(12) United States Patent
Moll et al.

(10) Patent No.: US 6,861,236 B2
(45) Date of Patent: Mar. 1, 2005

(54) EXPORT AND MODIFICATION OF (POLY) PEPTIDES IN THE LANTIBIOTIC WAY

(75) Inventors: Gert Nikolaas Moll, Groningen (NL); Cornelis Johannes Leenhouts, Haren (NL)

(73) Assignee: Applied Nanosystems B.V., Groningen (NL)

(*) Notice: Subject to any disclaimer, the term of this patent is extended or adjusted under 35 U.S.C. 154(b) by 0 days.

(21) Appl. No.: 10/360,101

(22) Filed: Feb. 7, 2003

(65) Prior Publication Data

US 2004/0009550 A1 Jan. 15, 2004

(30) Foreign Application Priority Data

May 24, 2002 (EP) .............................................. 02077060

(51) Int. Cl.[7] .............................................. C12P 21/02
(52) U.S. Cl. ....................... 435/69.1; 435/325; 530/323
(58) Field of Search ........................................ 435/69.1

(56) References Cited

U.S. PATENT DOCUMENTS

| | | | |
|---|---|---|---|
| 5,112,806 A | 5/1992 | Chatterjee et al. | |
| 5,218,101 A | 6/1993 | Hansen | |

(List continued on next page.)

FOREIGN PATENT DOCUMENTS

| | | |
|---|---|---|
| CA | 2209893 | 3/1999 |
| EP | 0 342 486 A1 | 11/1989 |
| EP | 0 342 658 B1 | 11/1989 |
| EP | 0 423 224 B1 | 4/1991 |
| EP | 0 444 759 A1 | 9/1991 |
| EP | 0 543 195 A2 | 5/1993 |
| EP | 0 597 997 B1 | 5/1994 |
| EP | 0 700 998 A1 | 3/1996 |
| EP | 0 712 935 A2 | 5/1996 |
| EP | 0 845 535 A2 | 6/1998 |
| GB | 2 282 813 A | 4/1995 |
| WO | WO 92/18633 | 10/1992 |
| WO | WO 93/03058 | 2/1993 |
| WO | WO 93/20213 | 10/1993 |
| WO | WO 94/12528 | 6/1994 |
| WO | WO 95/33765 | 12/1995 |
| WO | WO 96/16180 | 5/1996 |
| WO | WO 96/40757 | 12/1996 |
| WO | WO 97/11713 | 4/1997 |
| WO | WO 98/17685 | 4/1998 |
| WO | WO 98/56411 | 12/1998 |
| WO | WO 99/03352 | 1/1999 |
| WO | WO 00/46250 | 8/2000 |
| WO | WO 01/27143 A1 | 4/2001 |
| WO | WO 02/10336 A2 | 2/2002 |
| WO | WO 02/20610 A2 | 3/2002 |

OTHER PUBLICATIONS

Izaguirre et al. Appl. Environ. Microbiol. 63:3965–3971 (1997).*
Paul et al. FEMS Microbiology Letters 176:45–50 (1999).*
Burrage, et al., Biomimetic Synthesis of Lantibiotics, Chem. Eur. J., 2000, pp. 1455–1466, vol. 6, No. 8.
Okeley, et al., Facile Chemoselective Synthesis of Dehydroalanine–Containing Peptides, Organic Letters, 2000, pp. 3603–3606, vol. 2, No. 23.

(List continued on next page.)

*Primary Examiner*—Karen Cochrane Carlson
*Assistant Examiner*—Anand U Desai
(74) *Attorney, Agent, or Firm*—TraskBritt

(57) ABSTRACT

The invention includes a method for harvesting a polypeptide produced by a host cell, wherein the polypeptide has not undergone intracellular posttranslational modification, such as dehydration of a serine or a threonine, and/or thioether bridge formation. The invention also includes a method for producing thioether-containing peptides and dehydroalanine/dehydrobutyrine-containing.peptides, wherein thioether rings may be formed extracellularly.

13 Claims, 10 Drawing Sheets

Nisin

Subtilin

U.S. PATENT DOCUMENTS

| | | | |
|---|---|---|---|
| 5,516,682 A | | 5/1996 | Hansen |
| 5,576,420 A | | 11/1996 | Hansen |
| 5,594,103 A | | 1/1997 | De Vos et al. |
| 5,650,320 A | | 7/1997 | Caufield et al. |
| 5,811,392 A | | 9/1998 | Gilon et al. |
| 5,837,485 A | | 11/1998 | Entian et al. |
| 5,843,709 A | | 12/1998 | Entian et al. |
| 5,861,275 A | * | 1/1999 | Hansen ................ 435/69.1 |
| 5,872,001 A | | 2/1999 | Caufield et al. |
| 5,885,811 A | | 3/1999 | Hansen |
| 5,914,248 A | | 6/1999 | Kuipers et al. |
| 5,914,250 A | | 6/1999 | Hansen |
| 6,022,851 A | | 2/2000 | Vertesy et al. |
| 6,028,168 A | * | 2/2000 | Goodman et al. .......... 530/317 |
| 6,031,073 A | * | 2/2000 | Yu .............................. 530/317 |
| 6,100,056 A | | 8/2000 | Gasson et al. |
| 6,207,411 B1 | | 3/2001 | Ross et al. |
| 6,218,362 B1 | | 4/2001 | Lavoie et al. |
| 6,268,339 B1 | | 7/2001 | Goodman et al. |
| 6,342,385 B1 | | 1/2002 | Qi et al. |
| 2002/0019518 A1 | | 2/2002 | Hansen |

OTHER PUBLICATIONS

Jensen et al., Minimal Requirements for Exponential Growth of *Lactococcus lactis*, Applied and Environmental Microbiology, 1993, pp. 4363–4366, vol. 59, No. 12.

Kiesau et al., Evidence for a Multimeric Subtilin Synthetase Complex, Journal of Bacteriology, 1997, pp. 1475–1481, vol. 179, No. 5.

Kuipers et al., Autoregulation of Nisin Biosynthesis in *Lactococcus lactis* by Signal Transduction, The Journal of Biological Chemistry. 1995, pp. 27299–27304, vol. 270. No. 45.

Kuipers et al., Engineering Dehydrated Amino Acid Residues in the Antimicrobial Peptide Nisin. 1992, pp. 24340–24346, vol. 267, No. 34.

Kuipers et al., Characterization of the nisin gene cluster nisABTCIPR of *Lactococcus lactis*, Requirement of expression of the nisA and nial genes for development of immunity, Eur. J. of Biochem. 1993, pp. 281–291, vol. 216.

Kuipers et al., Protein engineering of lantibiotics, Antonie van Leeuwenhoek, 1996, pp. 161–170, vol. 69.

Kuipers et al., Controlled overproduction of proteins by lactic acid bacteria, TIBTECH, 1997, pp. 135–140, vol. 15.

Leenhouts et al., A general system for generating unlabelled gene replacements in bacterial chromosomes, Mol Gen Genet, 1996, pp. 217–224, vol. 253.

Mezo et al., Synthesis of Gonadotropin–Releasing Hormone III Analogs. Structure—Antitumor Activity Relationships, J. Med. Chem. 1997, pp. 3353–3358, vol. 40.

Nagai et al., Bicyclic Turned Dipeptide (BTD) as a Beta–Turn Mimetic; its Design Synthesis and Iacorporation into Bioactive Peptides. Tetrahedron, 1993, pp. 3577–3592, vol. 49– No. 17.

Banerjee et al., Structure and Expression of a Gene Encoding the Precursor of Subtilin, a Small Protein Antibiotic, The Journal of Biological Chemistry, 1988, pp. 9508–9514, vol. 263, No. 19.

Baneyx et al., Construction and Characterization of *Escherichia coli* Strains Deficient in Multiple Secreted Proteases: Protease III Degrades High–Molecular–Weight Substrates In Vivo, Journal of Bacteriology, 1991, pp. 2696–2703, vol. 173, No. 8.

Bienstock et al., Conformational Analysis of a Highly Potent Dicyclic Gonadotropin Releasing Hormone Antagonist by Nuclear Magnetic Resonance and Molecular Dynamics, J. Med. Chem., 1993, pp. 3265–3273, vol. 36.

Bierbaum et al., Engineering of a Novel Thioether Bridge and Role of Modified Residues in the Lantibiotic Pep5, Applied and Environmental Microbiology, 1996, pp. 385–392, vol. 62, No. 2.

Bierbaum, Genetics of Lantibiotic Biosynthesis, In: Amino Acids, Peptides, Porphyrins and Alkaloids, pp. 275–304, vol. 4.

Buchman et al., Structure, Expression, and Evolution of a Gene Encoding the Precursor of Nisin, a Small Protein Antibiotic, The Journal of Biological Chemistry, 1988, pp. 16260–16266, vol. 263, No. 31.

Buist et al., Molecular Cloning and Nucleotide Sequence of the Gene Encoding the Major Peptidoglycan Hydrolase of *Lactococcus lactis*, a Muramidase Needed for Cell Separation, Journal of Bacteriology, 1995, pp. 1554–1563, vol. 177, No. 6.

Entian et al., Genetics of subtilin and nisis biosyntheses, Antonic van Leeuwenhock, 1996, pp. 109–117, vol. 69.

Goodman et al., New Reagents, Reactions, and Peptidomimetics for Drug Design, Biopolymers, 2001, pp. 229–245, vol. 60.

Gross et al., The structure of Nisin, Journal of the American Chemical Society, 1971, pp. 4634–4635, vol. 93, No. 18.

Holo et al., Transformation of Lactococcus by Electroporation, In: Electroporation Protocols for Microorganisms, pp. 195–199, vol. 47.

Osapay et al., Lanthionine–Somatostatin Analogs: Synthesis, Characterization, Biological Activity, and Enzymatic Subility Studies, J. Med. Chem., 1997, pp. 2241–2251, vol. 40.

Poquet et al., HtrA is the unique surface housekeeping protease in *Lactococcus lactis* and is required for natural protein processing, Molecular Microbiology, 2000, pp. 1042–1051, vol. 35, No. 5.

Rivier et al., Design of Potent Dicyclic (1–5/4–10) Gonadotropin Releasing Hormone (GnRH) Antagonists, J. Med. Chem., 2000, pp. 807–818, vol. 43.

Rivier et al., Design of Monocyclic (1–3) and Dicyclic (1–3/4–10) Gonadotropin Releasing Hormone (GnRH) Antagonists, J. Med. Chem., 2000, pp. 797–806, vol. 43.

Rivier et al., Design of Potent Dicyclic (4–10/5–8) Gonadotropin Releasing Hormone (GnRH) Antagonists, J. Med. Chem., 2000, pp. 784–796, vol. 43.

Siegers et al., Biosynthesis of Lantibiotic Nisin, The Journal of Biological Chemistry, 1996 pp. 12294–12301, vol. 271, No. 21.

Siezen et al., Comparison of lantibiotic gene clusters and encoded proteins, 1996, pp. 171–184, vol. 69.

Terzaghi et al., Improved Medium for Lactic Streptococci and Their Bacteriophages, Antonie van Leeuwenhock, 1975, pp. 807–813, vol. 29, No. 6.

Van Der Meer et al., Influence of Amino Acid Substitutions in the Nisin Leader Peptide on Biosynthesis and Secretion of Nisin by *Lactococcus lactis*, The Journal of Biological Chemistry, 1994, pp. 3555–3562, vol. 269, No. 5.

Ye et al., NisP Is Related to Nisin Precursor Processing and Possibly to Immunity in *Lactococcus lactis*, Journal of Tongii Medical University, 1995, pp. 193–197, vol. 15, No. 4.

Novak et al., Cloning, Sequencing and Expression of an ABC Transporter Involved in the Production of the Lantibiotic Mutacin II in *Streptococcus mutans*, 96th ASM General Meeting, Abstract XP-000892159, 1996, USA.

Franke et al., Membrane Topology of the Lactococcal Bacteriocin ATP–binding Cassette Transporter Protein LenC, 1999, The Journal of Biological Chemistry, pp. 8484–8490, vol. 274, No. 13.

Qiao et al., Evidence for a role of NisT in transport of the lactibiotic nisin produced by *Lactococcus lactis* N8, 1996, pp. 89–93, FEMS Microbiology Letters, vol. 144.

Breukink et al., The lantibiotic nisin, a special case or not?, Biochimica et Biophysica Acta, 1999, pp. 223–234, vol. 1462.

McCauliffe et al., Lantibiotics: structure, biosynthesis and mode of action, FEMS Microbiology Reviews, 2001, pp. 285–308, vol. 25.

Fath et al., ABC Transporters: Bacterial Exporters, Microbiological Reviews, Dec. 1993, pp. 995–1017, vol. 57, No. 4.

* cited by examiner

Nisin

Subtilin

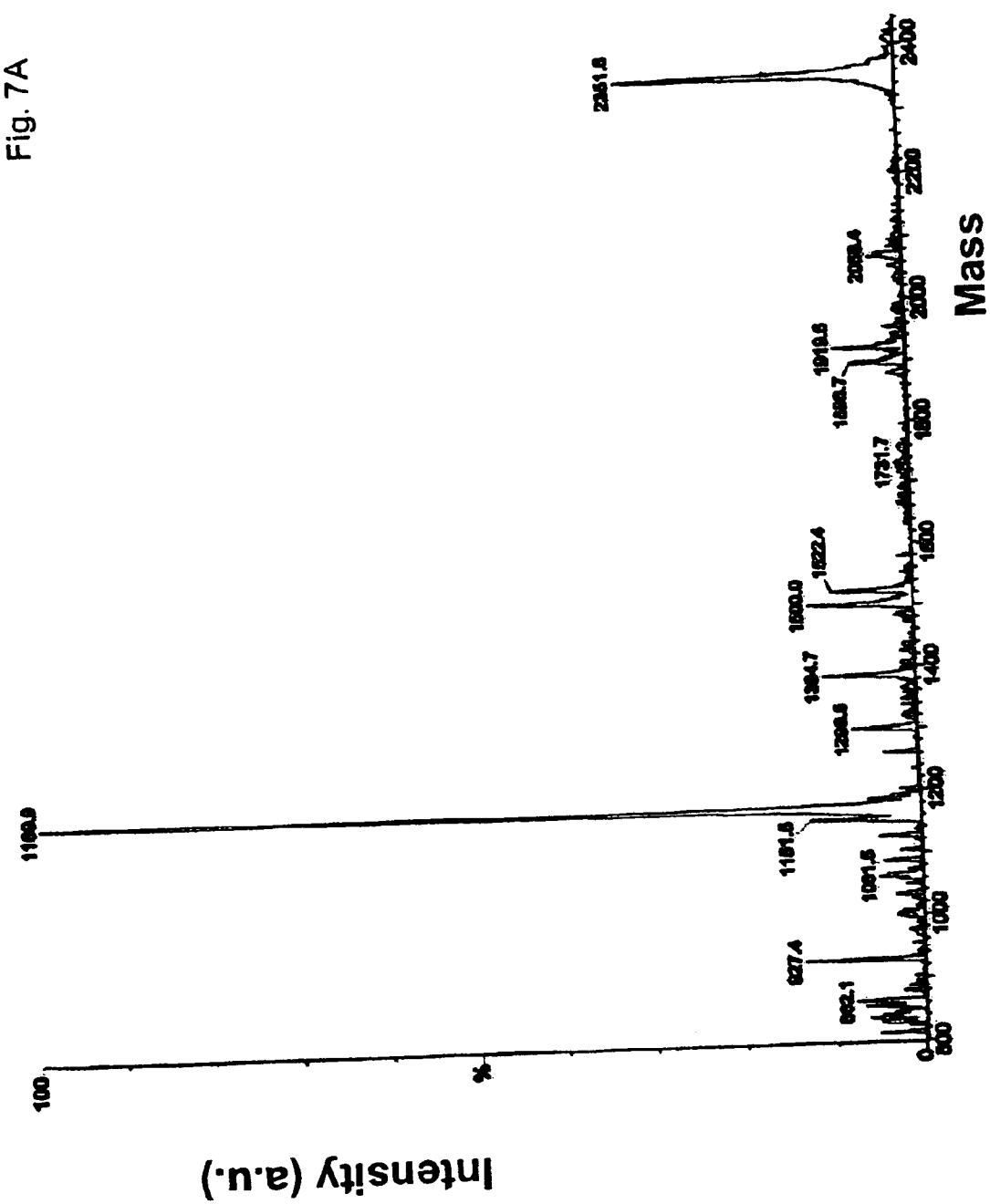

Fig. 7B

Nisin leader average mass

S T K D F N L D L V S V S K K D S G A S P R    2351.6

Thioether LHRH

LHRH1

Q H W S Y G L R P G

```
      ┌─S─┐
Q H W A Y A L R A G
```

```
      ┌─S─┐
Q H W A Y G A R P G
```

```
  ┌─S─┐
Q A W A Y G L R P G
```

```
    ┌─S─┐
Q H W A Y A L R P G
```

---

LHRH2

Q H W S H G W Y P G

```
      ┌─S─┐
Q H W A H A W Y A G
```

```
    ┌─S─┐
Q H W A H G A Y P G
```

```
  ┌─S─┐
Q A W A H G W Y P G
```

```
    ┌─S─┐
Q H W A H A W Y P G
```

EXPORT AND MODIFICATION OF (POLY) PEPTIDES IN THE LANTIBIOTIC WAY

TECHNICAL FIELD

The invention relates generally to biotechnology and, more particularly, to the field of lantibiotics and to the field of posttranslational modifications of (poly)peptides.

BACKGROUND

Lantibiotics form a group of unique ribosomally synthesized and posttranslationally modified antibiotic peptides that are produced by, and primarily act on, Gram-positive bacteria (for review, See McAuliffe et al., FEMS Microbiol. Rev. 25: 285–308 (2001)). Because by definition lantibiotics contain intramolecular thioether bridges or rings formed by the thioether amino acids lanthionine (Lan) and 3-methyllanthionine (MeLan) and lantibiotics all are peptide antibiotics with moderate to strong bactericidal activity, lantibiotics take their name from these most eye-catching properties.

Thioether rings protect peptides against proteolytic degradation. For instance, the lantibiotic nisin remains active after trypsin treatment. Thioether rings are also essential for some lantibiotic activities. For instance, opening of ring A or C in nisin causes deletion of the membrane permeabilization capacity. Ring A of nisin is necessary for its capacity to autoinduce its own synthesis and for nisin's capacity to block the peptidoglycan synthesis by interacting with lipid II. It is essential to have thioether rings and not disulfide rings since replacement of thioether rings by disulfide bridges leads to loss of antimicrobial activity.

Lantibiotics do not spoil the environment and are not toxic to animals or man. Lantibiotics may also have applications as biopreservatives in the preparation of food and beverages, or as a bactericidal agent in cosmetics and veterinary and medical products. Because the growing number of multidrug resistant pathogenic micro-organisms has created the threat of another "pre-antibiotic era" for many bacterial diseases, it is expected that lantibiotics also may serve as new lead compounds to remedy this alarming problem. For these reasons, lantibiotics have experienced a marked increase in basic and applied research activities in the past decade, leading to an extraordinary increase in the knowledge of the lantibiotics structural and functional properties, the mechanisms of action and of the genes and protein components involved in the biosynthesis and secretion of the lantibiotics. For example, lantibiotics have become subject to "protein engineering" projects, with the aim of altering, via site-directed mutagenesis, the lantibiotics activity, stability and spectrum of susceptible target cells. In this description, the linear (type A) lantibiotics are considered since at present, very little specific information is available for the circular (type B) lantibiotics.

The lantibiotics subtilin and nisin belong to, and are representative of, the peptide antibiotics or lantibiotics of type A. Subtilin and nisin contain the rare amino acids dehydroalanine (Dha), dehydrobutyrine (Dhb), meso-lanthionine and 3-methyllanthionine, as well as the characterizing thioether bridges.

Nisin is the most prominent lantibiotic and is used as a food preservative due to its high potency against certain Gram-positive bacteria. It is produced by *Lactococcus lactis* strains belonging to serological group N. The potent bactericidal activities of nisin and many other lantibiotics are based on their capacity to permeabilize the cytoplasmic membrane of target bacteria. Breakdown of the membrane potential is initiated by the formation of pores through which molecules of low molecular weight are released. In addition, nisin inhibits cell wall synthesis by binding to lipid II, a precursor of peptidoglycan synthesis, modulates the activity of autolytic enzymes and inhibits the outgrowth of spores (See also, Breukink and de Kruijff, Biochem. Biophys. Acta 1462: 223–234, 1999).

In several countries, nisin is used to prevent the growth of clostridia in cheese and canned food. The nisin peptide structure was first described by Gross & Morell (J. Am. Chem. Soc 93: 4634–4635, 1971), and its structural gene was isolated in 1988 (Buchmann et al., J. Biol. Chem. 263: 16260–16266, 1988). Nisin has two natural variants, nisin A and nisin Z, which differ in a single amino acid residue at position 27 (histidine in nisin A is replaced by asparagine in nisin Z).

Subtilin is produced by *Bacillus subtilis* (ATCC 6633). Subtilin's chemical structure was first unravelled by Gross & Kiltz (Biochem. Biophys. Res. Commun. 50: 559–565, 1973) and its structural gene was isolated in 1988 (Banerjee & Hansen, J. Biol. Chem. 263: 9508–9514, 1988). Subtilin has strong similarities to nisin with an identical organization of the lanthionine ring structures (FIG. 1). Further, nisin and subtilin possess similar antibiotic activities.

Due to its easy genetic analysis *B. subtilis* became a suitable model organism for the identification and characterization of genes and proteins involved in lantibiotic biosynthesis. The pathway by which nisin is produced is very similar to that of subtilin and the proteins involved share significant homologies over the entire proteins (for review, see also, De Vos et al., Mol. Microbiol. 17: 427–437, 1995).

Another well known and studied lantibiotic, produced by *Staphylococcus epidermis* 5, is Pep 5, which contains three ring structures (one MeLan and two Lan), an N-terminal oxobutyryl residue and two Dhb residues (Kellner et al., Angew. Chemie Int. Ed. Engl. 28: 616–619, 1989).

The respective genes of subtilin and nisin have been identified adjacent to the structural genes, and are organized in operon-like structures (FIG. 2). The genes are thought to be responsible for posttranslation modification, transport of the modified prepeptide, proteolytic cleavage and immunity which prevents toxic effects on the producing bacterium. Further, biosynthesis of subtilin and nisin is strongly regulated by a two-component regulatory system which includes a histidine kinase and a response regulator protein.

According to a present model (FIG. 3), it is assumed that an extracellular growth phase-dependent signal may activate the membrane localized histidine kinase. The nature of the signal may be different for subtilin and nisin biosynthesis. In nisin biosynthesis, nisin has an inducing function, whereas it was shown for subtilin biosynthesis that its biosynthesis is sporulation dependent.

According to the model, after nisin's auto-phosphorylation, the SpaK and NisK histidine kinase transfer the phosphate residue to the response regulator which in turn activates the genes necessary for subtilin and nisin biosynthesis. Thereafter, the prepeptide is modified at a membrane localized modification complex (lantionine synthetase) including the intracellular SpaB/SpaC and the NisB/NisC proteins, respectively. According to the model, the proteins are also associated with the SpaT and the NisT transporter, respectively.

As in any lantibiotic, the presubtilin or prenisin molecule includes a leader segment and a mature segment, wherein the leader segment is thought to play several roles in the biosynthetic pathway. The leader segment is thought not to be just a translocation signal sequence, but also thought to provide recognition signals for the modification enzymes and to suppress antimicrobial activity until the mature peptide is released from the cell. As also postulated by Qiao and Saris, (Fems Microbiol. Let. 144: 89–93(1996)), the modified prepeptide is thought to be proteolytically cleaved after its transport through the cellular membrane or cleavage of the leader from the modified peptide occurs inside the cell before secretion. In the case of nisin, cleavage is performed by NisP, whereas in the case of subtilin, no specific protease has been found within the operon-like structure. However, B. subtilis is rich in extracellular proteases and possibly subtilisin, which also recognizes proline at position-2, could cleave the modified pre-subtilin.

The gene clusters flanking the structural genes for various linear (type A) lantibiotics have recently been characterized (for review, see, Siezen et al., Antonie van Leeuwenhoek 69: 171–184, 1996)). The best studied representatives are those of nisin (nis), subtilin (spa), epidermin (epi), Pep5 (pep), cytolysin (cyl), lactocin S (las) and lacticin 481 (lct). Comparison of the antibiotic gene clusters shows that the clusters contain conserved genes that probably encode similar functions.

The nis, spa, epi and pep clusters contain lanB and lanC genes that are presumed to code for two types of enzymes that have been implicated in the modification reactions characteristic of all antibiotics, i.e. dehydration and thioether ring formation. The cyl, las and lct gene clusters have no homologue of the lanB gene, but do contain a much larger lanM gene that is the lanC gene homologue. Most antibiotic gene clusters contain a lanP gene encoding a serine protease that is presumably involved in the proteolytic processing of the prelantibiotics. All clusters contain a lanT gene encoding an ATP-binding cassette (ABC)-like transporter spanning the plasma membrane of a cell and likely is involved in the export of (precursors of) the lantibiotics from the cell. The lanE, lanF and lanG genes in the nis, spa and epi clusters encode another transport system that is possibly involved in self-protection. In the nisin and subtilin gene clusters two tandem genes, lanR and lank, have been located that code for a two-component regulatory system.

Non-homologous genes are also found in some lantibiotic gene clusters. The nisL and spaI genes encode lipoproteins that are involved in immunity, the pepL gene encodes a membrane-located immunity protein and epiD encodes an enzyme involved in a posttranslational modification found only in the C-terminus of epidermin. Several genes of unknown function are also found in the las gene cluster. Commonly, a host organism or cell carrying one or more of the genes (e.g., lanT, lanI, lanA, lanP, lanB and lanC) in the cluster are identified with a shorthand notation such as lanTIAPBC. The above identified genes appear to be different from genes encoding the secretion apparatus for the non-lantibiotic lactococcins that includes two membrane proteins LcnC and LcnD, as discussed in Franke et al., J. Biol. Chem 274: 8484–8490, (1999).

A database has been assembled for all putative gene products of type A lantibiotic gene clusters. Database searches, multiple sequence alignment and secondary structure prediction have been used to identify conserved sequence segments in the LanB, LanC, LanE, LanF, LanG, LanK, LanP, LanM, LanR and LanT gene products that may be essential for structure and function (Siezen et al., ibid). The database allows for a rapid screening of newly determined sequences in lantibiotic gene clusters.

However, despite the above cited recent knowledge obtained in the field, attempts to engineer novel lantibiotic-like peptides comprising newly synthesized unnaturally occurring thioether bridges have been scarce, if not rather unsuccessful. In U.S. Pat. No. 5,861,275, nisin-subtilin chimeras have been produced in the Gram-positive Bacillus subtilus that do not comprise thioether bridges other than those naturally occurring in either nisin or subtillin. In a different application (U.S. Patent Application Publication 2002/0019518), Bacillus subtilus was used to produce a chimeric polypeptide comprising a lantibiotic peptide and a subtilin leader segment, a lantibody, that remains associated within the cell wall.

A novel thioether bridge in lantibiotic Pep5 has been engineered by Bierbaum et al., Appl. Env. Microbiol. 62: 385–392, (1996) by modifying the Gram-positive bacterium Staphylococcus epidermis 5 by depleting the host organism of the gene cluster pepTIAPBC and replacing pepTIAPBC with a gene cluster pepIAPBC, wherein pepA was or was not replaced with mutated structural genes encoding for Pep 5 peptide and wherein amino acids were substituted; genes coding for peptides with substitutions C27A (Cysteine to Alanine at position 27), C33A, A19C, Dhb16A, Dhb20A, K18Dha were generated. The A19C substitution resulted in novel thioether ring formation. The clone corresponding to the A19C substitution produced a small amount of a peptide that showed only little activity. It was thought that prolonged exposure of the peptide to intracellular protease of the producing transformed cell was causal to this disappointing result.

The K18Dha substitution in Pep5 resulted in a clone that produced incompletely dehydrated serine at position 18. Kuipers et al. (J. Biol. Chem. 267: 24340–24346, 1992) engineered a new Dhb residue into nisinZ by substituting M17Q/G18T in the lantibiotic, but also obtained incomplete dehydration of the resulting threonine and no additional ring formation. The incomplete dehydration is generally thought to be a result of questionable substrate specificity of the dehydrating enzyme LanB in the transformed cell.

In short, no large measure of success has yet been achieved in providing novel thioether bridges to lantibiotics in Gram-positive organisms, let alone that engineered thioether bridge formation has been provided to polypeptides of non-lantibiotic descent or by organisms other than Gram-positive bacteria.

Paul, Leena K et al. (FEMS Microbiol. Lett. 176: 45–50, 1999) recently studied the subtilin leader peptide as a translocation signal in the Gram-negative E. coli. By default, devoid of a specific lantibiotic transporter system and provided a fusion-protein comprising the subtilin leader peptide and part of the mature subtilin attached to E. coli alkaline phosphatase (AP) to study the possible translocation. Although the fusion protein was translocated to the periplasmic side of the cytoplasmic membrane, the fusion protein remained associated with that membrane. In earlier work (Izaguirre & Hansen, Appl. Environ. Microbiol 63: 3965–3971, 1997), the same fusion protein was expressed in the Gram-positive Bacillus subtilis, where the fusion protein was cleaved off from the membrane after successful translocation, but where no dehydration of serines or threonines of the AP polypeptide, let alone thioether bridge formation, was observed. Novak J et al., ASM general meeting 96: 217 (1999), recently provided an E. coli host cell with an ORF (ORF1) encoding an ABC transporter of 341 amino acids thought to be involved in the translocation of the lantibiotic mutacinII in Streptococcus mutans.

However, an intact gene product of the ORF1 was not produced in E. coli, whereas a truncated protein of unknown identity or functionality was observed.

For the purpose of protein engineering of lantibiotics (for an extensive review see, Kuipers et al., Antonie van Leeuwenhoek 69: 161–170, 1996) or for the purpose of engineering newly designed (poly)peptides with lantibiotic-type posttranslational modifications, i.e., for example, for pharmaceutical use, much attention has recently (see, e.g., Entian & de Vos, Antoni van Leeuwenhoek supra; Siegers et al., J. Biol. Chem. 271: 1294–12301 (1996); Kiesau et al., J. Bacter. 179: 1475–1481 (1997)) been given to understanding the role of the LanB, LanC (or LanM) and LanT complex, the enzymes thought to be involved in dehydration, thioether ring formation and transportation of the lantibiotic out of the cell, respectively. However, the production of lantibiotic type heterologous proteins has not yet matured satisfactorily.

SUMMARY OF THE INVENTION

The invention provides a method allowing for the harvest of a desired (poly)peptide produced by a recombinant host cell. The method comprises the steps of a) selecting a recombinant host cell comprising a first nucleic acid comprising a first nucleic acid fragment encoding a leader peptide, and a second nucleic acid fragment encoding the desired (poly)peptide, whereby the first and second nucleic acid fragments are within the same open reading frame of the first nucleic acid and the leader peptide is at least functionally equivalent to a N-terminal leader peptide found with the prepeptide of a lantibiotic; b) selecting the host cell for the presence of a transporter protein commonly known as LanT or a functional equivalent thereof, and c) allowing the translation of the first nucleic acid and harvesting the desired (poly)peptide when the leader peptide (be it bound to or cleaved off from the desired (poly)peptide) is present in the culture medium of the cell.

In one embodiment, the leader peptide is freely available in the culture medium and is dissociated from host cell structures, such as the membrane or cell wall of the host cell. Considering the poor results obtained in the production of lantibiotic-type heterologous proteins, it was realized by the present inventors that until now, insufficient guidance was available on how to determine that a host cell system, thought to be suitably equipped with the machinery to provide for newly designed (poly)peptides with lantibiotic-type posttranslational modifications, was up to the task. As presented herein, it is realized that the presence of leader peptide in the culture medium of such a host cell system is a reliable measure of the capability of the system to produce such desired (poly)peptides.

It suffices to determine when, for a given host cell system, the presence or time point of appearance of such leader peptide in the culture system can be established to ascertain that actual production of the desired (poly)peptide (be it in modified or in as yet unmodified form) by the host cell system is expected and harvest can begin. The leader peptide can be detected each and every time in a host cell culture system set up to produce the desired (poly)peptide. However, for established cultures systems, harvest can be performed at time points which may be determined in pilot experiments with the culture systems.

The present invention shows that, until now, the field of the study of lantibiotic production has been looking on the wrong side of the cell membrane. The unmodified peptide coupled to its leader peptide can be transported out of the cell without prior modification, and LanB and LanC (or LanM) may act not inside, or outside of the cell (see also, FIG. 4). Now that this guidance for determining the suitability of a host cell culture system is available, as disclosed herein it is particularly useful for the production of desired heterologous (poly)peptides, which are of non-Gram-positive nature (i.e., Gram-negative prokaryotic), or essentially eukaryotic or viral descent.

Where it was earlier thought that LanB and LanC act in concert to modify the peptide only before it is translocated, it is disclosed herein that after transportation, the as yet unmodified peptide may undergo its specific posttranslational modification extracellularly leading to dehydration and thioether bridge formation, bringing the role of the transporter protein and the function of the leader peptide herein to central stage to modify a (poly)peptide in the lantibiotic way, it being a prerequisite to present the unmodified peptide to the modification machinery. It however also provides for improved production of unmodified or only partly modified heterologous proteins or peptides.

Thus, the invention also discloses the insight that dehydration of a serine or threonine of a (poly)peptide and subsequent thioether bridge formation can satisfactorily occur when a pre(poly)peptide has been transported out of the host cell wherein it was produced by translation, such as by a transporter protein such as an ABC transporter, or at least functionally corresponding to a transporter commonly identifiable as LanT. Dehydration (and optionally thioether bridge formation) is enzymatically catalyzed by an enzyme or enzymes that are at least functionally corresponding to LanB and/or LanC. The transporter transports the to-be-modified (poly)peptide through the membrane of the host cell where it is positioned in working proximity to extra-cellular located LanB for dehydration.

In a further embodiment, the invention discloses a method further comprising harvesting the desired (poly)peptide after detecting the presence of the leader peptide (be it bound to or cleaved off from the desired (poly)peptide) in the culture medium or supernatant of the cell (see also, FIG. 5). In the case of some small peptides, it is preferred to have not only the lantibiotic leader coding sequence in front of the desired peptide coding sequence, but the whole lantibiotic prepeptide coding sequence. The resulting fusion protein can be more easily detected and purified. Since, after ring formation, cleavage of the leader liberates the N-terminal site of the lantibiotic, very high sensitivity detection is possible by using the induction capacity of the lantibiotic. Furthermore, export is, in some cases, more efficient if the whole prepeptide precedes the desired peptide.

For detecting the presence, it is desirable that the medium contains a few nutrients, i.e., a so-called minimal medium. Also, it is desired that the presence is detected by harvesting the supernatant by aspirating and dispensing the supernatant into and out of a pipet tip (or other harvesting device) that contains a microvolume bed of affinity chromatography media fixed at the end of the tip that is without dead volume. This procedure is herein called "ziptipping" and allows, after subsequent elution, for relatively pure presentation of desired (poly)peptide for further analysis.

By using the combination of growth in minimal medium and ziptipping the supernatant of the culture, samples of sufficient purity can be obtained that are well suited for detection or analysis by high resolution MALDI-TOFMS. This allows a most significant measurement of leader peptide and, thus, prediction of desired (poly)peptide content, suitability of the host cell system used and suitable timeof-harvest of desired (poly)peptide. Detection of the leader peptide can, thus be used to ascertain the export of (poly) peptide coupled to this lantibiotic leader, such as in those cases where the leader peptidase acts extracellularly.

In a further embodiment, the invention discloses a method wherein the host cell producing the desired (poly)peptide is essentially devoid of leader peptidase (lanP) activity, thus allowing the production and extracellular harvest of desired (poly)peptide that is essentially still coupled to its leader peptide. In this way, potential intracellular toxic effects of desired (poly)peptide provided with thioether bridges are reduced. It suffices to design a leader peptide that cannot be cleaved by the leader peptidase of the host cell used. In both cases, the desired (poly)peptide can later be obtained free from the leader peptide, by, e.g., specific proteolytic cleavage using added lanP or another suitable protease capable of cleaving the leader peptide from the desired (poly)peptide.

It is also herein disclosed that in a desired (poly)peptide, a serine or serines that are N-terminally located from cysteines are dehydrated and coupled to more C-terminally located cysteines. As further exemplified herein, a (poly) peptide sequence with a serine and a cysteine '"S-C" contains (after thioether bridge formation) alanines in the positions of the serine and 'cysteine: "A—A." These alanines are coupled by, aside from the peptide backbone, a thioether bridge.

Generally, a method as provided herein allows a high detection level for measuring levels of (lantibiotic) (poly) peptides directly from the culture supernatant, considering that the ratio leader peptide versus desired (poly)peptide is essentially 1:1. Such guidance allows for efficient culture methods to produce the desired polypeptide and allows for determining appropriate or optimal time points at which the culture may be harvested.

In another embodiment, the invention discloses a method and a (poly)peptide wherein the desired (poly)peptide is selected from the group of peptide hormones, fragments of the peptide hormones or analogues from the peptide hormones originating from hypophysis and/or peptide hormones with similar actions including vasopressin, terlipressin, desmopressin, cispressin, oxytocin, adrenocorticotropic hormone and human growth hormone.

In yet another embodiment, the invention discloses a method and a (poly)peptide wherein the desired (poly) peptide is selected from the group of peptide hormones, fragments of the peptide hormones or analogues from the peptide hormones originating from hypothalamus, and/or peptide hormones with similar actions such as gonadoliberinII, luteinizing hormone, releasing hormone, leuprolide, and other synthetic analogues of LHRH including gonadorelin, goserelin, buserelin, leuproreline, nafarelin, triptorelin, cetrorelix, somatostatin, analogues of somatostatin, such as Octreotide, Somatostatine, corticotropin-inhibiting peptide, corticotropin-release factor, urocortin, urotensin II and growth hormone release factor. Specific LHRH-peptide analogues that are provided with a thioether ring structure is disclosed herein (see, Table 1).

Such distinct LHRH1 and LHRH2 and thioether bridge containing analogs are, for example, based on the peptide sequence of LHRH1 (SEQ ID NO: 1) or of LHRH2 (SEQ ID NO: 2). Such peptide sequences may be generated via recombinant means as described herein linked to a leader peptide, such as the nisin leader peptide (SEQ ID NO: 3). As disclosed herein, particular LHRH1- and LHRH2 thioether analogs were synthesized by exploiting the lantibiotic enzymes of the nisin producing *Lactococcus lactis* strain NZ9700. These enzymes involve a transporter molecule, NisT, a dehydrating enzyme, NisB that dehydrates serines and threonines and an enzyme, NisC that couples the dehydrated serines and threonines to cysteines giving the thioether ring.

Thioether bridged peptide-analogues were, for example, generated by cloning on a plasmid a nucleotide sequence that codes for a specific LHRH mutant behind the nisin leader (the particular LHRH analog coding sequence being followed by a stop codon).

In another embodiment, the invention discloses a method and a (poly)peptide wherein the desired (poly)peptide is selected from the group of peptide hormones, fragments of the peptide hormones or analogues from the peptide hormones originating from adrenocortex, adrenal medulla, kidney and heart and/or peptide hormones with similar actions such as adrenomedullin, angiotensin I, atrial natriuretic factor, bradykinin, brain natriuretic peptide, C-type natriuretic peptide and vasonatrin peptide.

In a further embodiment, the invention discloses a method and (poly)peptide wherein the desired (poly)peptide is selected from the group consisting of peptide hormones, fragments of the peptide hormones or analogues from the peptide hormones originating from other endocrine/exocrine organs such as the pancreas, thyroid, and parathyroid and/or peptide hormones with similar actions such as calcitonin, osteocalcin, glucagon, insulin, insulin-like growth factor-I or II, parathormone, and cholecystokinin.

In another embodiment, the invention disclosed a method and a (poly)peptide wherein the desired (poly)peptide is selected from the group of peptide hormones, fragments of the peptide hormones or (synthetic) analogues from the peptide hormones with antibiotic (-like) activity and/or peptide hormones with similar actions such as dermaseptin, defensin I, bombinin-like peptide, histatin-5, indolicidin, magainin-1 and ceratotoxin A.

In one embodiment, the invention discloses a method and a (poly)peptide wherein the desired (poly)peptide is selected from the group of biological active peptides, fragments of the biological active peptides and/or hormones or analogues from the biological active peptides and/or peptides with similar actions, such as exendin-3, secretin, human pancreatic polypeptide, peptide YY, gastric inhibitory polypeptide, big gastrin-I, pentagastrin, gastrin releasing peptide, motilin, neuropeptide Y, galanin, alpha-neurokinin, deltorphin, alpha-endorphin, beta-endorphin, leu-enkephalin, met-enkephalin, allatostatin I, anthopleurin-A, anti-inflammatory peptide 1, delta sleep inducing peptide, alpha-dendrotoxin, eledoisin, echistatin, small cardioactive peptide A or B, cerebellin, charybdotoxin, conopressin G, conotoxin EI, corazonin, experimental allergic encephalitogenic peptide, experimental autoimmune encephalomyelitis complementary peptide, tocinoic acid/pressinoic acid, brain-derived acidic fibroblast growth factor (1–11), brain derived acidic fibroblast growth factor (102–111), brain derived basic fibroblast growth factor (1–24), fibrinogen binding inhibitor peptide, fibroblast growth factor inhibitory peptide and transforming growth factor alpha.

In a further embodiment, the invention disclosed a method and a (poly)peptide wherein the desired (poly) peptide is selected from the group of biological active peptides, fragments of the biological active peptides and/or hormones or analogues from the biological active peptides and/or peptides with similar actions such as guanylin, helospectin I, hepatitis B surface antigen fragment, intercellular adhesion molecule, tachyplesin I, HIV (gp 120) antigenic peptide fragment, HIV (gp 41) antigenic peptide I fragment, HIV (gp41) antigenic peptide 5, HIV protease inhibitors, IGF II 69–84, interleukin-8 fragment, interleukin-2 fragment(60–70), leucokinin I, leukopyrokinin, mastoparan, melanin concentrating hormone, melittin, and ras oncogene related peptides.

Considering that lanthionine formation between, for example, dehydrobutyrine and cysteine is energetically possible at room temperature and can also occur spontaneously, the transported (poly)peptide can form thioether bridges spontaneously or where it is positioned in working proximity to extracellular located LanC for subsequent enzymatically induced thioether bridge formation. Alternatively, the transporter transports the to-be-modified polypeptide through the membrane of the host cell where it is positioned in working proximity to extracellularly located LanM for dehydration and subsequent thioether bridge formation.

The invention discloses a method from which several fields can benefit. In short, the invention discloses use of lantibiotic exporters (LanT) for export of peptides or proteins which may have been converted by lantibiotic enzyme(s), in particular, enabling extracellular formation of lanthionines and other rings. Amino acids are able to form short sequences (peptides) and longer sequences (proteins). Peptides and proteins (herein also referred to as "(poly)peptides") are both important classes of biomolecules for nutrition, for pest control and for fighting disease. The lantibiotics importance is illustrated by the number and range of therapies based on the antibiotics recently created by the biochemical and pharmaceutical industries. There is also a large number of protein and peptide based pharmaceuticals and it should also be understood that the use of therapeutic pharmaceuticals is not limited to humans, but also extends to animal, plant and other biosystems. However, the manufacture of many present and potential protein or peptide pharmaceuticals has limitations since many protein or peptide pharmaceuticals are prepared in living cells (in vivo), but the cells must be ruptured or lysed (killed) and the contents extracted, separated, and purified in order to provide a given quantity of the peptide or protein. Since this is a complex process, the amount of any desired peptide or protein in any cell at any time is limited.

The present invention bypasses this problem by introducing a factor into the living cells which allows the cells to continuously transport proteins or peptides and export them through the cell wall, so that the product produced intercellularly may be collected extracellularly and the cells may remain vital and continue to produce materials. It is evident that this permits a substantially easier and higher rate of production of the desired products.

Since it is known that the LanT transporter or functional equivalent thereof acts on unmodified (poly)peptide to which the leader is still attached, one field relates to the expression and production of recombinant (poly)peptides, other than bacterial descent, and relates to expression and/or production of a (poly)peptide of eukaryotic (i.e., plant, animal or fungal origin) or viral descent. Such peptides are widely produced by recombinant means for use in the production of pharmaceuticals, such as active compounds including a (poly)peptide hormone, or cytokine, or antibody fragment, or biopesticide agent, or as antigens for a vaccine or immunogenic composition. It is now possible to use a lantibiotic-type transporter system to export peptides of eukaryotic, viral, and of bacterial (prokaryotic) descent.

In one embodiment, the invention disclosed a method that allows for extracellular harvest of a desired (poly)peptide (which may be out of the realm of bacterial lantibiotics or even be of eukaryotic or viral descent) produced by a recombinant host cell. The method comprises a) selecting a recombinant host cell comprising or provided with a first recombinant nucleic acid having a first nucleic acid fragment encoding a leader peptide and a second nucleic acid fragment encoding the desired (poly)peptide wherein the first and second nucleic acid fragments are within the same open reading frame of the first nucleic acid and the leader peptide is at least functionally equivalent to a N-terminal leader peptide found with the prepeptide of a lantibiotic; and b) selecting the host cell for the presence of a lantibiotic transporter protein commonly known as LanT, (such a host cell can be a Gram-positive or Gram-negative prokaryote or an eukaryote provided with such a transporter) and allowing for the translation of the first nucleic acid. In this embodiment, the cell is essentially devoid of leader peptidase activity, or comprises leader peptidase that cannot cleave the specific leader peptide used. Such a host cell may be obtained by deleting or functionally deleting, the lanP gene.

In another embodiment, the invention discloses a method allowing for extracellular harvest of a desired (poly)peptide which has not undergone intracellular posttranslational modification comprising dehydration of a serine or a threonine and/or thioether bridge formation. As described herein, it is demonstrated how to obtain nisin prepeptide (i.e., nisin leader and unmodified nisin) extracellularly. The nisin prepeptide was obtained using a host cell selected for the presence of two plasmids, one plasmid encoding the nisin prepeptide and one plasmid encoding NisT, wherein the host cell is further characterized by at least the functional absence of at least one of the other gene products derived from the Nis-gene cluster, such as NisB, NisC, or NisP.

The invention thus discloses a (poly)peptide harvestable after the (poly)peptide has been transported from the producing host cell, obviating the need to lyse or disrupt the host cells to harvest the (poly)peptide. Alternatively, the desired polypeptide may be harvested from within the cell. Cultures of cells provided with the transporter protein can be kept alive and in use, wherein the desired (poly)peptide can be harvested from the supernatant of spun-down host cells. The host cells need not be of Gram-positive descent per se, since Gram-negative prokaryotes or even eukaryotes can be provided with a properly placed transporter. Thus, the gamut of expression systems that can be used to express and produce a desired (poly)peptide is enhanced.

Furthermore, the invention discloses a method allowing for extracellular modification of a desired (poly)peptide produced by a recombinant host cell. The method comprises a) selecting a recombinant host cell comprising a first nucleic acid comprising a first nucleic acid fragment encoding a leader peptide and a second nucleic acid fragment encoding the desired (poly)peptide, wherein the first and second nucleic acid fragments are within the same open reading frame of the first nucleic acid and the leader peptide is at least functionally equivalent to a N-terminal leader peptide found with the prepeptide of a wild-type lantibiotic; b) selecting the host cell for the presence of a transporter protein such as LanT, or a functional equivalent thereof; c) selecting the host cell for the presence of an essentially extracellular protein (such as LanB, LanC or LanM) capable of providing posttranslational modification; and d) allowing for the translation of the first nucleic acid.

In one embodiment, the invention discloses a method allowing for extracellular modification of a desired (poly)peptide which has not undergone intracellular posttranslational modification comprising dehydration of a serine or a threonine and/or thioether bridge formation. In this embodiment, the essentially extracellular, albeit preferably cell-surface-bound, enzyme is capable of dehydrating a serine or a threonine, or is capable of providing for thioether bridge formation.

Further, the invention disclosed a method for lantibiotic-type modification of nonlantibiotic polypeptides, even when the (poly)peptide is of essentially eukaryotic or viral descent. This is useful for altering various characteristics of such products, for example related to stability or pharmacological profiles of useful polypeptides. It is of course useful to use a leader peptide or functional equivalents thereof.

Furthermore, the invention discloses a method allowing for extracellular modification of a desired (poly)peptide produced by a recombinant host cell, wherein the modification comprises thioether bridge formation. The location of serines, threonines or cysteines in the desired (poly)peptide may be selected such that thioether ring formation by the enzyme system selected follows naturally. For example, serine and threonine dehydration, may be followed by thioether ring formation by coupling to cysteines as follows. In the case of lantibiotic enzymes belonging to the type B lantibiotics, ring formation may occur from dehydrated serines/threonines to more C-terminally or to more N-terminally located cysteines. In the case of lantibiotic enzymes belonging to type A lantibiotics, ring formation may occur from dehydrated serines/threonines to more C-terminally located cysteines. Conversion by enzymes belonging to type A lantibiotics occurs in time from N to C-terminal direction from dehydrated serines/threonines to the nearest more C-terminally located available cysteine. In the case of enzymes belonging to type A lantibiotics, a preferential distance of one to four amino acids to available cysteines is disclosed to form lanthionines. It is possible that 2 to 3 amino acids are between a dehydrated serine/threonine on the one hand and a cysteine on the other hand, wherein the optimal distance is two amino acids.

As disclosed in Table 1, peptides with the above preferred distances for optimal thioetherbridge formation may be selected. At distances between four and thirteen amino acids, lanthionine formation can occur but is less efficient. At these distances, dehydration of serines and threonines without subsequent lanthionine formation and next to no dehydration of serine/threonine occurs. It is possible to have flanking regions of serines and threonines that allow activity of the dehydrating enzyme. To achieve this, at least the six to eight amino acids (three to four on each side) surrounding dehydrated serines/threonines are substantially hydrophobic. At each of these positions in 40–80% of the cases, the amino acid is hydrophobic, in 20–40% hydrophilic, of which in 5–15% positively charged. For best efficiency, negatively charged amino acids rarely occur. The composition of the flanking regions on the desired (poly)peptide may differ from the one of serine and threonine in lantibiotic-type leader peptides. In leader peptides, serines and threonines occur, but are not dehydrated, whereas cysteines do not occur. The six to eight positions most proximate to leader serines/threonines contain less hydrophobic amino acids and more negatively charged amino acid than in positions around propeptide serine/threonine per position around 20–40% of the cases the amino acid is hydrophobic and around 20% of the cases a negatively charged amino acid is disclosed.

With respect to the peptidase cleavage site, at least two types of leader peptides exist from which guidance can be obtained to design better cleavable peptides or proteins. One type used the subtilisin-like serine protease LanP for cleavage, which occurs after Pro-Gln, Pro-Arg, Ala-Asp, or Ala-Glu. In the case of nisin, a positively charged residue at position −1 and a hydrophobic residue at position −4 appears necessary for interaction with NisP. This subtilisin-like serine protease LanP acts on the prepeptides of Pep5, Epilancin K7, Nisin A, Nisin-Z, Epidermin, and Gallidermin.

In the other type, the leader peptides are cleaved after Gly-Gly, Gly-Ala or Gly-Ser sequences. The latter holds for many other non lantibiotic bacteriocin leader peptides. The subtilisin like proteases are not known to cleave these sequences and a different type of protease is cleaving these leader peptides. It has been shown that in some bacteriocins, both lantibiotic and nonlantibiotic this second protease is a domain of the transport system LanT. This type of leader peptidase acts on prepeptides of Lacticin-481, Variacin, Mutacin-II, Streptococcin-A-FF22, Salivaricin-A, and Sublancin.

In addition, a two component lantibiotic, Cytolysin-LL/Cytolysin LS, exists of which each component is cleaved twice. One cleavage is by the "double glycine type" and the other cleavage is by the subtilisin-like peptidase.

The invention further disclosed a method for the modification of a desired polypeptide wherein the host cell is a Gram-negative prokaryote or a eukaryote. The invention also discloses a (poly)peptide modified, using a method of the invention.

The invention further discloses a host cell, such as a Gram-negative prokaryote or an eukaryote, provided with a recombinant nucleic acid comprising a first nucleic acid fragment encoding a leader peptide and a second nucleic acid fragment encoding a desired (poly)peptide, wherein the first and second nucleic acid fragments are within the same open reading frame of the first nucleic acid and the leader peptide is at least functionally equivalent to an N-terminal leader peptide found with the prepeptide of a lantibiotic. In one embodiment, a host cell is disclosed wherein the desired (poly)peptide is of essentially eukaryotic or viral descent, such as those disclosed in Table 1 and/or wherein the leader peptide is one of those disclosed in Table 2.

The invention also discloses a host cell provided with or selected for the presence of at least a LanT protein, or a functional equivalent thereof, wherein the host cell is further characterized by at least the functional absence of at least one of the other gene products derived from the Lan-gene cluster, such as LanB, LanC, (or a functional part from LanM) or LanP. The host cell comprises a Gram-negative prokaryote or a eukaryote.

The host cell disclosed herein has a specific use in a method of producing a (poly)peptide for harvest or modification, as disclosed herein above. For the purpose of harvest, LanT is present, but LanB and/or LanC (or LanM) are absent, or at least functionally absent, in that they are hampered in binding to or interfering with the polypeptide to be harvested. For the purpose of modification, LanT and an essentially extracellular protein allowing extracellular modification is present. The extracellular protein may be LanB, LanC, LanM, or an N-terminal) LanM fragment having LanB function, on a C-terminal LanM fragment having LanC function. A further extended or even complete lantibiotic gene-product cluster is preferably at least not functionally present.

The invention further discloses a recombinant nucleic acid comprising a first nucleic acid fragment encoding a leader peptide and a second nucleic acid fragment encoding a desired (poly)peptide, wherein the first and second nucleic acid fragments are within the same open reading frame of the first nucleic acid and the leader peptide is at least functionally equivalent to a N-terminal leader peptide found with the prepeptide of a lantibiotic, and wherein the desired (poly)peptide is of essentially eukaryotic or viral descent.

The invention also disclosed a proteinaceous substance comprising a polypeptide encoded by a nucleic acid. Such a proteinaceous substance can be harvested, or modified as previously disclosed herein. Use of a host cell, nucleic acid or proteinaceous substance of the present invention for the production of a desired (poly)peptide, and its use in producing a pharmaceutical composition are herein also disclosed. In particular, the invention discloses a (poly)peptide of Gram-negative prokaryotic, viral or eukaryotic descent (such as those of Table 1) wherein a serine or threonine has been dehydrated or which has been provided with a thioether bridge. The advantage of such a polypeptide lays in the creation of variants of known peptides or protein based drugs, where the dose or frequency of administration can be reduced to lower treatment cost, treatment time, and patient inconvenience.

The creation of variants of new protein or peptide based drugs, where the drug may not have been effective or admitted for use in an unstabilized form, and the creation of new therapeutic entities per se is further explained in the following detailed description.

BRIEF DESCRIPTION OF THE DRAWINGS

FIG. 7A: MALDI TOFMS analysis of ziptipped minimal medium supernatant from NZ9700+pNG-nisinleader-(L7C) LHRH. The peak at 1,169.9 Da corresponds to the thioether ring containing LHRH and the peak of 2,351.8 to the nisin leader. Secretion of the thioether ring stabilized (L7C) LHRH by *Lactococcus lactis* NZ9700. L7C-LHRH (a luteinizing hormone release hormone mutant) was fused to the nisin leader peptide by cloning the L7C-LHRH coding sequence behind the nisin leader in an expression vector. The lactococcal strain NZ9700 (a nisin producing *L. lactis* strain) is used for expression of the leader peptide-(L7C) LHRH fusion. The enzyme NisB dehydrates serine at position 4 and this dehydrated residue is coupled to the cysteine of position 7 by enzyme NisC to form a thioether bridge. The leader peptidase NisP cleaves of the leader peptide.

FIG. 7B: Structure of the nisin leader and thioether LHRH.

FIG. 8: Suitable LHRH analogues.

DETAILED DESCRIPTION

Figure 1:
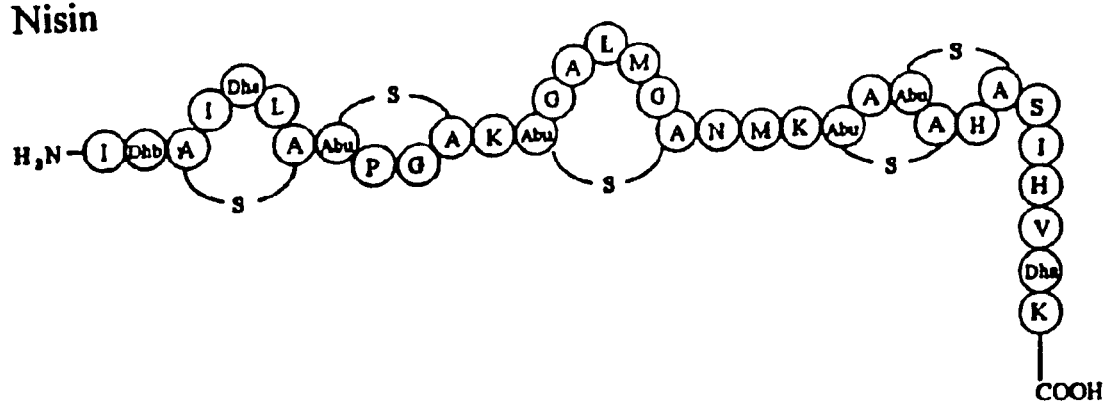
FIG. 1: Peptide structure of mature nisin and subtilin.
Figure 1:
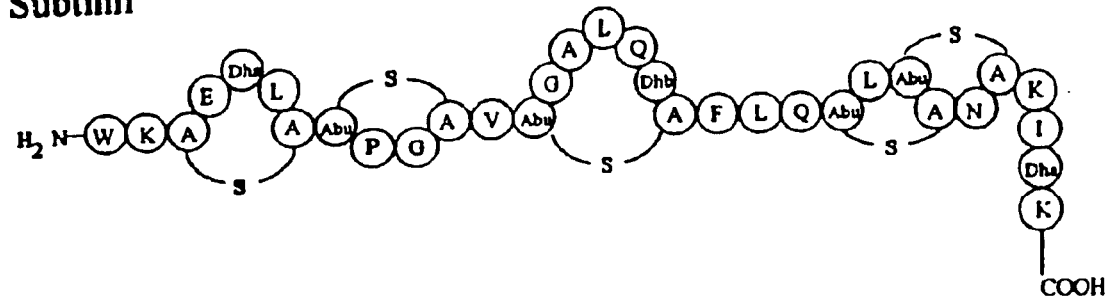
Figure 2:
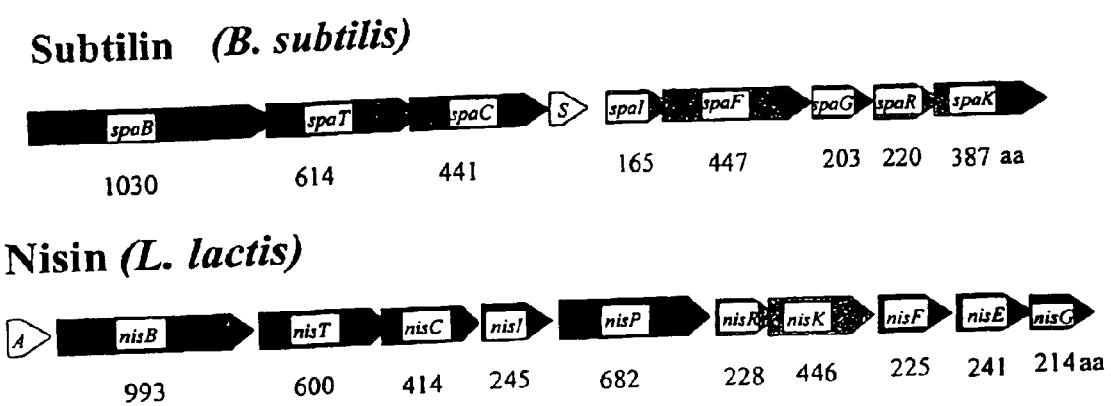
FIG. 2: Genomic organization of genes involved in subtilin and nisin biosynthesis.
Figure 3:
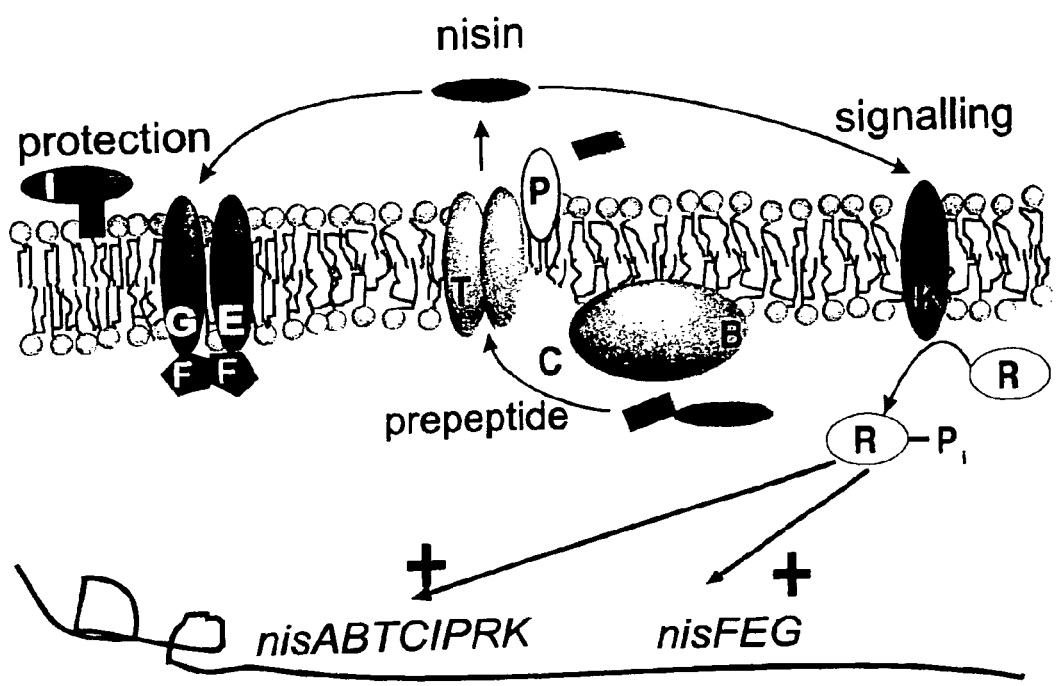
FIG. 3: Model for nisin biosynthesis wherein modification occurs intracellularly.
Figure 4:
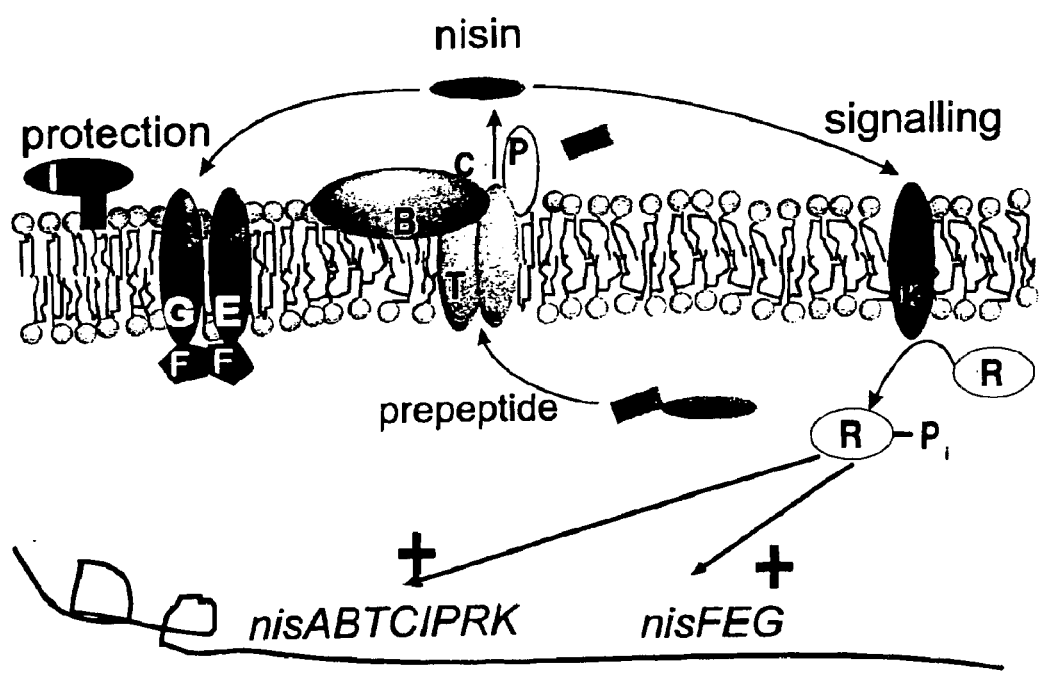
FIG. 4: Model for nisin biosynthesis wherein modification occurs extracellularly. Nisin prepeptide is exported by NisT ("T"), dehydrated by extracellular NisB (B) and subjected to thioether ring closure by extracellular NisC (C). Extracellular leader peptidase, NisP (P) cleaves of the leader peptide. Nisin interacts with a membrane bound histidine kinase NisK (K) which phosphorylates a response regulator NisR (R), which in its turn switches on transcription of the nis-genes (+, +). The producer cells are protected against nisin by the concerted action of the lipopeptide NisI and the transport system NisEFG.
Figure 5:
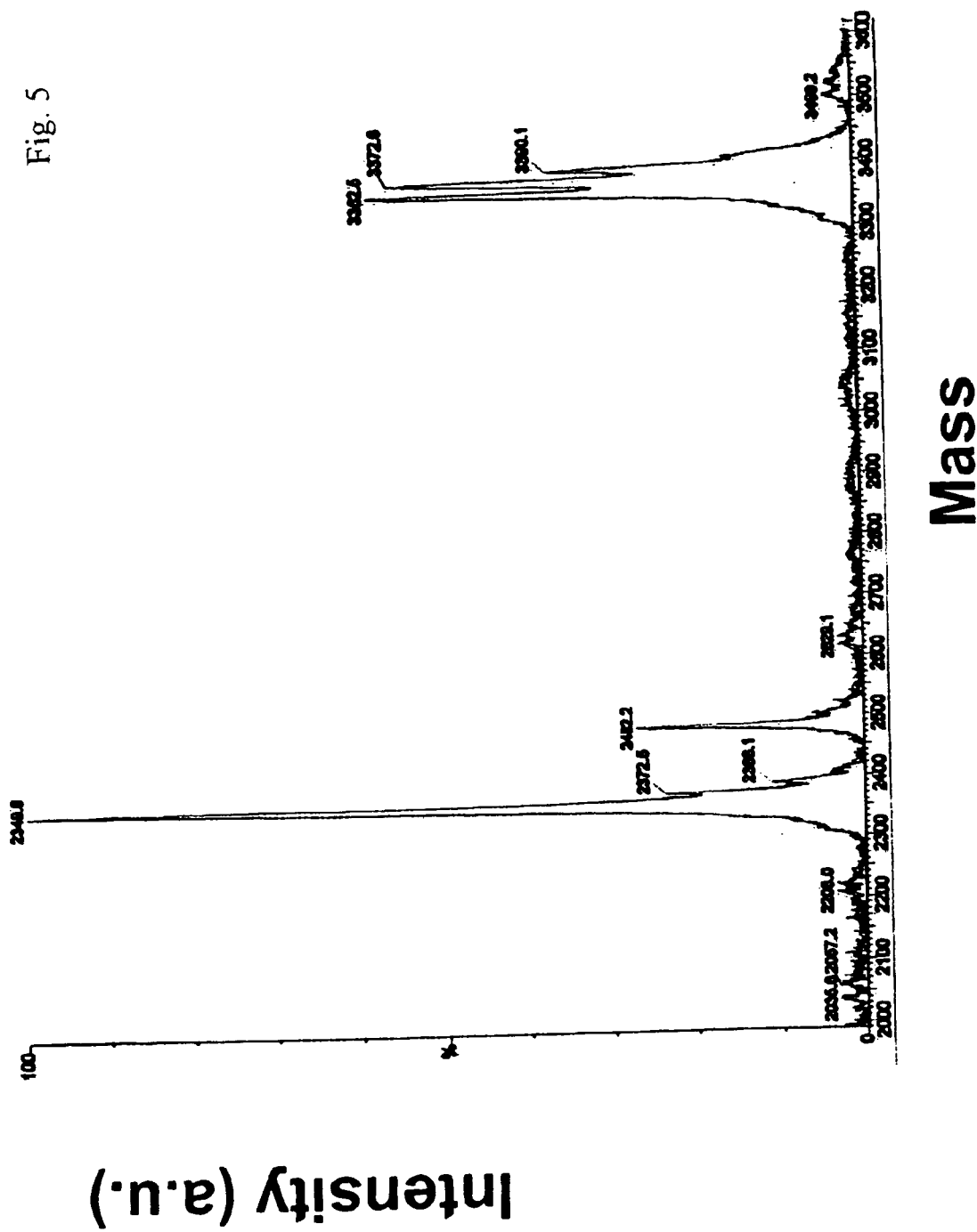
FIG. 5: Detection of lantibiotic leader peptide from the culture medium by MALDI-TOFMS. By using the combination of growth in minimal medium and ziptipping the supernatant of the culture, samples of sufficient purity were obtained for high resolution MALDI-TOFMS. This allowed most significant measurement of nisin leader peptide. The detection of lantibiotic leader peptide can be used to ascertain the export of (poly)peptide coupled to this lantibiotic leader, i.e., in those cases where the leader peptidase acts extracellularly. Generally the method allows a high detection level for measuring (lantibiotic) (poly)peptides directly from the culture supernatant.
Figure 6A:
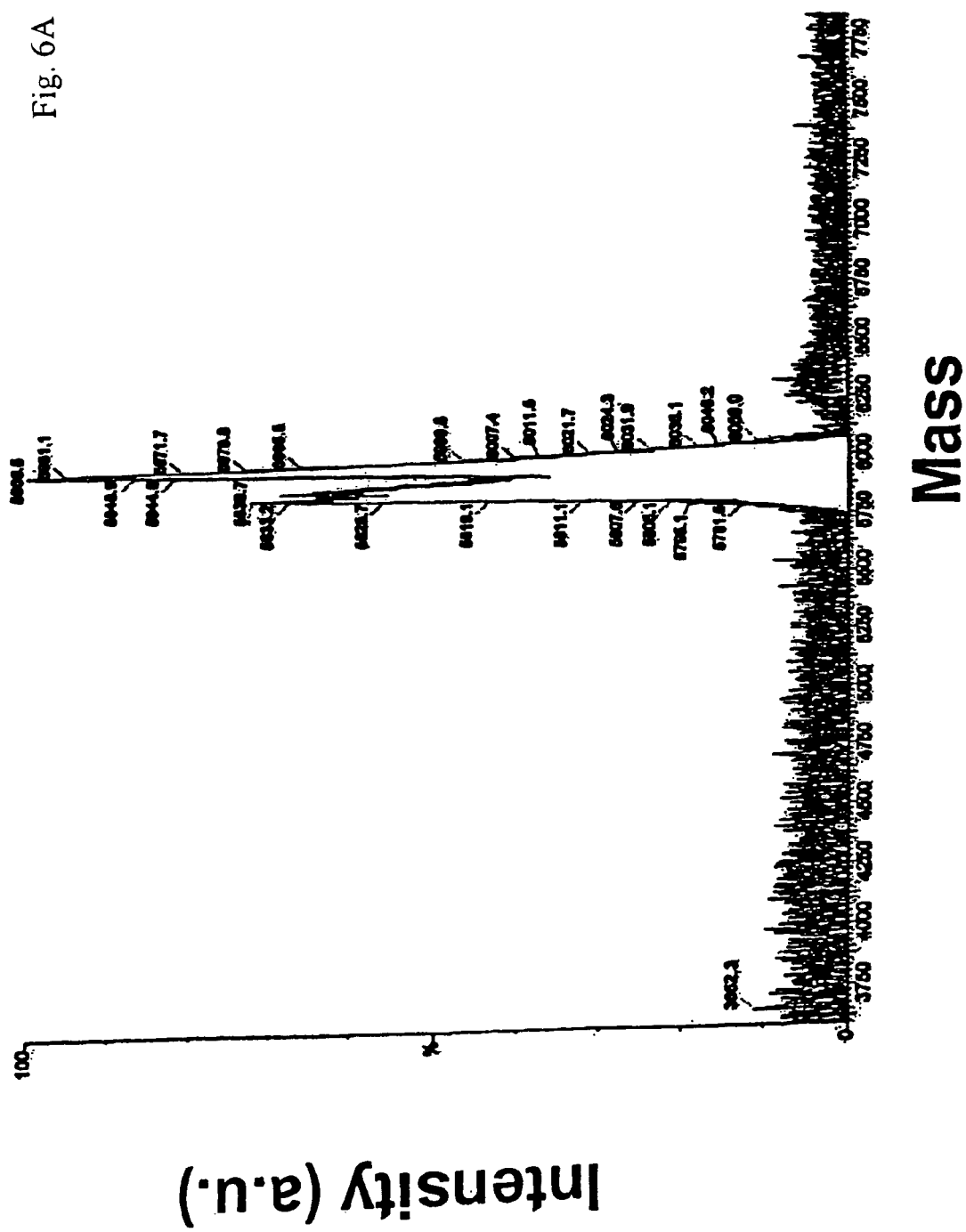
FIGS. 6A and 6B: The NisT transporter can transport unmodified nisin prepeptide. *Lactococcus lactis* strain NZ9000 with plasmids coding for the transporter, NisT and for the nisA product, nisin prepeptide, was grown in M17 medium and transcription of nisT and nisA was induced in minimal medium. Samples were prepared by ziptipping the culture supernatant and analyzed by MALDI TOFMS. A mass peak (theoretical mass of 5,831.8 Da) corresponding to unmodified nisin prepeptide was measured. A second peak has a mass consistent with the nisin prepeptide with methionine of position 1 still attached to it (theoretical mass of 5,963 Da). This demonstrates that NisT is sufficient for the transport of unmodified prepeptide to the exterior of the cell. For detailed information see example 1.
Figure 6B:
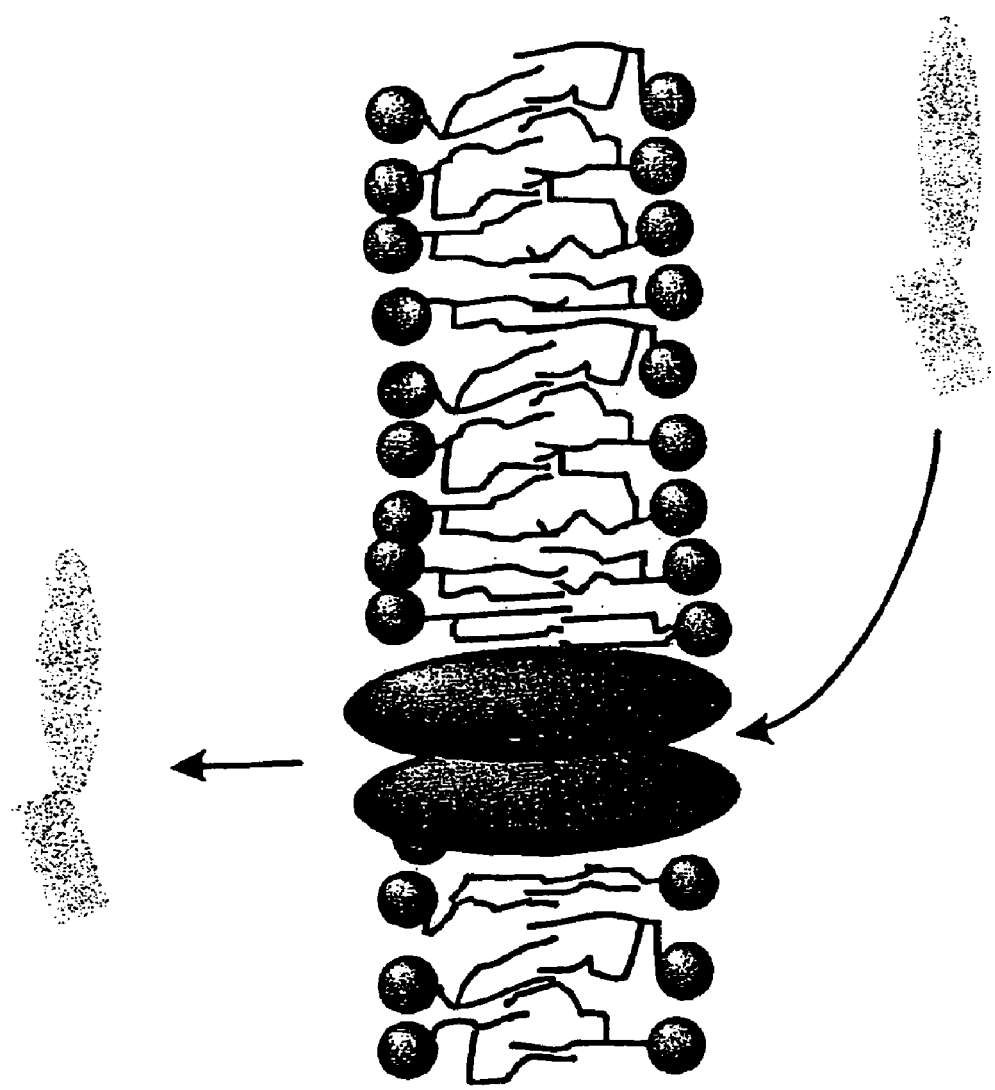

Lantibiotic enzymes are special. There is no strong homology with other enzymes. DNA and amino acid sequences of many lantibiotic enzymes are known, but no structures have been determined. The genes involved in the biosynthesis, processing and export of lantibiotics are present in a lanA B C/M (D) P R K T F E G I cluster. No uniform order or orientation of the genes in the different clusters exists indicating that rearrangements have occurred in the evolution.

Lanthionines are the most typical posttranslationally formed residues in antibiotics. They are formed via two steps. First, propeptide serines and threonines are dehydrated giving rise to dehydro-alanines and dehydrobutyrines, respectively. LanB has been proposed to play a role in dehydration, since it has a weak homology to IlvA, a threonine dehydratase from *E. coli*. It has also been shown that overexpression of NisB increases the occurrence of dehydration of serine 33 in nisin A, from 10% in the normal situation up to 50% in the case of overexpressed NisB. The LanB protein includes about 1,000 residues. LanB is a membrane associated protein.

LanC is thought to be responsible for the subsequent addition of cysteine SH groups to the dehydro amino acids, which results in the thioether rings. In the case of PepC, experimental data support this idea. Known LanC proteins include about 400 residues. In type A lantibiotics, the N-terminal part of lanthionine and methyllanthionine residues are formed by the dehydroalanine or dehydrobutyrine residues, whereas the C-terminal half is formed by the cysteine residues. Lanthionine formation between dehydrobutyrine and cysteine is energetically possible at room temperature and can also occur spontaneously.

Lantibiotic maturation and secretion is thought to occur at membrane-associated multimeric lanthionine synthetase complex including proteins LanB, LanC and the ABC transporter molecules LanT. At least two molecules of LanC and two molecules of LanT are part of the modification and transport complex. Some lantibiotics do not have the lanB gene, but have a larger lanM gene, whose product has some C-terminal homology with the lanC gene product. Since no lanB homologue is present in LanM-producing clusters, the N-terminal part of the LanM protein may perform the dehydration reaction typically performed by LanB.

Lantibiotics may be chemically synthesized, but the process is extremely costly and time consuming. Several mutant lantibiotics containing amino acid substitutions have been obtained by genetic engineering. However, despite many studies, only in the lantibiotic Pep5 one lanthionine ring has a new position been obtained.

The lantibiotic export systems, LanT, (whose sequences are known) are thought to be dedicated for the transport of the fully modified lantibiotic. The two enzymes involved in the lanthionine formation in nisin (NisB and NisC) have been reported to be located intracellularly in a NisBCT membrane associated complex (Siegers et al., 1996). Such intracellular localization suggests that the prepeptides are dehydrated by LanB where rings are formed by LanC and followed by export by LanT. Further, if the thioether ring-forming enzymes, NisB (which is responsible for dehydration, the first step in ring formation) or NisC (responsible for ring formation between dehydrated residues and cysteines) are inactivated by an in frame deletion of 61aa or by plasmid insertion respectively, no peptide is exported. The latter suggests that absence of (methyl) lanthionines prevent export.

However, it has been measured that prepeptide, such as nisin prepeptide, can be transported through the nisin transporter. This result was obtained using a strain with two plasmids, one plasmid coding for the nisin prepeptide and one plasmid coding for the nisin transporter. No prepeptide production was observed in a control experiment in which a strain with only the plasmid coding for the prepeptide was used. Some lantibiotics contain dehydrated serines/threonines that do not participate in thioether ring formation. From the latter, in combination with the observation that an unmodified peptide is exported, it may also be theorized that translocation of prepeptide without thioether rings, but with dehydrated residues, is possible. It is known that the second step in lanthionine ring formation is less difficult to achieve since it can also occur spontaneously at room temperature. After production of prepeptides with dehydrated residues, lanthionine rings can be formed extracellularly.

The finding disclosed herein provides the possibility to make new lantibiotics and, thus, to stabilize peptides/proteins by thioether rings, D-alanines or other residues formed by lantibiotic enzymes. Before (methyl)lanthionine formation, the distance of dehydrated residues to cysteines is typically 2–5 residues, but larger distances are possible. (Methyl)lanthionines can be formed from dehydrated residues to more N-terminally located or to more C-terminally located cysteines. In addition, the lantibiotic transport system can be used for the export of other proteins by inserting the sequence coding for the leader peptide in front of the protein DNA sequence.

Several uses are foreseen. For instance, peptide/protein drugs that are rapidly degraded in the blood plasma can be protected from proteolysis by thioether rings. Also, new lantibiotics can be used as antibiotics, especially against Gram-positive bacteria. This is useful since there is a growing and spreading resistance against classical antibiotics. New lantibiotics can be also be used as food additives to prevent bacterial growth and increase the shelf life of food products. Mastering the enzymatic synthesis of thioether rings further furnishes the possibility of synthesizing a broad variety of new antimicrobial peptides, which gives many possibilities to circumvent resistance. Lantibiotics have a variety of antimicrobial activities including membrane permeabilization, inhibition of cell wall synthesis, modulation of enzyme activities, and inhibition of outgrowth of spores. New lantibiotic-type peptides or proteins have modulated activity or a different spectrum of activity. A selection of such peptides or proteins is described herein in the examples given below.

EXAMPLE 1

The NisT Transporter can Transport Unmodified Nisin Prepeptide.

This example involves a *L. lactis* strain that lacks the entire chromosomal nisin gene cluster, but simultaneously produces plasmid encoded NisT and the NisA prepeptide. Unmodified NisA can be found in the culture supernatant, which demonstrates that NisT is sufficient for the transport of unmodified prepeptides to the exterior of the cell.

Materials and Methods. Use for the nisin inducible expression of nisT in *L. lactis*, a pNZ8048 (Kuipers et al. 1997, Tibtech. 15: 135–140) derived plasmid. The nisT gene was amplified using primers NisT.fw (5'-CGG TCT CCC ATG GAT GAA GTG AAA GAA TTC ACA TCA AAA C (SEQ ID NO: 4)) and NisT.rev (5'-CGG TCT CTC TAG ATT ATT CAT CAT TAT CCT CAT ATT GCT CTG (SEQ ID NO: 5)) with chromosomal DNA of NZ9700 (a nisin producing *L. lactis* strain; Kuipers et al. 1997, Tibtech. 15: 135–140) as a template. PCR conditions used include: 5 min 94° C., 30 times (30s 94° C., 30s 50° C., 3 min 72° C.), 10 min 72° C. The PCR products are purified with the Roche PCR-isolation kit. The expression vector is digested with NcoI/XbaI and the PCR fragments are digested with Eco31I (nucleotides 2–6 in the primers; the sticky ends it generated are at nucleotides 9–12 were compatible with NcoI and XhaI) and the fragments are subsequently ligated using T4 ligase (Roche). The resulting plasmid was designated pNG-nisT and contains a chloramphenicol (Cm) resistance gene as a selection marker.

Use for the nisin inducible production of the NisA prepeptide in *L. lactis*, a variant of pNZ8048 that contains an erythromycin (Em) resistance selection marker instead of a Cm marker. The nisA gene is amplified using primers NisA.fw (5'-CGG TCT CTC ATG AGT ACA AAA GAT TTT AAC TTG GAT TTG G (SEQ ID NO: 6)) and NisA.rev (5'-TAT ATG GAT CCT TTG CTT ACG TGA ATA CTA CAA TGA CAA G (SEQ ID NO: 7)) and chromosomal DNA of strain NZ9700 as a template under the same conditions as described above. The PCR product is purified with the Roche PCR-isolation kit. The expression vector was digested with NcoI/BamHI and the PCR fragment is digested with Eco31I and BamHI (nucleotides 2–6 in the primers; the sticky ends it generated are at nucleotides 9–12 were compatible with NcoI and BamHI) and the fragments are subsequently ligated using T4 ligase (Roche). The resulting plasmid is designated pNG-nisA.

*L. lactis* strains NZ9000 or PA1001 (a NZ9000 derivative lacking AcmA activity to abolish cell lysis (Buist et al. 1995, J. Bacteriol. 177: 1554–1563) and lacking HtrA to diminish extracellular proteolytic activity (Poquet et al. 2000, Mol. Microbiol. 35: 1042–1051)) with both pNG-nisT (Cm) and pNG-nisA (Em) are grown in M17-based medium (Terzaghi and Sandine, Appl. Microbiol., 29: 807–813 (1975)) to an $OD_{600}$ of 0.4. The cells are collected by centrifugation and resuspended in the same volume of Minimal Medium (Jensen and Hammer, 1993, Appl. Environ. Microbiol. 59: 4363–4366) and expression of NisT and NisA prepeptide was induced by addition of nisin as described (Kuipers et al. 1997, Tibtech. 15: 135–140). After overnight induction and subsequent centrifugation, the culture supernatants are pipeted up and down in C18 ZIPTIPS™ (Millipore) two times using 10 µl 50% acetonitril, followed by two times using 10 µl demineralized water, followed by eight times using 10 µl supernatant. The culture supernatants are then washed two times with 10 µl demineralized water, followed by elution two times with 10 µl 50% acetonitril containing 0.1% TFA. The final eluent is vacuum dried and stored at −20° C. until analysis by mass spectrometry. Prior to analysis, the dry material is resuspended in 2.5 µl of 50% acetonitril containing 0.1% TFA and 1 µl is applied to the target. After drying, 1 µl of matrix (10 mg/ml alpha-cyano-4-hydroxycinnamic acid completely dissolved (by mildly heating and vortexing) in 50% acetonitril containing 0.1% TFA) was applied to the target. The following MALDI-TOFMS (linear mode) laser settings were used: 100% coarse energy, 50% fine, source 20 KV, extra 19800, force 15000, suppression 500, pulse time 40, pulse voltage 2200, sampling rate 500 MHz, sensitivity 50 mV, shots 15.

Results: Analyze culture-supernatants of the following induced cultures and analyze by MALDI-TOFMS:

NZ9000 (or PA1001);

NZ9000 (pNG-nisA) (or PA1001(pNG-nisA)); and

NZ9000 (pNG-nisA+pNG-nisT) or (PA1001(pNG-nisA+pNG-nisT)).

No peaks were observed in samples derived from cultures A and B. Two main peaks were observed in sample C. The first peak is close to, or identical, to 5832.8 Da which corresponds to the unmodified nisin prepeptide: (5831.8 plus 1 proton). The second peak was about 130 Da higher mass than the first peak, which might correspond to the nisin prepeptide with two zinc atoms (Bierbaum, G. 1999, Ed. J. W. Kelly, Amino acids, Peptides, Porphyrins, Alkaloids 4, 275–301. Elsevier, Comprehensive Natural Products Chemistry, Eds. D. Barton, K. Nakanishi & O. Meth-Cohn) or the nisin prepeptide with the methionine in position 1 still present. This first peak is consistent with unmodified nisin prepeptide being transported by the nisin transporter NisT. This result demonstrates that NisT is sufficient for the transport of the nisin prepeptide and that modification is not required prior to transport.

EXAMPLE 2

Secretion of the Hydrophobin SC3 of the Fungus *Schizophyllum commune* by *Lactococcus lactis* through the use of the nisin A leader peptide and the nisin transport system NisT.

To study the role of the nisin A leader peptide in secretion through NisT in *L. lactis*, a strain that lacks the entire chromosomal nisin gene cluster was constructed, but produces simultaneously encoded plasmid NisT and the fungal hydrophobin SC3 fused to the NisA leader peptide. The fusion product is present in the culture supernatant, which demonstrates that the NisA leader peptide can be used to drive the transport of polypeptides other than nisin derivatives through the NisT transporter.

Materials and methods. A NisA leader peptide-SC3 fusion was constructed in a pNZ8048 expression vector that contains a c-myc epitope, which can be used for the detection of expressed polypeptides. For that purpose, a BglII-NcoI fragment upstream the c-myc epitope in the vector was replaced by a BglII-NcoI fragment of the NZ9700 chromosomal DNA that contains the nisA promoter and the nisA leader peptide (ending at amino acid sequence: . . . GASPR) (SEQ ID NO: 8)). A chromosomal fragment was obtained by PCR amplification using primers: NisA.fw3 (5'-CGG TCT CAG ATC AAT AGA AAC ATT AAC AAA TCT AAA ACA G (SEQ ID NO: 9)) and NisA.rev3 (5'-CGG TCT CA CAT GGA GCG TGG TGA TGC ACC TGA ATC (SEQ ID NO: 10)). The same PCR conditions used in Example 1 were applied. The PCR product was purified with the Roche PCR-isolation kit and digested with Eco31I (sites at nucleotides 2–6 in the primer sequences). This process results in a PCR fragment with BglII-NcoI sticky ends (at nucleotides 9–12 in the primer sequences). The BglII-NcoI digested vector and the cut PCR fragment were ligated and the newly obtained vector with the NisA leader peptide sequence upstream the c-myc epitope sequence was designated pNG-nisL. The SC3 gene was PCR amplified using primers SC3.fw2 (5'-CGG TCT CTA ATT CTT GGT GGC CAC CCG GGC ACG (SEQ ID NO: 11)) and SC3.rev2 (5'-CGG TCT CTA GCT CTT AGA GGA TGT TGA TGG GGG TGC (SEQ ID NO: 12)) with cDNA isolated from *Schizophyllum commune* as a template. The PCR product was purified with the Roche PCR-isolation kit. The vector pNG-NisL was digested with EcoRI and HindIII. The PCR product was cut with Eco31I (nucleotides 2–6 in the primer sequences) to generate EcoRI and HindIII sticky ends (at nucleotides 9–12 in the primer sequences). The two fragments were ligated and fused in the resulting plasmid, pNG-NisL-SC3, SC3, in frame, downstream from the NisA leader peptide and the c-myc epitope.

Plasmid pNG-NisT (Example 1) and pNG-NisL-SC3 were established together in *L. lactis* strain NZ9000 by Electroporation (Holo and Nes, 1995, Methods Mol. Biol. 47: 195–199). Expression was induced and secreted peptides were purified as described in Example 1. MALDI-TOFMS analysis was performed as described in Example 1 with the following modifications: 7 shots instead of 15 and suppression at 1,000 instead of 500. The same was performed for the control strains NZ9000, NZ9000(pNG-nisl-SC3).

Results. Culture-supernatants of the following induced cultures were analyzed by MALDI-TOFMS:

A. NZ9000;

B. NZ9000(pNG-NisL-SC3); and

C. NZ9000(pNG-NisL-SC3+pNG-nisT).

No peaks were observed in samples derived from cultures A and B. In sample C, the main peaks correspond to SC3, but are about 2351 Da larger mass, which corresponds to the mass of the NisA leader peptide. This shows that the eukaryotic SC3 preceded by the nisin A leader peptide is secreted by *L. lactis* via the nisin transporter NisT.

EXAMPLE 3

Export of nisin prepeptide across the cytoplasmic membrane of *Escherichia Coli* protease-deficient SF120 (Gram-negative bacterium), via the nisin transporter NisT.

Materials and methods. NisT was cloned in a suitable vector, such as the pBAD vector, and transformed at 25° C. to *E. coli* SF120 (Baneyx, F., and Georiou, G. 1991, J. Bacteriol. 173, 2696–2703). nisA was cloned in a second plasmid with a different antibiotic marker and transformed to the above strain. The resulting strain, as well as a control strain without pBAD-NisT, was grown and induced overnight with 0.3% arabinose and/or another adequate signal. The cells were pelleted and washed in milliQ to disrupting the outer membrane. The cells were pelleted and the supernatant was subjected to ZIPTIPPING™ and MALDI-TOFMS as in Example 1.

Results. A mass spectrometry signal was identical to Example 1, which is consistent with export of the nisin prepeptide across the cytoplasmic membrane in the strain with both plasmids, NisT and NisA.

EXAMPLE 4A

Export of nisin prepeptide across the cytoplasmic membrane of *Escherichia Coli* protease-deficient SF120 (Gram-negative bacterium) via the nisin transporter NisT and dehydration by NisB.

The nisin prepeptide includes a leader (SEQ ID NO: 13). Neither serines nor threonines are dehydrated in the leader. The second part of the prepeptide is the nisin propeptide (SEQ ID NO: 14). Most of the serines and all threonines can be dehydrated by NisB.

Materials and methods. NisBT is cloned in a suitable vector, such as the pBAD vector, and transformed at 25° C. to *E. coli* SF120. NisA is cloned in a second plasmid with a different antibiotic marker and transformed to the above strain. The resulting two-plasmid strains, as well as a control strain without pBAD-NisBT were grown and induced overnight with 0.3% arabinose and/or another adequate signal. The cells are pelleted and washed in milliQ and the outer membrane was disrupted. The cells were pelleted and the supernatant was subjected to ziptipping and MALDI-TOFMS as performed in example 1.

Results. A mass consistent with the export of the nisin prepeptide, with dehydrated serines and threonines in the propeptide region, across the cytoplasmic membrane in the strain with both plasmids (NisBT and NisA).

EXAMPLE 4B

Export of nisin prepeptide across the cytoplasmic membrane of *Escherichia coli* protease-deficient SF120 (Gram-negative bacterium) via the nisin transporter NisT and dehydration by NisB.

Materials and methods. NisABT was cloned with an inverted repeat between NisA and NisB, an organization as on the chromosome of *L. lactris* NZ9700, in a suitable vector, such as the pBAD vector, and transformed at 25° C. to *E. coli* SF120. The cells were grown at 25° C. and induced overnight with 0.3% arabinose and/or another adequate signal. The cells were pelleted and washed in milliQ to disrupt the outer membrane. The cells were pelleted and the supernatant is subjected to ziptipping and MALDI-TOFMS as in Example 1.

Results. A mass consistent with the export of the nisin prepeptide across the cytoplasmic membrane is present, with in the propeptide region most serines and all threonines dehydrated.

EXAMPLE 5

Export of nisin leader coupled to mature nisin across the cytoplasmic membrane of *Escherichia coli* protease-deficient SF120 (Gram-negative bacterium) via the nisin transporter NisT.

Materials and methods. NisABTC was cloned with an inverted repeat between NisA and NisB in a suitable vector, such as the pBAD vector, and transformed at 25° C. to *E coli* SF120. The resulting strain is grown at 25° C. and induced overnight with 0.3% arabinose and/or another adequate signal. The cells were pelleted and washed in milliQ and the outer membrane was disrupted. The cells remnants were pelleted and the supernatant was subjected to ziptipping and MALDI-TOFMS as in example 1.

The above ZIPTIPPED™ material and the crude supernatant is treated after outer membrane disruption with trypsin. This material is applied to the agar well assay to determine antibacterial activity. Also, the capacity of the trypsinated solutions to induce the nisin promoter was tested via the Gus assay (Kuipers et al., 1995, J. Biol. Chem. 270: 27299–27304).

Results. A mass spectrometry signal of about 5690 Da was consistent with export of the nisin prepeptide coupled to mature nisin across the cytoplasmic membrane. Trypsinated samples have antimicrobial activity in the agar well assay and nisin promoter induction capacity. These results show export of the nisin prepeptide which has undergone thioether ring formation, since trypsin cleaves off the leader and liberates the active nisin which has antimicrobial activity and induction capacity.

EXAMPLE 6

Export of alpha neurokinin (Table 1) across the cytoplasmic membrane of *Escherichia coli* protease-deficient SF120 (Gram-negative bacterium) via the variacin transporter VarT.

VarT has simultaneous transport and leader peptidase activity. As a consequence, export of the fusion protein including a variacin-leader (Table II) and alpha neurokinin (SEQ ID NO: 15) (Table 1) through VarT results in extracellular release of the alpha neurokinin without the leader.

Materials and methods. VarT was cloned in a suitable vector, such as the pBAD vector, and transformed at 25° C. to *E coli* SF120. A construct with leader variacin preceding neurokinin alpha is cloned in a second plasmid with a different antibiotic marker and transformed to the above strain. The resulting strain, as well as a control strain without pBAD-VarT, is grown and induced overnight with 0.3% arabinose and/or another adequate promoter related signal. The cells were pelleted and washed in milliQ and the outer membrane was disrupt. The cells remnants were pelleted and the supernatant was subjected to ziptipping and MALDI-TOFMS as in Example 1.

Results. A mass spectrometry signal corresponding to alpha neurokinin. This result was consistent with export of alpha neurokinin through VarT.

EXAMPLE 7

Export of glucagon (Table 1) via MutII T out of *Saccharomyces cerevisiae* (eukaryotic organism).

MutT has simultaneous transport and leader peptidase activity. As a consequence export of the fusion protein including a MutacinII-leader and glucagon through MutT results in extracellular release of glucagon without the leader.

The (C5,S24,C29)-Sequence of glucagon is presented at SEQ ID NO: 16.

Materials and methods. MutT was cloned in a suitable vector and transformed to *S. cerevisiae*. A construct was cloned with leader mutacinII preceding glucagon in a second plasmid which has a different antibiotic marker and the construct was transformed to the above strain. The resulting strain, as well as a control strain without MutT, was grown and induced overnight with an adequate signal. The cells were pelleted and the supernatant was subjected to ziptipping and MALDI-TOFMS as in Example 1.

Results. A mass spectrometry signal corresponds to glucagon. This shows that the mutacinII leader drives the export of glucagon out of *S. cerevisiae*.

EXAMPLE 8A

Export of nisin prepeptide via the nisin transporter NisT and modification by the nisin dehydrating enzyme NisB without subsequent enzymatic thioether bridge formation.

Materials and methods. NisBT was cloned as described in Example 1 using the primers NisB fw, (5'-CGG TCT CGC ATG ATA AAA AGT TCA TTT AAA GCT CAA CCG TTT TTA GTA AG (SEQ ID NO: 17)) and NisT rev (5'-CGG TCT CTC TAG ATT ATT CAT CAT TAT CCT CAT ATT GCT CTG (SEQ ID NO: 18)).

NZ9000+pNG-NisBT (Cm) were transformed with pNG-NisA (Em). NZ9000+pNG-NisBT+pNG-NisA cells were grown and induced as in Example 1. 50 µM TPEN (N,N,N',N'-Tetrakis(2-Pyrimidyl)ethylenediamine), a specific zinc chelator, was added to the supernatant and incubated 1 hour under stirring. The supernatant was ziptipped and analyzed by MALDI-TOFMS as performed in Example 1.

Results. A MALDI-TOFMS peak around 5690 Da in the sample derived from the supernatant from NZ9000+pNG-NisBT+pNG-NisA cells was present. Absence of the peak in samples derived from the supernatant of NZ9000+pNG-NisT+pNG-NisA (Example 1), which was consistent with dehydration of most serines and all threonines.

EXAMPLE 8B

Export of nisin prepeptide via the nisin transporter NisT and modification by the nisin dehydrating enzyme NisB without subsequent enzymatic thioether bridge formation.

Materials and methods. The plasmid pNG-NisABT was constructed similar to the organization of the genes in the wild type nisin producer NZ9700, which includes an inverted repeat between the NisA and the NisBT genes. This plasmid was transformed to NZ9000, grown and induced. After induction, NisBT was transcribed in low quantities by limited read through. The supernatant was subjected to TPEN treatment as in Example 8A followed by ziptipping and MALDI-TOFMS as in Example 1.

Results. A MALDI-TOFMS peak present around 5690 was consistent with export of the nisin prepeptide and dehydration of propeptide serines (most) and threonines (all).

EXAMPLE 9

Export of nisin prepeptide via the nisin transporter NisT and modification by the nisin dehydrating enzyme NisB followed by NisC-mediated thioether bridge formation, involving a pNG-NisABTC plasmid.

Materials and methods. The plasmid pNG-NisABTC was constructed similar to the organization of the genes in the wild type nisin producer NZ9700, which included an inverted repeat between the NisA and the NisB. NZ9000+ pNG-NisABTC were grown and induced. The supernatant is analyzed as in Example 1. Trypsin treated supernatant was subjected to the agar well assay by pouring the trypsinated supernatant in an agar well and overlaying with a nisin sensitive strain. In addition, the trypsinated supernatant was tested for its capacity to induce the nisin promoter with the Gus assay (Kuipers et al. 1995, J. Biol. Chem. 270:27299–27304).

Results. A peak with a mass corresponding to nisin prepeptide including the unmodifed leader peptide coupled to mature nisin, which has undergone dehydration reactions, and the lanthionine ring formation of nisin. Halos were present in the case of trypsinated supernatant and halos were absent, or significantly smaller, than halos in the case of trypsinated medium or untrypsinated supernatant.

These results were consistent with export of the nisin prepeptide which has undergone lanthionine bridge formation since trypsin cleaves off the leader and liberates active nisin which includes antimicrobial activity and induction capacity.

EXAMPLE 10

Secretion of thioether ring stabilized vasopressin by use of the NisA leader peptide in *Lactococcus lactis* NZ9800.

Vasopressin (SEQ ID NO: 19) is a 9 amino acid (aa) peptide antidiuretic hormone. It has cysteines in position 1 and 6 that form an internal disulfide bond. This example involves ring formation by interaction between aa1 and aa6 through the use of the nisin modification system that forms thioether bridges between a dehydrated serine or threonine and a downstream located cysteine. Conversion of the cysteine at position 1 by genetic modification into a serine enables thioether ring formation by the nisin modifying lantibiotic enzymes. This example involves a precise fusion of serine altered vasopressin (SerVaso) to the NisA leader peptide by genetic modification. The lactococcal strain NZ9800 (Kuipers et al. 1993, Eur. J. Biochem. 216, 281–291), used for expression of the leader peptide-Servaso fusion, contains all the components for the nisin secretion and modification machinery, but lacks the NisA structural gene.

Materials and methods. To obtain a precise and "in frame" fusion of SerVaso with the NisA leader peptide, a first plasmid pNG-NisL-SC3 (example 2) was converted into a general NisA leader peptide secretion vector. Suitable restriction sites were introduced and the c-myc-SC3 sequences were removed by PCR amplification of the entire plasmid using the following primers: pLP.1 (5'-CGG TCT CAG CGT GGT GAT GCA CCT GAA TC (SEQ ID NO: 20)) and pLP.2 (5'-CCA CGC TGA GAC CGC AGC TGG GAT CCG GCT TGA AAC GTT CAA TTG AAA TGG (SEQ ID NO: 21)). The PCR product was cut with Eco31I (nucleotides 2–7 in pLP.1 and nucleotides 8–13 in pLP.2), resulting in sticky ends (neucleotides 9–12 in pLP.1 and nucleotides 3–6 in pLP.2) that are compatible for self-ligation of the plasmid. After self-ligation, the resulting plasmid, pLP1, can be used for precise fusion of peptides and proteins after the . . . GASPR aa sequence of the NisA leader peptide by using the Eco31I restriction site. DNA fragments to be inserted at this position should contain a 5'-ACGC sticky end to allow ligation. At the 3'-end, the DNA fragment should contain a sticky end that is compatible with BamHI (site introduced by primer pLP.2, indicated in bold).

The SerVaso gene was obtained by annealing two oligo's: VP.1: 5'-ACG CTC ATA TTT TCA AAA TTG TCC TCG TGG TTA AG (SEQ ID NO: 22) and VP.2: 5'-GAT CCT TAA CCA CGA GGA CAA TTT TGA AAA TAT GA (SEQ ID NO: 23). The annealed fragment includes a stop codon and has the ACGC overhang at its 5'-end and a BamHI compatible sticky end at the 3'-end. The SerVaso gene fragment was ligated into Eco31I and BamHI digested pLP1 and the resulting plasmid was designated pLP1vp.

Strain NZ9800 carrying pLPvp was induced for expression as described in Example 1. The secreted peptide is purified and analyzed using MALDI-TOFMS (linear mode) essentially as described in Example 1.

Results. A MALDI-TOFMS mass consistent with production of processed and thioether ring modified vasopressin.

EXAMPLE 11

EpilancinBC-mediated synthesis by *Staphylococcus epidermis* (prokaryote, Gram-positive) of epilancin leader (Table 2) coupled to glucagon (Table 1) with thioether rings.

The (C5, S24, C29)-sequence of glucagon (SEQ ID NO: 16) (Table 1) allows the epilancin K7 enzymes to form thioether rings between S2-C5 and S24-C29.

Materials and methods. A construct leader epilancin K7 was cloned and followed in an open reading frame mutant glucagon. A plasmid with the above construct is transformed to wild type epilancin K7-producing *Staphylococcus epidermis*. Transcription of the leader-glucagon reading frame is induced. Overnight cell growth in minimal medium was performed, and the cells were centrifuged and ziptipping of the supernatant and MALDI-TOFMS analysis were performed (linear mode).

Results. A MALDI-TOFMS peak consistent with production of glucagon with dehydrated serines and threonines and thioether rings as indicated in Table 1 is present.

EXAMPLE 12

Production by *Streptococcus Salivarius* (prokaryote Gram-positive) of (S3, S12) tachyplesin I (Table 1) following export via SalT.

Materials and methods. A construct salivaricin-leader (Table 2) was cloned and followed in an open reading frame by mutant tachyplesin (Table 1). SalivaricinT was cloned on a second plasmid with a different antibiotic marker. Both plasmids were transformed to a *Streptococcus salivarius* strain devoid of salivaricin genes. Transcription of both plasmids was induced during 2–4 hours of continued growth. Every 30 min, 0.2 mM pmsf (protease inhibitor) was added. Ziptipping was performed as in Example 1 and analyzed by MALDI-TOFMS (linear mode).

Results. A mass spectrometry peak was present which corresponds to tachyplesin.

EXAMPLE 13A

Production by *Streptococcus salivarius* (prokaryote Gram-positive) of (S3, S12) tachyplesinI (Table 1) with salivaricinB-dehydrated Serine-3 and serine-12 without subsequent enzymatic thioether ring formation.

The (S3,S12) sequence of Tachyplesin can be found at SEQ ID NO: 24.

Materials and methods. A construct salivaricin leader (Table 2) was cloned and followed in an open reading frame by mutant tachyplesin (Table 1). SalivaricinBT was cloned on a second plasmid with a different antibiotic marker. This plasmid was transformed to a *Streptococcus salivarius* strain devoid of salivaricin genes. Transcription of both plasmids was induced during 2–4 hours of continued growth and ziptipping was performed as in Example 1 and analyzed by MALDI-TOFMS (linear mode).

Results. A mass spectrometry peak corresponding to tachyplesin with dehydrated serines was present.

EXAMPLE 13B

Production by *Streptococcus salivarius* (prokaryote Gram-positive) (S3, S12) tachyplesinI (Table 1) with salivaricinB-dehydrated S3 and S12 without Subsequent Enzymatic Thioether Ring Formation.

The (S3,S12) sequence of Tachyplesin can be found at SEQ ID NO: 24.

Materials and methods. A construct salivaricin-leader (Table 2) was cloned and followed in an open reading frame by mutant tachyplesin (Table 1) including an inverted repeat and, thereafter, salivaricinBT. This plasmid was transformed to a *Streptococcus salivarius* strain devoid of salivaricin genes. Transcription was induced during 2–4 hours of continued growth and ziptipping was performed as in Example 1 and analyzed by MALDI-TOFMS (linear mode).

Results. A mass spectrometry peak corresponding to tachyplesin with dehydrated serines was present.

EXAMPLE 14

Production by *Streptococcus salivarius* (prokaryote Gram-positive) of salivaricinBC-modified (S3, S12) tachyplesinI (Table 1) with salivaricinBC-mediated thioether rings instead of disulfide bridges.

The (S3,S12) sequence of Tachyplesin can be found at SEQ ID NO: 24.

This sequence allows the salivaricin enzymes to form thioether rings between S3-C7 and S12-C16.

Materials and methods. A construct salivaricin-leader (Table 2) was cloned and followed in an open reading frame by mutant tachyplesin (Table 1). A plasmid was transformed with the above construct into a wild type salivaricin producing *Streptococcus salivarius* (prokaryote Gram positive). Transcription of the salivaricin-leader-tachyplesin reading frame was induced during 2–4 hours of continued growth in minimal medium. The cells were centrifuged and ziptipping of the supernatant is performed as in Example 1 and MALDI-TOFMS analyzed (linear mode).

Results. A mass spectrometry peak corresponding to tachyplesin with thioether rings was present.

EXAMPLE 15

Production by *Lactococcus lactis* (prokaryote, Gram-positive) via lacticinT of vasonatrin (Table 1) without modifications.

Lacticin 481-T has leader peptidase activity and, thus, in this particular example, the supernatant of the cell culture vasonatrin is found without leader. Vasonatrin (SEQ ID NO :25) is amongst others involved in vaso relaxation.

Materials and methods. A construct lacticin 481-leader (Table 2) was cloned and followed in an open reading frame by vasonatrin (Table 1). Lacticin 481-T was cloned on a second plasmid having a different antibiotic marker. Both plasmids were transformed to a *L. Lactis* strain devoid of lacticin 481 genes. Transcription of both plasmids was induced during overnight growth in minimal medium and ziptipping was performed as in Example 1 and analyzed by MALDI-TOFMS (linear mode).

Results. A mass spectrometry peak corresponding to vasonatrin was present.

EXAMPLE 16

Production by *Lactococcus lactis* (prokaryote, Gram-positive) via lacticinT of vasonatrin (Table 1), with lacticinM mediated thioether rings.

Vasonatrin (SEQ ID NO: 25) is amongst others involved in vaso relaxation. It has an amino acid sequence that without mutations permits the formation of two lanthionine rings. The lanthionine rings can be formed from S3-C6 and from S16-C22.

Materials and methods. A construct lacticin 481-leader (Table 2) was cloned and followed in an open reading frame by vasonatrin (Table 1). The plasmid was transformed to a wild type lacticin 481 producing strain and transcription of the plasmid was induced during overnight growth in minimal medium. Ziptipping was performed as in Example 1 and analyzed by MALDI-TOFMS (reflectron mode).

Results. A mass spectrometry peak corresponding to vasonatrin with two thioether rings and two more dehydrated serines.

EXAMPLE 17

Production by *Escherichia coli* SF120 (prokaryote, Gram-negative) of epilancin K7 leader (Table 2) coupled to HIV (gp41) antigenic peptide 1 (SEQ ID NO: 26) (Table 1) without modifications.

Materials and methods. EpilancinT was cloned in a suitable vector, such as the pBAD vector, and transformed at 25° C. to *E coli* SF120. A construct with epilancin leader preceding HIV (gp41) antigenic peptide 1 was cloned in a second plasmid having a different antibiotic marker and transformed to the above strain. The resulting strain with the two plasmids and a control strain without pBAD-varT was grown at 25° C. and induced overnight with 0.3% arabinose and/or another adequate promoter related signal. The cells were pelleted and washed in milliQ and the outer membrane was disrupted. The cells remnants were pelleted and the supernatant was subjected to ziptipping and MALDI-TOFMS (linear mode) as in Example 1.

Results. A mass spectrometry signal corresponding to the epilancin leader coupled to HIV (gp41) antigenic peptide 1.

EXAMPLE 18A

Production by *E. coli* SF120 (prokaryote, Gram negative) of epilancin K7 leader (Table 2) coupled to HIV (gp41) antigenic peptide 1 (Table 1) with an epilancinB-dehydrated S2, without subsequent epilancinC-mediated thioether ring formation.

The sequence of HIV (gp41) antigenic peptide 1 can be found at SEQ ID NO: 26.

Materials and methods. EpilancinBT was cloned in a suitable vector, such as the pBAD vector, and transformed at 25° C. to *E coli* SF120. A construct with epilancin leader preceding HIV (gp41) antigenic peptide 1 was cloned in a second plasmid having a different antibiotic marker and transformed to the above strain. The resulting strain at and a control strain without pBAD-varBT were grown at 25° C. and induced overnight with 0.3% arabinose and/or another adequate-promoter related signal. The cells were pelleted and washed in milliQ prior to disruption of the outer membrane. The cells remnants were pelleted and the supernatant was subjected to ziptipping and MALDI-TOFMS (linear mode) as in Example 1.

Results. A mass spectrometry signal corresponding to the unmodified epilancin leader coupled to HIV (gp41) antigenic peptide 1, with dehydrated serines and threonines.

EXAMPLE 18B

Production by *E. coli* SF120 (prokaryote, Gram negative) of epilancin K7 leader (Table 2) coupled to HIV (gp41) antigenic peptide 1 (SEQ ID NO: 26) (Table 1) with an EpilancinB-dehydrated S2, without subsequent epilancinC-Mediated thioether ring formation.

Materials and methods. A plasmid, such as pBAD or another suitable vector, with epilancin-leader preceding HIV (gp41) antigenic peptide 1, preceding an inverted repeat, and preceding epilancinBT was constructed and transformed at 25° C. to *E coli* SF120. The resulting strain and a control strain without plasmid were grown at 25° C. and induced overnight with 0.3% arabinose and/or another adequate promoter related signal. The cells were pelleted and washed in milliQ and the outer membrane was disrupted. The cells remnants were pelleted and the supernatant was subjected to ziptipping and MALDI-TOFMS (linear mode) as in Example 1.

Results. A mass spectrometry signal corresponding to the unmodified epilancin leader coupled to HIV (gp41) antigenic peptide 1 with dehydrated serines and threonines was present.

EXAMPLE 19

Production by *E. coli* SF120 (prokaryote, Gram negative) of epilancin K7 leader (Table 2) coupled to HIV (gp41) antigenic peptide 1 (Table 1) with an EpilancinBC synthesized thioether ring.

HIV (gp41) antigenic peptide 1 (SEQ ID NO: 26) sequence allows the epilancin enzymes formation of the thioether ring S2-C8.

Materials and methods. A plasmid such as pBAD, or another suitable vector, with epilancin leader preceding HIV (gp41) antigenic peptide 1, preceding an inverted repeat, and preceding EpilancinBTC was cloned and transformed at 25° C. to *E. coli* SF120. The resulting strain and a control strain without plasmid were grown at 25° C. and induced overnight with 0.3% arabinose and/or another adequate promoter-related signal. The cells were pelleted and washed in milliQ prior to disrupting the outer membrane. The cells remnants were pelleted and the supernatant was subjected to ziptipping and MALDI-TOFMS (linear mode) as in Example 1.

Results. A mass spectrometry signal corresponding to the unmodified epilancin leader part coupled to modified HIV (gp41) antigenic peptide 1 with one thioether ring and dehydrated serines and threonines.

EXAMPLE 20

Production by *S. cerevisiae* (eukaryote) of epicidium leader (Table 2) coupled to (S1) calcitonin (Table 1) via EpicidiumT without modifications.

The (S1)-sequence of calcitonin can be found at SEQ ID NO: 27.

Materials and methods. EpicidiumT was cloned in a suitable vector and transformed to *Saccharomyces cerevisiae*. A construct with epicidium leader preceding calcitonin (Table 1) was cloned in a second plasmid having a different antibiotic marker and transformed to the above strain. The resulting strain and a control strain without epicidiumT were grown and induced overnight with an adequate promoter related signal in the presence of a 2 times added mixture of protease inhibitors. The cells were pelleted and t the supernatant was subjected to ziptipping and MALDI-TOFMS (linear mode) as in Example 1.

Results. A mass spectrometry signal corresponding to the epicidium leader coupled to calcitonin.

EXAMPLE 21A

Production by *S. cerevisiae* of epicidium leader (Table 2) coupled to (S1) calcitonin (Table 1) with EpicidumB-dehydrated serines and threonines without enzymatic thioether ring formation.

The (S1)-sequence of calcitonin can be found at SEQ ID NO: 27.

Materials and methods. EpicidiumBT was cloned in a suitable vector and transformed to *Saccharomyces cerevisiae*. A construct with epicidium leader preceding calcitonin (Table 1) was cloned in a second plasmid having a different antibiotic marker and transformed to the above strain. The resulting strain and a control strain without EpicidiumT were grown and induced overnight with an adequate promoter-related signal in the presence of a 2 times added mixture of protease inhibitors. The cells were pelleted and the supernatant was subjected to ziptipping and MALDI-TOFMS (linear mode) as in Example 1.

Results. A mass spectrometry signal corresponding to the unmodifed epicidium leader coupled to modified calcitonin with dehydrated serines and threonines.

EXAMPLE 21B

Production by *Saccharomyces cerevisiae* (eukaryote) of epicidium leader (Table2) coupled to (S1) calcitonin (Table 1) with EpicidiumB-dehydrated serines and threonines without enzymatic thioether ring formation to cys7.

Materials and methods. A construct with epicidium leader preceding calcitonin preceding a stop triplet preceding EpicidiumBT was cloned in a suitable plasmid and transformed to *S. cerevisiae*. The resulting strain was grown and induced overnight with an adequate promoter-related signal in the presence of a 2 times added mixture of protease inhibitors. The cells were pelleted and the supernatant was subjected to ziptipping and MALDI-TOFMS (linear mode) as in Example 1.

Results. A mass spectrometry signal corresponding to the unmodified epicidium leader coupled to modified calcitonin with dehydrated serines and threonines was present.

EXAMPLE 22

Production by *S. cerevisiae* of epicidium leader (Table 2) coupled to (S1) calcitonin (Table 1) with dehydrated serines and threonines and one EpicidiumBC-mediated thioether ring. The (S1)-sequence of calcitonin (SEQ ID NO: 27) allows the epicidium enzymes to form the lanthionine S1-C7.

Materials and methods. A construct with epicidium-leader preceding calcitonin preceding a stop triplet preceding EpicidiumBTC was inserted in a suitable plasmid and transformed to *Saccharomyces cerevisiae*. The resulting strain was grown and induced overnight with an adequate promoter-related signal. The cells were pelleted and the supernatant was subjected to ziptipping and MALDI-TOFMS (linear mode) as in Example 1.

Results. A mass spectrometry signal corresponding to the unmodified epicidium leader coupled to modified calcitonin with dehydrated serines and threonines and one thioether ring was present.

EXAMPLE 23

Secretion of thioether ring stabilized (L7C)LHRH by use of the NisA leader peptide in *Lactococcus lactis* NZ9700.

L7C-LHRH (luteinizing hormone release hormone) is a 10-amino acid (aa) peptide. Replacing the leucine at position 7 with a cysteine enables thioether ring formation by the nisin modifying lantibiotic enzymes. These modifying enzymes form a complex with the transporter NisT and the modifications are coupled to transport. Therefore, the (poly) peptide to be modified should be preceded by the nisin leader which directs the fusion peptide to the nisin transporter. This example involves the precise fusion of L7C-LHRH to the nisin leader peptide by genetic modification. The lactococcal strain NZ9700 (a nisin producing *L. lactis* strain; Kuipers et al. 1997, Tibtech. 15: 135–140) is used for expression of the leader peptide-(L7C)LHRH fusion and contains the components for the nisin secretion (NisT) and modification machinery (NisB and NisC). The enzyme NisB dehydrates serine at position 4 and the dehydrated residue is coupled to the cysteine of position 7 by enzyme NisC to form a thioether bridge.

Materials and methods. A pNZ8048-derived plasmid (Kuipers et al. 1997, Tibtech. 15:135–140) was used for the nisin inducible expression of (L7C)LHRH preceded by the nisin leader in *Lactococcus lactis*. The plasmid, termed pLP1, was constructed in such a way that precise fusion of peptides and proteins after the . . . GASPR aa sequence of the NisA leader peptide by making use of an Eco31I restriction site. DNA fragments to be inserted at this position should contain a 5'-ACGC sticky end to allow ligation. The DNA fragment should contain a sticky end at the 3'-end that is compatible with BamHI.

The (L7C)LHRH gene is obtained by annealing two oligo's: LHRH1: 5'-A CGC CAA CAC TGG TCA TAT GGT TGT CGT CCT GGT TAA G (SEQ ID NO: 28) and LHRH2: 5'-GA TCC TTA ACC AGG ACG ACA ACC ATA TGA CCA GTG TTG (SEQ ID NO: 29). The annealed fragment includes a stop codon and includes the ACGC overhang at the 5'-end and a BamHI compatible sticky end at the 3'-end. The (L7C)LHRH gene fragment is ligated into Eco31I and BamHI and digested pLP1 and the resulting plasmid is designated pLP1-LHRH1.

The vector pLP1-LHRH1 is transformed to *Lactococcus lactis* NZ9700 (a nisin producing *L. lactis* strain; Kuipers et al. 1997, Tibtech. 15: 135–140). The resulting NZ9700+ pLP1-LHRH1 was grown in M17-based medium (Terzaghi and Sandine, 1975, Appl. Microbiol. 29: 807–813) to an $OD_{600}$ of 0.4. The cells were collected by centrifugation and resuspended in the same volume of Minimal Medium (Jensen and Hammer, 1993, Appl. Environ. Microbiol. 59: 4363–4366). After overnight incubation and subsequent centrifugation, samples were prepared using C18 ziptips (Millipore) as follows: pipet two times with 10 µl 50% acetonitril, followed by two times with 10 µl milliQ water, followed by eight times with 10 µl supernatant, followed by two times washing with 10 µl MilliQ water, followed by elution two times with 10 µl 50% acetonitril containing 0.1% TFA. The final eluent is vacuum dried and stored at −20° C. until analysis by mass spectrometry. Prior to analysis, the dry material was resuspended in 6 µl of 50% acetonitril containing 0.1% TFA and 1 µl was applied to the target. After drying, 1 µl of matrix (10 mg/ml alpha-cyano-4-hydroxycinnamic acid completely dissolved (by mildly heating and vortexing) in 50% acetonitril containing 0.1% TFA) was applied to the target. The following MALDI-TOFMS (linear mode) laser settings were used: 100% coarse energy, 90% fine, source 20 KV, extra 19800, force 15000, suppression 350, pulse time 40, pulse voltage 1400, sampling rate 500 MHz, sensitivity 50 mV, shots 15.

EXAMPLE 24

This Example Describes the Production of a Lantibiotic with the leader peptide still attached to it by using a strain that does not express the leader peptidase. In the case of some novel lanthionine containing (poly)peptides, this provides the advantage of reduced toxicity of the novel lantibiotic towards the producer cell.

Materials and methods. A ΔNisP strain from *Lactococcus lactis* NZ9700 is constructed.

A delta NisP strain is made using the plasmid pOR1280 (Leenhouts et al., 1996, Mol. Gen. Genet. 253, 217–224.). This disruption of NisP is made by removing the start codon of the coding gene. The advantage is the absence of the whole protein without a major alteration of the mRNA. Two PCR products of about 1 Kb were generated wherein one product starts before the gene ending before the mutated start codon and the second product starts from the start codon. These PCR products were coupled by a second PCR reaction and cloned in the pOR1280 vector in the multiple cloning site. The result was a 2 Kb genomic fragment with the changed stop codon in the middle. Finally, two subsequent single crossovers transfer the mutation into the genome.

Sequence around start codon NisP:

(SEQ ID NO: 30)

```
GCTTGCAACGAAGGTAGGAA ACTAGA TGAAAAAAATACTAGGTTTCCTTTTTATCG
TTTGTTCGTTGGG
CGAACGTTGCTTCCATCCTTTGATCTCACTTTTTTTATGATCCAAAGGAAAAATAGCA
AACAAGCAACCC
```

The amino acid sequence at SEQ ID NO: 31 is one possible open reading frame of NisP beginning at position 27 of the NisP nucleotide sequence above and ending at position 71.

The priming sites are nucleotides 38–65 and 74–99, the start codon is shown in bold face and the boxed area is replaced by NotI restriction site in the mutant strain.

The following primers are used dnisp1:

5'-cggtctctctagacctcctgattatgacgtgattg-3' (SEQ ID NO: 32)

Eco31I site is at nucleotides 2–6; XbaI site is at nucleotides 8–13.

dnisp2:

5'-gtagcgggacctctagtttcctaccttcgttgc-3' (SEQ ID NO: 33)

NotI site at nucleotides 4–11; changed start codon (into stop codon) at nucleotides 12–14.

dnisp3:

5'-gtagcggccgcactaggtttccttttatcgtttgttcg-3' (SEQ ID NO: 34)

NotI site at nucleotides 4–11.

dnisp4:

5'-cggtctctagatctccataaacatattggtaccagccag-3' (SEQ ID NO: 35)

Eco31I site at nucleotides 2–7; BglII site at nucleotides 8–13.

Two separate PCRs were performed on chromosomal DNA of the NZ9700 strain. One PCR was performed with primers dnisp1 and dnisp2 to form product of about 1.5 kb in length. A second PCR was performed with primers dnisp3 and dnisp4 to form a product of about 1.5 kb. Both fragments were purified and digested with NotI. The fragments were ligated together and a third PCR was performed on the ligation mixture with primers dnisp1 and dnisp4 to form a product of about 3 kb.

The product was digested with Eco31I or BglII/XbaI and cloned in pOR1280. The plasmid was transformed to *L. lactis* NZ9700 and growth was selected on erythromycin plates. Specific insertions into NisP gene (PCR, decrease in nisin production) were positively identified by growing a colony for 36 generations, plating out on X-gal/IPTG plates and screening for white colonies. The white colonies should be sensitive to erythromycin and be hampered in nisin production (no or small halo formation). The produced nisin should contain the leader sequence attached to the nisin.

The mutation was checked by PCR and sequencing. The above-generated ΔNisP strain was grown overnight in M17 medium (Terzaghi and Sandine, 1975, Appl. Microbiol. 29: 807–813), diluted 100 fold and grown to $OD_{600}$ equal to 0.4. Subsequently, the cells were pelleted and resuspended in minimal medium (Jensen and Hammer, 1993, Appl. Environ. Microbiol. 59: 4363–4366) supplemented with protease inhibitors 0.2 mM pmsf, 0.2 mM TPCK and filtered supernatant of the nisin producing *L. lactis* NZ9700 at 1000 fold dilution. After 1, 2 and 3 hours, more 0.2 mM pmsf, 0.2 mM TPCK are added and followed by overnight incubation. The cells were pelleted and the supernatant of the samples was subjected to: a) ziptipping as in described Example 1 and analyzed by MALDI-TOFMS using the settings given in Example 1; b) treatment with leader peptidase or trypsin and followed by either ziptipping and MALDI-TOFMS, or a halo assay; or c) binding to a column with antibodies against the nisin leader peptide. Elution and experiments a) and b).

Results: a) a mass spectrometry signal consistent with nisin (with all its thioether rings) to which the leader is still attached was present; b) a nisin mass spectrometry signal was present or halo formation by the samples treated by leader peptidase or trypsin was observed; and c) results as under a) and b) respectively.

EXAMPLE 25

Growth medium. When analyzing peptide and protein samples by mass spectrometry, the purity of the samples is a major issue. Contamination of the sample may drastically decrease the detection level of peptides and proteins. In order to prepare samples that have a relatively high purity and allow an optimal sensitivity when measuring exported peptides and proteins by matrix-assisted laser desorption/ionization time-of-flight mass spectrometry (MALDI TOFMS), bacterial cells are grown in a very poor medium. The poor medium essentially contains a mixture of specific salts, specific vitamins, glucose, asparagine and casamino acids. The medium does not contain: trypton, soya peptone, meat digest or yeast extract.

The following minimal medium can be prepared for use with Lactococci:

Stock solutions:

| SOLUTION A | |
|---|---|
| $(NH_4)_2SO_4$ | 2.0 g; |
| $Na_2HPO_4$ | 6.0 g; |
| $KH_2PO_4$ | 3.0 g; |
| $Na_2SO_4$ | 0.011 g; and |
| NaCl | 1.0 g are dissolved in 200 ml $H_2O$. |
| SOLUTION B | |
| Casamino acids | 10.0 g; |
| Na-acetate | 2.0 g; |
| Asparagine | 0.08 g; |
| $MgCl_2$ | 0.2 g; |
| $CaCl_2$ | 0.01 g; and |
| $FeCl_3(7H_2O)$ | 0.0006 g are dissolved in 800 ml $H_2O$. |
| GLUCOSE 20% | |
| Glucose | 20 g is dissolved in 100 ml $H_2O$. |
| VITAMIN MIX | |
| biotin | 0.01 g; |
| folic acid | 0.1 g; |
| riboflavin | 0.1 g; |
| nicotinic acid | 0.1 g; |
| pantotheic acid | 0.1 g; and |
| pyridoxal | 0.2 g are dissolved in 100 ml $H_2O$. |

Solution A, B and the glucose solution are autoclaved separately, while the vitamin mix is filter sterilized.

To prepare 100 ml of medium, after sterilization (and cooling down), 20 ml of solution A is added to 80 ml of solution B, 2.5 ml glucose 20% is added and 100 ul of vitamin mix is added. If necessary, appropriate antibiotics are added.

EXAMPLE 26

Purification of peptides and proteins from minimal culture medium. Peptide and protein samples for analysis by matrix-assisted laser desorption/ionization time-of-flight mass spectrometry (MALDI TOFMS) was prepared as follows. Cultures of bacteria grown in minimal medium were centrifuged in order to pellet the cells. The supernatant was aspirated and dispensed several times into and out of a pipet tip that contains a microvolume bed of affinity chromatography media fixed at the end of the tip that is without dead volume. This procedure has been referred to herein as "ziptipping." A washing step follows in order to wash away contaminants and unwanted biomolecules. The washing step was performed by aspirating and dispensing, for instance, milliQ water. Finally, the peptide or protein was eluted in 1–20 µl of suitable solvent and applied directly on the target, or vial, or speedvacced and stored at −20° C. Prior to MALDI TOFMS analysis, the sample was resuspended in 1 to 5 µl (or further dilution) of a suitable solvent of which 1 µl was applied on the target or vial.

Table 1: (poly)peptides of which the coding DNA is preceded by lantibiotic leader coding DNA in an open reading frame. Mutation possibilities allowing posttranslational thioether ring(s) formation given, for example, for vasopressin applies also to other sequences, including those which have already one ring, within other (poly)peptides in Table 1, taking into account the description of thioether ring formation mentioned in the text.

TABLE 1A

Vasopressin: Function: as an antidiuretic hormone:

(S1, R8)-sequence (SEQ ID NO: 36); lanthionine ring S1-C6
(S1, C2, R8)-sequence (SEQ ID NO: 37); lanthionine ring S1-C2
(S1, C3, R8)-sequence (SEQ ID NO: 38); lanthionine ring S1-C3
(S1, C4, R8)-sequence (SEQ ID NO: 39); lanthionine ring S1-C4
(S1, C5, R8)-sequence (SEQ ID NO: 40); lanthionine ring S1-C5
(S1, A6, C7, R8)-sequence (SEQ ID NO: 41); lanthionine ring S1-C7
(S1, A6, C8)-sequence (SEQ ID NO: 42); lanthionine ring S1-C8
(S1, R8, C9)-sequence (SEQ ID NO: 43); lanthionine ring S1-C9
(A1, S2, R8)-sequence (SEQ ID NO: 44); lanthionine ring S2-C6
(A1, S2, C3, R8)-sequence (SEQ ID NO: 45); lanthionine ring S2-C3
(A1, S2, C4, R8)-sequence (SEQ ID NO: 46); lanthionine ring S2-C4
(A1, S2, C5, R8)-sequence (SEQ ID NO: 47); lanthionine ring S2-C5
(A1, S2, A6, C7, R8)-sequence (SEQ ID NO: 48); lanthionine ring S2-C7
(A1, S2, A6, C8)-sequence (SEQ ID NO: 49); lanthionine ring S2-C8
(A1, S2, A6, R8, C9)-sequence (SEQ ID NO: 50); lanthionine ring S2-C9
(A1, S3, R8)-sequence (SEQ ID NO: 51); lanthionine ring S3-C6
(A1, S3, C4, R8)-sequence (SEQ ID NO: 52); lanthionine ring S3-C4
(A1, S3, C5, R8)-sequence (SEQ ID NO: 53); lanthionine ring S3-C5
(A1, S3, A6, C7, R8)-sequence (SEQ ID NO: 54); lanthionine ring S3-C7
(A1, S3, A6, C8)-sequence (SEQ ID NO: 55); lanthionine ring S3-C8
(A1, S3, A6, R8, C9)-sequence (SEQ ID NO: 56); lanthionine ring S3-C9
(A1, S4, R8)-sequence (SEQ ID NO: 57); lanthionine ring S4-C6
(A1, S4, C5, R8)-sequence (SEQ ID NO: 58); lanthionine ring S4-C5
(A1, S4, A6, C7, R8)-sequence (SEQ ID NO: 59); lanthionine ring S4-C7
(A1, S4, A6, C8)-sequence (SEQ ID NO: 60); lanthionine ring S4-C8
(A1, S4, A6, R8, C9)-sequence (SEQ ID NO: 61); lanthionine ring S4-C9
(A1, S5, R8)-sequence (SEQ ID NO: 62); lanthionine ring S5-C6
(A1, S5, A6, C7, R8)-sequence (SEQ ID NO: 63); lanthionine ring S5-C7
(A1, S5, A6, C8)-sequence (SEQ ID NO: 64); lanthionine ring S5-C8
(A1, S5, A6, R8, C9)-sequence (SEQ ID NO: 65); lanthionine ring S5-C9
(A1, S6, C7, R8)-sequence (SEQ ID NO: 66); lanthionine ring S6-C7
(A1, S6, C8)-sequence (SEQ ID NO: 67); lanthionine ring S6-C8
(A1, S6, R8, C9)-sequence (SEQ ID NO: 68); lanthionine ring S6-C9

TABLE 1A-continued

Vasopressin: Function: as an antidiuretic hormone:

(A1, S7, C8)-sequence (SEQ ID NO: 69); lanthionine ring S7-C8
(A1, S7, R8, C9)-sequence (SEQ ID NO: 70); lanthionine ring S7-C9
(A1, S7, C9)-sequence (SEQ ID NO: 71); lanthionine ring S8-C9.

Terlipressin (antidiuretic hormone):

S4-Sequence (SEQ ID NO: 72)

Posttranslational lanthionine: S4-C9.

Cispressin (antidiuretic hormone):

S1-Sequence (SEQ ID NO: 73)

Posttranslational lanthionine ring: S1-C6.

Adrenomedullin Hypotensive peptide, may function as a hormone in circulation control A13,S16-Sequence (SEQ ID NO: 74)

Posttranslational lanthionine: S16-C21.

Allatostatin I (neuropeptide inhibitor of juvenile hormone synthesis)

C6-Sequence (SEQ ID NO: 75)

Posttranslational lanthionine: S3-C6.

Angiotensin I

S7,C10-Sequence (SEQ ID NO: 76)

Posttranslational lanthionine S7-C10

Function: In response to lowered pressure, the enzyme renin cleaves angiotensin I, from angiotensinogen, then removes a dipeptide to yield the physiologically active angiotensin II, the most potent pressor substance known, which helps regulate volume and mineral balance of body fluids.

Anthopleurin-A (neuropeptide)

A4-Sequence (SEQ ID NO: 77)

Posttranslational lanthionine rings: S3-C6, S27-C31, S33-C38, T44-C48.

Anti-inflammatory peptide 1 (anti-inflammation)

S1,C6-Sequence (SEQ ID NO: 78)

Posttranslational lanthionine: S1-C6

Dermaseptin (antimicrobial peptide)

C10-Sequence (SEQ ID NO: 79)

Posttranslational lanthionine: T5-C10.

Bombinin-like peptide (antimicrobial peptide)

C8-Sequence (SEQ ID NO: 80)

Posttranslational lanthionine: S5-C8.

Histatin-5 (antimicrobial salivary peptide)

S4,C7-Sequence (SEQ ID NO: 81)

Posttranslational lanthionine: S4-C7.

Indolicidin (antimicrobial peptide)

S2,C5-Sequence (SEQ ID NO: 82)

Posttranslational lanthionine: S2-C5.

Magainin-1 (antimicrobial peptide)

C13-Sequence (SEQ ID NO: 83)

Posttranslational lanthionine: S8-C13.

Atrial Natriuretic Factor (potent vasoactive substance with a key role in cardiovascular homeostasis and cGMP-stimulating activity).

(SEQ ID NO: 84)

Posttranslational lanthionines: S1-C7, S19-C23.

Bradykinin (important role in renal physiology and behavior).
C9-Sequence (SEQ ID NO: 85)
Posttranslational lanthionine: S6-C9.
Brain Natriuretic Peptide (acts as a cardiac hormone involved in natriuresis, diuresis, vasorelaxation, inhibition of renin and aldosteron secretion, improves heart function)
S16,C19-Sequence (SEQ ID NO: 86)
Posttranslational lanthionine: S8-C10, S16-$C_{19}$
C-type Natriuretic peptide (exhibits natriuretic and vasodepressor activity)
(SEQ ID NO: 87)
Posttranslational lanthionine ring: S34-C37, S47-C53.
Vasonatrin peptide (vasorelaxation)
(SEQ ID NO: 88)
Posttranslational lanthionine ring: S3-C6,S17-C22.
Delta sleep inducing peptide (delta sleep induction)
S2,C6-Sequence (SEQ ID NO: 89)
Posttranslational lanthionine ring: S2-C6.
Alpha-dendrotoxin
S11,S26-Sequence (SEQ ID NO: 90)
Posttranslational lanthionine: S11-C15, S26-C31
Function: affects potassium channels.
Eledoisin
C4-Sequence (SEQ ID NO: 91)
Posttranslational lanthionine ring: S2-C4
Function: neuron excitation, causing behavioral responses, vasodilators, secretagogues, causing contraction of smooth muscles.
Echistatin
(SEQ ID NO: 92)
Posttranslational lanthionine rings: S4-C7, T18-C20, T36-C37
Function: Inhibitor of fibrinogen-dependent platelet aggregation.
alpha-endorphin
S2,C6-Sequence (SEQ ID NO: 93)
Posttranslational lanthionine ring: S2-C6
Function: opioid.
beta-endorphin
S21,C26-Sequence (SEQ ID NO: 94)
Posttranslational lanthionine ring: S21-C26
Function: opioid.
Defensin I
S2,S 12-Sequence (SEQ ID NO: 95)
Posttranslational lanthionine rings: S2-C4, S13-C19
Function: antimicrobial peptide.
Secretin
S23,C26-Sequence (SEQ ID NO: 96)
Posttranslational lanthionine ring:S23-C26
Function: pH regulation in the stomach.
Urocortin
C19-Sequence (SEQ ID NO: 97)
Posttranslational lanthionine ring: T16-C19
Function: stimulates ACTH secretion.
Urotensin II
S5-Sequence (SEQ ID NO: 98)
Posttranslational lanthionine rings: T3-C6, S5-C11
Function: osmoregulation and corticotropin release factor.
Small Cardioactive Peptide A
S4,C7-Sequence (SEQ ID NO: 99)
Posttranslational lanthionine:S4-C7
Function: inhibits acetylcholine release
Small Cardioactive peptide B
S4,C7-Sequence (SEQ ID NO: 100)
Posttranslational lanthionine: S4-C7
Function: stimulates contraction in the gut, increases amplitude of the heart beat.
Ceratotoxin A
C9-Sequence (SEQ ID NO: 101)
Posttranslational lanthionine: S4-C9
Function: antimicrobial, hemolytic peptide with activity against Gram-positive and Gram-negative bacteria, stable at 100° C.
Cerebellin
C7-Sequence (SEQ ID NO: 102)
Posttranslational lanthionine: S3-C7
Function: neuromudulation, stimulation of norepinephrine release, enhances indirectly adrenocortical secretion.
Charybdotoxin
S33-Sequence (SEQ ID NO: 103)
Posttranslational (methyl)lanthionine: T3-C7, T8-C13, S15-C17, T23-C28, S33-C35
Function: inhibitor calcium—and voltage activated potassium channels.
Cholecystokinin
C8-Sequence (SEQ ID NO: 104)
Posttranslational lanthionine: S4-C8
Function: Gall bladder contraction and release of pancreatic enzymes in the gut.
Conopressin G
S1-Sequence (SEQ ID NO: 105)
Posttranslational lanthionine: S1-C6
Function: behavioral control.
alpha-Conotoxin EI
S2,S5-Sequence (SEQ ID NO: 106)
Posttranslational lanthionine: S2-C4, S5-C10, S13-C18
Function: blocking nicotinic acetylcholine receptors.
Corazonin
C9-Sequence (SEQ ID NO: 107)
Posttranslational lanthionine: S5-C9
Function: Regulation heart beat.
Leu-enkephalin
S2,C3-Sequence (SEQ ID NO: 108)
Posttranslational lanthionine ring: S2-C3
Function: opioid
Met-enkephalin
S2,C3-Sequence (SEQ ID NO: 109)
Posttranslational lanthionine ring: S2-C3
Function: opioid.
Oxytocin
(S1)-Sequence (SEQ ID NO: 110)
Posttranslational lanthionine ring S1-C6
Function: Oxytocin stimulates uterine contraction and lactation; increases $Na^+$ secretion;
stimulates myometrial GTPase and phospholipase C.
Exendin-3
C35-Sequence (SEQ ID NO: 111)
Posttranslational lanthionine ring: S32-C35

Function: secretin-like.
Experimental Allergic Encephalitogenic peptide
C5-Sequence (SEQ ID NO: 112)
Posttranslational lanthionine ring: S2-C5
Function: myelin membrane stabilization.
Experimental Autoimmune Encephalomyelitis Complementary peptide
S4,C7-Sequence (SEQ ID NO: 113)
Posttranslational lanthionine ring: S4-C7
Effect: having a role in autoimmune encephalomyelitis.
GonadoliberinII
(C9)-sequence (SEQ ID NO: 114)
Posttranslational lanthionine ring: S4-C9
Function: stimulates the secretion of gonadotropins; it stimulates the secretion of both luteinizing and follicle stimulating hormones.
Tocinoic acid/pressinoic acid
(S1,I3)-Sequence (SEQ ID NO: 115)
posttranslational lanthionine ring S1-C6
Function: Tocinoic acid is an oxytocin inhibitor, induces maternal behavior.
Leuprolide
Sequences:
(SEQ ID NO: 116)
Posttranslational thioether ring: S4-C7
(SEQ ID NO: 117)
Posttranslational thioether ring: S4-C7
Function: LHRH agonist.
Calcitonin
Accession number: P01258
(S1)-Sequence (SEQ ID NO: 118)
Posttranslational thioether ring S1-C7
Function: CaPi incorporation in bones.
ACTH, Adrenocorticotropic hormone
(Q5, C6)-Sequence (SEQ ID NO: 119)
posttranslational lanthionine ring S1-C6
Function: ACTH stimulates synthesis and secretion of glucocorticoids by adrenal cortex.
Corticotropin inhibiting peptide
S4,C8-Sequence (SEQ ID NO: 120)
Posttranslational lanthionine: S4-C8
Function: inhibition ACTH.
Corticotropin-Release Factor
S30,C33-Sequence (SEQ ID NO: 121)
Posttranslational lanthionine: S30-C33
Function: release of corticotrophin.
Somatostatin
(S3)-Sequence (SEQ ID NO: 122)
posttranslational lanthionine ring S3-C14
Function:somatotropin release inhibition factor, growth hormone release inhibiting factor.
Human pancreatic polypeptide
(S18, C21)-Sequence (SEQ ID NO: 123)
Posttranslational lanthionine ring S18-C21
Function: Agonist at Y4 neuropeptide receptors.
Peptide YY
(S22,C25,T29,C32)-Sequence
(SEQ ID NO: 124)
Posttranslational (methyl)lanthionine rings S22-C25, T29-C32

Function: Gut hormone that inhibits both secretin- and cholecystokinin-stimulated pancreatic secretion.
Glucagon
(C5,S24,C29)-Sequence (SEQ ID NO: 125)
Posttranslational lanthionine rings S1-C5, S24-C29
Function: restoring blood glucose level when too low.
alpha-neurokinin
(C9)-sequence (SEQ ID NO: 15)
posttranslational lanthionine ring S5-C9
function: tachykinin antagonist.
LHRH1, Luteinizing Hormone Releasing Hormone
Function: regulates secretion of gonadotropins, luteinizing hormone and sex steroids.
(Q1, C7)-Sequence (SEQ ID NO: 126)
Posttranslational lanthionine ring S4-C7

| | | |
|---|---|---|
| (S1, C4)-Sequence: | (SEQ ID NO: 127) | posttr. ring: S1-C4 |
| (S1, A4, C5)-Sequence: | (SEQ ID NO: 128) | posttr. ring: S1-C5 |
| (S1, A4, C6)-Sequence: | (SEQ ID NO: 129) | posttr. ring: S1-C6 |
| (Q1, S2, A4, C5)-Sequence: | (SEQ ID NO: 130) | posttr. ring: S2-C5 |
| (Q1, S2, A4, C6)-sequence: | (SEQ ID NO: 131) | posttr. ring: S2-C6 |
| (Q1, S2, A4, C7)-sequence: | (SEQ ID NO: 132) | posttr. ring: S2-C7 |
| (Q1, S3, A4, C6)-sequence: | (SEQ ID NO: 133) | posttr. ring: S3-C6 |
| (Q1, S3, A4, C7)-sequence: | (SEQ ID NO: 134) | posttr. ring: S3-C7 |
| (Q1, S3, A4, C8)-sequence: | (SEQ ID NO: 135) | posttr. ring: S3-C8 |
| (Q1, C8)-sequence: | (SEQ ID NO: 136) | posttr. ring: S4-C8 |
| (Q1, C9)-sequence: | (SEQ ID NO: 137) | posttr. ring: S4-C9 |
| (Q1, A4, S5, C8)-sequence: | (SEQ ID NO: 138) | posttr. ring: S5-C8 |
| (Q1, A4, S5, C9)-sequence: | (SEQ ID NO: 139) | posttr. ring: S5-C9 |
| (Q1, A4, S5, C10)-sequence: | (SEQ ID NO: 140) | posttr. ring: S5-C10 |
| (Q1, A4, S6, C9)-sequence: | (SEQ ID NO: 141) | posttr. ring: S6-C9 |
| (Q1, A4, S6, C10)-sequence: | (SEQ ID NO: 142) | posttr. ring: S6-C10 |
| (Q1, A4, S7, C10)-sequence: | (SEQ ID NO: 143) | posttr. ring: S7-C10. |

LHRH2, Luteinizing Hormone Releasing Hormone fragment
Function: regulates secretion of gonadotropins, luteinizing hormone and sex steroids.
(Q1, C7)-Sequence (SEQ ID NO: 309)
Posttranslational lanthionine ring S4-C7

| | | |
|---|---|---|
| (S1, C4)-Sequence: | (SEQ ID NO: 144) | posttr. ring: S1-C4 |
| (S1, A4, C5)-Sequence: | (SEQ ID NO: 145) | posttr. ring: S1-C5 |
| (S1, A4, C6)-Sequence: | (SEQ ID NO: 146) | posttr. ring: S1-C6 |
| (Q1, S2, A4, C5)-Sequence: | (SEQ ID NO: 147) | posttr. ring: S2-C5 |
| (Q1, S2, A4, C6)-sequence: | (SEQ ID NO: 148) | posttr. ring: S2-C6 |
| (Q1, S2, A4, C7)-sequenee: | (SEQ ID NO: 149) | posttr. ring: S2-C7 |
| (Q1, S3, A4, C6)-sequence: | (SEQ ID NO: 150) | posttr. ring: S3-C6 |
| (Q1, S3, A4, C7)-sequence: | (SEQ ID NO: 151) | posttr. ring: S3-C7 |
| (Q1, S3, A4, C8)-sequenee: | (SEQ ID NO: 152) | posttr. ring: S3-C8 |
| (Q1, C8)-sequence: | (SEQ ID NO: 153) | posttr. ring: S4-C8 |
| (Q1, C9)-sequence: | (SEQ ID NO: 154) | posttr. ring: S4-C9 |
| (Q1, A4, S5, C8)-sequence: | (SEQ ID NO: 155) | posttr. ring: S5-C8 |
| (Q1, A4, S5, C9)-sequence: | (SEQ ID NO: 156) | posttr. ring: S5-C9 |
| (Q1, A4, S5, C10)-sequence: | (SEQ ID NO: 157) | posttr. ring: S5-C10 |
| (Q1, A4, S6, C9)-sequence: | (SEQ ID NO: 158) | posttr. ring: S6-C9 |
| (Q1, A4, S6, C10)-sequence: | (SEQ ID NO: 159) | posttr. ring: S6-C10 |
| (Q1, A4, S7, C10)-sequence: | (SEQ ID NO: 160) | posttr. ring: S7-C10. |

Brain derived acidic fibroblast growth factor (102–111)
(S103,C109)-Sequence (SEQ ID NO: 161)
Posttranslational lanthionine ring S103-C109
Function: growth factor.
Brain derived basic fibroblast growth factor (1–24)
(SEQ ID NO: 162)
Posttranslational lanthionine ring S11-C17

Function: growth factor.
Insulin
Sequences:
alpha-chain (SEQ ID NO: 163)
(S9-C14, T27-C30)
beta chain (SEQ ID NO: 164)
Posttranslational (methyl)lanthionine rings S9-C14, T27-C30
disulfide bonds: alpha 6–11 alpha 7-beta 7, alpha 20-beta 19
function: diabetes treatment.
Parathormone:
(S36-C39, T79-C82)-Sequence (SEQ ID NO: 165)
Posttranslational (methyl)lanthionine rings S36-C39, T79-C82
Function: modulation of serum calcium content affecting the mineral and bone physiology.
Fibrinogen Binding Inhibitor peptide
S6,C9-Sequence (SEQ ID NO: 166)
Posttranslational lanthionine: S6-C9.
Fibroblast growth factor inhibitory peptide
S1,C3-Sequence (SEQ ID NO: 167)
Posttranslational lanthionine ring: S1-C3
Effect: inhibition fibroblast growth factor.
Galanin
C10-Sequence (SEQ ID NO: 168)
Posttranslational lanthionine ring: S6-C10
Function: contracts smooth muscle of the gastrointestinal and genitourinary tract, regulates growth hormone release, modulates insulin release.
Gastric Inhibitory Polypeptide
S28,C31-Sequence (SEQ ID NO: 169)
Function: potent stimulation of insulin secretion and relatively poor inhibitor of gastric acid secretion.
Big Gastrin-I
S8,C 11-Sequence (SEQ ID NO: 170)
Posttranslational lanthionine ring: S8-C11
Function: stimulates gastric HCl secretion, pancreatic enzyme secretion, smooth muscle contraction and increases blood circulation and water secretion in the stomach and intestine.
Pentagastrin
S1,C4-Sequence (SEQ ID NO: 171)
Posttranslational lanthionine ring: S1-C4
Gastrin Releasing Peptide
S9,C 12-Sequence (SEQ ID NO: 172)
Posttranslational lanthionine ring: S9-C12
Function: gastrin release.
Transforming growth factor alpha
(SEQ ID NO: 173)
Posttranslational (methyl)lanthionine ring: S3-C8, T21-C22, S37-C44
Function: TGF alpha is a mitogenic polypeptide that is able to bind to the egf receptor and act synergistically with TGF beta to promote anchorage-independent cell proliferation in soft agar.
Human growth hormone
C7-Sequence (SEQ ID NO: 174)
Posttranslational methyllanthionine ring: T3-C7
Function: growth hormone, stimulates amongst others protein synthesis and amino acid uptake.
Growth hormone release factor
C22-Sequence (SEQ ID NO: 175)
Posttranslational lanthionine ring: S18-C22
Function: release of growth hormone.
Guanylin
(SEQ ID NO: 176)
Posttranslational lanthionine ring: T3-C4, T13-C15
Function: activator of guanylate cyclase.
Helospectin I
S15,C 18-Sequence (SEQ ID NO: 177)
Posttranslational lanthionine ring: S15-C18
Hepatitis B surface antigen fragment
C6-Sequence (SEQ ID NO: 178)
Posttranslational methyllanthionine ring: T3-C6
Function: exendin-1: secretin-like.
Intercellular adhesion molecule
(SEQ ID NO: 179)
Posttranslational lanthionine ring: S18-C23
Function: anti-hiv.
Tachyplesin I
(S3,S12)-Sequence (SEQ ID NO: 180)
Posttranslational lanthionine rings S3-C7, S12-C16
Function Hiv cell fusion inhibitor, anti tumor peptide, antimicrobial peptide.
HIV (gp120) antigenic peptide fragment
(S10,C 14)-Sequence (SEQ ID NO: 181)
Posttranslational lanthionine ring S10-C14.
HIV (gp 41) antigenic peptide 1 fragment
(S2)-Sequence (SEQ ID NO: 26)
Posttranslational lanthionine S2-C8.
HIV (gp41) antigenic peptide 5
(S20)-Sequence (SEQ ID NO: 182)
Posttranslational lanthionine ring S20-C26.
HIV protease inhibitors
(SEQ ID NO: 183)
Posttranslational lanthionine ring T1-C5
Function: inhibitor HIV protease.
Insulin-like growth factor-I analog
S1,C4-Sequence (SEQ ID NO: 184)
Posttranslational lanthionine rings: S1-C4, S11-C12.
IGF II 69–84:
(C7)-Sequence (SEQ ID NO: 185)
Posttranslational lanthionine ring S3-C7.
Interleukin-8 fragment:
(S6, C10)-Sequence (SEQ ID NO: 186)
Posttranslational lanthionine ring S6-C 10
Function: attraction neutrophils, basophils and T-cells, but not monocytes. It is involved in neutrophil activation and is released from several cell-types in response to inflammation.
Interleukin-2 fragment(60–70) (T-cell growth factor)
(SEQ ID NO: 187)
Posttranslational lanthionine ring S67-C70.
Leucokinin I (neuroactive peptide)
C8-Sequence (SEQ ID NO: 188)
Posttranslational lanthionine ring: S6-C8.
Leukopyrokinin
C4-Sequence (SEQ ID NO: 189)
Posttranslational lanthionine ring:T1-C4

Function: mediates visceral muscle contractile activity.
Mastoparan
S5,C8-Sequence (SEQ ID NO: 190)
Posttranslational lanthionine ring: S5-C8
Function: Wasp venom membrane-active toxin.
Melanin concentrating hormone
S11-Sequence (SEQ ID NO: 191)
Posttranslational lanthionine ring: S11-C16
Function: possible neurotransmitter, involved in the regulation of goal directed behavior.
Melittin
C14-Sequence (SEQ ID NO: 192)
Posttranslational lanthionine ring: T10-C14
Function: Bee venom membrane-active peptide.
Motilin
C9-Sequence (SEQ ID NO: 193)
Posttranslational lanthionine ring: T6-C9
Function: regulation of interdigestive gastrointestinal motility.
Neuropeptide Y
C26-Sequence (SEQ ID NO: 194)
Posttranslational lanthionine ring S22-C26
Function:control of feeding and secretion of gonadotropin-release hormone.
Osteocalcin
S4,C8-Sequence (SEQ ID NO: 195)
Posttranslational lanthionine ring: S4-C8
Function: constitutes 1–2% of the total bone protein, it binds strongly to apatite and calcium.
(N-acetyl-)beta-endorphin 1–27
(C21)-Sequence (SEQ ID NO: 196)
Posttranslational methyllanthionine T16-C21
Functions: analgesia, behavioral changes, growth hormone release.
Ras oncogene related peptide
HU-ras$^{ha}$
(S2, C5)-Sequence (SEQ ID NO: 197)
Posttranslational lanthionine ring S2-C5.
Ras oncogene related peptide
Hu-ras$^{T24}$
(S2, C5)-Sequence (SEQ ID NO: 198)
Posttranslational lanthionine ring S2-C5.
Ras oncogene-related peptide
Hu-(Hu-ras$^{t24}$)-Lys
(S3, C6)-Sequence (SEQ ID NO: 199)
Posttranslational lanthionine ring S3-C6.

TABLE 1B

| Albumin |
| --- |
| Accession number: P02768 (SEQ ID NO: 200) |

Disulfide bonds: 77–86;99–115; 114–125; 148–193; 192–201;224–270;269–277;289–303;302–313;340–385;384–393;416–462;461–472;485–501;500–511; 538–583;582–591 (numbers correspond to the precursor protein which contains 24 amino acids more, N-terminally)
Function: regulation colloidal osmotic pressure of the blood plasma, binding blood plasma molecules.
Alglucerase
Accession number: P04062
(SEQ ID NO: 201)
Function: glucosylceramidase.
Alpha-galactosidase
Accession number: P06280
(SEQ ID NO: 202)
Function: galactosidase.
Alteplase
Accession number: P00750
(SEQ ID NO: 203)
Disulfide: 41–71; 69–78; 86–97; 91–108;110–119; 127–208; 148–190; 179–203; 215–296;236–278; 267–291; 299–430; 342–358; 350–419; 444–519; 476–492;509–537 (counted with 35 additional N-terminal aa)
Function: cleaves plasminogen to form plasmin
Antithrombin III
Accession number: P01008
(SEQ ID NO: 204)
Disulfide: 40–160;53–127; 279–462 (counted with 32 aa signal sequence)
Function: inhibition coagulation.
Aprotinin
Accession number: P00974
Disulfide: 40–90; 49–73; 65–86 (counting with 35 aa N-terminal)
Function: Inhibits trypsin, kallikrein, chymotrypsin and plasmin.
Asparaginase
Accession number: P20933
Sequence:
alpha-chain (SEQ ID NO: 206)
beta-chain (SEQ ID NO: 207)
Disulfide: 64–69; 163–179; 286–306; 317–345 (counted with 23 extra N-terminal aa)
Function: Cleaving glycoproteins.
Becaplermin
Accession number: P01127
(SEQ ID NO: 208)
Disulfide: 97–141; 130–178; 134–180;124–124 INTERCHAIN; 133–133 INTERCHAIN. (counting with 81 aa N-terminal)
Function: growth factor from platelet.
Bone morphogenic protein 7
Accession number: P34819
(SEQ ID NO: 209)
Function: induces bone formation, involved in Ca regulation.
Catalase
Accession number: P04040
(SEQ ID NO: 210)
Function: protection against $H_2O_2$.
Cecropin B
Accession number: P01508
(SEQ ID NO: 211)
Function: Antibacterial.
Cellulase
Accession number: P23548
(SEQ ID NO: 212)
Function: hydrolysis cellulose.
Choriogonadotropin alpha Accession number: P01215
(SEQ ID NO: 213)
Function: A heterodimer of a common alpha chain and a unique beta chain confers biological specificity to thyrotropin, lutropin, follitropin and gonadotropin.
Choriogonadotropin beta
Accession number: P01233
(SEQ ID NO: 214)
Disulfide: 29–77; 43–92; 46–130; 54–108; 58–110; 113–120
Function: stimulates steroid production.
Chymopapain
Accession number: P14080
(SEQ ID NO: 215)
Disulfide: 156–197; 190–229; 287–338 (counting with 134 aa N-terminal)
Function: Thiol protease.
Chymotrypsin
Accession number: P54414
(SEQ ID NO: 216
Function: serine protease.
Big Endothelin
(SEQ ID NO: 217)
Function: endothelins are endothelium derived vasoconstrictor peptides.
Clostridium botulinum toxin type A
Accession number: Q45894
Sequence A-light chain (SEQ ID NO: 218)
Sequence A-heavy chain (SEQ ID NO: 219)
Disulfide: 429–453 INTERCHAIN (BY SIMILARITY); 1234–1279
Function: blocking neurotransmitter release by hydrolysis of snap25.
Clostridium botulinum toxin type B
Accession number: P10844
(SEQ ID NO: 220)
Disulfide: 436–445 INTERCHAIN (PROBABLE).
Function: endopeptidase that cleaves synaptobrevin-2 and thus blocks neurotransmission.
Collagen
Accession number: P30754
(SEQ ID NO: 221)
Function: fibril formation
Collagenase
Accession number: P08897
(SEQ ID NO: 222)
Disulfide: 60–76; 181–196; 206–234
Function: Serine protease.
Corticotropin, ACTH
Accession number: P01189
(SEQ ID NO: 223)
Disulfide: 28–50 (counting with 26 aa signal)
Function: melanocyte stimulation.
Dornase alfa
Accession number: P24855
(SEQ ID NO: 224)
Disulfide: 123–126; 195–231 (counted with 21 aa extra N-terminal)
Function: endonucleolytic, binds G-actin.
Eptacog alpha (factor VII)
Accession number: P08709
(SEQ ID NO: 225)
Disulfide: 77–82; 110–121; 115–130; 132–141; 151–162; 158–172; 174–187; 195–322; 219–224; 238–254; 370–389; 400–428 (counted with 61 aa N-terminally)
Function: coagulation.
Etanercept
Accession number: P20333
(SEQ ID NO: 226)
Disulfide: 40–53; 54–67; 57–75; 78–93; 96–110; 100–118; 120–126; 134–143; 137–161; 164 179 (counted with 22 aa extra N-terminally)
Function: receptor TNF-alpha.
Erythropoietin
Accession number: P01588
(SEQ ID NO: 227)
Disulfide: 34–188; disulfide: 56–60 (counted with 27 aa N-terminally)
Function: erythropoiese.
Exendin-4
Accession number: P26349
(SEQ ID NO: 228)
86 AMIDATION (G-87 PROVIDE AMIDE GROUP). (counted with 23 aa signal N-terminally)
Function: secretin-like.
Factor VIII
Accession number: P00451
(SEQ ID NO: 229)
Disulfide: 172–198;547–573; 1851–1877; 2040–2188; 2193–2345 (counted with 19 aa extra N-terminally)
Function: coagulation.
Factor IX
Accession number: P00740
Sequence:
Light chain: (SEQ ID NO: 230)
Heavy chain: (SEQ ID NO: 231)
Disulfide: 64–69; 97–108; 102–117; 119–128; 134–145; 141–155; 157–170 (counted in the precursor)
Function: coagulation.
Factor X
Accession number: P00742
Sequence:
Light chain: (SEQ ID NO: 232)
Heavy chain: (SEQ ID NO: 223)
Disulfide: 90–101; 95–110; 112–121; 129–140; 136–149; 151–164; 172–342; 241–246; 261 277; 390–404; 415–443 (counted with 40 aa signal sequence)
Function: coagulation, factor Xa (part of factor X-heavy chain) is a vitamin K-dependent glycoprotein that converts prothrombin into thrombin in the presence of amongst others anionic phospholipid.
Factor XIII
Accession number: P00488
(SEQ ID NO: 234)
Function: coagulation, indirectly stabilizing fibrin chains.
Fibronectin
Accession number: P02751
(SEQ ID NO: 235)
Disulfide: 52–78; 76–87; 97–125; 123–135; 141–169; 167–179; 186–215; 213–225; 231–260; 258–308–335;

333–342; 360–386; 374–401; 420–446; 434–461; 470–498; 496–508; 518 545; 543–555; 561–589; 587–599; 2206–2235; 2233–2245; 2251–2278; 2276–2288; 2295–2319; 2317–2333; 2367—2367; 2371—2371 INTERCHAIN (WITH 2367 OF OTHER CHAIN). (counted with 31 aa extra N-terminally)

Function: wound healing, cell shape.

Fibrinogen

Accession number: P02671

(SEQ ID NO: 236)

Disulfide: 47—47 INTERCHAIN (WITH C-47'); 55—55 INTERCHAIN (WITH C-95 IN BETA); 64—64 INTERCHAIN (WITH C-49 IN GAMMA); 68—68 INTERCHAIN (WITH C-106 IN BETA); 180—180 INTERCHAIN (WITH C-165 IN GAMMA); 184—184 INTERCHAIN (WITH C-223 IN BETA); 461–491

Function: fibrin formation, platelet aggregation.

Filgrastim

Accession number: P09919

(SEQ ID NO: 237)

Disulfide: 69–75; 97–107 (counted with 30 aa N-terminally)

Function: granulocyte stimulation.

Follitropin alpha

Accession number: P37036

(SEQ ID NO: 238)

Disulfde: 11–35; 14–64; 32–86; 36–88; 63–91

Function: follicle stimulation.

Follitropin beta

Accession numbers: P01225

(SEQ ID NO: 239)

Disulfide: 21–69; 35–84; 38–122; 46–100; 50–102; 105–112 (counted with 18 aa N-terminally)

Function: follicle stimulation.

Growth hormone releasing hormone

Accession number: P48144

(SEQ ID NO: 240)

Function: growth hormone release.

Pituitary adenylate cyclase activating polypeptide

Accession number: P48144

(SEQ ID NO: 241)

Function: see name.

Hyaluronidase

Accession number: P38567

(SEQ ID NO: 242)

Function: glycosyl hydrolase.

Hirudin II

Accession number: P28504

(SEQ ID NO: 243)

Disulfide: 6–14; 16–28; 22–39

Function: thrombin inhibitor.

Imiglucerase

Accession number: P04062

(SEQ ID NO: 244)

Function: Glucohydrolase.

Interleukin 2

Accession number: P01585

(SEQ ID NO: 245)

Disulfide: 78–125 (counted with 20 aa signal N-terminally)

Function: growth factor.

Interferon alpha-4

Accession numbers: P01562

(SEQ ID NO: 246)

Disulfide: 24–122; 52–162 (counted with 23 aa N-terminally)

Function: Antiviral, interferon stimulates the production of two enzymes, a protein kinase and an oligoadenylate synthetase.

Interferon-beta

Accession numbers: P01575

(SEQ ID NO: 247)

Function: antiviral, antibacterial and anticancer.

Intrinsic factor

Accession number: P27352

(SEQ ID NO: 248)

Disulfide: 26–246; 103–288; 143–182 (counted with 18 aa N-terminally extra)

Function: cobalamin endocytosis.

Invertase

Accession number: Q60115

(SEQ ID NO: 249)

Function: sucrase.

Lepirudin

Accession number: P01050

(SEQ ID NO: 250)

Disulfides: 6–14; 16–28

Function: thrombin inhibitor.

Lutropin beta

Accession number: P01229

(SEQ ID NO: 251)

Disulfide: 29–77; 43–92; 46–130; 54–108; 58–110; 113–120

Function: stimulates synthesis of steroids.

Lysozyme

Accession number: P21270

(SEQ ID NO: 252)

Function: hydrolysis peptidoglycan.

Metalloproteinase inhibitor

Accession number: P16035

Accession number: P21270

(SEQ ID NO: 253)

Disulfides: 27–98; 29–127; 39–152; 154–201; 159–164; 172–193 (counted with 26 aa N-terminally)

Function: inactivation protease.

Neurophysin

Accession number: P01185

(SEQ ID NO: 254)

Disulfide: 41–85; 44–58; 52–75; 59–65; 92–104; 98–116; 105–110

Function: Neurophysin binds vasopressin.

Papain

Accession number: P00784

(SEQ ID NO: 255)

Disulfide: 155–196; 189–228; 286–333 (counted with 18 aa N-terminally)

Function: Proteinase.

Pepsin

Accession number: P00790

(SEQ ID NO: 256)

Disulfide: 107–112; 268–272; 311–344 (counted with 62 aa N-terminally)

Function: Peptidase.

Plasminogen

Accession number: P00747

(SEQ ID NO: 257)

Disulfide: 49–73; 53–61; 103–181; 124–164; 152–176; 185–262; 188–316; 206–245; 234–257; 275–352; 296–335; 324–347; 377–454; 398–437; 426–449; 481–560; 502–543; 531–555; 567–685; 577–585; 607–623; 699–766; 729–745; 756–784

Function: Protease.

Protamine

Accession number: P04554

(SEQ ID NO: 258)

Function: histon substitution.

Prothrombin

Accession number: P12259

(SEQ ID NO: 259)

Disulfide: 167–193; 500–526; 1725–1751; 1907–2061; 2066–2221 (counted with 28 N-terminal aa)

Function: Coagulation.

Protirelin

Accession number: P20396

(SEQ ID NO: 260)

Function: thyrotropin release.

SC3

Accession number: P16933

(SEQ ID NO: 261)

Function: hydrophobin.

Sermorelin

Accession number: P01286

(SEQ ID NO: 262)

Function: growth hormone release.

Streptodornase

Accession number: P26295

(SEQ ID NO: 263)

Function: DNAse.

Streptokinase

Accession number: P00779

(SEQ ID NO: 264)

Function: activating plasminogen.

Thyroglobulin

Accession number: P01266

(SEQ ID NO: 265)

Function: precursor thyroid hormone.

Urokinase accession: P00749

(SEQ ID NO: 266)

Function: plasminogen activation.

TABLE 2

| Leader Peptides: | |
|---|---|
| Epicidin-280 | (SEQ ID NO: 267) |
| Pep-5 | (SEQ ID NO: 268) |
| Epilancin-K7 | (SEQ ID NO: 269) |
| Nisin-A/Z | (SEQ ID NO: 270) |
| Subtilin | (SEQ ID NO: 271) |
| Epidermin | (SEQ ID NO: 272) |
| Gallidermin | (SEQ ID NO: 273) |
| Mutacin-1140/III | (SEQ ID NO: 274) |
| Lacticin-481 | (SEQ ID NO: 275) |
| Variacin | (SEQ ID NO: 276) |
| Mutacin-II | (SEQ ID NO: 277) |
| Streptococcin-A-FF22 | (SEQ ID NO: 278) |
| Salivaricin-A | (SEQ ID NO: 279) |
| Sublancin | (SEQ ID NO: 280) |
| Lactocin-S | (SEQ ID NO: 281) |
| Ruminococcin A | (SEQ ID NO: 282) |
| Butyrivibriocin OR79A | (SEQ ID NO: 283) |
| Streptococcin A-M49 | (SEQ ID NO: 284) |
| Bacteriocin J46 | (SEQ ID NO: 285) |
| Salivaricin A1 | (SEQ ID NO: 286) |
| Streptin | (SEQ ID NO: 287) |
| Plantaricin-W alpha | (SEQ ID NO: 288) |
| Lacticin-3147A1 | (SEQ ID NO: 289) |
| Staphylococcin-C55 alpha | (SEQ ID NO: 290) |
| Plantaricin-W beta | (SEQ ID NO: 291) |
| Lacticin-3147A2 | (SEQ ID NO: 292) |
| Staphylococcin-C55 beta | (SEQ ID NO: 293) |
| Cytolysin-LL | (SEQ ID NO: 294) |
| Cytolysin-LS | (SEQ ID NO: 295) |
| Cinnamycin | (SEQ ID NO: 296) |
| Mersacidin | (SEQ ID NO: 297) |

What is claimed is:

1. A method for producing a thioether bridge containing polypeptide of a non-Gram positive bacterium origin in a host cell, said method comprising: selecting a host cell having a nucleic acid molecule comprising:
   a first nucleic acid fragment encoding a leader peptide;
   a second nucleic acid fragment encoding a polypeptide comprising a sequence selected from the group of sequences consisting of Ser-Cys, Ser-Xaa$_{1-20}$-Cys (SEQ ID NO: 310), Thr-Cys, and Thr-Xaa$_{1-20}$-Cys (SEQ ID NO: 311), wherein Xaa is any amino acid and the polypeptide is of the non-Gram positive bacterium origin;
   wherein the first and second nucleic acid fragments are within the same open reading frame as the nucleic acid molecule; and
   wherein the leader peptide acts as a translocation signal sequence and a recognition signal such that the thioether bridge formation may occur;
   selecting the host cell for the presence of the transporter protein LanT or a functional equivalent thereof having LanT activity;
   translating the nucleic acid molecule, thus producing the leader peptide and the polypeptide comprising the sequence selected from the group of sequences consisting of Ser-Cys, Ser-Xaa$_{1-20}$-Cys (SEQ ID NO: 310), Thr-Cys, and Thr-Xaa$_{1-20}$-Cys (SEQ ID NO: 311); and
   harvesting the polypeptide containing the thioether bridge from a medium of the host cell.

2. The method according to claim 1, further comprising harvesting the polypeptide containing the thioether bridge after the leader peptide is detected in the medium of the host cell.

3. The method according to claim 1, wherein the leader peptide is selected from the group consisting of the leader peptides of Table 2.

4. The method according to claim 1, wherein the host cell is of a Gram-negative or eukaryotic origin.

5. The method according to claim 1, wherein the polypeptide containing the thioether bridge has not undergone intra-cellular post-translational modification.

6. The method according to claim 1, wherein the host cell is not provided with a LanB protein or a functional equivalent thereof having LanB activity.

7. The method according to claim 1, wherein the host cell is not provided with a LanC protein or a functional equivalent thereof having LanC activity.

8. The method according to claim 6, wherein the host cell is of Gram-negative or eukaryotic origin.

9. The method according to claim 7, wherein the host cell is of Gram-negative or eukaryotic origin.

10. The method according to claim 5, wherein the intra-cellular post-translational modification comprises dehydration of a serine, dehydration of a threonine or thioether bridge formation.

11. The method according to claim 1, wherein the polypeptide comprises the sequence Ser-Xaa$_{2-15}$-Cys (SEQ ID NO: 312) or Thr- Xaa$_{2-15}$-Cys (SEQ ID NO: 313).

12. A method for producing a thioether bridge containing polypeptide of a non-Gram positive bacterium origin, said method comprising: providing a host cell having a nucleic acid molecule, the nucleic acid molecule comprising:
   a first nucleic acid fragment encoding a leader peptide of a nisin peptide origin;
   a second nucleic acid fragment encoding a pre-polypeptide comprising a sequence selected from the group of sequences consisting of Ser-Cys, Ser-Xaa$_{1-20}$-Cys (SEQ ID NO: 310), Thr-Cys, and Thr-Xaa$_{1-20}$-Cys (SEQ ID NO: 311), wherein Xaa is any amino acid and the pre-polypeptide is of the non-Gram positive bacterium origin;
   wherein the first and second nucleic acid fragments are within the same open reading frame as the nucleic acid molecule;
   translating the nucleic acid molecule, thus expressing the leader peptide and the pre-polypeptide; and
   harvesting the thioether bridge containing polypeptide from a medium of the host cell.

13. The method according to claim 12, wherein the pre-polypeptide comprises the sequence Ser-Xaa$_{2-15}$-Cys (SEQ ID NO: 312) or Thr- Xaa$_{2-15}$-Cys (SEQ ID NO: 313).

* * * * *

SEQUENCE LISTING

<160> NUMBER OF SEQ ID NOS: 313

<210> SEQ ID NO 1
<211> LENGTH: 10
<212> TYPE: PRT
<213> ORGANISM: Artificial Sequence
<220> FEATURE:
<223> OTHER INFORMATION: LHRH1 sequence

<400> SEQUENCE: 1

-continued

```
Gln His Trp Ser Tyr Gly Leu Arg Pro Gly
1               5                   10

<210> SEQ ID NO 2
<211> LENGTH: 10
<212> TYPE: PRT
<213> ORGANISM: Artificial Sequence
<220> FEATURE:
<223> OTHER INFORMATION: LHRH2 sequence

<400> SEQUENCE: 2

Gln His Trp Ser His Gly Trp Tyr Pro Gly
1               5                   10

<210> SEQ ID NO 3
<211> LENGTH: 22
<212> TYPE: PRT
<213> ORGANISM: Lactococcus lactis
<220> FEATURE:
<221> NAME/KEY: SITE
<222> LOCATION: (1)..(22)
<223> OTHER INFORMATION: Note = nisin leader peptide

<400> SEQUENCE: 3

Ser Thr Lys Asp Phe Asn Leu Asp Leu Val Ser Val Ser Lys Lys Asp
1               5                   10                  15

Ser Gly Ala Ser Pro Arg
            20

<210> SEQ ID NO 4
<211> LENGTH: 40
<212> TYPE: DNA
<213> ORGANISM: Artificial Sequence
<220> FEATURE:
<223> OTHER INFORMATION: primer NisT.fw

<400> SEQUENCE: 4
cggtctccca tggatgaagt gaaagaattc acatcaaaac                              40

<210> SEQ ID NO 5
<211> LENGTH: 42
<212> TYPE: DNA
<213> ORGANISM: Artificial Sequence
<220> FEATURE:
<223> OTHER INFORMATION: primer NisT.rev

<400> SEQUENCE: 5
cggtctctct agattattca tcattatcct catattgctc tg                           42

<210> SEQ ID NO 6
<211> LENGTH: 40
<212> TYPE: DNA
<213> ORGANISM: Artificial Sequence
<220> FEATURE:
<223> OTHER INFORMATION: primer NisA.fw

<400> SEQUENCE: 6
cggtctctca tgagtacaaa agattttaac ttggatttgg                              40

<210> SEQ ID NO 7
<211> LENGTH: 40
<212> TYPE: DNA
<213> ORGANISM: Artificial Sequence
<220> FEATURE:
<223> OTHER INFORMATION: primer NisA.rev
```

-continued

```
<400> SEQUENCE: 7
tatatggatc ctttgcttac gtgaatacta caatgacaag                           40

<210> SEQ ID NO 8
<211> LENGTH: 5
<212> TYPE: PRT
<213> ORGANISM: Artificial Sequence
<220> FEATURE:
<223> OTHER INFORMATION: end of nisA leader peptide

<400> SEQUENCE: 8

Gly Ala Ser Pro Arg
1               5

<210> SEQ ID NO 9
<211> LENGTH: 40
<212> TYPE: DNA
<213> ORGANISM: Artificial Sequence
<220> FEATURE:
<223> OTHER INFORMATION: primer NisA.fw3

<400> SEQUENCE: 9
cggtctcaga tcaatagaaa cattaacaaa tctaaaacag                           40

<210> SEQ ID NO 10
<211> LENGTH: 35
<212> TYPE: DNA
<213> ORGANISM: Artificial Sequence
<220> FEATURE:
<223> OTHER INFORMATION: primer NisA.rev3

<400> SEQUENCE: 10
cggtctcaca tggagcgtgg tgatgcacct gaatc                                35

<210> SEQ ID NO 11
<211> LENGTH: 33
<212> TYPE: DNA
<213> ORGANISM: Artificial Sequence
<220> FEATURE:
<223> OTHER INFORMATION: primer SC3.fw2

<400> SEQUENCE: 11
cggtctctaa ttcttggtgg ccacccgggc acg                                  33

<210> SEQ ID NO 12
<211> LENGTH: 36
<212> TYPE: DNA
<213> ORGANISM: Artificial Sequence
<220> FEATURE:
<223> OTHER INFORMATION: primer SC3.rev2

<400> SEQUENCE: 12
cggtctctag ctcttagagg atgttgatgg gggtgc                               36

<210> SEQ ID NO 13
<211> LENGTH: 23
<212> TYPE: PRT
<213> ORGANISM: Lactococcus lactis
<220> FEATURE:
<221> NAME/KEY: SITE
<222> LOCATION: (1)..(23)
<223> OTHER INFORMATION: Note = leader sequence of nisin prepeptide

<400> SEQUENCE: 13

Met Ser Thr Lys Asp Phe Asn Leu Asp Leu Val Ser Val Ser Lys Lys
1               5                   10                  15
```

```
Asp Ser Gly Ala Ser Pro Arg
            20

<210> SEQ ID NO 14
<211> LENGTH: 34
<212> TYPE: PRT
<213> ORGANISM: Lactococcus lactis
<220> FEATURE:
<221> NAME/KEY: SITE
<222> LOCATION: (1)..(34)
<223> OTHER INFORMATION: Note = nisin propeptide

<400> SEQUENCE: 14

Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30

Ser Lys

<210> SEQ ID NO 15
<211> LENGTH: 10
<212> TYPE: PRT
<213> ORGANISM: Artificial Sequence
<220> FEATURE:
<223> OTHER INFORMATION: (C9)- sequence of alpha neurokinin

<400> SEQUENCE: 15

His Lys Thr Asp Ser Phe Val Gly Cys Met
1               5                   10

<210> SEQ ID NO 16
<211> LENGTH: 29
<212> TYPE: PRT
<213> ORGANISM: Artificial Sequence
<220> FEATURE:
<223> OTHER INFORMATION: (C5, C24, C29) -sequence of glucagon

<400> SEQUENCE: 16

His Ser Gln Gly Cys Phe Thr Ser Asp Tyr Ser Lys Tyr Leu Asp Ser
1               5                   10                  15

Arg Arg Ala Gln Asp Phe Val Ser Trp Leu Met Asn Cys
            20                  25

<210> SEQ ID NO 17
<211> LENGTH: 50
<212> TYPE: DNA
<213> ORGANISM: Artificial Sequence
<220> FEATURE:
<223> OTHER INFORMATION: primer nisB fw

<400> SEQUENCE: 17
cggtctcgca tgataaaaag ttcatttaaa gctcaaccgt ttttagtaag            50

<210> SEQ ID NO 18
<211> LENGTH: 42
<212> TYPE: DNA
<213> ORGANISM: Artificial Sequence
<220> FEATURE:
<223> OTHER INFORMATION: primer NisT rev

<400> SEQUENCE: 18
cggtctctct agattattca tcattatcct catattgctc tg                    42

<210> SEQ ID NO 19
```

```
<211> LENGTH: 9
<212> TYPE: PRT
<213> ORGANISM: Artificial Sequence
<220> FEATURE:
<223> OTHER INFORMATION: vasopressin

<400> SEQUENCE: 19

Cys Tyr Phe Gln Asn Cys Pro Arg Gly
1               5

<210> SEQ ID NO 20
<211> LENGTH: 29
<212> TYPE: DNA
<213> ORGANISM: Artificial Sequence
<220> FEATURE:
<223> OTHER INFORMATION: primer pLP.1

<400> SEQUENCE: 20
cggtctcagc gtggtgatgc acctgaatc                              29

<210> SEQ ID NO 21
<211> LENGTH: 51
<212> TYPE: DNA
<213> ORGANISM: Artificial Sequence
<220> FEATURE:
<223> OTHER INFORMATION: primer pLP.2

<400> SEQUENCE: 21
ccacgctgag accgcagctg ggatccggct tgaaacgttc aattgaaatg g      51

<210> SEQ ID NO 22
<211> LENGTH: 35
<212> TYPE: DNA
<213> ORGANISM: Artificial Sequence
<220> FEATURE:
<223> OTHER INFORMATION: oligo VP.1

<400> SEQUENCE: 22
acgctcatat tttcaaaatt gtcctcgtgg ttaag                        35

<210> SEQ ID NO 23
<211> LENGTH: 35
<212> TYPE: DNA
<213> ORGANISM: Artificial Sequence
<220> FEATURE:
<223> OTHER INFORMATION: oligo VP.2

<400> SEQUENCE: 23
gatccttaac cacgaggaca attttgaaaa tatga                        35

<210> SEQ ID NO 24
<211> LENGTH: 17
<212> TYPE: PRT
<213> ORGANISM: Artificial Sequence
<220> FEATURE:
<223> OTHER INFORMATION: (S3,S12)-sequence of tachyplesin

<400> SEQUENCE: 24

Lys Trp Ser Phe Arg Val Cys Tyr Arg Gly Ile Ser Tyr Arg Arg Cys
1               5                   10                  15
Arg

<210> SEQ ID NO 25
<211> LENGTH: 27
<212> TYPE: PRT
<213> ORGANISM: Artificial Sequence
```

```
<220> FEATURE:
<223> OTHER INFORMATION: vasonatrin

<400> SEQUENCE: 25

Gly Leu Ser Lys Gly Cys Phe Gly Leu Lys Leu Asp Arg Ile Gly Ser
1               5                   10                  15

Met Ser Gly Leu Gly Cys Asn Ser Phe Arg Tyr
            20                  25

<210> SEQ ID NO 26
<211> LENGTH: 17
<212> TYPE: PRT
<213> ORGANISM: Artificial Sequence
<220> FEATURE:
<223> OTHER INFORMATION: HIV (gp41) antigenic peptide 1

<400> SEQUENCE: 26

Gly Ser Ser Gly Lys Leu Ile Cys Thr Thr Ala Val Pro Trp Asn Ala
1               5                   10                  15

Ser

<210> SEQ ID NO 27
<211> LENGTH: 32
<212> TYPE: PRT
<213> ORGANISM: Artificial Sequence
<220> FEATURE:
<223> OTHER INFORMATION: (S1)-sequence of calcitonin

<400> SEQUENCE: 27

Ser Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 28
<211> LENGTH: 38
<212> TYPE: DNA
<213> ORGANISM: Artificial Sequence
<220> FEATURE:
<223> OTHER INFORMATION: oligo LHRH1

<400> SEQUENCE: 28
acgccaacac tggtcatatg gttgtcgtcc tggttaag                         38

<210> SEQ ID NO 29
<211> LENGTH: 38
<212> TYPE: DNA
<213> ORGANISM: Artificial Sequence
<220> FEATURE:
<223> OTHER INFORMATION: oligo LHRH2

<400> SEQUENCE: 29
gatccttaac caggacgaca accatatgac cagtgttg                         38

<210> SEQ ID NO 30
<211> LENGTH: 140
<212> TYPE: DNA
<213> ORGANISM: Artificial Sequence
<220> FEATURE:
<223> OTHER INFORMATION: part of NisP sequence

<400> SEQUENCE: 30
gcttgcaacg aaggtaggaa actagagtga aaaaatact aggtttcctt tttatcgttt   60
gttcgttggg cgaacgttgc ttccatcctt tgatctcact tttttatga tccaaaggaa  120
```
aaatagcaaa caagcaaccc                                              140

<210> SEQ ID NO 31
<211> LENGTH: 15
<212> TYPE: PRT
<213> ORGANISM: Artificial Sequence
<220> FEATURE:
<223> OTHER INFORMATION: part of amino acid sequence of NisP

<400> SEQUENCE: 31

Val Lys Lys Ile Leu Gly Phe Leu Phe Ile Val Cys Ser Leu Gly
1               5                   10                  15

<210> SEQ ID NO 32
<211> LENGTH: 35
<212> TYPE: DNA
<213> ORGANISM: Artificial Sequence
<220> FEATURE:
<223> OTHER INFORMATION: primer dnisp1

<400> SEQUENCE: 32
cggtctctct agacctcctg attatgacgt gattg                              35

<210> SEQ ID NO 33
<211> LENGTH: 36
<212> TYPE: DNA
<213> ORGANISM: Artificial Sequence
<220> FEATURE:
<223> OTHER INFORMATION: primer dnisp2

<400> SEQUENCE: 33
gtagcggccg cctatctagt ttcctacctt cgttgc                             36

<210> SEQ ID NO 34
<211> LENGTH: 39
<212> TYPE: DNA
<213> ORGANISM: Artificial Sequence
<220> FEATURE:
<223> OTHER INFORMATION: primer dnisp3

<400> SEQUENCE: 34
gtagcggccg cactaggttt cctttttatc gtttgttcg                          39

<210> SEQ ID NO 35
<211> LENGTH: 38
<212> TYPE: DNA
<213> ORGANISM: Artificial Sequence
<220> FEATURE:
<223> OTHER INFORMATION: primer dnisp4

<400> SEQUENCE: 35
cggtctcaga tctccataaa catattggta ccagccag                           38

<210> SEQ ID NO 36
<211> LENGTH: 9
<212> TYPE: PRT
<213> ORGANISM: Artificial Sequence
<220> FEATURE:
<223> OTHER INFORMATION: (S1,R8)-sequence of vasopressin

<400> SEQUENCE: 36

Ser Tyr Phe Gln Asn Cys Pro Arg Gly
1               5

<210> SEQ ID NO 37

```
<211> LENGTH: 9
<212> TYPE: PRT
<213> ORGANISM: Artificial Sequence
<220> FEATURE:
<223> OTHER INFORMATION: (S1,C2,R8)-sequence of vasopressin

<400> SEQUENCE: 37

Ser Cys Phe Gln Asn Cys Pro Arg Gly
1               5

<210> SEQ ID NO 38
<211> LENGTH: 9
<212> TYPE: PRT
<213> ORGANISM: Artificial Sequence
<220> FEATURE:
<223> OTHER INFORMATION: (S1,C3,R8)-sequence of vasopressin

<400> SEQUENCE: 38

Ser Tyr Cys Gln Asn Cys Pro Arg Gly
1               5

<210> SEQ ID NO 39
<211> LENGTH: 9
<212> TYPE: PRT
<213> ORGANISM: Artificial Sequence
<220> FEATURE:
<223> OTHER INFORMATION: (S1,C4,R8)-sequence of vasopressin

<400> SEQUENCE: 39

Ser Tyr Phe Cys Asn Cys Pro Arg Gly
1               5

<210> SEQ ID NO 40
<211> LENGTH: 9
<212> TYPE: PRT
<213> ORGANISM: Artificial Sequence
<220> FEATURE:
<223> OTHER INFORMATION: (S1,C5,R8)-sequence of vasopressin

<400> SEQUENCE: 40

Ser Tyr Phe Gln Cys Cys Pro Arg Gly
1               5

<210> SEQ ID NO 41
<211> LENGTH: 9
<212> TYPE: PRT
<213> ORGANISM: Artificial Sequence
<220> FEATURE:
<223> OTHER INFORMATION: (S1,A6,C7,R8)-sequence of vasopressin

<400> SEQUENCE: 41

Ser Tyr Phe Gln Asn Ala Cys Arg Gly
1               5

<210> SEQ ID NO 42
<211> LENGTH: 9
<212> TYPE: PRT
<213> ORGANISM: Artificial Sequence
<220> FEATURE:
<223> OTHER INFORMATION: (S1,A6,C8)-sequence of vasopressin

<400> SEQUENCE: 42

Ser Tyr Phe Gln Asn Ala Pro Cys Gly
1               5

<210> SEQ ID NO 43
<211> LENGTH: 9
```

<212> TYPE: PRT
<213> ORGANISM: Artificial Sequence
<220> FEATURE:
<223> OTHER INFORMATION: (S1,R8,C9)-sequence of vasopressin

<400> SEQUENCE: 43

Ser Tyr Phe Gln Asn Cys Pro Arg Cys
1               5

<210> SEQ ID NO 44
<211> LENGTH: 9
<212> TYPE: PRT
<213> ORGANISM: Artificial Sequence
<220> FEATURE:
<223> OTHER INFORMATION: (A1,S2,R8)-sequence of vasopressin

<400> SEQUENCE: 44

Ala Ser Phe Gln Asn Cys Pro Arg Gly
1               5

<210> SEQ ID NO 45
<211> LENGTH: 9
<212> TYPE: PRT
<213> ORGANISM: Artificial Sequence
<220> FEATURE:
<223> OTHER INFORMATION: (A1,S2,C3,R8)-sequence of vasopressin

<400> SEQUENCE: 45

Ala Ser Cys Gln Asn Cys Pro Arg Gly
1               5

<210> SEQ ID NO 46
<211> LENGTH: 9
<212> TYPE: PRT
<213> ORGANISM: Artificial Sequence
<220> FEATURE:
<223> OTHER INFORMATION: (A1,S2,C4,R8)-sequence of vasopressin

<400> SEQUENCE: 46

Ala Ser Phe Cys Asn Cys Pro Arg Gly
1               5

<210> SEQ ID NO 47
<211> LENGTH: 9
<212> TYPE: PRT
<213> ORGANISM: Artificial Sequence
<220> FEATURE:
<223> OTHER INFORMATION: (A1,S2,C5,R8)-sequence of vasopressin

<400> SEQUENCE: 47

Ala Ser Phe Gln Cys Cys Pro Arg Gly
1               5

<210> SEQ ID NO 48
<211> LENGTH: 9
<212> TYPE: PRT
<213> ORGANISM: Artificial Sequence
<220> FEATURE:
<223> OTHER INFORMATION: (A1,S2,A6,C7,R8)-sequence of vasopressin

<400> SEQUENCE: 48

Ala Ser Phe Gln Asn Ala Cys Arg Gly
1               5

<210> SEQ ID NO 49
<211> LENGTH: 9
<212> TYPE: PRT

```
<213> ORGANISM: Artificial Sequence
<220> FEATURE:
<223> OTHER INFORMATION: (A1,S2,A6,C8)-sequence of vasopressin

<400> SEQUENCE: 49

Ala Ser Phe Gln Asn Ala Pro Cys Gly
1               5

<210> SEQ ID NO 50
<211> LENGTH: 9
<212> TYPE: PRT
<213> ORGANISM: Artificial Sequence
<220> FEATURE:
<223> OTHER INFORMATION: (A1,S2,A6,R8,C9)-sequence of vasopressin

<400> SEQUENCE: 50

Ala Ser Phe Gln Asn Ala Pro Arg Cys
1               5

<210> SEQ ID NO 51
<211> LENGTH: 9
<212> TYPE: PRT
<213> ORGANISM: Artificial Sequence
<220> FEATURE:
<223> OTHER INFORMATION: (A1,S3,R8)-sequence of vasopressin

<400> SEQUENCE: 51

Ala Tyr Ser Gln Asn Cys Pro Arg Gly
1               5

<210> SEQ ID NO 52
<211> LENGTH: 9
<212> TYPE: PRT
<213> ORGANISM: Artificial Sequence
<220> FEATURE:
<223> OTHER INFORMATION: (A1,S3,C4,R8)-sequence of vasopressin

<400> SEQUENCE: 52

Ala Tyr Ser Cys Asn Cys Pro Arg Gly
1               5

<210> SEQ ID NO 53
<211> LENGTH: 9
<212> TYPE: PRT
<213> ORGANISM: Artificial Sequence
<220> FEATURE:
<223> OTHER INFORMATION: (A1,S3,C5,R8)-sequence of vasopressin

<400> SEQUENCE: 53

Ala Tyr Ser Gln Cys Cys Pro Arg Gly
1               5

<210> SEQ ID NO 54
<211> LENGTH: 9
<212> TYPE: PRT
<213> ORGANISM: Artificial Sequence
<220> FEATURE:
<223> OTHER INFORMATION: (A1,S3,A6,C7,R8)-sequence of vasopressin

<400> SEQUENCE: 54

Ala Tyr Ser Gln Asn Ala Cys Arg Gly
1               5

<210> SEQ ID NO 55
<211> LENGTH: 9
<212> TYPE: PRT
<213> ORGANISM: Artificial Sequence
```

```
<220> FEATURE:
<223> OTHER INFORMATION: (A1,S3,A6,C8)-sequence of vasopressin

<400> SEQUENCE: 55

Ala Tyr Ser Gln Asn Ala Pro Cys Gly
1               5

<210> SEQ ID NO 56
<211> LENGTH: 9
<212> TYPE: PRT
<213> ORGANISM: Artificial Sequence
<220> FEATURE:
<223> OTHER INFORMATION: (A1,S3,A6,R8,C9)-sequence of vasopressin

<400> SEQUENCE: 56

Ala Tyr Ser Gln Asn Ala Pro Arg Cys
1               5

<210> SEQ ID NO 57
<211> LENGTH: 9
<212> TYPE: PRT
<213> ORGANISM: Artificial Sequence
<220> FEATURE:
<223> OTHER INFORMATION: (A1,S4,R8)-sequence of vasopressin

<400> SEQUENCE: 57

Ala Tyr Phe Ser Asn Cys Pro Arg Gly
1               5

<210> SEQ ID NO 58
<211> LENGTH: 9
<212> TYPE: PRT
<213> ORGANISM: Artificial Sequence
<220> FEATURE:
<223> OTHER INFORMATION: (A1,S4,C5,R8)-sequence of vasopressin

<400> SEQUENCE: 58

Ala Tyr Phe Ser Cys Cys Pro Arg Gly
1               5

<210> SEQ ID NO 59
<211> LENGTH: 9
<212> TYPE: PRT
<213> ORGANISM: Artificial Sequence
<220> FEATURE:
<223> OTHER INFORMATION: (A1,S4,A6,C7,R8)-sequence of vasopressin

<400> SEQUENCE: 59

Ala Tyr Phe Ser Asn Ala Cys Arg Gly
1               5

<210> SEQ ID NO 60
<211> LENGTH: 9
<212> TYPE: PRT
<213> ORGANISM: Artificial Sequence
<220> FEATURE:
<223> OTHER INFORMATION: (A1,S4,A6,C8)-sequence of vasopressin

<400> SEQUENCE: 60

Ala Tyr Phe Ser Asn Ala Pro Cys Gly
1               5

<210> SEQ ID NO 61
<211> LENGTH: 9
<212> TYPE: PRT
<213> ORGANISM: Artificial Sequence
<220> FEATURE:
```

<223> OTHER INFORMATION: (A1,S4,A6,R8,C9)-sequence of vasopressin

<400> SEQUENCE: 61

Ala Tyr Phe Ser Asn Ala Pro Arg Cys
1               5

<210> SEQ ID NO 62
<211> LENGTH: 9
<212> TYPE: PRT
<213> ORGANISM: Artificial Sequence
<220> FEATURE:
<223> OTHER INFORMATION: (A1,S5,R8)-sequence of vasopressin

<400> SEQUENCE: 62

Ala Tyr Phe Gln Ser Cys Pro Arg Gly
1               5

<210> SEQ ID NO 63
<211> LENGTH: 9
<212> TYPE: PRT
<213> ORGANISM: Artificial Sequence
<220> FEATURE:
<223> OTHER INFORMATION: (A1,S5,A6,C7,R8)-sequence of vasopressin

<400> SEQUENCE: 63

Ala Tyr Phe Gln Ser Ala Cys Arg Gly
1               5

<210> SEQ ID NO 64
<211> LENGTH: 9
<212> TYPE: PRT
<213> ORGANISM: Artificial Sequence
<220> FEATURE:
<223> OTHER INFORMATION: (A1,S5,A6,C8)-sequence of vasopressin

<400> SEQUENCE: 64

Ala Tyr Phe Gln Ser Ala Pro Cys Gly
1               5

<210> SEQ ID NO 65
<211> LENGTH: 9
<212> TYPE: PRT
<213> ORGANISM: Artificial Sequence
<220> FEATURE:
<223> OTHER INFORMATION: (A1,S5,A6,R8,C9)-sequence of vasopressin

<400> SEQUENCE: 65

Ala Tyr Phe Gln Ser Ala Pro Arg Cys
1               5

<210> SEQ ID NO 66
<211> LENGTH: 9
<212> TYPE: PRT
<213> ORGANISM: Artificial Sequence
<220> FEATURE:
<223> OTHER INFORMATION: (A1,S6,C7,R8)-sequence of vasopressin

<400> SEQUENCE: 66

Ala Tyr Phe Gln Asn Ser Cys Arg Gly
1               5

<210> SEQ ID NO 67
<211> LENGTH: 9
<212> TYPE: PRT
<213> ORGANISM: Artificial Sequence
<220> FEATURE:
<223> OTHER INFORMATION: (A1,S6,C8)-sequence of vasopressin

```
<400> SEQUENCE: 67

Ala Tyr Phe Gln Asn Ser Pro Cys Gly
1               5

<210> SEQ ID NO 68
<211> LENGTH: 9
<212> TYPE: PRT
<213> ORGANISM: Artificial Sequence
<220> FEATURE:
<223> OTHER INFORMATION: (A1,S6,R8,C9)-sequence of vasopressin

<400> SEQUENCE: 68

Ala Tyr Phe Gln Asn Ser Pro Cys Gly
1               5

<210> SEQ ID NO 69
<211> LENGTH: 9
<212> TYPE: PRT
<213> ORGANISM: Artificial Sequence
<220> FEATURE:
<223> OTHER INFORMATION: (A1,S7,C8)-sequence of vasopressin

<400> SEQUENCE: 69

Ala Tyr Phe Gln Asn Cys Ser Cys Gly
1               5

<210> SEQ ID NO 70
<211> LENGTH: 9
<212> TYPE: PRT
<213> ORGANISM: Artificial Sequence
<220> FEATURE:
<223> OTHER INFORMATION: (A1,S7,R8,C9)-sequence of vasopressin

<400> SEQUENCE: 70

Ala Tyr Phe Gln Asn Cys Ser Arg Cys
1               5

<210> SEQ ID NO 71
<211> LENGTH: 9
<212> TYPE: PRT
<213> ORGANISM: Artificial Sequence
<220> FEATURE:
<223> OTHER INFORMATION: (A1,S7,C9)-sequence of vasopressin

<400> SEQUENCE: 71

Ala Tyr Phe Gln Asn Cys Ser Arg Cys
1               5

<210> SEQ ID NO 72
<211> LENGTH: 12
<212> TYPE: PRT
<213> ORGANISM: Artificial Sequence
<220> FEATURE:
<223> OTHER INFORMATION: S4-sequence of terlipressin

<400> SEQUENCE: 72

Gly Gly Gly Ser Tyr Phe Gln Asn Cys Pro Lys Gly
1               5                   10

<210> SEQ ID NO 73
<211> LENGTH: 11
<212> TYPE: PRT
<213> ORGANISM: Artificial Sequence
<220> FEATURE:
<223> OTHER INFORMATION: S4-sequence of cispressin
```

<400> SEQUENCE: 73

Gly Gly Gly Ser Tyr Phe Asn Cys Pro Lys Gly
1               5                   10

<210> SEQ ID NO 74
<211> LENGTH: 52
<212> TYPE: PRT
<213> ORGANISM: Artificial Sequence
<220> FEATURE:
<223> OTHER INFORMATION: A13,S16-sequence of Adrenomedullin Hypotensive peptide

<400> SEQUENCE: 74

Tyr Arg Gln Ser Met Asn Asn Phe Gln Gly Leu Arg Ala Phe Gly Ser
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50

<210> SEQ ID NO 75
<211> LENGTH: 13
<212> TYPE: PRT
<213> ORGANISM: Artificial Sequence
<220> FEATURE:
<223> OTHER INFORMATION: C6-sequence of allatostatin I

<400> SEQUENCE: 75

Ala Pro Ser Gly Ala Cys Arg Leu Tyr Gly Phe Gly Leu
1               5                   10

<210> SEQ ID NO 76
<211> LENGTH: 10
<212> TYPE: PRT
<213> ORGANISM: Artificial Sequence
<220> FEATURE:
<223> OTHER INFORMATION: S7,C10-sequence of angiotensin I

<400> SEQUENCE: 76

Asp Arg Val Tyr Ile His Ser Phe His Cys
1               5                   10

<210> SEQ ID NO 77
<211> LENGTH: 49
<212> TYPE: PRT
<213> ORGANISM: Artificial Sequence
<220> FEATURE:
<223> OTHER INFORMATION: A4-sequence of anthopleurin-A

<400> SEQUENCE: 77

Gly Val Ser Ala Leu Cys Asp Ser Asp Gly Pro Ser Val Arg Gly Asn
1               5                   10                  15

Thr Leu Ser Gly Thr Leu Thr Leu Tyr Pro Ser Gly Cys Pro Ser Gly
            20                  25                  30

Trp His Asn Cys Lys Ala His Gly Pro Thr Ile Gly Trp Cys Cys Lys
        35                  40                  45

Gln

<210> SEQ ID NO 78
<211> LENGTH: 9
<212> TYPE: PRT
<213> ORGANISM: Artificial Sequence

```
<220> FEATURE:
<223> OTHER INFORMATION: S1,C6-sequence of anti-inflammatory peptide 1

<400> SEQUENCE: 78

Ser Gln Met Lys Lys Cys Leu Asp Ser
1               5

<210> SEQ ID NO 79
<211> LENGTH: 34
<212> TYPE: PRT
<213> ORGANISM: Artificial Sequence
<220> FEATURE:
<223> OTHER INFORMATION: C10-sequence of dermaseptin

<400> SEQUENCE: 79

Ala Leu Trp Lys Thr Met Leu Lys Lys Cys Gly Thr Met Ala Leu His
1               5                   10                  15

Ala Gly Lys Ala Ala Leu Gly Ala Ala Asp Thr Ile Ser Gln Gly
            20                  25                  30

Thr Gln

<210> SEQ ID NO 80
<211> LENGTH: 27
<212> TYPE: PRT
<213> ORGANISM: Artificial Sequence
<220> FEATURE:
<223> OTHER INFORMATION: C8-sequence of bombinin-like peptide

<400> SEQUENCE: 80

Gly Ile Gly Ala Ser Ile Leu Cys Ala Gly Lys Ser Ala Leu Lys Gly
1               5                   10                  15

Leu Ala Lys Gly Leu Ala Glu His Phe Ala Asn
            20                  25

<210> SEQ ID NO 81
<211> LENGTH: 24
<212> TYPE: PRT
<213> ORGANISM: Artificial Sequence
<220> FEATURE:
<223> OTHER INFORMATION: S4,C7-sequence of histatin-5

<400> SEQUENCE: 81

Asp Ser His Ser Lys Arg Cys His Gly Tyr Lys Arg Lys Phe His Asp
1               5                   10                  15

Lys His His Ser His Arg Gly Tyr
            20

<210> SEQ ID NO 82
<211> LENGTH: 13
<212> TYPE: PRT
<213> ORGANISM: Artificial Sequence
<220> FEATURE:
<223> OTHER INFORMATION: S2-C5-sequence of indolicidin

<400> SEQUENCE: 82

Ile Ser Pro Trp Cys Trp Pro Trp Trp Pro Trp Arg Arg
1               5                   10

<210> SEQ ID NO 83
<211> LENGTH: 23
<212> TYPE: PRT
<213> ORGANISM: Artificial Sequence
<220> FEATURE:
<223> OTHER INFORMATION: C13-sequence of magainin-1
```

```
<400> SEQUENCE: 83

Gly Ile Gly Lys Phe Leu His Ser Ala Gly Lys Phe Cys Lys Ala Phe Val
1               5                   10                  15

Gly Glu Ile Met Lys Ser
            20

<210> SEQ ID NO 84
<211> LENGTH: 28
<212> TYPE: PRT
<213> ORGANISM: Artificial Sequence
<220> FEATURE:
<223> OTHER INFORMATION: sequence of Atrial Natriuretic Factor

<400> SEQUENCE: 84

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 85
<211> LENGTH: 9
<212> TYPE: PRT
<213> ORGANISM: Artificial Sequence
<220> FEATURE:
<223> OTHER INFORMATION: C9-sequence of bradykinin

<400> SEQUENCE: 85

Arg Pro Pro Gly Phe Ser Pro Phe Cys
1               5

<210> SEQ ID NO 86
<211> LENGTH: 32
<212> TYPE: PRT
<213> ORGANISM: Artificial Sequence
<220> FEATURE:
<223> OTHER INFORMATION: S16,C19-sequence of Brain Natriuretic peptide

<400> SEQUENCE: 86

Ser Pro Lys Met Val Gln Gly Ser Gly Cys Phe Gly Arg Lys Met Ser
1               5                   10                  15

Arg Ile Cys Ser Ser Ser Gly Leu Gly Cys Lys Val Leu Arg Arg His
            20                  25                  30

<210> SEQ ID NO 87
<211> LENGTH: 53
<212> TYPE: PRT
<213> ORGANISM: Artificial Sequence
<220> FEATURE:
<223> OTHER INFORMATION: sequence of C-type Natriuretic peptide

<400> SEQUENCE: 87

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
    50

<210> SEQ ID NO 88
<211> LENGTH: 27
<212> TYPE: PRT
```

```
<213> ORGANISM: Artificial Sequence
<220> FEATURE:
<223> OTHER INFORMATION: sequence of vasonatrin peptide

<400> SEQUENCE: 88

Gly Leu Ser Lys Gly Cys Phe Gly Leu Lys Leu Asp Arg Ile Gly Ser
1               5                   10                  15

Met Ser Gly Leu Gly Cys Asn Ser Phe Arg Tyr
            20                  25

<210> SEQ ID NO 89
<211> LENGTH: 9
<212> TYPE: PRT
<213> ORGANISM: Artificial Sequence
<220> FEATURE:
<223> OTHER INFORMATION: S2,C6-sequence of delta sleep inducing peptide

<400> SEQUENCE: 89

Trp Ser Gly Gly Asn Cys Ser Gly Glu
1               5

<210> SEQ ID NO 90
<211> LENGTH: 58
<212> TYPE: PRT
<213> ORGANISM: Artificial Sequence
<220> FEATURE:
<223> OTHER INFORMATION: S11,S26-sequence of alpha-dendrotoxin

<400> SEQUENCE: 90

Pro Arg Arg Lys Leu Cys Ile Leu His Arg Ser Pro Gly Arg Cys Tyr
1               5                   10                  15

Asp Lys Ile Pro Ala Phe Tyr Tyr Asn Ser Lys Lys Lys Gln Cys Glu
            20                  25                  30

Arg Phe Asp Trp Ser Gly Cys Gly Gly Asn Ser Asn Arg Phe Lys Thr
        35                  40                  45

Ile Glu Glu Cys Arg Arg Thr Cys Ile Gly
    50                  55

<210> SEQ ID NO 91
<211> LENGTH: 10
<212> TYPE: PRT
<213> ORGANISM: Artificial Sequence
<220> FEATURE:
<223> OTHER INFORMATION: C4-sequence of eledoisin

<400> SEQUENCE: 91

Pro Ser Lys Cys Ala Phe Ile Gly Leu Met
1               5                   10

<210> SEQ ID NO 92
<211> LENGTH: 49
<212> TYPE: PRT
<213> ORGANISM: Artificial Sequence
<220> FEATURE:
<223> OTHER INFORMATION: sequence of echistatin

<400> SEQUENCE: 92

Glu Cys Glu Ser Gly Pro Cys Cys Arg Asn Cys Lys Phe Leu Lys Glu
1               5                   10                  15

Gly Thr Ile Cys Lys Arg Ala Arg Gly Asp Asp Met Asp Asp Tyr Cys
            20                  25                  30

Asn Gly Lys Thr Cys Asp Cys Pro Arg Asn Pro His Lys Gly Pro Ala
        35                  40                  45
```

Thr

<210> SEQ ID NO 93
<211> LENGTH: 16
<212> TYPE: PRT
<213> ORGANISM: Artificial Sequence
<220> FEATURE:
<223> OTHER INFORMATION: S2,C6-sequence of alpha-endorphin

<400> SEQUENCE: 93

Tyr Ser Gly Phe Met Cys Ser Glu Lys Ser Gln Thr Pro Leu Val Thr
1               5                   10                  15

<210> SEQ ID NO 94
<211> LENGTH: 31
<212> TYPE: PRT
<213> ORGANISM: Artificial Sequence
<220> FEATURE:
<223> OTHER INFORMATION: S21,C26-sequence of beta-endorphin

<400> SEQUENCE: 94

Tyr Gly Gly Phe Met Thr Ser Glu Lys Ser Gln Thr Pro Leu Val Thr
1               5                   10                  15

Leu Phe Lys Asn Ser Ile Ile Lys Asn Cys Tyr Lys Lys Gly Glu
            20                  25                  30

<210> SEQ ID NO 95
<211> LENGTH: 30
<212> TYPE: PRT
<213> ORGANISM: Artificial Sequence
<220> FEATURE:
<223> OTHER INFORMATION: S2,S12-sequence of defensin I

<400> SEQUENCE: 95

Ala Ser Tyr Cys Arg Ile Pro Ala Cys Ile Ala Gly Ser Arg Arg Tyr
1               5                   10                  15

Gly Thr Cys Thr Tyr Gln Gly Arg Leu Trp Ala Phe Cys Cys
            20                  25                  30

<210> SEQ ID NO 96
<211> LENGTH: 27
<212> TYPE: PRT
<213> ORGANISM: Artificial Sequence
<220> FEATURE:
<223> OTHER INFORMATION: S23,C26-sequence of secretin

<400> SEQUENCE: 96

His Ser Asp Gly Thr Phe Thr Ser Glu Leu Ser Arg Leu Arg Glu Phe
1               5                   10                  15

Ala Arg Leu Gln Arg Leu Ser Gln Gly Cys Val
            20                  25

<210> SEQ ID NO 97
<211> LENGTH: 40
<212> TYPE: PRT
<213> ORGANISM: Artificial Sequence
<220> FEATURE:
<223> OTHER INFORMATION: C19-sequence of urocortin

<400> SEQUENCE: 97

Asp Asn Pro Ser Leu Ser Ile Asp Leu Thr Phe His Leu Leu Arg Thr
1               5                   10                  15

Leu Leu Cys Leu Ala Arg Thr Gln Ser Gln Arg Glu Arg Ala Glu Gln
            20                  25                  30

-continued

```
Asn Arg Ile Ile Phe Asp Ser Val
        35                  40

<210> SEQ ID NO 98
<211> LENGTH: 12
<212> TYPE: PRT
<213> ORGANISM: Artificial Sequence
<220> FEATURE:
<223> OTHER INFORMATION: S5-sequence of urotensin II

<400> SEQUENCE: 98

Ala Gly Thr Ala Ser Cys Phe Trp Lys Tyr Cys Val
1               5                   10

<210> SEQ ID NO 99
<211> LENGTH: 11
<212> TYPE: PRT
<213> ORGANISM: Artificial Sequence
<220> FEATURE:
<223> OTHER INFORMATION: S4,C7-sequence of Small Cardioactive peptide A

<400> SEQUENCE: 99

Ala Arg Pro Ser Tyr Leu Cys Phe Pro Arg Met
1               5                   10

<210> SEQ ID NO 100
<211> LENGTH: 9
<212> TYPE: PRT
<213> ORGANISM: Artificial Sequence
<220> FEATURE:
<223> OTHER INFORMATION: S4,C7-sequence of Small Cardioactive peptide B

<400> SEQUENCE: 100

Met Asn Tyr Ser Ala Phe Cys Arg Met
1               5

<210> SEQ ID NO 101
<211> LENGTH: 29
<212> TYPE: PRT
<213> ORGANISM: Artificial Sequence
<220> FEATURE:
<223> OTHER INFORMATION: C9-sequence of ceratoxin A

<400> SEQUENCE: 101

Ser Ile Gly Ser Ala Leu Lys Lys Cys Leu Pro Val Ala Lys Lys Ile
1               5                   10                  15

Gly Lys Ile Ala Leu Pro Ile Ala Lys Ala Ala Leu Pro
            20                  25

<210> SEQ ID NO 102
<211> LENGTH: 16
<212> TYPE: PRT
<213> ORGANISM: Artificial Sequence
<220> FEATURE:
<223> OTHER INFORMATION: C7-sequence of cerebellin

<400> SEQUENCE: 102

Ser Gly Ser Ala Lys Val Cys Phe Ser Ala Ile Arg Ser Thr Asn His
1               5                   10                  15

<210> SEQ ID NO 103
<211> LENGTH: 36
<212> TYPE: PRT
<213> ORGANISM: Artificial Sequence
<220> FEATURE:
<223> OTHER INFORMATION: S33-sequence of charybdotoxin
```

-continued

```
<400> SEQUENCE: 103

Phe Thr Asn Val Ser Cys Thr Thr Ser Lys Glu Cys Trp Ser Val Cys
1               5                   10                  15

Gln Arg Leu His Asn Thr Ser Arg Gly Lys Cys Met Asn Lys Lys Ser
            20                  25                  30

Arg Cys Tyr Ser
        35

<210> SEQ ID NO 104
<211> LENGTH: 32
<212> TYPE: PRT
<213> ORGANISM: Artificial Sequence
<220> FEATURE:
<223> OTHER INFORMATION: C8-sequence of cholecystokinin

<400> SEQUENCE: 104

Lys Ala Pro Ser Gly Arg Met Cys Ile Val Lys Asn Leu Gln Gln Leu
1               5                   10                  15

Asp Pro Ser His Arg Ile Ser Asp Arg Tyr Met Gly Trp Met Asp Phe
            20                  25                  30

<210> SEQ ID NO 105
<211> LENGTH: 9
<212> TYPE: PRT
<213> ORGANISM: Artificial Sequence
<220> FEATURE:
<223> OTHER INFORMATION: S1-sequence of conopressin G

<400> SEQUENCE: 105

Ser Phe Ile Arg Asn Cys Pro Lys Gly
1               5

<210> SEQ ID NO 106
<211> LENGTH: 18
<212> TYPE: PRT
<213> ORGANISM: Artificial Sequence
<220> FEATURE:
<223> OTHER INFORMATION: S2,S5-sequence of alpha-conotoxin EI

<400> SEQUENCE: 106

Arg Ser His Cys Ser Tyr His Pro Thr Cys Asn Met Ser Asn Pro Gln
1               5                   10                  15

Ile Cys

<210> SEQ ID NO 107
<211> LENGTH: 10
<212> TYPE: PRT
<213> ORGANISM: Artificial Sequence
<220> FEATURE:
<223> OTHER INFORMATION: C9-sequence of corazonin

<400> SEQUENCE: 107

Thr Phe Gln Tyr Ser Arg Gly Trp Cys Asn
1               5                   10

<210> SEQ ID NO 108
<211> LENGTH: 5
<212> TYPE: PRT
<213> ORGANISM: Artificial Sequence
<220> FEATURE:
<223> OTHER INFORMATION: S2,C3-sequence of Leu-enkephalin

<400> SEQUENCE: 108

Tyr Ser Cys Phe Leu
```

```
<210> SEQ ID NO 109
<211> LENGTH: 5
<212> TYPE: PRT
<213> ORGANISM: Artificial Sequence
<220> FEATURE:
<223> OTHER INFORMATION: S2,C3-sequence of Met-enkephalin

<400> SEQUENCE: 109

Tyr Ser Cys Phe Met
1               5

<210> SEQ ID NO 110
<211> LENGTH: 9
<212> TYPE: PRT
<213> ORGANISM: Artificial Sequence
<220> FEATURE:
<223> OTHER INFORMATION: (S1)-sequence of oxytocin

<400> SEQUENCE: 110

Ser Tyr Ile Gln Asn Cys Pro Leu Gly
1               5

<210> SEQ ID NO 111
<211> LENGTH: 39
<212> TYPE: PRT
<213> ORGANISM: Artificial Sequence
<220> FEATURE:
<223> OTHER INFORMATION: C35-sequence of exendin-3

<400> SEQUENCE: 111

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Cys Pro Pro Pro Ser
        35

<210> SEQ ID NO 112
<211> LENGTH: 9
<212> TYPE: PRT
<213> ORGANISM: Artificial Sequence
<220> FEATURE:
<223> OTHER INFORMATION: C5-sequence of Experimental Allergic Encephali
      togenic peptide

<400> SEQUENCE: 112

Phe Ser Trp Gly Cys Glu Gly Gln Arg
1               5

<210> SEQ ID NO 113
<211> LENGTH: 11
<212> TYPE: PRT
<213> ORGANISM: Artificial Sequence
<220> FEATURE:
<223> OTHER INFORMATION: S4,C7-sequence of Experimental Autoimmune Ence
      phalitomyelitis Complementary peptide

<400> SEQUENCE: 113

Val Phe Ile Ser Gly Pro Cys Arg Leu Leu Gly
1               5                   10

<210> SEQ ID NO 114
<211> LENGTH: 10
<212> TYPE: PRT
```

```
<213> ORGANISM: Artificial Sequence
<220> FEATURE:
<223> OTHER INFORMATION: (C9)-sequence of gonadoliberin II

<400> SEQUENCE: 114

Gln His Trp Ser His Gly Trp Tyr Cys Gly
1               5                   10

<210> SEQ ID NO 115
<211> LENGTH: 6
<212> TYPE: PRT
<213> ORGANISM: Artificial Sequence
<220> FEATURE:
<223> OTHER INFORMATION: (S1,13)-sequence of tocinoic acid / pressinoic
      acid

<400> SEQUENCE: 115

Ser Tyr Ile Gln Asn Cys
1               5

<210> SEQ ID NO 116
<211> LENGTH: 10
<212> TYPE: PRT
<213> ORGANISM: Artificial Sequence
<220> FEATURE:
<223> OTHER INFORMATION: sequence of leuprolide
<220> FEATURE:
<221> NAME/KEY: MISC_FEATURE
<222> LOCATION: (1)..(10)
<223> OTHER INFORMATION: Note = "Xaa" at pos. 1 and 10 may be any amino
      acid

<400> SEQUENCE: 116

Xaa His Trp Ser Tyr Gly Cys Arg Pro Xaa
1               5                   10

<210> SEQ ID NO 117
<211> LENGTH: 9
<212> TYPE: PRT
<213> ORGANISM: Artificial Sequence
<220> FEATURE:
<223> OTHER INFORMATION: sequence of leuprolide
<220> FEATURE:
<221> NAME/KEY: MISC_FEATURE
<222> LOCATION: (1)..(9)
<223> OTHER INFORMATION: Note = "Xaa" on pos. 1, 6 and 9 may be any
      amino acid

<400> SEQUENCE: 117

Xaa His Trp Ser Tyr Xaa Cys Arg Xaa
1               5

<210> SEQ ID NO 118
<211> LENGTH: 32
<212> TYPE: PRT
<213> ORGANISM: Artificial Sequence
<220> FEATURE:
<223> OTHER INFORMATION: (S1)-sequence of calcitonin

<400> SEQUENCE: 118

Ser Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 119
<211> LENGTH: 39
<212> TYPE: PRT
```

```
<213> ORGANISM: Artificial Sequence
<220> FEATURE:
<223> OTHER INFORMATION: (Q5,C6)-sequence of ACTH, Adrenocorticotropic
      hormone

<400> SEQUENCE: 119

Ser Tyr Ser Met Gln Cys Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu Phe
        35

<210> SEQ ID NO 120
<211> LENGTH: 31
<212> TYPE: PRT
<213> ORGANISM: Artificial Sequence
<220> FEATURE:
<223> OTHER INFORMATION: S4,C8-sequence of corticotropin inhibiting
      peptide

<400> SEQUENCE: 120

Phe Arg Trp Ser Lys Pro Val Cys Lys Lys Arg Arg Pro Val Lys Val
1               5                   10                  15

Tyr Pro Asn Gly Ala Glu Asp Ser Ala Glu Ala Phe Pro Leu Glu
            20                  25                  30

<210> SEQ ID NO 121
<211> LENGTH: 41
<212> TYPE: PRT
<213> ORGANISM: Artificial Sequence
<220> FEATURE:
<223> OTHER INFORMATION: S30,C33-sequence of Corticotropin-Release
      Factor

<400> SEQUENCE: 121

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Ser Ala His
            20                  25                  30

Cys Asn Arg Lys Leu Met Glu Ile Ile
        35                  40

<210> SEQ ID NO 122
<211> LENGTH: 14
<212> TYPE: PRT
<213> ORGANISM: Artificial Sequence
<220> FEATURE:
<223> OTHER INFORMATION: (S3)-sequence of somatostatin

<400> SEQUENCE: 122

Ala Gly Ser Lys Asn Phe Phe Trp Lys Thr Phe Thr Ser Cys
1               5                   10

<210> SEQ ID NO 123
<211> LENGTH: 36
<212> TYPE: PRT
<213> ORGANISM: Artificial Sequence
<220> FEATURE:
<223> OTHER INFORMATION: (S18,C21)-sequence of human pancreatic peptide
<220> FEATURE:
<221> NAME/KEY: MISC_FEATURE
<222> LOCATION: (1)..(27)
<223> OTHER INFORMATION: Note = Note = "Xaa" at pos. 27 may be any amino
      acid
```

```
<400> SEQUENCE: 123

Ala Pro Leu Glu Pro Val Tyr Pro Gly Asp Asn Ala Thr Pro Glu Gln
1               5                   10                  15

Met Ser Gln Tyr Cys Ala Asp Leu Arg Arg Xaa Ile Asn Met Leu Thr
            20                  25                  30

Arg Pro Arg Tyr
        35

<210> SEQ ID NO 124
<211> LENGTH: 36
<212> TYPE: PRT
<213> ORGANISM: Artificial Sequence
<220> FEATURE:
<223> OTHER INFORMATION: (S22,C25,T29,C32)-sequence of peptide YY

<400> SEQUENCE: 124

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 125
<211> LENGTH: 29
<212> TYPE: PRT
<213> ORGANISM: Artificial Sequence
<220> FEATURE:
<223> OTHER INFORMATION: (C5,S24,C29)-sequence of glucagon

<400> SEQUENCE: 125

His Ser Gln Gly Cys Phe Thr Ser Asp Tyr Ser Lys Tyr Leu Asp Ser
1               5                   10                  15

Arg Arg Ala Gln Asp Phe Val Ser Trp Leu Met Asn Cys
            20                  25

<210> SEQ ID NO 126
<211> LENGTH: 10
<212> TYPE: PRT
<213> ORGANISM: Artificial Sequence
<220> FEATURE:
<223> OTHER INFORMATION: (Q1,C7)-sequence of LHRH1

<400> SEQUENCE: 126

Gln His Trp Ser Tyr Gly Cys Arg Pro Gly
1               5                   10

<210> SEQ ID NO 127
<211> LENGTH: 10
<212> TYPE: PRT
<213> ORGANISM: Artificial Sequence
<220> FEATURE:
<223> OTHER INFORMATION: (S1,C4)-sequence of LHRH1

<400> SEQUENCE: 127

Ser His Trp Cys Tyr Gly Leu Arg Pro Gly
1               5                   10

<210> SEQ ID NO 128
<211> LENGTH: 10
<212> TYPE: PRT
<213> ORGANISM: Artificial Sequence
<220> FEATURE:
<223> OTHER INFORMATION: (S1,A4,C5)-sequence of LHRH1
```

```
<400> SEQUENCE: 128

Ser His Trp Ala Cys Gly Leu Arg Pro Gly
1               5                   10

<210> SEQ ID NO 129
<211> LENGTH: 10
<212> TYPE: PRT
<213> ORGANISM: Artificial Sequence
<220> FEATURE:
<223> OTHER INFORMATION: (S1,A4,C6)-sequence of LHRH1

<400> SEQUENCE: 129

Ser His Trp Ala Tyr Cys Leu Arg Pro Gly
1               5                   10

<210> SEQ ID NO 130
<211> LENGTH: 10
<212> TYPE: PRT
<213> ORGANISM: Artificial Sequence
<220> FEATURE:
<223> OTHER INFORMATION: (Q1,S2,A4,C5)-sequence of LHRH1

<400> SEQUENCE: 130

Gln Ser Trp Ala Cys Gly Leu Arg Pro Gly
1               5                   10

<210> SEQ ID NO 131
<211> LENGTH: 10
<212> TYPE: PRT
<213> ORGANISM: Artificial Sequence
<220> FEATURE:
<223> OTHER INFORMATION: (Q1,S2,A4,C6)-sequence of LHRH1

<400> SEQUENCE: 131

Gln Ser Trp Ala Tyr Cys Leu Arg Pro Gly
1               5                   10

<210> SEQ ID NO 132
<211> LENGTH: 10
<212> TYPE: PRT
<213> ORGANISM: Artificial Sequence
<220> FEATURE:
<223> OTHER INFORMATION: (Q1,S2,A4,C7)-sequence of LHRH1

<400> SEQUENCE: 132

Gln Ser Trp Ala Tyr Gly Cys Arg Pro Gly
1               5                   10

<210> SEQ ID NO 133
<211> LENGTH: 10
<212> TYPE: PRT
<213> ORGANISM: Artificial Sequence
<220> FEATURE:
<223> OTHER INFORMATION: (Q1,S3,A4,C6)-sequence of LHRH1

<400> SEQUENCE: 133

Gln His Ser Ala Tyr Cys Leu Arg Pro Gly
1               5                   10

<210> SEQ ID NO 134
<211> LENGTH: 10
<212> TYPE: PRT
<213> ORGANISM: Artificial Sequence
<220> FEATURE:
<223> OTHER INFORMATION: (Q1,S3,A4,C7)-sequence of LHRH1
```

-continued

```
<400> SEQUENCE: 134

Gln His Ser Ala Tyr Gly Cys Arg Pro Gly
1               5                   10

<210> SEQ ID NO 135
<211> LENGTH: 10
<212> TYPE: PRT
<213> ORGANISM: Artificial Sequence
<220> FEATURE:
<223> OTHER INFORMATION: (Q1,S3,A4,C8)-sequence of LHRH1

<400> SEQUENCE: 135

Gln His Ser Ala Tyr Gly Leu Cys Pro Gly
1               5                   10

<210> SEQ ID NO 136
<211> LENGTH: 10
<212> TYPE: PRT
<213> ORGANISM: Artificial Sequence
<220> FEATURE:
<223> OTHER INFORMATION: (Q1,C8)-sequence of LHRH1

<400> SEQUENCE: 136

Gln His Trp Ser Tyr Gly Leu Cys Pro Gly
1               5                   10

<210> SEQ ID NO 137
<211> LENGTH: 10
<212> TYPE: PRT
<213> ORGANISM: Artificial Sequence
<220> FEATURE:
<223> OTHER INFORMATION: (Q1,C9)-sequence of LHRH1

<400> SEQUENCE: 137

Gln His Trp Ser Tyr Gly Leu Arg Cys Gly
1               5                   10

<210> SEQ ID NO 138
<211> LENGTH: 10
<212> TYPE: PRT
<213> ORGANISM: Artificial Sequence
<220> FEATURE:
<223> OTHER INFORMATION: (Q1,A4,S5,C8)-sequence of LHRH1

<400> SEQUENCE: 138

Gln His Trp Ala Ser Gly Leu Cys Pro Gly
1               5                   10

<210> SEQ ID NO 139
<211> LENGTH: 10
<212> TYPE: PRT
<213> ORGANISM: Artificial Sequence
<220> FEATURE:
<223> OTHER INFORMATION: (Q1,A4,S5,C9)-sequence of LHRH1

<400> SEQUENCE: 139

Gln His Trp Ala Ser Gly Leu Arg Cys Gly
1               5                   10

<210> SEQ ID NO 140
<211> LENGTH: 10
<212> TYPE: PRT
<213> ORGANISM: Artificial Sequence
<220> FEATURE:
<223> OTHER INFORMATION: (Q1,A4,S5,C10)-sequence of LHRH1

<400> SEQUENCE: 140
```

Gln His Trp Ala Ser Gly Leu Arg Pro Cys
1               5                   10

<210> SEQ ID NO 141
<211> LENGTH: 10
<212> TYPE: PRT
<213> ORGANISM: Artificial Sequence
<220> FEATURE:
<223> OTHER INFORMATION: (Q1,A4,S6,C9)-sequence of LHRH1

<400> SEQUENCE: 141

Gln His Trp Ala Tyr Ser Leu Arg Cys Gly
1               5                   10

<210> SEQ ID NO 142
<211> LENGTH: 10
<212> TYPE: PRT
<213> ORGANISM: Artificial Sequence
<220> FEATURE:
<223> OTHER INFORMATION: (Q1,A4,S6,C10)-sequence of LHRH1

<400> SEQUENCE: 142

Gln His Trp Ala Tyr Ser Leu Arg Pro Cys
1               5                   10

<210> SEQ ID NO 143
<211> LENGTH: 10
<212> TYPE: PRT
<213> ORGANISM: Artificial Sequence
<220> FEATURE:
<223> OTHER INFORMATION: (Q1,A4,S7,C10)-sequence of LHRH1

<400> SEQUENCE: 143

Gln His Trp Ala Tyr Gly Ser Arg Pro Cys
1               5                   10

<210> SEQ ID NO 144
<211> LENGTH: 10
<212> TYPE: PRT
<213> ORGANISM: Artificial Sequence
<220> FEATURE:
<223> OTHER INFORMATION: (S1,C4)-sequence of LHRH2

<400> SEQUENCE: 144

Ser His Trp Cys His Gly Trp Tyr Pro Gly
1               5                   10

<210> SEQ ID NO 145
<211> LENGTH: 10
<212> TYPE: PRT
<213> ORGANISM: Artificial Sequence
<220> FEATURE:
<223> OTHER INFORMATION: (S1,A4,C5)-sequence of LHRH2

<400> SEQUENCE: 145

Ser His Trp Ala Cys Gly Trp Tyr Pro Gly
1               5                   10

<210> SEQ ID NO 146
<211> LENGTH: 10
<212> TYPE: PRT
<213> ORGANISM: Artificial Sequence
<220> FEATURE:
<223> OTHER INFORMATION: (S1,A4,C6)-sequence of LHRH2

<400> SEQUENCE: 146

```
Ser His Trp Ala His Cys Trp Tyr Pro Gly
1               5                   10
```

<210> SEQ ID NO 147
<211> LENGTH: 10
<212> TYPE: PRT
<213> ORGANISM: Artificial Sequence
<220> FEATURE:
<223> OTHER INFORMATION: (Q1,S2,A4,C5)-sequence of LHRH2

<400> SEQUENCE: 147

```
Gln Ser Trp Ala Cys Gly Trp Tyr Pro Gly
1               5                   10
```

<210> SEQ ID NO 148
<211> LENGTH: 10
<212> TYPE: PRT
<213> ORGANISM: Artificial Sequence
<220> FEATURE:
<223> OTHER INFORMATION: (Q1,S2,A4,C6)-sequence of LHRH2

<400> SEQUENCE: 148

```
Gln Ser Trp Ala His Cys Trp Tyr Pro Gly
1               5                   10
```

<210> SEQ ID NO 149
<211> LENGTH: 10
<212> TYPE: PRT
<213> ORGANISM: Artificial Sequence
<220> FEATURE:
<223> OTHER INFORMATION: (Q1,S2,A4,C7)-sequence of LHRH2

<400> SEQUENCE: 149

```
Gln Ser Trp Ala His Gly Cys Tyr Pro Gly
1               5                   10
```

<210> SEQ ID NO 150
<211> LENGTH: 10
<212> TYPE: PRT
<213> ORGANISM: Artificial Sequence
<220> FEATURE:
<223> OTHER INFORMATION: (Q1,S3,A4,C6)-sequence of LHRH2

<400> SEQUENCE: 150

```
Gln His Ser Ala His Cys Trp Tyr Pro Gly
1               5                   10
```

<210> SEQ ID NO 151
<211> LENGTH: 10
<212> TYPE: PRT
<213> ORGANISM: Artificial Sequence
<220> FEATURE:
<223> OTHER INFORMATION: (Q1,S3,A4,C7)-sequence of LHRH2

<400> SEQUENCE: 151

```
Gln His Ser Ala His Gly Cys Tyr Pro Gly
1               5                   10
```

<210> SEQ ID NO 152
<211> LENGTH: 10
<212> TYPE: PRT
<213> ORGANISM: Artificial Sequence
<220> FEATURE:
<223> OTHER INFORMATION: (Q1,S3,A4,C8)-sequence of LHRH2

<400> SEQUENCE: 152

```
Gln His Ser Ala His Gly Trp Cys Pro Gly
```

-continued

<210> SEQ ID NO 153
<211> LENGTH: 10
<212> TYPE: PRT
<213> ORGANISM: Artificial Sequence
<220> FEATURE:
<223> OTHER INFORMATION: (Q1,C8)-sequence of LHRH2

<400> SEQUENCE: 153

Gln His Trp Ser His Gly Trp Cys Pro Gly
1               5                   10

<210> SEQ ID NO 154
<211> LENGTH: 10
<212> TYPE: PRT
<213> ORGANISM: Artificial Sequence
<220> FEATURE:
<223> OTHER INFORMATION: (Q1,C9)-sequence of LHRH2

<400> SEQUENCE: 154

Gln His Trp Ser His Gly Trp Tyr Cys Gly
1               5                   10

<210> SEQ ID NO 155
<211> LENGTH: 10
<212> TYPE: PRT
<213> ORGANISM: Artificial Sequence
<220> FEATURE:
<223> OTHER INFORMATION: (Q1,A4,S5,C8)-sequence of LHRH2

<400> SEQUENCE: 155

Gln His Trp Ala Ser Gly Trp Cys Pro Gly
1               5                   10

<210> SEQ ID NO 156
<211> LENGTH: 10
<212> TYPE: PRT
<213> ORGANISM: Artificial Sequence
<220> FEATURE:
<223> OTHER INFORMATION: (Q1,A4,S5,C9)-sequence of LHRH2

<400> SEQUENCE: 156

Gln His Trp Ala Ser Gly Trp Tyr Cys Gly
1               5                   10

<210> SEQ ID NO 157
<211> LENGTH: 10
<212> TYPE: PRT
<213> ORGANISM: Artificial Sequence
<220> FEATURE:
<223> OTHER INFORMATION: (Q1,A4,S5,C10)-sequence of LHRH2

<400> SEQUENCE: 157

Gln His Trp Ala Ser Gly Trp Tyr Pro Cys
1               5                   10

<210> SEQ ID NO 158
<211> LENGTH: 10
<212> TYPE: PRT
<213> ORGANISM: Artificial Sequence
<220> FEATURE:
<223> OTHER INFORMATION: (Q1,A4,S6,C9)-sequence of LHRH2

<400> SEQUENCE: 158

Gln His Trp Ala His Ser Trp Tyr Cys Gly
1               5                   10

<210> SEQ ID NO 159
<211> LENGTH: 10
<212> TYPE: PRT
<213> ORGANISM: Artificial Sequence
<220> FEATURE:
<223> OTHER INFORMATION: (Q1,A4,S6,C10)-sequence of LHRH2

<400> SEQUENCE: 159

Gln His Trp Ala His Ser Trp Tyr Pro Cys
1               5                   10

<210> SEQ ID NO 160
<211> LENGTH: 10
<212> TYPE: PRT
<213> ORGANISM: Artificial Sequence
<220> FEATURE:
<223> OTHER INFORMATION: (Q1,A4,S7,C10)-sequence of LHRH2

<400> SEQUENCE: 160

Gln His Trp Ala His Gly Ser Tyr Pro Cys
1               5                   10

<210> SEQ ID NO 161
<211> LENGTH: 10
<212> TYPE: PRT
<213> ORGANISM: Artificial Sequence
<220> FEATURE:
<223> OTHER INFORMATION: (S103,C109)-sequence of brain derived acidic
      fibroblast growth factor (102-111)

<400> SEQUENCE: 161

His Ser Gln Lys His Trp Phe Cys Gly Leu
1               5                   10

<210> SEQ ID NO 162
<211> LENGTH: 24
<212> TYPE: PRT
<213> ORGANISM: Artificial Sequence
<220> FEATURE:
<223> OTHER INFORMATION: sequence of brain derived acidic fibroblast
      growth factor (1-24)

<400> SEQUENCE: 162

Pro Ala Leu Pro Glu Asp Gly Gly Ser Gly Ala Phe Pro Pro Cys His
1               5                   10                  15

Phe Lys Asp Pro Lys Arg Leu Tyr
            20

<210> SEQ ID NO 163
<211> LENGTH: 21
<212> TYPE: PRT
<213> ORGANISM: Artificial Sequence
<220> FEATURE:
<223> OTHER INFORMATION: alpha chain sequence of insulin

<400> SEQUENCE: 163

Gly Ile Val Glu Gln Cys Cys Ala Ser Val Cys Ser Leu Tyr Gln Leu
1               5                   10                  15

Glu Asn Tyr Cys Asn
            20

<210> SEQ ID NO 164
<211> LENGTH: 30
<212> TYPE: PRT
<213> ORGANISM: Artificial Sequence

```
<220> FEATURE:
<223> OTHER INFORMATION: (S9-C14,T27-C30)-beta-chain sequence of insulin

<400> SEQUENCE: 164

Phe Val Asn Gln His Leu Cys Gly Ser His Leu Val Glu Cys Leu Tyr
1               5                   10                  15

Leu Val Cys Gly Glu Arg Gly Phe Phe Tyr Thr Pro Lys Cys
            20                  25                  30

<210> SEQ ID NO 165
<211> LENGTH: 84
<212> TYPE: PRT
<213> ORGANISM: Artificial Sequence
<220> FEATURE:
<223> OTHER INFORMATION: (S36-C39, T79-C82)-sequence of parathormone

<400> SEQUENCE: 165

Ser Val Ser Glu Ile Glu Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ser Leu Gly Cys Pro Leu Ala Pro Arg Asp Ala Gly Ser
        35                  40                  45

Glu Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Cys Ser Glu

<210> SEQ ID NO 166
<211> LENGTH: 12
<212> TYPE: PRT
<213> ORGANISM: Artificial Sequence
<220> FEATURE:
<223> OTHER INFORMATION: S6,C9-sequence of Fibrinogen Binding Inhibitor
      peptide

<400> SEQUENCE: 166

His His Leu Gly Gly Ser Lys Gln Cys Gly Asp Val
1               5                   10

<210> SEQ ID NO 167
<211> LENGTH: 8
<212> TYPE: PRT
<213> ORGANISM: Artificial Sequence
<220> FEATURE:
<223> OTHER INFORMATION: sequence of S1,C3-sequence of fibroblast
      growth factor inhibitory peptide

<400> SEQUENCE: 167

Ser Pro Cys Gly His Tyr Lys Gly
1               5

<210> SEQ ID NO 168
<211> LENGTH: 30
<212> TYPE: PRT
<213> ORGANISM: Artificial Sequence
<220> FEATURE:
<223> OTHER INFORMATION: C10-sequence of galanin

<400> SEQUENCE: 168

Gly Trp Thr Leu Asn Ser Ala Gly Tyr Cys Leu Gly Pro His Ala Val
1               5                   10                  15
```

Gly Asn His Arg Ser Phe Ser Asp Lys Asn Gly Leu Thr Ser
            20                  25                  30

<210> SEQ ID NO 169
<211> LENGTH: 42
<212> TYPE: PRT
<213> ORGANISM: Artificial Sequence
<220> FEATURE:
<223> OTHER INFORMATION: S28,C31-sequence of Gastric Inhibitory
      Polypeptide

<400> SEQUENCE: 169

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ser Gln Lys Cys Lys
            20                  25                  30

Lys Asn Asp Trp Lys His Asn Ile Thr Gln
            35                  40

<210> SEQ ID NO 170
<211> LENGTH: 33
<212> TYPE: PRT
<213> ORGANISM: Artificial Sequence
<220> FEATURE:
<223> OTHER INFORMATION: S8,C11-sequence of Big Gastrin-1

<400> SEQUENCE: 170

Leu Gly Pro Gln Gly Pro Pro Ser Leu Val Cys Asp Pro Ser Lys Lys
1               5                   10                  15

Gln Gly Pro Trp Leu Glu Glu Glu Glu Ala Tyr Gly Trp Met Asp
            20                  25                  30

Phe

<210> SEQ ID NO 171
<211> LENGTH: 5
<212> TYPE: PRT
<213> ORGANISM: Artificial Sequence
<220> FEATURE:
<223> OTHER INFORMATION: S1,C4 Boc-beta-sequence of pentagastrin

<400> SEQUENCE: 171

Ser Trp Met Cys Phe
1               5

<210> SEQ ID NO 172
<211> LENGTH: 27
<212> TYPE: PRT
<213> ORGANISM: Artificial Sequence
<220> FEATURE:
<223> OTHER INFORMATION: S9,C12-sequence of Gastrin Releasing Peptide

<400> SEQUENCE: 172

Val Pro Leu Pro Ala Gly Gly Ser Val Leu Cys Lys Met Tyr Pro
1               5                   10                  15

Arg Gly Asn His Trp Ala Val Gly His Leu Met
            20                  25

<210> SEQ ID NO 173
<211> LENGTH: 50
<212> TYPE: PRT
<213> ORGANISM: Artificial Sequence
<220> FEATURE:
<223> OTHER INFORMATION: sequence of transforming growth factor alpha

<400> SEQUENCE: 173

```
Val Val Ser His Phe Asn Asp Cys Pro Asp Ser His THr Gln Phe Cys
1               5                   10                  15

Phe His Gly Thr Cys Arg Phe Leu Val Gln Glu Asp Lys Pro Ala Cys
            20                  25                  30

Val Cys His Ser Gly Tyr Val Gly Ala Arg Cys Glu His Ala Asp Leu
        35                  40                  45

Leu Ala
    50

<210> SEQ ID NO 174
<211> LENGTH: 43
<212> TYPE: PRT
<213> ORGANISM: Artificial Sequence
<220> FEATURE:
<223> OTHER INFORMATION: C7-sequence of human growth hormone

<400> SEQUENCE: 174

Phe Pro Thr Ile Pro Leu Cys Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser
        35                  40

<210> SEQ ID NO 175
<211> LENGTH: 44
<212> TYPE: PRT
<213> ORGANISM: Artificial Sequence
<220> FEATURE:
<223> OTHER INFORMATION: C22-sequence of growth hormone release factor

<400> SEQUENCE: 175

Tyr Ala Asp Ala Ile Phe Thr Asn Ser Tyr Arg Lys Val Leu Gly Gln
1               5                   10                  15

Leu Ser Ala Arg Lys Cys Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 176
<211> LENGTH: 15
<212> TYPE: PRT
<213> ORGANISM: Artificial Sequence
<220> FEATURE:
<223> OTHER INFORMATION: sequence of guanylin

<400> SEQUENCE: 176

Pro Gly Thr Cys Glu Ile Cys Ala Tyr Ala Ala Cys Thr Gly Cys
1               5                   10                  15

<210> SEQ ID NO 177
<211> LENGTH: 38
<212> TYPE: PRT
<213> ORGANISM: Artificial Sequence
<220> FEATURE:
<223> OTHER INFORMATION: S15, C18-sequence of helospectin I

<400> SEQUENCE: 177

His Ser Asp Ala Thr Phe Thr Ala Glu Tyr Ser Lys Leu Leu Ser Lys
1               5                   10                  15

Leu Cys Leu Gln Lys Tyr Leu Glu Ser Ile Leu Gly Ser Ser Thr Ser
            20                  25                  30
```

```
Pro Arg Pro Pro Ser Ser
        35

<210> SEQ ID NO 178
<211> LENGTH: 21
<212> TYPE: PRT
<213> ORGANISM: Artificial Sequence
<220> FEATURE:
<223> OTHER INFORMATION: C6-sequence of Hepatitis B surface antigen
      fragment

<400> SEQUENCE: 178

Met Gly Thr Asn Leu Cys Val Pro Asn Pro Leu Gly Phe Phe Pro Asp
1               5                  10                  15
His Gln Leu Asp Pro
           20

<210> SEQ ID NO 179
<211> LENGTH: 23
<212> TYPE: PRT
<213> ORGANISM: Artificial Sequence
<220> FEATURE:
<223> OTHER INFORMATION: sequence of intercellular adhesion molecule

<400> SEQUENCE: 179

Asn Ala Gln Thr Ser Val Ser Pro Ser Lys Val Ile Leu Pro Arg Gly
1               5                  10                  15
Gly Ser Val Leu Val Thr Cys
           20

<210> SEQ ID NO 180
<211> LENGTH: 17
<212> TYPE: PRT
<213> ORGANISM: Artificial Sequence
<220> FEATURE:
<223> OTHER INFORMATION: (S3,S12)-sequence of tachyplesin I

<400> SEQUENCE: 180

Lys Trp Ser Phe Arg Val Cys Tyr Arg Gly Ile Ser Tyr Arg Arg Cys
1               5                  10                  15
Arg

<210> SEQ ID NO 181
<211> LENGTH: 24
<212> TYPE: PRT
<213> ORGANISM: Artificial Sequence
<220> FEATURE:
<223> OTHER INFORMATION: (S10, C14)-sequence of HIV (gp 120) antigenic
      peptide fragment

<400> SEQUENCE: 181

Cys Gly Lys Ile Glu Pro Leu Gly Val Ser Pro Thr Lys Cys Lys Arg
1               5                  10                  15
Arg Val Val Gln Arg Glu Lys Arg
           20

<210> SEQ ID NO 182
<211> LENGTH: 36
<212> TYPE: PRT
<213> ORGANISM: Artificial Sequence
<220> FEATURE:
<223> OTHER INFORMATION: (S20)-sequence of HIV (gp 41) antigenic peptide
      5

<400> SEQUENCE: 182

Arg Val Thr Ala Ile Glu Lys Tyr Leu Gln Asp Gln Ala Arg Leu Asn
```

```
                1               5                  10                 15
Ser Trp Gly Ser Ala Phe Arg Gln Val Cys His Thr Thr Val Pro Trp
                20                 25                 30

Val Asn Asp Ser
        35

<210> SEQ ID NO 183
<211> LENGTH: 6
<212> TYPE: PRT
<213> ORGANISM: Artificial Sequence
<220> FEATURE:
<223> OTHER INFORMATION: sequence of HIV protease inhibitors

<400> SEQUENCE: 183

Thr Val Ser Phe Cys Phe
1               5

<210> SEQ ID NO 184
<211> LENGTH: 12
<212> TYPE: PRT
<213> ORGANISM: Artificial Sequence
<220> FEATURE:
<223> OTHER INFORMATION: S1,C4-sequence of insulin-like growth factor-I
      analog

<400> SEQUENCE: 184

Ser Tyr Ala Cys Pro Leu Lys Pro Ala Lys Ser Cys
1               5                  10

<210> SEQ ID NO 185
<211> LENGTH: 16
<212> TYPE: PRT
<213> ORGANISM: Artificial Sequence
<220> FEATURE:
<223> OTHER INFORMATION: (C7)-sequence of IGF II 69-84

<400> SEQUENCE: 185

Asp Val Ser Thr Pro Pro Cys Val Leu Pro Asp Asn Phe Pro Arg Tyr
1               5                  10                 15

<210> SEQ ID NO 186
<211> LENGTH: 10
<212> TYPE: PRT
<213> ORGANISM: Artificial Sequence
<220> FEATURE:
<223> OTHER INFORMATION: (S6,C10)-sequence of interleukin-8 fragment

<400> SEQUENCE: 186

Ala Val Leu Pro Arg Ser Ala Lys Glu Cys
1               5                  10

<210> SEQ ID NO 187
<211> LENGTH: 11
<212> TYPE: PRT
<213> ORGANISM: Artificial Sequence
<220> FEATURE:
<223> OTHER INFORMATION: sequence of interleukin-2 fragment (60-70)
      (T-cell growth factor)

<400> SEQUENCE: 187

Leu Thr Phe Lys Phe Tyr Met Ser Lys Lys Cys
1               5                  10

<210> SEQ ID NO 188
<211> LENGTH: 8
<212> TYPE: PRT
```

```
<213> ORGANISM: Artificial Sequence
<220> FEATURE:
<223> OTHER INFORMATION: C8-sequence of leucokinin I (neuroactive
      peptide)

<400> SEQUENCE: 188

Asp Pro Ala Phe Asn Ser Trp Cys
1               5

<210> SEQ ID NO 189
<211> LENGTH: 7
<212> TYPE: PRT
<213> ORGANISM: Artificial Sequence
<220> FEATURE:
<223> OTHER INFORMATION: C4-sequence of leukopyrokinin

<400> SEQUENCE: 189

Thr Ser Phe Cys Pro Arg Leu
1               5

<210> SEQ ID NO 190
<211> LENGTH: 14
<212> TYPE: PRT
<213> ORGANISM: Artificial Sequence
<220> FEATURE:
<223> OTHER INFORMATION: S5,C8-sequence of mastoparan

<400> SEQUENCE: 190

Ile Asn Leu Lys Ser Leu Ala Cys Leu Ala Lys Lys Ile Leu
1               5                   10

<210> SEQ ID NO 191
<211> LENGTH: 19
<212> TYPE: PRT
<213> ORGANISM: Artificial Sequence
<220> FEATURE:
<223> OTHER INFORMATION: S11-sequence of melanin concentrating hormone

<400> SEQUENCE: 191

Asp Phe Asp Met Leu Arg Cys Met Leu Gly Ser Val Tyr Arg Pro Cys
1               5                   10                  15

Trp Gln Val

<210> SEQ ID NO 192
<211> LENGTH: 25
<212> TYPE: PRT
<213> ORGANISM: Artificial Sequence
<220> FEATURE:
<223> OTHER INFORMATION: C14-sequence of melittin

<400> SEQUENCE: 192

Gly Ile Gly Ala Val Leu Lys Val Leu Thr Gly Leu Pro Cys Leu Ile
1               5                   10                  15

Ser Trp Ile Lys Arg Lys Arg Gln Gln
            20                  25

<210> SEQ ID NO 193
<211> LENGTH: 22
<212> TYPE: PRT
<213> ORGANISM: Artificial Sequence
<220> FEATURE:
<223> OTHER INFORMATION: C9-sequence of motilin

<400> SEQUENCE: 193

Phe Val Pro Ile Phe Thr Tyr Gly Cys Leu Gln Arg Met Gln Glu Lys
1               5                   10                  15
```

```
Glu Arg Asn Lys Gly Gln
            20

<210> SEQ ID NO 194
<211> LENGTH: 36
<212> TYPE: PRT
<213> ORGANISM: Artificial Sequence
<220> FEATURE:
<223> OTHER INFORMATION: C26-sequence of neuropeptide Y

<400> SEQUENCE: 194

Tyr Pro Ser Lys Pro Asp Asn Pro Gly Glu Asp Ala Pro Ala Glu Asp
1               5                   10                  15

Met Ala Arg Tyr Tyr Ser Ala Leu Arg Cys Tyr Ile Asn Leu Ile Thr
            20                  25                  30

Arg Asn Arg Tyr
            35

<210> SEQ ID NO 195
<211> LENGTH: 35
<212> TYPE: PRT
<213> ORGANISM: Artificial Sequence
<220> FEATURE:
<223> OTHER INFORMATION: S4,C8-sequence of osteocalcin

<400> SEQUENCE: 195

Tyr Leu Tyr Ser Trp Leu Gly Cys Pro Val Pro Tyr Pro Asp Pro Asp
1               5                   10                  15

Glu Leu Ala Asp His Ile Gly Phe Gln Glu Ala Tyr Arg Arg Phe Tyr
            20                  25                  30

Gly Pro Val
        35

<210> SEQ ID NO 196
<211> LENGTH: 27
<212> TYPE: PRT
<213> ORGANISM: Artificial Sequence
<220> FEATURE:
<223> OTHER INFORMATION: (C21)-sequence of (N-acetyl-)beta-endorphin
      1-27

<400> SEQUENCE: 196

Tyr Gly Gly Phe Met Thr Ser Glu Lys Ser Gln Thr Pro Leu Val Thr
1               5                   10                  15

Leu Phe Lys Asn Cys Ile Ile Lys Asn Ala Tyr
            20                  25

<210> SEQ ID NO 197
<211> LENGTH: 8
<212> TYPE: PRT
<213> ORGANISM: Artificial Sequence
<220> FEATURE:
<223> OTHER INFORMATION: (S2,C5)-sequence of ras oncogene related
      peptide

<400> SEQUENCE: 197

Gly Ser Gly Gly Cys Gly Lys Ser
1               5

<210> SEQ ID NO 198
<211> LENGTH: 8
<212> TYPE: PRT
<213> ORGANISM: Artificial Sequence
<220> FEATURE:
```

```
<223> OTHER INFORMATION: (S2,C5)-sequence of ras oncogene related
      peptide

<400> SEQUENCE: 198

Gly Ser Val Gly Cys Gly Lys Ser
1               5

<210> SEQ ID NO 199
<211> LENGTH: 10
<212> TYPE: PRT
<213> ORGANISM: Artificial Sequence
<220> FEATURE:
<223> OTHER INFORMATION: (S3,C6)-sequence of ras oncogene related
      peptide

<400> SEQUENCE: 199

Tyr Gly Ser Val Gly Cys Gly Lys Ser Lys
1               5                   10

<210> SEQ ID NO 200
<211> LENGTH: 583
<212> TYPE: PRT
<213> ORGANISM: Artificial Sequence
<220> FEATURE:
<223> OTHER INFORMATION: sequence of albumin

<400> SEQUENCE: 200

Asp Thr His Lys Ser Glu Ile Ala His Arg Phe Lys Asp Leu Gly Glu
1               5                   10                  15

Glu His Phe Lys Gly Leu Val Leu Ile Ala Phe Ser Gln Tyr Leu Gln
                20                  25                  30

Gln Cys Pro Phe Asp Glu His Val Lys Leu Val Asn Glu Leu Thr Glu
            35                  40                  45

Phe Ala Lys Thr Cys Val Ala Asp Glu Ser His Ala Gly Cys Glu Lys
        50                  55                  60

Ser Leu His Thr Leu Phe Gly Asp Glu Leu Cys Lys Val Ala Ser Leu
65                  70                  75                  80

Arg Glu Thr Tyr Gly Asp Met Ala Asp Cys Cys Glu Lys Gln Glu Pro
                85                  90                  95

Glu Arg Asn Glu Cys Phe Leu Ser His Lys Asp Asp Ser Pro Asp Leu
            100                 105                 110

Pro Lys Leu Lys Pro Asp Pro Asn Thr Leu Cys Asp Glu Phe Lys Ala
        115                 120                 125

Asp Glu Lys Lys Phe Trp Gly Lys Tyr Leu Tyr Glu Ile Ala Arg Arg
    130                 135                 140

His Pro Tyr Phe Tyr Ala Pro Glu Leu Leu Tyr Tyr Ala Asn Lys Tyr
145                 150                 155                 160

Asn Gly Val Phe Gln Glu Cys Cys Gln Ala Glu Asp Lys Gly Ala Cys
                165                 170                 175

Leu Leu Pro Lys Ile Glu Thr Met Arg Glu Lys Val Leu Ala Ser Ser
            180                 185                 190

Ala Arg Gln Arg Leu Arg Cys Ala Ser Ile Gln Lys Phe Gly Glu Arg
        195                 200                 205

Ala Leu Lys Ala Trp Ser Val Ala Arg Leu Ser Gln Lys Phe Pro Lys
    210                 215                 220

Ala Glu Phe Val Glu Val Thr Lys Leu Val Thr Asp Leu Thr Lys Val
225                 230                 235                 240

His Lys Glu Cys Cys His Gly Asp Leu Leu Glu Cys Ala Asp Asp Arg
                245                 250                 255
```

```
Ala Asp Leu Ala Lys Tyr Ile Cys Asp Asn Gln Asp Thr Ile Ser Ser
            260                 265                 270

Lys Leu Lys Glu Cys Cys Asp Lys Pro Leu Leu Glu Lys Ser His Cys
        275                 280                 285

Ile Ala Glu Val Glu Lys Asp Ala Ile Pro Glu Asn Leu Pro Pro Leu
        290                 295                 300

Thr Ala Asp Phe Ala Glu Asp Lys Asp Val Cys Lys Asn Tyr Gln Glu
305                 310                 315                 320

Ala Lys Asp Ala Phe Leu Gly Ser Phe Leu Tyr Glu Tyr Ser Arg Arg
                325                 330                 335

His Pro Glu Tyr Ala Val Ser Val Leu Leu Arg Leu Ala Lys Glu Tyr
            340                 345                 350

Glu Ala Thr Leu Glu Glu Cys Cys Ala Lys Asp Asp Pro His Ala Cys
        355                 360                 365

Tyr Ser Thr Val Phe Asp Lys Leu Lys His Leu Val Asp Glu Pro Gln
370                 375                 380

Asn Leu Ile Lys Gln Asn Cys Asp Gln Phe Glu Lys Leu Gly Glu Tyr
385                 390                 395                 400

Gly Phe Gln Asn Ala Leu Ile Val Arg Tyr Thr Arg Lys Val Pro Gln
                405                 410                 415

Val Ser Thr Pro Thr Leu Val Glu Val Ser Arg Ser Leu Gly Lys Val
            420                 425                 430

Gly Thr Arg Cys Cys Thr Lys Pro Glu Ser Glu Arg Met Pro Cys Thr
        435                 440                 445

Glu Asp Tyr Leu Ser Leu Ile Leu Asn Arg Leu Cys Val Leu His Glu
450                 455                 460

Lys Thr Pro Val Ser Glu Lys Val Thr Lys Cys Cys Thr Glu Ser Leu
465                 470                 475                 480

Val Asn Arg Arg Pro Cys Phe Ser Ala Leu Thr Pro Asp Glu Thr Tyr
                485                 490                 495

Val Pro Lys Ala Phe Asp Glu Lys Leu Phe Thr Phe His Ala Asp Ile
            500                 505                 510

Cys Thr Leu Pro Asp Thr Glu Lys Gln Ile Lys Lys Gln Thr Ala Leu
        515                 520                 525

Val Glu Leu Leu Lys His Lys Pro Lys Ala Thr Glu Glu Gln Leu Lys
        530                 535                 540

Thr Val Met Glu Asn Phe Val Ala Phe Val Asp Lys Cys Cys Ala Ala
545                 550                 555                 560

Asp Asp Lys Glu Ala Cys Phe Ala Val Glu Gly Pro Lys Leu Val Val
                565                 570                 575

Ser Thr Gln Thr Ala Leu Ala
            580

<210> SEQ ID NO 201
<211> LENGTH: 497
<212> TYPE: PRT
<213> ORGANISM: Artificial Sequence
<220> FEATURE:
<223> OTHER INFORMATION: sequence of alglucerase

<400> SEQUENCE: 201

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30
```

```
Ala Leu Gly Thr Phe Ser Arg Tyr Glu Ser Thr Arg Ser Gly Arg Arg
             35                  40                  45

Met Glu Leu Ser Met Gly Pro Ile Gln Ala Asn His Thr Gly Thr Gly
 50                  55                  60

Leu Leu Leu Thr Leu Gln Pro Glu Gln Lys Phe Gln Lys Val Lys Gly
 65                  70                  75                  80

Phe Gly Ala Met Thr Asp Ala Ala Leu Asn Ile Leu Ala Leu
                 85                  90                  95

Ser Pro Pro Ala Gln Asn Leu Leu Lys Ser Tyr Phe Ser Glu Glu
             100                 105                 110

Gly Ile Gly Tyr Asn Ile Ile Arg Val Pro Met Ala Ser Cys Asp Phe
             115                 120                 125

Ser Ile Arg Thr Tyr Thr Tyr Ala Asp Thr Pro Asp Asp Phe Gln Leu
 130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                 165                 170                 175

Ser Pro Trp Thr Ser Pro Thr Trp Leu Lys Thr Asn Gly Ala Val Asn
                 180                 185                 190

Gly Lys Gly Ser Leu Lys Gly Gln Pro Gly Asp Ile Tyr His Gln Thr
             195                 200                 205

Trp Ala Arg Tyr Phe Val Lys Phe Leu Asp Ala Tyr Ala Glu His Lys
 210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                 245                 250                 255

Arg Asp Phe Ile Ala Arg Asp Leu Gly Pro Thr Leu Ala Asn Ser Thr
                 260                 265                 270

His His Asn Val Arg Leu Leu Met Leu Asp Asp Gln Arg Leu Leu Leu
             275                 280                 285

Pro His Trp Ala Lys Val Val Leu Thr Asp Pro Glu Ala Ala Lys Tyr
 290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                 325                 330                 335

Phe Ala Ser Glu Ala Cys Val Gly Ser Lys Phe Trp Glu Gln Ser Val
             340                 345                 350

Arg Leu Gly Ser Trp Asp Arg Gly Met Gln Tyr Ser His Ser Ile Ile
             355                 360                 365

Thr Asn Leu Leu Tyr His Val Val Gly Trp Thr Asp Trp Asn Leu Ala
             370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                 405                 410                 415

Phe Tyr His Leu Gly His Phe Ser Lys Phe Ile Pro Glu Gly Ser Gln
                 420                 425                 430

Arg Val Gly Leu Val Ala Ser Gln Lys Asn Asp Leu Asp Ala Val Ala
             435                 440                 445
```

-continued

```
Leu Met His Pro Asp Gly Ser Ala Val Val Val Leu Asn Arg Ser
    450             455             460

Ser Lys Asp Val Pro Leu Thr Ile Lys Asp Pro Ala Val Gly Phe Leu
465                 470             475                 480

Glu Thr Ile Ser Pro Gly Tyr Ser Ile His Thr Tyr Leu Trp His Arg
                485             490                 495

Gln

<210> SEQ ID NO 202
<211> LENGTH: 398
<212> TYPE: PRT
<213> ORGANISM: Artificial Sequence
<220> FEATURE:
<223> OTHER INFORMATION: sequence of alpha-galactosidase

<400> SEQUENCE: 202

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Pro Asp Ser Cys
                20                  25                  30

Ile Ser Glu Lys Leu Phe Met Glu Met Ala Glu Leu Met Val Ser Glu
            35                  40                  45

Gly Trp Lys Asp Ala Gly Tyr Glu Tyr Leu Cys Ile Asp Asp Cys Trp
    50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
        115                 120                 125

Ala Asp Trp Gly Val Asp Leu Leu Lys Phe Asp Gly Cys Tyr Cys Asp
    130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
    210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
        275                 280                 285

Asn Gln Asp Pro Leu Gly Lys Gln Gly Tyr Gln Leu Arg Gln Gly Asp
    290                 295                 300

Asn Phe Glu Val Trp Glu Arg Pro Leu Ser Gly Leu Ala Trp Ala Val
```

```
                305                 310                 315                 320
Ala Met Ile Asn Arg Gln Glu Ile Gly Gly Pro Arg Ser Tyr Thr Ile
                    325                 330                 335

Ala Val Ala Ser Leu Gly Lys Gly Val Ala Cys Asn Pro Ala Cys Phe
                340                 345                 350

Ile Thr Gln Leu Leu Pro Val Lys Arg Lys Leu Gly Phe Tyr Glu Trp
                    355                 360                 365

Thr Ser Arg Leu Arg Ser His Ile Asn Pro Thr Gly Thr Val Leu Leu
                370                 375                 380

Gln Leu Glu Asn Thr Met Gln Met Ser Leu Lys Asp Leu Leu
385                 390                 395
```

<210> SEQ ID NO 203
<211> LENGTH: 527
<212> TYPE: PRT
<213> ORGANISM: Artificial Sequence
<220> FEATURE:
<223> OTHER INFORMATION: sequence of alteplase

<400> SEQUENCE: 203

```
Ser Tyr Gln Val Ile Cys Arg Asp Glu Lys Thr Gln Met Ile Tyr Gln
1               5                   10                  15

Gln His Gln Ser Trp Leu Arg Pro Val Leu Arg Ser Asn Arg Val Glu
                20                  25                  30

Tyr Cys Trp Cys Asn Ser Gly Arg Ala Gln Cys His Ser Val Pro Val
            35                  40                  45

Lys Ser Cys Ser Glu Pro Arg Cys Phe Asn Gly Gly Thr Cys Gln Gln
    50                  55                  60

Ala Leu Tyr Phe Ser Asp Phe Val Cys Gln Cys Pro Glu Gly Phe Ala
65                  70                  75                  80

Gly Lys Cys Cys Glu Ile Asp Thr Arg Ala Thr Cys Tyr Glu Asp Gln
                85                  90                  95

Gly Ile Ser Tyr Arg Gly Thr Trp Ser Thr Ala Glu Ser Gly Ala Glu
                100                 105                 110

Cys Thr Asn Trp Asn Ser Ser Ala Leu Ala Gln Lys Pro Tyr Ser Gly
            115                 120                 125

Arg Arg Pro Asp Ala Ile Arg Leu Gly Leu Gly Asn His Asn Tyr Cys
    130                 135                 140

Arg Asn Pro Asp Arg Asp Ser Lys Pro Trp Cys Tyr Val Phe Lys Ala
145                 150                 155                 160

Gly Lys Tyr Ser Ser Glu Phe Cys Ser Thr Pro Ala Cys Ser Glu Gly
                165                 170                 175

Asn Ser Asp Cys Tyr Phe Gly Asn Gly Ser Ala Tyr Arg Gly Thr His
                180                 185                 190

Ser Leu Thr Glu Ser Gly Ala Ser Cys Leu Pro Trp Asn Ser Met Ile
            195                 200                 205

Leu Ile Gly Lys Val Tyr Thr Ala Gln Asn Pro Ser Ala Gln Ala Leu
    210                 215                 220

Gly Leu Gly Lys His Asn Tyr Cys Arg Asn Pro Asp Gly Asp Ala Lys
225                 230                 235                 240

Pro Trp Cys His Val Leu Lys Asn Arg Arg Leu Thr Trp Glu Tyr Cys
                245                 250                 255

Asp Val Pro Ser Cys Ser Thr Cys Gly Leu Arg Gln Tyr Ser Gln Pro
                260                 265                 270

Gln Phe Arg Ile Lys Gly Gly Leu Phe Ala Asp Ile Ala Ser His Pro
```

```
                    275                 280                 285
Trp Gln Ala Ala Ile Phe Ala Lys His Arg Arg Ser Pro Gly Glu Arg
    290                 295                 300

Phe Leu Cys Gly Gly Ile Leu Ile Ser Ser Cys Trp Ile Leu Ser Ala
305                 310                 315                 320

Ala His Cys Phe Gln Glu Arg Phe Pro His His Leu Thr Val Ile
                325                 330                 335

Leu Gly Arg Thr Tyr Arg Val Val Pro Gly Glu Glu Gln Lys Phe
            340                 345                 350

Glu Val Glu Lys Tyr Ile Val His Lys Glu Phe Asp Asp Thr Tyr
        355                 360                 365

Asp Asn Asp Ile Ala Leu Leu Gln Leu Lys Ser Asp Ser Ser Arg Cys
    370                 375                 380

Ala Gln Glu Ser Ser Val Val Arg Thr Val Cys Leu Pro Pro Ala Asp
385                 390                 395                 400

Leu Gln Leu Pro Asp Trp Thr Glu Cys Glu Leu Ser Gly Tyr Gly Lys
                405                 410                 415

His Glu Ala Leu Ser Pro Phe Tyr Ser Glu Arg Leu Lys Glu Ala His
            420                 425                 430

Val Arg Leu Tyr Pro Ser Ser Arg Cys Thr Ser Gln His Leu Leu Asn
        435                 440                 445

Arg Thr Val Thr Asp Asn Met Leu Cys Ala Gly Asp Thr Arg Ser Gly
    450                 455                 460

Gly Pro Gln Ala Asn Leu His Asp Ala Cys Gln Gly Asp Ser Gly Gly
465                 470                 475                 480

Pro Leu Val Cys Leu Asn Asp Gly Arg Met Thr Leu Val Gly Ile Ile
                485                 490                 495

Ser Trp Gly Leu Gly Cys Gly Gln Lys Asp Val Pro Gly Val Tyr Thr
            500                 505                 510

Lys Val Thr Asn Tyr Leu Asp Trp Ile Arg Asp Asn Met Arg Pro
        515                 520                 525

<210> SEQ ID NO 204
<211> LENGTH: 432
<212> TYPE: PRT
<213> ORGANISM: Artificial Sequence
<220> FEATURE:
<223> OTHER INFORMATION: sequence of antithrombin III

<400> SEQUENCE: 204

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
```

```
                115                 120                     125
Arg Leu Tyr Arg Lys Ala Asn Lys Ser Ser Lys Leu Val Ser Ala Asn
            130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
            165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
            195                 200                 205

Glu Leu Thr Val Leu Val Leu Val Asn Thr Ile Tyr Phe Lys Gly Leu
            210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
            245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
            275                 280                 285

Glu Lys Ser Leu Ala Lys Val Glu Lys Glu Leu Thr Pro Glu Val Leu
            290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
            325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
            355                 360                 365

His Lys Ala Phe Leu Glu Val Asn Glu Glu Gly Ser Glu Ala Ala Ala
            370                 375                 380

Ser Thr Ala Val Val Ile Ala Gly Arg Ser Leu Asn Pro Asn Arg Val
385                 390                 395                 400

Thr Phe Lys Ala Asn Arg Pro Phe Leu Val Phe Ile Arg Glu Val Pro
            405                 410                 415

Leu Asn Thr Ile Ile Phe Met Gly Arg Val Ala Asn Pro Cys Val Lys
            420                 425                 430

<210> SEQ ID NO 205
<211> LENGTH: 58
<212> TYPE: PRT
<213> ORGANISM: Artificial Sequence
<220> FEATURE:
<223> OTHER INFORMATION: sequence of aprotinin

<400> SEQUENCE: 205

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55
```

-continued

<210> SEQ ID NO 206
<211> LENGTH: 181
<212> TYPE: PRT
<213> ORGANISM: Artificial Sequence
<220> FEATURE:
<223> OTHER INFORMATION: alpha-chain sequence of asparaginase

<400> SEQUENCE: 206

```
Ser Pro Leu Pro Leu Val Val Asn Thr Trp Pro Phe Lys Asn Ala Thr
1               5                   10                  15

Glu Ala Ala Trp Arg Ala Leu Ala Ser Gly Gly Ser Ala Leu Asp Ala
            20                  25                  30

Val Glu Ser Gly Cys Ala Met Cys Glu Arg Glu Gln Cys Asp Gly Ser
        35                  40                  45

Val Gly Phe Gly Gly Ser Pro Asp Glu Leu Gly Glu Thr Thr Leu Asp
    50                  55                  60

Ala Met Ile Met Asp Gly Thr Thr Met Asp Val Gly Ala Val Gly Asp
65                  70                  75                  80

Leu Arg Arg Ile Lys Asn Ala Ile Gly Val Ala Arg Lys Val Leu Glu
                85                  90                  95

His Thr Thr His Thr Leu Leu Val Gly Glu Ser Ala Thr Thr Phe Ala
            100                 105                 110

Gln Ser Met Gly Phe Ile Asn Glu Asp Leu Ser Thr Ser Ala Ser Gln
        115                 120                 125

Ala Leu His Ser Asp Trp Leu Ala Arg Asn Cys Gln Pro Asn Tyr Trp
    130                 135                 140

Arg Asn Val Ile Pro Asp Pro Ser Lys Tyr Cys Gly Pro Tyr Lys Pro
145                 150                 155                 160

Pro Gly Ile Leu Lys Gln Asp Ile Pro Ile His Lys Glu Thr Glu Asp
                165                 170                 175

Asp Arg Gly His Asp
            180
```

<210> SEQ ID NO 207
<211> LENGTH: 141
<212> TYPE: PRT
<213> ORGANISM: Artificial Sequence
<220> FEATURE:
<223> OTHER INFORMATION: beta-chain sequence of asparaginase

<400> SEQUENCE: 207

```
Thr Ile Gly Met Val Val Ile His Lys Thr Gly His Ile Ala Ala Gly
1               5                   10                  15

Thr Ser Thr Asn Gly Ile Lys Phe Lys Ile His Gly Arg Val Gly Asp
            20                  25                  30

Ser Pro Ile Pro Gly Ala Gly Ala Tyr Ala Asp Asp Thr Ala Gly Ala
        35                  40                  45

Ala Ala Ala Thr Gly Asn Gly Asp Ile Leu Met Arg Phe Leu Pro Ser
    50                  55                  60

Tyr Gln Ala Val Glu Tyr Met Arg Arg Gly Glu Asp Pro Thr Ile Ala
65                  70                  75                  80

Cys Gln Lys Val Ile Ser Arg Ile Gln Lys His Phe Pro Glu Phe Phe
                85                  90                  95

Gly Ala Val Ile Cys Ala Asn Val Thr Gly Ser Tyr Gly Ala Ala Cys
            100                 105                 110
```

```
Asn Lys Leu Ser Thr Phe Thr Gln Phe Ser Phe Met Val Tyr Asn Ser
        115                 120                 125

Glu Lys Asn Gln Pro Thr Glu Glu Lys Val Asp Cys Ile
    130                 135                 140

<210> SEQ ID NO 208
<211> LENGTH: 159
<212> TYPE: PRT
<213> ORGANISM: Artificial Sequence
<220> FEATURE:
<223> OTHER INFORMATION: sequence of becaplermin

<400> SEQUENCE: 208

Ser Leu Gly Ser Leu Thr Ile Ala Glu Pro Ala Met Ile Ala Glu Cys
1               5                   10                  15

Lys Thr Arg Thr Glu Val Phe Glu Ile Ser Arg Arg Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Asn Val Gln Cys Arg Pro Thr Gln
    50                  55                  60

Val Gln Leu Arg Pro Val Gln Val Arg Lys Ile Glu Ile Val Arg Lys
65                  70                  75                  80

Lys Pro Ile Phe Lys Lys Ala Thr Val Thr Leu Glu Asp His Leu Ala
                85                  90                  95

Cys Lys Cys Glu Thr Val Ala Ala Ala Arg Pro Val Thr Arg Ser Pro
            100                 105                 110

Gly Gly Ser Gln Glu Gln Arg Ala Lys Thr Pro Gln Thr Arg Val Thr
        115                 120                 125

Ile Arg Thr Val Arg Val Arg Arg Pro Pro Lys Gly Lys His Arg Lys
    130                 135                 140

Phe Lys His Thr His Asp Lys Thr Ala Leu Lys Glu Thr Leu Gly
145                 150                 155

<210> SEQ ID NO 209
<211> LENGTH: 187
<212> TYPE: PRT
<213> ORGANISM: Artificial Sequence
<220> FEATURE:
<223> OTHER INFORMATION: sequence of bone morphogenic protein 7

<400> SEQUENCE: 209

Gly Lys His Asn Ser Ala Pro Met Phe Met Leu Asp Leu Tyr Asn Ala
1               5                   10                  15

Met Ala Val Glu Glu Gly Gly Pro Ala Gly Gln Gly Phe Ser Tyr
            20                  25                  30

Pro Tyr Lys Ala Val Phe Ser Thr Gln Gly Pro Pro Leu Ala Ser Leu
        35                  40                  45

Gln Asp Ser His Phe Leu Thr Asp Ala Asp Met Val Met Ser Phe Val
    50                  55                  60

Asn Leu Val Glu His Asp Lys Glu Phe Phe His Pro Arg Tyr His His
65                  70                  75                  80

Arg Glu Phe Arg Phe Asp Leu Ser Lys Ile Pro Glu Gly Glu Ala Val
                85                  90                  95

Thr Ala Ala Glu Phe Arg Ile Tyr Lys Asp Tyr Ile Arg Glu Arg Phe
            100                 105                 110

Asp Asn Glu Thr Phe Arg Ile Ser Val Tyr Gln Val Leu Gln Glu His
        115                 120                 125
```

```
Leu Gly Arg Glu Ser Asp Leu Phe Leu Leu Asp Ser Arg Thr Leu Trp
            130                 135                 140

Ala Ser Glu Glu Gly Trp Leu Val Phe Asp Ile Thr Ala Thr Ser Asn
145                 150                 155                 160

His Trp Val Val Asn Pro Arg His Asn Leu Gly Leu Gln Leu Cys Val
                165                 170                 175

Glu Thr Leu Asp Gly Gln Ser Ile Asn Pro Lys
            180                 185

<210> SEQ ID NO 210
<211> LENGTH: 526
<212> TYPE: PRT
<213> ORGANISM: Artificial Sequence
<220> FEATURE:
<223> OTHER INFORMATION: sequence of catalase

<400> SEQUENCE: 210

Ala Asp Ser Arg Asp Pro Ala Ser Asp Gln Met Gln His Trp Lys Glu
1               5                   10                  15

Gln Arg Ala Ala Gln Lys Ala Asp Val Leu Thr Thr Gly Ala Gly Asn
            20                  25                  30

Pro Val Gly Asp Lys Leu Asn Val Ile Thr Val Gly Pro Arg Gly Pro
        35                  40                  45

Leu Leu Val Gln Asp Val Val Phe Thr Asp Glu Met Ala His Phe Asp
    50                  55                  60

Arg Glu Arg Ile Pro Glu Arg Val Val His Ala Lys Gly Ala Gly Ala
65                  70                  75                  80

Phe Gly Tyr Phe Glu Val Thr His Asp Ile Thr Lys Tyr Ser Lys Ala
                85                  90                  95

Lys Val Phe Glu His Ile Gly Lys Lys Thr Pro Ile Ala Val Arg Phe
            100                 105                 110

Ser Thr Val Ala Gly Glu Ser Gly Ser Ala Asp Thr Val Arg Asp Pro
        115                 120                 125

Arg Gly Phe Ala Val Lys Phe Tyr Thr Glu Asp Gly Asn Trp Asp Leu
    130                 135                 140

Val Gly Asn Asn Thr Pro Ile Phe Phe Ile Arg Asp Pro Ile Leu Phe
145                 150                 155                 160

Pro Ser Phe Ile His Ser Gln Lys Arg Asn Pro Gln Thr His Leu Lys
                165                 170                 175

Asp Pro Asp Met Val Trp Asp Phe Trp Ser Leu Arg Pro Glu Ser Leu
            180                 185                 190

His Gln Val Ser Phe Leu Phe Ser Asp Arg Gly Ile Pro Asp Gly His
        195                 200                 205

Arg His Met Asn Gly Tyr Gly Ser His Thr Phe Lys Leu Val Asn Ala
    210                 215                 220

Asn Gly Glu Ala Val Tyr Cys Lys Phe His Tyr Lys Thr Asp Gln Gly
225                 230                 235                 240

Ile Lys Asn Leu Ser Val Glu Asp Ala Ala Arg Leu Ser Gln Glu Asp
                245                 250                 255

Pro Asp Tyr Gly Ile Arg Asp Leu Phe Asn Ala Ile Ala Thr Gly Lys
            260                 265                 270

Tyr Pro Ser Trp Thr Phe Tyr Ile Gln Val Met Thr Phe Asn Gln Ala
        275                 280                 285

Glu Thr Phe Pro Phe Asn Pro Phe Asp Leu Thr Lys Val Trp Pro His
    290                 295                 300
```

```
Lys Asp Tyr Pro Leu Ile Pro Val Gly Lys Leu Val Leu Asn Arg Asn
305                 310                 315                 320

Pro Val Asn Tyr Phe Ala Glu Val Glu Gln Ile Ala Phe Asp Pro Ser
                325                 330                 335

Asn Met Pro Pro Gly Ile Glu Ala Ser Pro Asp Lys Met Leu Gln Gly
            340                 345                 350

Arg Leu Phe Ala Tyr Pro Asp Thr His Arg His Arg Leu Gly Pro Asn
        355                 360                 365

Tyr Leu His Ile Pro Val Asn Cys Pro Tyr Arg Ala Arg Val Ala Asn
370                 375                 380

Tyr Gln Arg Asp Gly Pro Met Cys Met Gln Asp Asn Gln Gly Gly Ala
385                 390                 395                 400

Pro Asn Tyr Tyr Pro Asn Ser Phe Gly Ala Pro Glu Gln Gln Pro Ser
                405                 410                 415

Ala Leu Glu His Ser Ile Gln Tyr Ser Gly Glu Val Arg Arg Phe Asn
            420                 425                 430

Thr Ala Asn Asp Asp Asn Val Thr Gln Val Arg Ala Phe Tyr Val Asn
        435                 440                 445

Val Leu Asn Glu Glu Gln Arg Lys Arg Leu Cys Glu Asn Ile Ala Gly
    450                 455                 460

His Leu Lys Asp Ala Gln Ile Phe Ile Gln Lys Lys Ala Val Lys Asn
465                 470                 475                 480

Phe Thr Glu Val His Pro Asp Tyr Gly Ser His Ile Gln Ala Leu Leu
                485                 490                 495

Asp Lys Tyr Asn Ala Glu Lys Pro Lys Asn Ala Ile His Thr Phe Val
            500                 505                 510

Gln Ser Gly Ser His Leu Ala Ala Arg Glu Lys Ala Asn Leu
        515                 520                 525

<210> SEQ ID NO 211
<211> LENGTH: 36
<212> TYPE: PRT
<213> ORGANISM: Artificial Sequence
<220> FEATURE:
<223> OTHER INFORMATION: sequence of cecropin B

<400> SEQUENCE: 211

Lys Trp Lys Val Phe Lys Lys Ile Glu Lys Met Gly Arg Asn Ile Arg
1               5                   10                  15

Asn Gly Ile Val Lys Ala Gly Pro Ala Ile Ala Val Leu Gly Glu Ala
            20                  25                  30

Lys Ala Leu Gly
        35

<210> SEQ ID NO 212
<211> LENGTH: 397
<212> TYPE: PRT
<213> ORGANISM: Artificial Sequence
<220> FEATURE:
<223> OTHER INFORMATION: sequence of cellulase

<400> SEQUENCE: 212

Met Lys Lys Lys Gly Leu Lys Lys Thr Phe Phe Val Ile Ala Ser Leu
1               5                   10                  15

Val Met Gly Phe Thr Leu Tyr Gly Tyr Thr Pro Val Ser Ala Asp Ala
            20                  25                  30

Ala Ser Val Lys Gly Tyr Tyr His Thr Gln Gly Asn Lys Ile Val Asp
```

-continued

```
                35                  40                  45
Glu Ser Gly Lys Glu Ala Ala Phe Asn Gly Leu Asn Trp Phe Gly Leu
 50                  55                  60
Glu Thr Pro Asn Tyr Thr Leu His Gly Leu Trp Ser Arg Ser Met Asp
 65                  70                  75                  80
Asp Met Leu Asp Gln Val Lys Lys Glu Gly Tyr Asn Leu Ile Arg Leu
                 85                  90                  95
Pro Tyr Ser Asn Gln Leu Phe Asp Ser Ser Arg Pro Asp Ser Ile
                100                 105                 110
Asp Tyr His Lys Asn Pro Asp Leu Val Gly Leu Asn Pro Ile Gln Ile
                115                 120                 125
Met Asp Lys Leu Ile Glu Lys Ala Gly Gln Arg Gly Ile Gln Ile Ile
130                 135                 140
Leu Asp Arg His Arg Pro Gly Ser Gly Gly Gln Ser Glu Leu Trp Tyr
145                 150                 155                 160
Thr Ser Gln Tyr Pro Glu Ser Arg Trp Ile Ser Asp Trp Lys Met Leu
                165                 170                 175
Ala Asp Arg Tyr Lys Asn Asn Pro Thr Val Ile Gly Ala Asp Leu His
                180                 185                 190
Asn Glu Pro His Gly Gln Ala Ser Trp Gly Thr Gly Asn Ala Ser Thr
                195                 200                 205
Asp Trp Arg Leu Ala Ala Gln Arg Ala Gly Asn Ala Ile Leu Ser Val
                210                 215                 220
Asn Pro Asn Trp Leu Ile Leu Val Glu Gly Val Asp His Asn Val Gln
225                 230                 235                 240
Gly Asn Asn Ser Gln Tyr Trp Trp Gly Gly Asn Leu Thr Gly Val Ala
                245                 250                 255
Asn Tyr Pro Val Val Leu Asp Val Pro Asn Arg Val Val Tyr Ser Pro
                260                 265                 270
His Asp Tyr Gly Pro Gly Val Ser Gln Pro Trp Phe Asn Asp Pro
                275                 280                 285
Ala Phe Pro Ser Asn Leu Pro Ala Ile Trp Asp Gln Thr Trp Gly Tyr
290                 295                 300
Ile Ser Lys Gln Asn Ile Ala Pro Val Leu Val Gly Glu Phe Gly Gly
305                 310                 315                 320
Arg Asn Val Asp Leu Ser Cys Pro Glu Gly Lys Trp Gln Asn Ala Leu
                325                 330                 335
Val His Tyr Ile Gly Ala Asn Asn Leu Tyr Phe Thr Tyr Trp Ser Leu
                340                 345                 350
Asn Pro Asn Ser Gly Asp Thr Gly Leu Leu Leu Asp Asp Trp Thr
                355                 360                 365
Thr Trp Asn Arg Pro Lys Gln Asp Met Leu Gly Arg Ile Met Lys Pro
370                 375                 380
Val Val Ser Val Ala Gln Ala Glu Ala Ala Glu
385                 390                 395
```

<210> SEQ ID NO 213
<211> LENGTH: 92
<212> TYPE: PRT
<213> ORGANISM: Artificial Sequence
<220> FEATURE:
<223> OTHER INFORMATION: sequence of choriogonadotropin alpha

<400> SEQUENCE: 213

Ala Pro Asp Val Gln Asp Cys Pro Glu Cys Thr Leu Gln Glu Asn Pro

```
           1               5                  10                  15
         Phe Phe Ser Gln Pro Gly Ala Pro Ile Leu Gln Cys Met Gly Cys Cys
                     20                  25                  30
         Phe Ser Arg Ala Tyr Pro Thr Pro Leu Arg Ser Lys Lys Thr Met Leu
                     35                  40                  45
         Val Gln Lys Asn Val Thr Ser Glu Ser Thr Cys Cys Val Ala Lys Ser
                 50                  55                  60
         Tyr Asn Arg Val Thr Val Met Gly Gly Phe Lys Val Glu Asn His Thr
         65                  70                  75                  80
         Ala Cys His Cys Ser Thr Cys Tyr Tyr His Lys Ser
                             85                  90

SEQ ID NO 214
LENGTH: 145
TYPE: PRT
ORGANISM: Artificial Sequence
FEATURE:
OTHER INFORMATION: sequence of choriogonadotropin beta

SEQUENCE: 214

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
                20                  25                  30

Ile Cys Ala Gly Tyr Cys Pro Thr Met Thr Arg Val Leu Gln Gly Val
            35                  40                  45

Leu Pro Ala Leu Pro Gln Val Val Cys Asn Tyr Arg Asp Val Arg Phe
        50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
                100                 105                 110

Pro Arg Phe Gln Asp Ser Ser Ser Lys Ala Pro Pro Pro Ser Leu
            115                 120                 125

Pro Ser Pro Ser Arg Leu Pro Gly Pro Ser Asp Thr Pro Ile Leu Pro
        130                 135                 140

Gln
145

<210> SEQ ID NO 215
<211> LENGTH: 217
<212> TYPE: PRT
<213> ORGANISM: Artificial Sequence
<220> FEATURE:
<223> OTHER INFORMATION: sequence of chymopapain

<400> SEQUENCE: 215

Pro Gln Ser Ile Asp Trp Arg Ala Lys Gly Ala Val Thr Pro Val Lys
1               5                   10                  15

Asn Gln Gly Ala Cys Gly Ser Cys Trp Ala Phe Ser Thr Ile Ala Thr
                20                  25                  30

Val Glu Gly Ile Asn Lys Ile Val Thr Gly Asn Leu Leu Glu Leu Ser
            35                  40                  45

Glu Gln Glu Leu Val Asp Cys Asp Lys His Ser Tyr Gly Cys Lys Gly
        50                  55                  60

Gly Tyr Gln Thr Thr Ser Leu Gln Tyr Val Ala Asn Gly Val His
65                  70                  75                  80

Thr Ser Lys Val Tyr Pro Tyr Gln Ala Lys Gln Tyr Lys Cys Arg Ala
                85                  90                  95
```

-continued

```
Thr Asp Lys Pro Gly Pro Lys Val Lys Ile Thr Gly Tyr Lys Arg Val
            100                 105                 110
Pro Ser Asn Cys Glu Thr Ser Phe Leu Gly Ala Leu Ala Asn Gln Pro
            115                 120                 125
Leu Ser Val Leu Val Glu Ala Gly Gly Lys Pro Phe Gln Leu Tyr Lys
        130                 135                 140
Ser Gly Val Phe Asp Gly Pro Cys Gly Thr Lys Leu Asp His Ala Val
145                 150                 155                 160
Thr Ala Val Gly Tyr Gly Thr Ser Asp Gly Lys Asn Tyr Ile Ile Ile
                165                 170                 175
Lys Asn Ser Trp Gly Pro Asn Trp Gly Glu Lys Gly Tyr Met Arg Leu
            180                 185                 190
Lys Arg Gln Ser Gly Asn Ser Gln Gly Thr Cys Gly Val Tyr Lys Ser
            195                 200                 205
Ser Tyr Tyr Pro Phe Lys Gly Phe Ala
        210                 215
```

<210> SEQ ID NO 216
<211> LENGTH: 199
<212> TYPE: PRT
<213> ORGANISM: Artificial Sequence
<220> FEATURE:
<223> OTHER INFORMATION: sequence of chymotrypsin

<400> SEQUENCE: 216

```
Met Thr Thr Ser Ala Ala Arg Lys Gly Leu Arg Thr Arg Gly Ser Ala
1               5                   10                  15
Cys Pro Arg Ala Thr Arg Ser Ala Ser Ser Ile Ser Ser Arg Ala Gln
            20                  25                  30
Val Ile Val Ala Gly Pro Ile Thr Asp Lys Leu Ala Gln Arg Thr Val
        35                  40                  45
Ala His Leu Leu Ala Leu Ala Glu Asp Ser Asp Glu Pro Ile Asn Met
    50                  55                  60
Leu Ile Ser Ser Pro Gly Gly His Val Glu Ser Gly Asp Met Ile His
65                  70                  75                  80
Asp Val Ile Lys Phe Ile Arg Pro Thr Val Arg Thr Ile Gly Leu Ala
                85                  90                  95
Trp Val Ala Ser Ala Gly Ala Leu Ile Phe Val Gly Ala Asp Lys Glu
            100                 105                 110
Asn Arg Tyr Cys Leu Pro Asn Thr Arg Phe Leu Ile His Gln Pro Ser
            115                 120                 125
Val Gly Ile Gly Gly Thr Ser Thr Asp Met Met Ile Gln Ala Glu Gln
        130                 135                 140
Val Arg Leu Met Arg Asp Arg Leu Asn Gln Ile Phe Ala Glu Ala Thr
145                 150                 155                 160
Gly Gln Pro Val Glu Arg Ile Glu Lys Asp Thr Gln Arg Asp Phe Trp
                165                 170                 175
Leu Asn Thr Gln Glu Ala Leu Asp Tyr Gly Leu Leu Gly Lys Val Ile
            180                 185                 190
Arg Ser Val Asp Glu Leu Lys
        195
```

<210> SEQ ID NO 217
<211> LENGTH: 38
<212> TYPE: PRT
<213> ORGANISM: Artificial Sequence -continued

```
<220> FEATURE:
<223> OTHER INFORMATION: sequence of big endothelin

<400> SEQUENCE: 217

Cys Ser Cys Ser Ser Leu Met Asp Lys Glu Cys Val Tyr Phe Cys His
1               5                   10                  15

Leu Asp Ile Ile Trp Val Asn Thr Pro Glu His Val Val Pro Tyr Gly
            20                  25                  30

Leu Gly Ser Pro Arg Ser
            35

<210> SEQ ID NO 218
<211> LENGTH: 447
<212> TYPE: PRT
<213> ORGANISM: Artificial Sequence
<220> FEATURE:
<223> OTHER INFORMATION: sequence A-light chain of clostridium botulinum toxin type A

<400> SEQUENCE: 218

Pro Phe Val Asn Lys Gln Phe Asn Tyr Lys Asp Pro Val Asn Gly Val
1               5                   10                  15

Asp Ile Ala Tyr Ile Lys Ile Pro Asn Ala Gly Gln Met Gln Pro Val
            20                  25                  30

Lys Ala Phe Lys Ile His Asn Lys Ile Trp Val Ile Pro Glu Arg Asp
        35                  40                  45

Thr Phe Thr Asn Pro Glu Glu Gly Asp Leu Asn Pro Pro Glu Ala
    50                  55                  60

Lys Gln Val Pro Val Ser Tyr Tyr Asp Ser Thr Tyr Leu Ser Thr Asp
65                  70                  75                  80

Asn Glu Lys Asp Asn Tyr Leu Lys Gly Val Thr Lys Leu Phe Glu Arg
                85                  90                  95

Ile Tyr Ser Thr Asp Leu Gly Arg Met Leu Leu Thr Ser Ile Val Arg
            100                 105                 110

Gly Ile Pro Phe Trp Gly Gly Ser Thr Ile Asp Thr Glu Leu Lys Val
        115                 120                 125

Ile Asp Thr Asn Cys Ile Asn Val Ile Gln Pro Asp Gly Ser Tyr Arg
    130                 135                 140

Ser Glu Glu Leu Asn Leu Val Ile Ile Gly Pro Ser Ala Asp Ile Ile
145                 150                 155                 160

Gln Phe Glu Cys Lys Ser Phe Gly His Asp Val Leu Asn Leu Thr Arg
                165                 170                 175

Asn Gly Tyr Gly Ser Thr Gln Tyr Ile Arg Phe Ser Pro Asp Phe Thr
            180                 185                 190

Phe Gly Phe Glu Glu Ser Leu Glu Val Asp Thr Asn Pro Leu Leu Gly
        195                 200                 205

Ala Gly Lys Phe Ala Thr Asp Pro Ala Val Thr Leu Ala His Glu Leu
    210                 215                 220

Ile His Ala Glu His Arg Leu Tyr Gly Ile Ala Ile Asn Pro Asn Arg
225                 230                 235                 240

Val Phe Lys Val Asn Thr Asn Ala Tyr Tyr Glu Met Ser Gly Leu Glu
                245                 250                 255

Val Ser Phe Glu Glu Leu Arg Thr Phe Gly Gly His Asp Ala Lys Phe
            260                 265                 270

Ile Asp Ser Leu Gln Glu Asn Glu Phe Arg Leu Tyr Tyr Tyr Asn Lys
        275                 280                 285

Phe Lys Asp Val Ala Ser Thr Leu Asn Lys Ala Lys Ser Ile Ile Gly
```

```
            290                 295                 300
Thr Thr Ala Ser Leu Gln Tyr Met Lys Asn Val Phe Lys Glu Lys Tyr
305                 310                 315                 320

Leu Leu Ser Glu Asp Thr Ser Gly Lys Phe Ser Val Asp Lys Leu Lys
                325                 330                 335

Phe Asp Lys Leu Tyr Lys Met Leu Thr Glu Ile Tyr Thr Glu Asp Asn
            340                 345                 350

Phe Val Asn Phe Phe Lys Val Ile Asn Arg Lys Thr Tyr Leu Asn Phe
        355                 360                 365

Asp Lys Ala Val Phe Arg Ile Asn Ile Val Pro Asp Glu Asn Tyr Thr
    370                 375                 380

Ile Lys Asp Gly Phe Asn Leu Lys Gly Ala Asn Leu Ser Thr Asn Phe
385                 390                 395                 400

Asn Gly Gln Asn Thr Glu Ile Asn Ser Arg Asn Phe Thr Arg Leu Lys
                405                 410                 415

Asn Phe Thr Gly Leu Phe Glu Phe Tyr Lys Leu Leu Cys Val Arg Gly
            420                 425                 430

Ile Ile Pro Phe Lys Thr Lys Ser Leu Asp Glu Gly Tyr Asn Lys
        435                 440                 445

<210> SEQ ID NO 219
<211> LENGTH: 848
<212> TYPE: PRT
<213> ORGANISM: Artificial Sequence
<220> FEATURE:
<223> OTHER INFORMATION: sequence A-heavy chain of clostridium botulinum
      toxin type A

<400> SEQUENCE: 219

Ala Leu Asn Asp Leu Cys Ile Lys Val Asn Asn Trp Asp Leu Phe Phe
1               5                   10                  15

Ser Pro Ser Glu Asp Asn Phe Thr Asn Asp Leu Asp Lys Val Glu Glu
            20                  25                  30

Ile Thr Ala Asp Thr Asn Ile Glu Ala Ala Glu Glu Asn Ile Ser Leu
        35                  40                  45

Asp Leu Ile Gln Gln Tyr Tyr Leu Thr Phe Asp Phe Asp Asn Glu Pro
    50                  55                  60

Glu Asn Ile Ser Ile Glu Asn Leu Ser Ser Asp Ile Ile Gly Gln Leu
65                  70                  75                  80

Glu Pro Met Pro Asn Ile Glu Arg Phe Pro Asn Gly Lys Lys Tyr Glu
                85                  90                  95

Leu Asp Lys Tyr Thr Met Phe His Tyr Leu Arg Ala Gln Glu Phe Glu
            100                 105                 110

His Gly Asp Ser Arg Ile Ile Leu Thr Asn Ser Ala Glu Glu Ala Leu
        115                 120                 125

Leu Lys Pro Asn Val Ala Tyr Thr Phe Ser Ser Lys Tyr Val Lys
    130                 135                 140

Lys Ile Asn Lys Ala Val Glu Ala Phe Met Phe Leu Asn Trp Ala Glu
145                 150                 155                 160

Glu Leu Val Tyr Asp Phe Thr Asp Glu Thr Asn Glu Val Thr Thr Met
                165                 170                 175

Asp Lys Ile Ala Asp Ile Thr Ile Ile Val Pro Tyr Ile Gly Pro Ala
            180                 185                 190

Leu Asn Ile Gly Asn Met Leu Ser Lys Gly Glu Phe Val Glu Ala Ile
        195                 200                 205
```

-continued

```
Ile Phe Thr Gly Val Val Ala Met Leu Glu Phe Ile Pro Glu Tyr Ala
210                 215                 220
Leu Pro Val Phe Gly Thr Phe Ala Ile Val Ser Tyr Ile Ala Asn Lys
225                 230                 235                 240
Val Leu Thr Val Gln Thr Ile Asn Asn Ala Leu Ser Lys Arg Asn Glu
                245                 250                 255
Lys Trp Asp Glu Val Tyr Lys Tyr Thr Val Thr Asn Trp Leu Ala Lys
                260                 265                 270
Val Asn Thr Gln Ile Asp Leu Ile Arg Glu Lys Met Lys Lys Ala Leu
            275                 280                 285
Glu Asn Gln Ala Glu Ala Thr Lys Ala Ile Ile Asn Tyr Gln Tyr Asn
        290                 295                 300
Gln Tyr Thr Glu Glu Lys Asn Asn Ile Asn Phe Asn Ile Asp Asp
305                 310                 315                 320
Leu Ser Ser Lys Leu Asn Glu Ser Ile Asn Ser Ala Met Ile Asn Ile
                325                 330                 335
Asn Lys Phe Leu Asp Gln Cys Ser Val Ser Tyr Leu Met Asn Ser Met
                340                 345                 350
Ile Pro Tyr Ala Val Lys Arg Leu Lys Asp Phe Asp Ala Ser Val Arg
                355                 360                 365
Asp Val Leu Leu Lys Tyr Ile Tyr Asp Asn Arg Gly Thr Leu Val Leu
370                 375                 380
Gln Val Asp Arg Leu Lys Asp Glu Val Asn Asn Thr Leu Ser Ala Asp
385                 390                 395                 400
Ile Pro Phe Gln Leu Ser Lys Tyr Val Asp Asn Lys Lys Leu Leu Ser
                405                 410                 415
Thr Phe Thr Glu Tyr Ile Lys Asn Ile Val Asn Thr Ser Ile Leu Ser
                420                 425                 430
Ile Val Tyr Lys Lys Asp Asp Leu Ile Asp Leu Ser Arg Tyr Gly Ala
            435                 440                 445
Lys Ile Asn Ile Gly Asp Arg Val Tyr Tyr Asp Ser Ile Asp Lys Asn
450                 455                 460
Gln Ile Lys Leu Ile Asn Leu Glu Ser Ser Thr Ile Glu Val Ile Leu
465                 470                 475                 480
Lys Asn Ala Ile Val Tyr Asn Ser Met Tyr Glu Asn Phe Ser Thr Ser
                485                 490                 495
Phe Trp Ile Lys Ile Pro Lys Tyr Phe Ser Lys Ile Asn Leu Asn Asn
                500                 505                 510
Glu Tyr Thr Ile Ile Asn Cys Ile Glu Asn Asn Ser Gly Trp Lys Val
            515                 520                 525
Ser Leu Asn Tyr Gly Glu Ile Ile Trp Thr Leu Gln Asp Asn Lys Gln
530                 535                 540
Asn Ile Gln Arg Val Val Phe Lys Tyr Ser Gln Met Val Asn Ile Ser
545                 550                 555                 560
Asp Tyr Ile Asn Arg Trp Ile Phe Val Thr Ile Thr Asn Asn Arg Leu
                565                 570                 575
Thr Lys Ser Lys Ile Tyr Ile Asn Gly Arg Leu Ile Asp Gln Lys Pro
                580                 585                 590
Ile Ser Asn Leu Gly Asn Ile His Ala Ser Asn Lys Ile Met Phe Lys
            595                 600                 605
Leu Asp Gly Cys Arg Asp Pro Arg Arg Tyr Ile Met Ile Lys Tyr Phe
610                 615                 620
Asn Leu Phe Asp Lys Glu Leu Asn Glu Lys Glu Ile Lys Asp Leu Tyr
```

-continued

```
                625                 630                 635                 640
Asp Ser Gln Ser Asn Ser Gly Ile Leu Lys Asp Phe Trp Gly Asn Tyr
                    645                 650                 655
Leu Gln Tyr Asp Lys Pro Tyr Tyr Met Leu Asn Leu Phe Asp Pro Asn
                    660                 665                 670
Lys Tyr Val Asp Val Asn Asn Ile Gly Ile Arg Gly Tyr Met Tyr Leu
                    675                 680                 685
Lys Gly Pro Arg Gly Ser Val Val Thr Thr Asn Ile Tyr Leu Asn Ser
                    690                 695                 700
Thr Leu Tyr Glu Gly Thr Lys Phe Ile Ile Lys Lys Tyr Ala Ser Gly
705                 710                 715                 720
Asn Glu Asp Asn Ile Val Arg Asn Asn Asp Arg Val Tyr Ile Asn Val
                    725                 730                 735
Val Val Lys Asn Lys Glu Tyr Arg Leu Ala Thr Asn Ala Ser Gln Ala
                    740                 745                 750
Gly Val Glu Lys Ile Leu Ser Ala Leu Glu Ile Pro Asp Val Gly Asn
                    755                 760                 765
Leu Ser Gln Val Val Val Met Lys Ser Lys Asp Asp Gln Gly Ile Arg
770                 775                 780
Asn Lys Cys Lys Met Asn Leu Gln Asp Asn Asn Gly Asn Asp Ile Gly
785                 790                 795                 800
Phe Ile Gly Phe His Leu Tyr Asp Asn Ile Ala Lys Leu Val Ala Ser
                    805                 810                 815
Asn Trp Tyr Asn Arg Gln Val Gly Lys Ala Ser Arg Thr Phe Gly Cys
                    820                 825                 830
Ser Trp Glu Phe Ile Pro Val Asp Asp Gly Trp Gly Glu Ser Ser Leu
                    835                 840                 845
```

<210> SEQ ID NO 220
<211> LENGTH: 1290
<212> TYPE: PRT
<213> ORGANISM: Artificial Sequence
<220> FEATURE:
<223> OTHER INFORMATION: sequence of clostridium botulinum toxin type B

<400> SEQUENCE: 220

```
Pro Val Thr Ile Asn Asn Phe Asn Tyr Asn Asp Pro Ile Asp Asn Asn
1               5                   10                  15
Asn Ile Ile Met Met Glu Pro Pro Phe Ala Arg Gly Thr Gly Arg Tyr
                20                  25                  30
Tyr Lys Ala Phe Lys Ile Thr Asp Arg Ile Trp Ile Ile Pro Glu Arg
            35                  40                  45
Tyr Thr Phe Gly Tyr Lys Pro Glu Asp Phe Asn Lys Ser Ser Gly Ile
        50                  55                  60
Phe Asn Arg Asp Val Cys Glu Tyr Tyr Asp Pro Asp Tyr Leu Asn Thr
65                  70                  75                  80
Asn Asp Lys Lys Asn Ile Phe Leu Gln Thr Met Ile Lys Leu Phe Asn
                85                  90                  95
Arg Ile Lys Ser Lys Pro Leu Gly Glu Lys Leu Leu Glu Met Ile Ile
                100                 105                 110
Asn Gly Ile Pro Tyr Leu Gly Asp Arg Arg Val Pro Leu Glu Glu Phe
            115                 120                 125
Asn Thr Asn Ile Ala Ser Val Thr Val Asn Lys Leu Ile Ser Asn Pro
        130                 135                 140
Gly Glu Val Glu Arg Lys Lys Gly Ile Phe Ala Asn Leu Ile Ile Phe
```

```
              145                 150                 155                 160
    Gly Pro Gly Pro Val Leu Asn Glu Asn Glu Thr Ile Asp Ile Gly Ile
                    165                 170                 175

Gln Asn His Phe Ala Ser Arg Glu Gly Phe Gly Gly Ile Met Gln Met
                    180                 185                 190

Lys Phe Cys Pro Glu Tyr Val Ser Val Phe Asn Asn Val Gln Glu Asn
                    195                 200                 205

Lys Gly Ala Ser Ile Phe Asn Arg Arg Gly Tyr Phe Ser Asp Pro Ala
                    210                 215                 220

Leu Ile Leu Met His Glu Leu Ile His Val Leu His Gly Leu Tyr Gly
    225                 230                 235                 240

Ile Lys Val Asp Asp Leu Pro Ile Val Pro Asn Glu Lys Lys Phe Phe
                    245                 250                 255

Met Gln Ser Thr Asp Ala Ile Gln Ala Glu Glu Leu Tyr Thr Phe Gly
                    260                 265                 270

Gly Gln Asp Pro Ser Ile Ile Thr Pro Ser Thr Asp Lys Ser Ile Tyr
                    275                 280                 285

Asp Lys Val Leu Gln Asn Phe Arg Gly Ile Val Asp Arg Leu Asn Lys
    290                 295                 300

Val Leu Val Cys Ile Ser Asp Pro Asn Ile Asn Ile Asn Ile Tyr Lys
    305                 310                 315                 320

Asn Lys Phe Lys Asp Lys Tyr Lys Phe Val Glu Asp Ser Glu Gly Lys
                    325                 330                 335

Tyr Ser Ile Asp Val Glu Ser Phe Asp Lys Leu Tyr Lys Ser Leu Met
                    340                 345                 350

Phe Gly Phe Thr Glu Thr Asn Ile Ala Glu Asn Tyr Lys Ile Lys Thr
                    355                 360                 365

Arg Ala Ser Tyr Phe Ser Asp Ser Leu Pro Pro Val Lys Ile Lys Asn
                    370                 375                 380

Leu Leu Asp Asn Glu Ile Tyr Thr Ile Glu Glu Gly Phe Asn Ile Ser
    385                 390                 395                 400

Asp Lys Asp Met Glu Lys Glu Tyr Arg Gly Gln Asn Lys Ala Ile Asn
                    405                 410                 415

Lys Gln Ala Tyr Glu Glu Ile Ser Lys Glu His Leu Ala Val Tyr Lys
                    420                 425                 430

Ile Gln Met Cys Lys Ser Val Lys Ala Pro Gly Ile Cys Ile Asp Val
                    435                 440                 445

Asp Asn Glu Asp Leu Phe Phe Ile Ala Asp Lys Asn Ser Phe Ser Asp
                    450                 455                 460

Asp Leu Ser Lys Asn Glu Arg Ile Glu Tyr Asn Thr Gln Ser Asn Tyr
    465                 470                 475                 480

Ile Glu Asn Asp Phe Pro Ile Asn Glu Leu Ile Leu Asp Thr Asp Leu
                    485                 490                 495

Ile Ser Lys Ile Glu Leu Pro Ser Glu Asn Thr Glu Ser Leu Thr Asp
                    500                 505                 510

Phe Asn Val Asp Val Pro Val Tyr Glu Lys Gln Pro Ala Ile Lys Lys
                    515                 520                 525

Ile Phe Thr Asp Glu Asn Thr Ile Phe Gln Tyr Leu Tyr Ser Gln Thr
                    530                 535                 540

Phe Pro Leu Asp Ile Arg Asp Ile Ser Leu Thr Ser Ser Phe Asp Asp
    545                 550                 555                 560

Ala Leu Leu Phe Ser Asn Lys Val Tyr Ser Phe Phe Ser Met Asp Tyr
                    565                 570                 575
```

-continued

```
Ile Lys Thr Ala Asn Lys Val Val Glu Ala Gly Leu Phe Ala Gly Trp
            580                 585                 590
Val Lys Gln Ile Val Asn Asp Phe Val Ile Glu Ala Asn Lys Ser Asn
        595                 600                 605
Thr Met Asp Lys Ile Ala Asp Ile Ser Leu Ile Val Pro Tyr Ile Gly
        610                 615                 620
Leu Ala Leu Asn Val Gly Asn Glu Thr Ala Lys Gly Asn Phe Glu Asn
625                 630                 635                 640
Ala Phe Glu Ile Ala Gly Ala Ser Ile Leu Leu Glu Phe Ile Pro Glu
                645                 650                 655
Leu Leu Ile Pro Val Val Gly Ala Phe Leu Leu Glu Ser Tyr Ile Asp
            660                 665                 670
Asn Lys Asn Lys Ile Ile Lys Thr Ile Asp Asn Ala Leu Thr Lys Arg
        675                 680                 685
Asn Glu Lys Trp Ser Asp Met Tyr Gly Leu Ile Val Ala Gln Trp Leu
        690                 695                 700
Ser Thr Val Asn Thr Gln Phe Tyr Thr Ile Lys Glu Gly Met Tyr Lys
705                 710                 715                 720
Ala Leu Asn Tyr Gln Ala Gln Ala Leu Glu Glu Ile Ile Lys Tyr Arg
                725                 730                 735
Tyr Asn Ile Tyr Ser Glu Lys Glu Lys Ser Asn Ile Asn Ile Asp Phe
            740                 745                 750
Asn Asp Ile Asn Ser Lys Leu Asn Glu Gly Ile Asn Gln Ala Ile Asp
        755                 760                 765
Asn Ile Asn Asn Phe Ile Asn Gly Cys Ser Val Ser Tyr Leu Met Lys
        770                 775                 780
Lys Met Ile Pro Leu Ala Val Glu Lys Leu Leu Asp Phe Asp Asn Thr
785                 790                 795                 800
Leu Lys Lys Asn Leu Leu Asn Tyr Ile Asp Glu Asn Lys Leu Tyr Leu
                805                 810                 815
Ile Gly Ser Ala Glu Tyr Glu Lys Ser Lys Val Asn Lys Tyr Leu Lys
            820                 825                 830
Thr Ile Met Pro Phe Asp Leu Ser Ile Tyr Thr Asn Asp Thr Ile Leu
        835                 840                 845
Ile Glu Met Phe Asn Lys Tyr Asn Ser Glu Ile Leu Asn Asn Ile Ile
        850                 855                 860
Leu Asn Leu Arg Tyr Lys Asp Asn Asn Leu Ile Asp Leu Ser Gly Tyr
865                 870                 875                 880
Gly Ala Lys Val Glu Val Tyr Asp Gly Val Glu Leu Asn Asp Lys Asn
                885                 890                 895
Gln Phe Lys Leu Thr Ser Ser Ala Asn Ser Lys Ile Arg Val Thr Gln
            900                 905                 910
Asn Gln Asn Ile Ile Phe Asn Ser Val Phe Leu Asp Phe Ser Val Ser
        915                 920                 925
Phe Trp Ile Arg Ile Pro Lys Tyr Lys Asn Asp Gly Ile Gln Asn Tyr
        930                 935                 940
Ile His Asn Glu Tyr Thr Ile Ile Asn Cys Met Lys Asn Asn Ser Gly
945                 950                 955                 960
Trp Lys Ile Ser Ile Arg Gly Asn Arg Ile Ile Trp Thr Leu Ile Asp
                965                 970                 975
Ile Asn Gly Lys Thr Lys Ser Val Phe Phe Glu Tyr Asn Ile Arg Glu
            980                 985                 990
```

-continued

```
Asp Ile Ser Glu Tyr Ile Asn Arg  Trp Phe Phe Val Thr  Ile Thr Asn
        995                 1000                 1005

Asn Leu  Asn Asn Ala Lys Ile  Tyr Ile Asn Gly Lys  Leu Glu Ser
    1010                 1015                 1020

Asn Thr Asp Ile Lys Asp Ile  Arg Glu Val Ile Ala  Asn Gly Glu
    1025                 1030                 1035

Ile Ile  Phe Lys Leu Asp Gly  Asp Ile Asp Arg Thr  Gln Phe Ile
    1040                 1045                 1050

Trp Met Lys Tyr Phe Ser Ile  Phe Asn Thr Glu Leu  Ser Gln Ser
    1055                 1060                 1065

Asn Ile  Glu Glu Arg Tyr Lys  Ile Gln Ser Tyr Ser  Glu Tyr Leu
    1070                 1075                 1080

Lys Asp  Phe Trp Gly Asn Pro  Leu Met Tyr Asn Lys  Glu Tyr Tyr
    1085                 1090                 1095

Met Phe  Asn Ala Gly Asn Lys  Asn Ser Tyr Ile Lys  Leu Lys Lys
    1100                 1105                 1110

Asp Ser  Pro Val Gly Glu Ile  Leu Thr Arg Ser Lys  Tyr Asn Gln
    1115                 1120                 1125

Asn Ser  Lys Tyr Ile Asn Tyr  Arg Asp Leu Tyr Ile  Gly Glu Lys
    1130                 1135                 1140

Phe Ile  Ile Arg Arg Lys Ser  Asn Ser Gln Ser Ile  Asn Asp Asp
    1145                 1150                 1155

Ile Val  Arg Lys Glu Asp Tyr  Ile Tyr Leu Asp Phe  Phe Asn Leu
    1160                 1165                 1170

Asn Gln  Glu Trp Arg Val Tyr  Thr Tyr Lys Tyr Phe  Lys Lys Glu
    1175                 1180                 1185

Glu Glu  Lys Leu Phe Leu Ala  Pro Ile Ser Asp Ser  Asp Glu Phe
    1190                 1195                 1200

Tyr Asn  Thr Ile Gln Ile Lys  Glu Tyr Asp Glu Gln  Pro Thr Tyr
    1205                 1210                 1215

Ser Cys  Gln Leu Leu Phe Lys  Lys Asp Glu Glu Ser  Thr Asp Glu
    1220                 1225                 1230

Ile Gly  Leu Ile Gly Ile His  Arg Phe Tyr Glu Ser  Gly Ile Val
    1235                 1240                 1245

Phe Glu  Glu Tyr Lys Asp Tyr  Phe Cys Ile Ser Lys  Trp Tyr Leu
    1250                 1255                 1260

Lys Glu  Val Lys Arg Lys Pro  Tyr Asn Leu Lys Leu  Gly Cys Asn
    1265                 1270                 1275

Trp Gln  Phe Ile Pro Lys Asp  Glu Gly Trp Thr Glu
    1280                 1285                 1290

<210> SEQ ID NO 221
<211> LENGTH: 1027
<212> TYPE: PRT
<213> ORGANISM: Artificial Sequence
<220> FEATURE:
<223> OTHER INFORMATION: sequence of collagen
<220> FEATURE:
<221> NAME/KEY: MISC_FEATURE
<222> LOCATION: (96)..(937)
<223> OTHER INFORMATION: Note = Note = "Xaa" at positions 96 through 937 may be any amino acid

<400> SEQUENCE: 221

Tyr Arg Ala Gly Pro Arg Tyr Ile Gln Ala Gln Val Gly Pro Ile Gly
1               5                   10                  15

Pro Arg Gly Pro Pro Gly Pro Pro Gly Ser Pro Gly Gln Gln Gly Tyr
            20                  25                  30
```

-continued

```
Gln Gly Leu Arg Gly Glu Pro Gly Asp Ser Gly Pro Met Gly Pro Ile
             35                  40                  45
Gly Lys Arg Gly Pro Pro Gly Pro Ala Gly Ile Ala Gly Lys Ser Gly
         50                  55                  60
Asp Asp Gly Arg Asp Gly Glu Pro Gly Pro Arg Gly Gly Ile Gly Pro
 65                  70                  75                  80
Met Gly Pro Arg Gly Ala Gly Gly Met Pro Gly Met Pro Gly Pro Xaa
                 85                  90                  95
Gly His Arg Gly Phe Arg Gly Leu Ser Gly Ser Xaa Gly Glu Gln Gly
                100                 105                 110
Lys Ser Gly Asn Gln Gly Pro Asp Gly Gly Pro Gly Pro Ala Gly Pro
            115                 120                 125
Ser Gly Pro Ile Gly Pro Arg Gly Gln Thr Gly Glu Arg Gly Arg Asp
        130                 135                 140
Gly Lys Ser Gly Leu Pro Gly Leu Arg Gly Val Asp Gly Leu Ala Gly
145                 150                 155                 160
Pro Pro Gly Pro Pro Gly Pro Ile Gly Ser Thr Gly Ser Pro Gly Phe
                165                 170                 175
Pro Gly Thr Pro Gly Ser Lys Gly Asp Arg Gly Gln Ser Gly Ile Xaa
                180                 185                 190
Gly Ala Gln Gly Leu Gln Gly Pro Val Gly Leu Ser Gly Gln Pro Gly
            195                 200                 205
Val Ala Gly Glu Asn Gly His Pro Gly Met Pro Gly Met Asp Gly Ala
        210                 215                 220
Asn Gly Glu Pro Gly Ala Ser Gly Glu Ser Gly Leu Pro Gly Pro Ser
225                 230                 235                 240
Gly Phe Pro Gly Pro Arg Gly Met Pro Gly Thr Ala Gly Ser Pro Gly
                245                 250                 255
Gln Ala Gly Ala Xaa Gly Asp Gly Gly Pro Thr Gly Glu Gln Gly Arg
                260                 265                 270
Pro Gly Ala Pro Gly Val Xaa Gly Ser Ser Gly Pro Pro Gly Asp Val
            275                 280                 285
Gly Ala Pro Gly His Ala Gly Glu Ala Gly Lys Arg Gly Ser Pro Gly
        290                 295                 300
Ser Pro Gly Pro Ala Gly Ser Pro Gly Pro Gln Gly Asp Arg Gly Leu
305                 310                 315                 320
Pro Gly Ser Arg Gly Leu Pro Gly Met Thr Gly Ala Ser Gly Ala Met
                325                 330                 335
Gly Ile Pro Gly Glu Lys Gly Pro Ser Gly Glu Pro Gly Ala Lys Gly
            340                 345                 350
Pro Thr Gly Asp Thr Gly Arg Gln Gly Asn Gln Gly Thr Pro Gly Ile
        355                 360                 365
Ala Gly Leu Pro Gly Asn Pro Gly Ser Asp Gly Arg Pro Gly Lys Asp
        370                 375                 380
Gly Arg Pro Gly Ile Arg Gly Lys Asp Gly Lys Gln Gly Glu Gln Gly
385                 390                 395                 400
Pro Gln Gly Pro Gln Gly Leu Ala Gly Leu Gln Gly Arg Ala Gly Pro
                405                 410                 415
Pro Gly Ala Arg Gly Glu Pro Gly Lys Asn Gly Ala Pro Gly Glu Pro
            420                 425                 430
Gly Ala His Gly Glu Gln Gly Asp Ala Gly Lys Asp Gly Glu Thr Gly
        435                 440                 445
```

-continued

```
Ala Ala Gly Pro Pro Gly Ala Ala Gly Pro Thr Gly Ala Arg Gly Pro
    450                 455                 460
Pro Gly Pro Arg Gly Gln Gln Gly Phe Gln Gly Leu Ala Gly Ala Gln
465                 470                 475                 480
Gly Thr Pro Gly Glu Ala Gly Lys Thr Gly Glu Arg Gly Ala Val Gly
                485                 490                 495
Ala Thr Gly Pro Ser Gly Pro Ala Gly Pro Gly Glu Arg Gly Ala
            500                 505                 510
Pro Gly Asp Arg Gly Asn Val Gly Pro Arg Gly Met Pro Gly Glu Arg
        515                 520                 525
Gly Ala Thr Gly Pro Ala Gly Pro Thr Gly Ser Pro Gly Val Ala Gly
    530                 535                 540
Ala Lys Gly Gln Gly Gly Pro Pro Gly Pro Ala Gly Leu Val Gly Leu
545                 550                 555                 560
Pro Gly Glu Arg Gly Pro Lys Gly Val Gly Gly Ser Xaa Gly Ser Arg
                565                 570                 575
Gly Asp Ile Gly Pro Arg Gly Lys Ala Gly Glu Arg Gly Lys Asp Gly
            580                 585                 590
Glu Arg Gly Glu Arg Gly Glu Asn Gly Leu Pro Gly Pro Ser Gly Leu
        595                 600                 605
Ala Ala Ser Xaa Gly Glu Arg Gly Asp Met Gly Ser Pro Gly Glu Arg
    610                 615                 620
Gly Ser Pro Gly Pro Ala Gly Glu Arg Gly Pro Ala Gly Ser Gln Gly
625                 630                 635                 640
Ile Gln Gly Gln Pro Gly Pro Gly Asp Ala Gly Pro Ala Gly Thr
                645                 650                 655
Xaa Gly Asp Ile Gly Phe Pro Gly Glu Arg Gly Thr Arg Gly Ala Thr
            660                 665                 670
Gly Lys Gln Gly Ala Arg Gly Pro Arg Gly Leu Ala Gly Lys Arg Gly
        675                 680                 685
Leu Arg Gly Ala Gly Gly Ser Arg Gly Glu Thr Gly Ala Gln Gly Glu
    690                 695                 700
Ile Gly Leu Pro Gly Ser Pro Gly Gln Pro Gly Leu Pro Gly Pro Ser
705                 710                 715                 720
Gly Gln Pro Gly Pro Ser Gly Pro Ala Gly Thr Ala Gly Lys Gln Gly
                725                 730                 735
Val Xaa Gly Ala Arg Gly Ser Pro Gly Leu Val Gly Lys Gln Gly Asp
            740                 745                 750
Arg Gly Ser Asp Gly Glu Pro Gly Arg Asp Gly Thr Xaa Gly Glu Arg
        755                 760                 765
Gly Glu Asp Gly Pro Pro Gly Val Ser Gly Pro Thr Gly Ala Pro Gly
    770                 775                 780
Gln Gln Gly Glu Arg Gly Met Pro Gly Met Val Gly Leu Arg Gly Glu
785                 790                 795                 800
Thr Gly Pro Met Gly Gly Gln Gly Met Xaa Gly Asp Gly Gly Pro Pro
                805                 810                 815
Gly Pro Ser Gly Asp Arg Gly Glu Arg Gly Asn Ala Gly Pro Gln Gly
            820                 825                 830
Pro Thr Gly Pro Ser Gly Gln Ala Gly Ala Pro Gly Gln Glu Gly Ala
        835                 840                 845
Pro Gly Lys Asp Gly Leu Pro Gly Leu Ala Gly Arg Pro Gly Glu Arg
    850                 855                 860
Gly Glu Pro Gly Val Ala Gly Arg Ala Gly Ser Gln Gly Leu Ala Gly
```

-continued

```
                865                 870                 875                 880
Leu Met Gly Gln Arg Gly Leu Pro Gly Ala Ala Gly Pro Pro Gly Asp
                    885                 890                 895
Arg Gly Glu Arg Gly Glu Pro Gly Gly Gln Gly Val Gln Gly Pro Val
                900                 905                 910
Gly Ala Pro Gly Ser Gln Gly Pro Ala Gly Ile Met Gly Met Xaa Gly
            915                 920                 925
Glu Ala Gly Gly Lys Gly Ala Xaa Gly Asp Lys Gly Trp Thr Gly Leu
    930                 935                 940
Pro Gly Leu Gln Gly Leu Gln Gly Thr Pro Gly His Ser Gly Glu Ser
945                 950                 955                 960
Gly Pro Pro Gly Ala Pro Gly Pro Arg Gly Ala Arg Gly Glu Ala Gly
                965                 970                 975
Gly Arg Gly Ser Gln Gly Pro Pro Gly Lys Asp Gly Gln Pro Gly Pro
                980                 985                 990
Ser Gly Arg Val Gly Pro Arg Gly  Pro Ser Gly Asp Asp  Gly Arg Ser
                995                 1000                1005
Gly Pro  Pro Gly Pro Pro Gly  Pro Pro Gly Pro Pro  Gly Asn Ser
    1010                1015                1020
Asp Tyr  Gly Ala
    1025
```

<210> SEQ ID NO 222
<211> LENGTH: 230
<212> TYPE: PRT
<213> ORGANISM: Artificial Sequence
<220> FEATURE:
<223> OTHER INFORMATION: sequence of collagenase

<400> SEQUENCE: 222

```
Ile Ile Asn Gly Tyr Glu Ala Tyr Thr Gly Leu Phe Pro Tyr Gln Ala
1               5                   10                  15
Gly Leu Asp Ile Thr Leu Gln Asp Gln Arg Arg Val Trp Cys Gly Gly
                20                  25                  30
Ser Leu Ile Asp Asn Lys Trp Ile Leu Thr Ala Ala His Cys Val His
            35                  40                  45
Asp Ala Val Ser Val Val Tyr Leu Gly Ser Ala Val Gln Tyr Glu
    50                  55                  60
Gly Glu Ala Val Val Asn Ser Glu Arg Ile Ile Ser His Ser Met Phe
65                  70                  75                  80
Asn Pro Asp Thr Tyr Leu Asn Asp Val Ala Leu Ile Lys Ile Pro His
                85                  90                  95
Val Glu Tyr Thr Asp Asn Ile Gln Pro Ile Arg Leu Pro Ser Gly Glu
                100                 105                 110
Glu Leu Asn Asn Lys Phe Glu Asn Ile Trp Ala Thr Val Ser Gly Trp
            115                 120                 125
Gly Gln Ser Asn Thr Asp Thr Val Ile Leu Gln Tyr Thr Tyr Asn Leu
    130                 135                 140
Val Ile Asp Asn Asp Arg Cys Ala Gln Glu Tyr Pro Pro Gly Ile Ile
145                 150                 155                 160
Val Glu Ser Thr Ile Cys Gly Asp Thr Cys Asp Gly Lys Ser Pro Cys
                165                 170                 175
Phe Gly Asp Ser Gly Gly Pro Phe Val Leu Ser Asp Lys Asn Leu Leu
            180                 185                 190
Ile Gly Val Val Ser Phe Val Ser Gly Ala Gly Cys Glu Ser Gly Lys
    195                 200                 205
```

-continued

```
Pro Val Gly Phe Ser Arg Val Thr Ser Tyr Met Asp Trp Ile Gln Gln
    210                 215                 220

Asn Thr Gly Ile Ile Phe
225             230

<210> SEQ ID NO 223
<211> LENGTH: 241
<212> TYPE: PRT
<213> ORGANISM: Artificial Sequence
<220> FEATURE:
<223> OTHER INFORMATION: sequence of corticotropin ACTH

<400> SEQUENCE: 223

Trp Cys Leu Glu Ser Ser Gln Cys Gln Asp Leu Thr Thr Glu Ser Asn
1               5                   10                  15

Leu Leu Glu Cys Ile Arg Ala Cys Lys Pro Asp Leu Ser Ala Glu Thr
                20                  25                  30

Pro Met Phe Pro Gly Asn Gly Asp Glu Gln Pro Leu Thr Glu Asn Pro
            35                  40                  45

Arg Lys Tyr Val Met Gly His Phe Arg Trp Asp Arg Phe Gly Arg Arg
    50                  55                  60

Asn Ser Ser Ser Gly Ser Ser Gly Ala Gly Gln Lys Arg Glu Asp
65                  70                  75                  80

Val Ser Ala Gly Glu Asp Cys Gly Pro Leu Pro Glu Gly Gly Pro Glu
                85                  90                  95

Pro Arg Ser Asp Gly Ala Lys Pro Gly Pro Arg Glu Gly Lys Arg Ser
            100                 105                 110

Tyr Ser Met Glu His Phe Arg Trp Gly Lys Pro Val Gly Lys Lys Arg
        115                 120                 125

Arg Pro Val Lys Val Tyr Pro Asn Gly Ala Glu Asp Glu Ser Ala Glu
    130                 135                 140

Ala Phe Pro Leu Glu Phe Lys Arg Glu Leu Thr Gly Gln Arg Leu Arg
145                 150                 155                 160

Glu Gly Asp Gly Pro Asp Gly Pro Ala Asp Asp Gly Ala Gly Ala Gln
                165                 170                 175

Ala Asp Leu Glu His Ser Leu Leu Val Ala Ala Glu Lys Lys Asp Glu
            180                 185                 190

Gly Pro Tyr Arg Met Glu His Phe Arg Trp Gly Ser Pro Pro Lys Asp
        195                 200                 205

Lys Arg Tyr Gly Gly Phe Met Thr Ser Glu Lys Ser Gln Thr Pro Leu
    210                 215                 220

Val Thr Leu Phe Lys Asn Ala Ile Ile Lys Asn Ala Tyr Lys Lys Gly
225                 230                 235                 240

Glu

<210> SEQ ID NO 224
<211> LENGTH: 260
<212> TYPE: PRT
<213> ORGANISM: Artificial Sequence
<220> FEATURE:
<223> OTHER INFORMATION: sequence of dornase alfa

<400> SEQUENCE: 224

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
                20                  25                  30
```

-continued

```
Asp Ile Ala Leu Val Gln Glu Val Arg Asp Ser His Leu Thr Ala Val
         35                  40                  45

Gly Lys Leu Leu Asp Asn Leu Asn Gln Asp Ala Pro Asp Thr Tyr His
 50                  55                  60

Tyr Val Val Ser Glu Pro Leu Gly Arg Asn Ser Tyr Lys Glu Arg Tyr
 65                  70                  75                  80

Leu Phe Val Tyr Arg Pro Asp Gln Val Ser Ala Val Asp Ser Tyr Tyr
                 85                  90                  95

Tyr Asp Asp Gly Cys Glu Pro Cys Gly Asn Asp Thr Phe Asn Arg Glu
            100                 105                 110

Pro Ala Ile Val Arg Phe Phe Ser Arg Phe Thr Glu Val Arg Glu Phe
            115                 120                 125

Ala Ile Val Pro Leu His Ala Ala Pro Gly Asp Ala Val Ala Glu Ile
        130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 225
<211> LENGTH: 405
<212> TYPE: PRT
<213> ORGANISM: Artificial Sequence
<220> FEATURE:
<223> OTHER INFORMATION: sequence of eptacog alpha (factor VII)

<400> SEQUENCE: 225

Asn Ala Phe Leu Glu Glu Leu Arg Pro Gly Ser Leu Glu Arg Glu Cys
 1               5                  10                  15

Lys Glu Glu Gln Cys Ser Phe Glu Glu Ala Arg Glu Ile Phe Lys Asp
                20                  25                  30

Ala Glu Arg Thr Lys Leu Phe Trp Ile Ser Tyr Ser Asp Gly Asp Gln
             35                  40                  45

Cys Ala Ser Ser Pro Cys Gln Asn Gly Gly Ser Cys Lys Asp Gln Leu
 50                  55                  60

Gln Ser Tyr Ile Cys Phe Cys Leu Pro Ala Phe Glu Gly Arg Asn Cys
 65                  70                  75                  80

Glu Thr His Lys Asp Asp Gln Leu Ile Cys Val Asn Glu Asn Gly Gly
                 85                  90                  95

Cys Glu Gln Tyr Cys Ser Asp His Thr Gly Thr Lys Arg Ser Cys Arg
            100                 105                 110

Cys His Glu Gly Tyr Ser Leu Leu Ala Asp Gly Val Ser Cys Thr Pro
        115                 120                 125
```

```
Thr Val Glu Tyr Pro Cys Gly Lys Ile Pro Ile Leu Glu Lys Arg Asn
            130                 135                 140

Ala Ser Lys Pro Gln Gly Arg Ile Val Gly Lys Val Cys Pro Lys
145                 150                 155                 160

Gly Glu Cys Pro Trp Gln Val Leu Leu Leu Val Asn Gly Ala Gln Leu
                165                 170                 175

Cys Gly Gly Thr Leu Ile Asn Thr Ile Trp Val Val Ser Ala Ala His
            180                 185                 190

Cys Phe Asp Lys Ile Lys Asn Trp Arg Asn Leu Ile Ala Val Leu Gly
        195                 200                 205

Glu His Asp Leu Ser Glu His Asp Gly Asp Glu Gln Ser Arg Arg Val
    210                 215                 220

Ala Gln Val Ile Ile Pro Ser Thr Tyr Val Pro Gly Thr Thr Asn His
225                 230                 235                 240

Asp Ile Ala Leu Leu Arg Leu His Gln Pro Val Val Leu Thr Asp His
                245                 250                 255

Val Val Pro Leu Cys Leu Pro Glu Arg Thr Phe Ser Glu Arg Thr Leu
            260                 265                 270

Ala Phe Val Arg Phe Ser Leu Val Ser Gly Trp Gly Gln Leu Leu Asp
        275                 280                 285

Arg Gly Ala Thr Ala Leu Glu Leu Met Val Leu Asn Val Pro Arg Leu
    290                 295                 300

Met Thr Gln Asp Cys Leu Gln Gln Ser Arg Lys Val Gly Asp Ser Pro
305                 310                 315                 320

Asn Ile Thr Glu Tyr Met Phe Cys Ala Gly Tyr Ser Asp Gly Ser Lys
                325                 330                 335

Asp Ser Cys Lys Gly Asp Ser Gly Gly Pro His Ala Thr His Tyr Arg
            340                 345                 350

Gly Thr Trp Tyr Leu Thr Gly Ile Val Ser Trp Gly Gln Gly Cys Ala
        355                 360                 365

Thr Val Gly His Phe Gly Val Tyr Thr Arg Val Ser Gln Tyr Ile Glu
    370                 375                 380

Trp Leu Gln Lys Leu Met Arg Ser Glu Pro Arg Pro Gly Val Leu Leu
385                 390                 395                 400

Arg Ala Pro Phe Pro
                405

<210> SEQ ID NO 226
<211> LENGTH: 439
<212> TYPE: PRT
<213> ORGANISM: Artificial Sequence
<220> FEATURE:
<223> OTHER INFORMATION: sequence of etanercept

<400> SEQUENCE: 226

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80
```

-continued

```
Asp Gln Val Glu Thr Gln Ala Cys Thr Arg Glu Gln Asn Arg Ile Cys
                 85                  90                  95
Thr Cys Arg Pro Gly Trp Tyr Cys Ala Leu Ser Lys Gln Glu Gly Cys
            100                 105                 110
Arg Leu Cys Ala Pro Leu Arg Lys Cys Arg Pro Gly Phe Gly Val Ala
        115                 120                 125
Arg Pro Gly Thr Glu Thr Ser Asp Val Val Cys Lys Pro Cys Ala Pro
    130                 135                 140
Gly Thr Phe Ser Asn Thr Thr Ser Ser Thr Asp Ile Cys Arg Pro His
145                 150                 155                 160
Gln Ile Cys Asn Val Val Ala Ile Pro Gly Asn Ala Ser Arg Asp Ala
                165                 170                 175
Val Cys Thr Ser Thr Ser Pro Thr Arg Ser Met Ala Pro Gly Ala Val
            180                 185                 190
His Leu Pro Gln Pro Val Ser Thr Arg Ser Gln His Thr Gln Pro Thr
        195                 200                 205
Pro Glu Pro Ser Thr Ala Pro Ser Thr Ser Phe Leu Leu Pro Met Gly
    210                 215                 220
Pro Ser Pro Pro Ala Glu Gly Ser Thr Gly Asp Phe Ala Leu Pro Val
225                 230                 235                 240
Gly Leu Ile Val Gly Val Thr Ala Leu Gly Leu Leu Ile Ile Gly Val
                245                 250                 255
Val Asn Cys Val Ile Met Thr Gln Val Lys Lys Pro Leu Cys Leu
            260                 265                 270
Gln Arg Glu Ala Lys Val Pro His Leu Pro Ala Asp Lys Ala Arg Gly
        275                 280                 285
Thr Gln Gly Pro Glu Gln Gln His Leu Leu Ile Thr Ala Pro Ser Ser
    290                 295                 300
Ser Ser Ser Ser Leu Glu Ser Ser Ala Ser Ala Leu Asp Arg Arg Ala
305                 310                 315                 320
Pro Thr Arg Asn Gln Pro Gln Ala Pro Gly Val Glu Ala Ser Gly Ala
                325                 330                 335
Gly Glu Ala Arg Ala Ser Thr Gly Ser Ser Asp Ser Ser Pro Gly Gly
            340                 345                 350
His Gly Thr Gln Val Asn Val Thr Cys Ile Val Asn Val Cys Ser Ser
        355                 360                 365
Ser Asp His Ser Ser Gln Cys Ser Ser Gln Ala Ser Ser Thr Met Gly
    370                 375                 380
Asp Thr Asp Ser Ser Pro Ser Glu Ser Pro Lys Asp Glu Gln Val Pro
385                 390                 395                 400
Phe Ser Lys Glu Glu Cys Ala Phe Arg Ser Gln Leu Glu Thr Pro Glu
                405                 410                 415
Thr Leu Leu Gly Ser Thr Glu Glu Lys Pro Leu Pro Leu Gly Val Pro
            420                 425                 430
Asp Ala Gly Met Lys Pro Ser
        435
```

<210> SEQ ID NO 227
<211> LENGTH: 166
<212> TYPE: PRT
<213> ORGANISM: Artificial Sequence
<220> FEATURE:
<223> OTHER INFORMATION: sequence of erythropoietin

<400> SEQUENCE: 227

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145             150                 155                 160

Cys Arg Thr Gly Asp Arg
                165

<210> SEQ ID NO 228
<211> LENGTH: 64
<212> TYPE: PRT
<213> ORGANISM: Artificial Sequence
<220> FEATURE:
<223> OTHER INFORMATION: sequence of exendin-4

<400> SEQUENCE: 228

Met Pro Val Glu Ser Gly Leu Ser Ser Glu Asp Ser Ala Ser Ser Glu
1               5                   10                  15

Ser Phe Ala Ser Lys Ile Lys Arg His Gly Glu Gly Thr Phe Thr Ser
            20                  25                  30

Asp Leu Ser Lys Gln Met Glu Glu Ala Val Arg Leu Phe Ile Glu
            35                  40                  45

Trp Leu Lys Asn Gly Gly Pro Ser Ser Gly Ala Pro Pro Ser Gly
    50                  55                  60

<210> SEQ ID NO 229
<211> LENGTH: 2332
<212> TYPE: PRT
<213> ORGANISM: Artificial Sequence
<220> FEATURE:
<223> OTHER INFORMATION: sequence of factor VIII

<400> SEQUENCE: 229

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
```

```
            65                  70                  75                  80
Tyr Asp Thr Val Val Ile Thr Leu Lys Asn Met Ala Ser His Pro Val
                    85                  90                  95
Ser Leu His Ala Val Gly Val Ser Tyr Trp Lys Ala Ser Glu Gly Ala
                   100                 105                 110
Glu Tyr Asp Asp Gln Thr Ser Gln Arg Glu Lys Glu Asp Asp Lys Val
                   115                 120                 125
Phe Pro Gly Gly Ser His Thr Tyr Val Trp Gln Val Leu Lys Glu Asn
                   130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                   165                 170                 175
Leu Val Cys Arg Glu Gly Ser Leu Ala Lys Glu Lys Thr Gln Thr Leu
                   180                 185                 190
His Lys Phe Ile Leu Leu Phe Ala Val Phe Asp Glu Gly Lys Ser Trp
                   195                 200                 205
His Ser Glu Thr Lys Asn Ser Leu Met Gln Asp Arg Asp Ala Ala Ser
                   210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                   245                 250                 255
Val Ile Gly Met Gly Thr Thr Pro Glu Val His Ser Ile Phe Leu Glu
                   260                 265                 270
Gly His Thr Phe Leu Val Arg Asn His Arg Gln Ala Ser Leu Glu Ile
                   275                 280                 285
Ser Pro Ile Thr Phe Leu Thr Ala Gln Thr Leu Leu Met Asp Leu Gly
                   290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                   325                 330                 335
Met Lys Asn Asn Glu Glu Ala Glu Asp Tyr Asp Asp Asp Leu Thr Asp
                   340                 345                 350
Ser Glu Met Asp Val Val Arg Phe Asp Asp Asp Asn Ser Pro Ser Phe
                   355                 360                 365
Ile Gln Ile Arg Ser Val Ala Lys Lys His Pro Lys Thr Trp Val His
                   370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                   405                 410                 415
Gln Arg Ile Gly Arg Lys Tyr Lys Lys Val Arg Phe Met Ala Tyr Thr
                   420                 425                 430
Asp Glu Thr Phe Lys Thr Arg Glu Ala Ile Gln His Glu Ser Gly Ile
                   435                 440                 445
Leu Gly Pro Leu Leu Tyr Gly Glu Val Gly Asp Thr Leu Leu Ile Ile
                   450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                   485                 490                 495
```

```
His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
            690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
            755                 760                 765

Thr Asp Pro Trp Phe Ala His Arg Thr Pro Met Pro Lys Ile Gln Asn
            770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
            850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910
```

-continued

```
Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185

Asn Gln Glu Lys Lys Ile Gln Glu Glu Ile Glu Lys Lys Glu Thr
    1190                1195                1200

Leu Ile Gln Glu Asn Val Val Leu Pro Gln Ile His Thr Val Thr
    1205                1210                1215

Gly Thr Lys Asn Phe Met Lys Asn Leu Phe Leu Leu Ser Thr Arg
    1220                1225                1230

Gln Asn Val Glu Gly Ser Tyr Asp Gly Ala Tyr Ala Pro Val Leu
    1235                1240                1245

Gln Asp Phe Arg Ser Leu Asn Asp Ser Thr Asn Arg Thr Lys Lys
    1250                1255                1260

His Thr Ala His Phe Ser Lys Lys Gly Glu Glu Glu Asn Leu Glu
    1265                1270                1275

Gly Leu Gly Asn Gln Thr Lys Gln Ile Val Glu Lys Tyr Ala Cys
    1280                1285                1290

Thr Thr Arg Ile Ser Pro Asn Thr Ser Gln Gln Asn Phe Val Thr
    1295                1300                1305

Gln Arg Ser Lys Arg Ala Leu Lys Gln Phe Arg Leu Pro Leu Glu
```

-continued

|   | 1310 |   |   |   | 1315 |   |   |   | 1320 |   |   |
|---|------|---|---|---|------|---|---|---|------|---|---|

Glu Thr Glu Leu Glu Lys Arg Ile Ile Val Asp Asp Thr Ser Thr
1325                  1330                  1335

Gln Trp Ser Lys Asn Met Lys His Leu Thr Pro Ser Thr Leu Thr
1340                  1345                  1350

Gln Ile Asp Tyr Asn Glu Lys Glu Lys Gly Ala Ile Thr Gln Ser
1355                  1360                  1365

Pro Leu Ser Asp Cys Leu Thr Arg Ser His Ser Ile Pro Gln Ala
1370                  1375                  1380

Asn Arg Ser Pro Leu Pro Ile Ala Lys Val Ser Ser Phe Pro Ser
1385                  1390                  1395

Ile Arg Pro Ile Tyr Leu Thr Arg Val Leu Phe Gln Asp Asn Ser
1400                  1405                  1410

Ser His Leu Pro Ala Ala Ser Tyr Arg Lys Lys Asp Ser Gly Val
1415                  1420                  1425

Gln Glu Ser Ser His Phe Leu Gln Gly Ala Lys Lys Asn Asn Leu
1430                  1435                  1440

Ser Leu Ala Ile Leu Thr Leu Glu Met Thr Gly Asp Gln Arg Glu
1445                  1450                  1455

Val Gly Ser Leu Gly Thr Ser Ala Thr Asn Ser Val Thr Tyr Lys
1460                  1465                  1470

Lys Val Glu Asn Thr Val Leu Pro Lys Pro Asp Leu Pro Lys Thr
1475                  1480                  1485

Ser Gly Lys Val Glu Leu Leu Pro Lys Val His Ile Tyr Gln Lys
1490                  1495                  1500

Asp Leu Phe Pro Thr Glu Thr Ser Asn Gly Ser Pro Gly His Leu
1505                  1510                  1515

Asp Leu Val Glu Gly Ser Leu Leu Gln Gly Thr Glu Gly Ala Ile
1520                  1525                  1530

Lys Trp Asn Glu Ala Asn Arg Pro Gly Lys Val Pro Phe Leu Arg
1535                  1540                  1545

Val Ala Thr Glu Ser Ser Ala Lys Thr Pro Ser Lys Leu Leu Asp
1550                  1555                  1560

Pro Leu Ala Trp Asp Asn His Tyr Gly Thr Gln Ile Pro Lys Glu
1565                  1570                  1575

Glu Trp Lys Ser Gln Glu Lys Ser Pro Glu Lys Thr Ala Phe Lys
1580                  1585                  1590

Lys Lys Asp Thr Ile Leu Ser Leu Asn Ala Cys Glu Ser Asn His
1595                  1600                  1605

Ala Ile Ala Ala Ile Asn Glu Gly Gln Asn Lys Pro Glu Ile Glu
1610                  1615                  1620

Val Thr Trp Ala Lys Gln Gly Arg Thr Glu Arg Leu Cys Ser Gln
1625                  1630                  1635

Asn Pro Pro Val Leu Lys Arg His Gln Arg Glu Ile Thr Arg Thr
1640                  1645                  1650

Thr Leu Gln Ser Asp Gln Glu Glu Ile Asp Tyr Asp Asp Thr Ile
1655                  1660                  1665

Ser Val Glu Met Lys Lys Glu Asp Phe Asp Ile Tyr Asp Glu Asp
1670                  1675                  1680

Glu Asn Gln Ser Pro Arg Ser Phe Gln Lys Lys Thr Arg His Tyr
1685                  1690                  1695

Phe Ile Ala Ala Val Glu Arg Leu Trp Asp Tyr Gly Met Ser Ser
1700                  1705                  1710

-continued

```
Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860

Asn Pro Ala His Gly Arg Gln Val Thr Val Gln Glu Phe Ala Leu
1865                1870                1875

Phe Phe Thr Ile Phe Asp Glu Thr Lys Ser Trp Tyr Phe Thr Glu
1880                1885                1890

Asn Met Glu Arg Asn Cys Arg Ala Pro Cys Asn Ile Gln Met Glu
1895                1900                1905

Asp Pro Thr Phe Lys Glu Asn Tyr Arg Phe His Ala Ile Asn Gly
1910                1915                1920

Tyr Ile Met Asp Thr Leu Pro Gly Leu Val Met Ala Gln Asp Gln
1925                1930                1935

Arg Ile Arg Trp Tyr Leu Leu Ser Met Gly Ser Asn Glu Asn Ile
1940                1945                1950

His Ser Ile His Phe Ser Gly His Val Phe Thr Val Arg Lys Lys
1955                1960                1965

Glu Glu Tyr Lys Met Ala Leu Tyr Asn Leu Tyr Pro Gly Val Phe
1970                1975                1980

Glu Thr Val Glu Met Leu Pro Ser Lys Ala Gly Ile Trp Arg Val
1985                1990                1995

Glu Cys Leu Ile Gly Glu His Leu His Ala Gly Met Ser Thr Leu
2000                2005                2010

Phe Leu Val Tyr Ser Asn Lys Cys Gln Thr Pro Leu Gly Met Ala
2015                2020                2025

Ser Gly His Ile Arg Asp Phe Gln Ile Thr Ala Ser Gly Gln Tyr
2030                2035                2040

Gly Gln Trp Ala Pro Lys Leu Ala Arg Leu His Tyr Ser Gly Ser
2045                2050                2055

Ile Asn Ala Trp Ser Thr Lys Glu Pro Phe Ser Trp Ile Lys Val
2060                2065                2070

Asp Leu Leu Ala Pro Met Ile Ile His Gly Ile Lys Thr Gln Gly
2075                2080                2085

Ala Arg Gln Lys Phe Ser Ser Leu Tyr Ile Ser Gln Phe Ile Ile
2090                2095                2100
```

```
Met Tyr Ser Leu Asp Gly Lys Lys Trp Gln Thr Tyr Arg Gly Asn
    2105            2110                2115

Ser Thr Gly Thr Leu Met Val Phe Phe Gly Asn Val Asp Ser Ser
    2120            2125                2130

Gly Ile Lys His Asn Ile Phe Asn Pro Pro Ile Ile Ala Arg Tyr
    2135            2140                2145

Ile Arg Leu His Pro Thr His Tyr Ser Ile Arg Ser Thr Leu Arg
    2150            2155                2160

Met Glu Leu Met Gly Cys Asp Leu Asn Ser Cys Ser Met Pro Leu
    2165            2170                2175

Gly Met Glu Ser Lys Ala Ile Ser Asp Ala Gln Ile Thr Ala Ser
    2180            2185                2190

Ser Tyr Phe Thr Asn Met Phe Ala Thr Trp Ser Pro Ser Lys Ala
    2195            2200                2205

Arg Leu His Leu Gln Gly Arg Ser Asn Ala Trp Arg Pro Gln Val
    2210            2215                2220

Asn Asn Pro Lys Glu Trp Leu Gln Val Asp Phe Gln Lys Thr Met
    2225            2230                2235

Lys Val Thr Gly Val Thr Thr Gln Gly Val Lys Ser Leu Leu Thr
    2240            2245                2250

Ser Met Tyr Val Lys Glu Phe Leu Ile Ser Ser Ser Gln Asp Gly
    2255            2260                2265

His Gln Trp Thr Leu Phe Phe Gln Asn Gly Lys Val Lys Val Phe
    2270            2275                2280

Gln Gly Asn Gln Asp Ser Phe Thr Pro Val Val Asn Ser Leu Asp
    2285            2290                2295

Pro Pro Leu Leu Thr Arg Tyr Leu Arg Ile His Pro Gln Ser Trp
    2300            2305                2310

Val His Gln Ile Ala Leu Arg Met Glu Val Leu Gly Cys Glu Ala
    2315            2320                2325

Gln Asp Leu Tyr
    2330

<210> SEQ ID NO 230
<211> LENGTH: 144
<212> TYPE: PRT
<213> ORGANISM: Artificial Sequence
<220> FEATURE:
<223> OTHER INFORMATION: light chain sequence of factor IX

<400> SEQUENCE: 230

Asn Ser Gly Lys Leu Glu Glu Phe Val Gln Gly Asn Leu Glu Arg Glu
1               5                   10                  15

Cys Met Glu Glu Lys Cys Ser Phe Glu Glu Ala Arg Glu Val Phe Glu
            20                  25                  30

Asn Thr Glu Arg Thr Thr Glu Phe Trp Lys Gln Tyr Val Asp Gly Asp
        35                  40                  45

Gln Cys Glu Ser Asn Pro Cys Leu Asn Gly Gly Ser Cys Lys Asp Asp
    50                  55                  60

Ile Asn Ser Tyr Glu Cys Trp Cys Pro Phe Gly Phe Glu Gly Lys Asn
65                  70                  75                  80

Cys Glu Leu Asp Val Thr Cys Asn Ile Lys Asn Gly Arg Cys Glu Gln
                85                  90                  95

Phe Cys Lys Asn Ser Ala Asp Asn Lys Val Val Cys Ser Cys Thr Glu
            100                 105                 110
```

```
Gly Tyr Arg Leu Ala Glu Asn Gln Lys Ser Cys Glu Pro Ala Val Pro
            115                 120                 125

Phe Pro Cys Gly Arg Val Ser Val Ser Gln Thr Ser Lys Leu Thr Arg
        130                 135                 140
```

<210> SEQ ID NO 231
<211> LENGTH: 270
<212> TYPE: PRT
<213> ORGANISM: Artificial Sequence
<220> FEATURE:
<223> OTHER INFORMATION: heavy chain sequence of factor IX

<400> SEQUENCE: 231

```
Ala Glu Ala Val Phe Pro Asp Val Asp Tyr Val Asn Ser Thr Glu Ala
1               5                   10                  15

Glu Thr Ile Leu Asp Asn Ile Thr Gln Ser Thr Gln Ser Phe Asn Asp
            20                  25                  30

Phe Thr Arg Val Val Gly Gly Glu Asp Ala Lys Pro Gly Gln Phe Pro
        35                  40                  45

Trp Gln Val Val Leu Asn Gly Lys Val Asp Ala Phe Cys Gly Gly Ser
    50                  55                  60

Ile Val Asn Glu Lys Trp Ile Val Thr Ala Ala His Cys Val Glu Thr
65                  70                  75                  80

Gly Val Lys Ile Thr Val Val Ala Gly Glu His Asn Ile Glu Glu Thr
                85                  90                  95

Glu His Thr Glu Gln Lys Arg Asn Val Ile Arg Ile Ile Pro His His
            100                 105                 110

Asn Tyr Asn Ala Ala Ile Asn Lys Tyr Asn His Asp Ile Ala Leu Leu
        115                 120                 125

Glu Leu Asp Glu Pro Leu Val Leu Asn Ser Tyr Val Thr Pro Ile Cys
    130                 135                 140

Ile Ala Asp Lys Glu Tyr Thr Asn Ile Phe Leu Lys Phe Gly Ser Gly
145                 150                 155                 160

Tyr Val Ser Gly Trp Gly Arg Val Phe His Lys Gly Arg Ser Ala Leu
                165                 170                 175

Val Leu Gln Tyr Leu Arg Val Pro Leu Val Asp Arg Ala Thr Cys Leu
            180                 185                 190

Arg Ser Thr Lys Phe Thr Ile Tyr Asn Asn Met Phe Cys Ala Gly Phe
        195                 200                 205

His Glu Gly Gly Arg Asp Ser Cys Gln Gly Asp Ser Gly Gly Pro His
    210                 215                 220

Val Thr Glu Val Glu Gly Thr Ser Phe Leu Thr Gly Ile Ile Ser Trp
225                 230                 235                 240

Gly Glu Glu Cys Ala Met Lys Gly Lys Tyr Gly Ile Tyr Thr Lys Val
                245                 250                 255

Ser Arg Tyr Val Asn Trp Ile Lys Glu Lys Thr Lys Leu Thr
            260                 265                 270
```

<210> SEQ ID NO 232
<211> LENGTH: 139
<212> TYPE: PRT
<213> ORGANISM: Artificial Sequence
<220> FEATURE:
<223> OTHER INFORMATION: light chain sequence of factor X

<400> SEQUENCE: 232

```
Ala Asn Ser Phe Leu Glu Glu Met Lys Lys Gly His Leu Glu Arg Glu
1               5                   10                  15
```

```
Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
            35                  40                  45

Gln Cys Glu Thr Ser Pro Cys Gln Asn Gln Gly Lys Cys Lys Asp Gly
            50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Gln Asn Ser Val Val Cys Ser Cys Ala
            100                 105                 110

Arg Gly Tyr Thr Leu Ala Asp Asn Gly Lys Ala Cys Ile Pro Thr Gly
            115                 120                 125

Pro Tyr Pro Cys Gly Lys Gln Thr Leu Glu Arg
            130                 135
```

<210> SEQ ID NO 233
<211> LENGTH: 309
<212> TYPE: PRT
<213> ORGANISM: Artificial Sequence
<220> FEATURE:
<223> OTHER INFORMATION: heavy chain sequence of factor X

<400> SEQUENCE: 233

```
Arg Lys Arg Ser Val Ala Gln Ala Thr Ser Ser Ser Gly Glu Ala Pro
1               5                   10                  15

Asp Ser Ile Thr Trp Lys Pro Tyr Asp Ala Ala Asp Leu Asp Pro Thr
            20                  25                  30

Glu Asn Pro Phe Asp Leu Leu Asp Phe Asn Gln Thr Gln Pro Glu Arg
            35                  40                  45

Gly Asp Asn Asn Leu Thr Arg Ile Val Gly Gly Gln Glu Cys Lys Asp
            50                  55                  60

Gly Glu Cys Pro Trp Gln Ala Leu Leu Ile Asn Glu Glu Asn Glu Gly
65                  70                  75                  80

Phe Cys Gly Gly Thr Ile Leu Ser Glu Phe Tyr Ile Leu Thr Ala Ala
                85                  90                  95

His Cys Leu Tyr Gln Ala Lys Arg Phe Lys Val Arg Val Gly Asp Arg
            100                 105                 110

Asn Thr Glu Gln Glu Glu Gly Gly Glu Ala Val His Glu Val Glu Val
            115                 120                 125

Val Ile Lys His Asn Arg Phe Thr Lys Glu Thr Tyr Asp Phe Asp Ile
            130                 135                 140

Ala Val Leu Arg Leu Lys Thr Pro Ile Thr Phe Arg Met Asn Val Ala
145                 150                 155                 160

Pro Ala Cys Leu Pro Glu Arg Asp Trp Ala Glu Ser Thr Leu Met Thr
                165                 170                 175

Gln Lys Thr Gly Ile Val Ser Gly Phe Gly Arg Thr His Glu Lys Gly
            180                 185                 190

Arg Gln Ser Thr Arg Leu Lys Met Leu Glu Val Pro Tyr Val Asp Arg
            195                 200                 205

Asn Ser Cys Lys Leu Ser Ser Ser Phe Ile Ile Thr Gln Asn Met Phe
            210                 215                 220

Cys Ala Gly Tyr Asp Thr Lys Gln Glu Asp Ala Cys Gln Gly Asp Ser
225                 230                 235                 240
```

-continued

Gly Gly Pro His Val Thr Arg Phe Lys Asp Thr Tyr Phe Val Thr Gly
                245                 250                 255

Ile Val Ser Trp Gly Glu Gly Cys Ala Arg Lys Gly Lys Tyr Gly Ile
            260                 265                 270

Tyr Thr Lys Val Thr Ala Phe Leu Lys Trp Ile Asp Arg Ser Met Lys
        275                 280                 285

Thr Arg Gly Leu Pro Lys Ala Lys Ser His Ala Pro Glu Val Ile Thr
    290                 295                 300

Ser Ser Pro Leu Lys
305

<210> SEQ ID NO 234
<211> LENGTH: 693
<212> TYPE: PRT
<213> ORGANISM: Artificial Sequence
<220> FEATURE:
<223> OTHER INFORMATION: sequence of factor XIII

<400> SEQUENCE: 234

Val Asn Leu Gln Glu Phe Leu Asn Val Thr Ser Val His Leu Phe Lys
1               5                   10                  15

Glu Arg Trp Asp Thr Asn Lys Val Asp His His Thr Asp Lys Tyr Glu
            20                  25                  30

Asn Asn Lys Leu Ile Val Arg Arg Gly Gln Ser Phe Tyr Val Gln Ile
        35                  40                  45

Asp Phe Ser Arg Pro Tyr Asp Pro Arg Arg Asp Leu Phe Arg Val Glu
    50                  55                  60

Tyr Val Ile Gly Arg Tyr Pro Gln Glu Asn Lys Gly Thr Tyr Ile Pro
65                  70                  75                  80

Val Pro Ile Val Ser Glu Leu Gln Ser Gly Lys Trp Gly Ala Lys Ile
                85                  90                  95

Val Met Arg Glu Asp Arg Ser Val Arg Leu Ser Ile Gln Ser Ser Pro
            100                 105                 110

Lys Cys Ile Val Gly Lys Phe Arg Met Tyr Val Ala Val Trp Thr Pro
        115                 120                 125

Tyr Gly Val Leu Arg Thr Ser Arg Asn Pro Glu Thr Asp Thr Tyr Ile
    130                 135                 140

Leu Phe Asn Pro Trp Cys Glu Asp Asp Ala Val Tyr Leu Asp Asn Glu
145                 150                 155                 160

Lys Glu Arg Glu Glu Tyr Val Leu Asn Asp Ile Gly Val Ile Phe Tyr
                165                 170                 175

Gly Glu Val Asn Asp Ile Lys Thr Arg Ser Trp Ser Tyr Gly Gln Phe
            180                 185                 190

Glu Asp Gly Ile Leu Asp Thr Cys Leu Tyr Val Met Asp Arg Ala Gln
        195                 200                 205

Met Asp Leu Ser Gly Arg Gly Asn Pro Ile Lys Val Ser Arg Val Gly
    210                 215                 220

Ser Ala Met Val Asn Ala Lys Asp Asp Glu Gly Val Leu Val Gly Ser
225                 230                 235                 240

Trp Asp Asn Ile Tyr Ala Tyr Gly Val Pro Pro Ser Ala Trp Thr Gly
                245                 250                 255

Ser Val Asp Ile Leu Leu Glu Tyr Arg Ser Ser Glu Asn Pro Val Arg
            260                 265                 270

Tyr Gly Gln Cys Trp Val Phe Ala Gly Val Phe Asn Thr Phe Leu Arg
        275                 280                 285

-continued

```
Cys Leu Gly Ile Pro Ala Arg Ile Val Thr Asn Tyr Phe Ser Ala His
    290                 295                 300

Asp Asn Asp Ala Asn Leu Gln Met Asp Ile Phe Leu Glu Glu Asp Gly
305                 310                 315                 320

Asn Val Asn Ser Lys Leu Thr Lys Asp Ser Val Trp Asn Tyr His Cys
                325                 330                 335

Trp Asn Glu Ala Trp Met Thr Arg Pro Asp Leu Pro Val Gly Phe Gly
            340                 345                 350

Gly Trp Gln Ala Val Asp Ser Thr Pro Gln Glu Asn Ser Asp Gly Met
        355                 360                 365

Tyr Arg Cys Gly Pro Ala Ser Val Gln Ala Ile Lys His Gly His Val
    370                 375                 380

Cys Phe Gln Phe Asp Ala Pro Phe Val Phe Ala Glu Val Asn Ser Asp
385                 390                 395                 400

Leu Ile Tyr Ile Thr Ala Lys Lys Asp Gly Thr His Val Val Glu Asn
                405                 410                 415

Val Asp Ala Thr His Ile Gly Lys Leu Ile Val Thr Lys Gln Ile Gly
            420                 425                 430

Gly Asp Gly Met Met Asp Ile Thr Asp Thr Tyr Lys Phe Gln Glu Gly
        435                 440                 445

Gln Glu Glu Glu Arg Leu Ala Leu Glu Thr Ala Leu Met Tyr Gly Ala
    450                 455                 460

Lys Lys Pro Leu Asn Thr Glu Gly Val Met Lys Ser Arg Ser Asn Val
465                 470                 475                 480

Asp Met Asp Phe Glu Val Glu Asn Ala Val Leu Gly Lys Asp Phe Lys
                485                 490                 495

Leu Ser Ile Thr Phe Arg Asn Asn Ser His Asn Arg Tyr Thr Ile Thr
            500                 505                 510

Ala Tyr Leu Ser Ala Asn Ile Thr Phe Tyr Thr Gly Val Pro Lys Ala
        515                 520                 525

Glu Phe Lys Lys Glu Thr Phe Asp Val Thr Leu Glu Pro Leu Ser Phe
    530                 535                 540

Lys Lys Glu Ala Val Leu Ile Gln Ala Gly Glu Tyr Met Gly Gln Leu
545                 550                 555                 560

Leu Glu Gln Ala Ser Leu His Phe Phe Val Thr Ala Arg Ile Asn Glu
                565                 570                 575

Thr Arg Asp Val Leu Ala Lys Gln Lys Ser Thr Val Leu Thr Ile Pro
            580                 585                 590

Glu Ile Ile Ile Lys Val Arg Gly Thr Gln Val Val Gly Ser Asp Met
        595                 600                 605

Thr Val Thr Val Gln Phe Thr Asn Pro Leu Lys Glu Thr Leu Arg Asn
    610                 615                 620

Val Trp Val His Leu Asp Gly Pro Gly Val Thr Arg Pro Met Lys Lys
625                 630                 635                 640

Met Phe Arg Glu Ile Arg Pro Asn Ser Thr Val Gln Trp Glu Glu Val
                645                 650                 655

Cys Arg Pro Trp Val Ser Gly His Arg Lys Leu Ile Ala Ser Met Ser
            660                 665                 670

Ser Asp Ser Leu Arg His Val Tyr Gly Glu Leu Asp Val Gln Ile Gln
        675                 680                 685

Arg Arg Pro Ser Met
    690
```

<210> SEQ ID NO 235
<211> LENGTH: 2355
<212> TYPE: PRT
<213> ORGANISM: Artificial Sequence
<220> FEATURE:
<223> OTHER INFORMATION: sequence of fibronectin

<400> SEQUENCE: 235

```
Gln Ala Gln Gln Met Val Gln Pro Gln Ser Pro Val Ala Val Ser Gln
1               5                   10                  15

Ser Lys Pro Gly Cys Tyr Asp Asn Gly Lys His Tyr Gln Ile Asn Gln
            20                  25                  30

Gln Trp Glu Arg Thr Tyr Leu Gly Asn Ala Leu Val Cys Thr Cys Tyr
        35                  40                  45

Gly Gly Ser Arg Gly Phe Asn Cys Glu Ser Lys Pro Glu Ala Glu Glu
    50                  55                  60

Thr Cys Phe Asp Lys Tyr Thr Gly Asn Thr Tyr Arg Val Gly Asp Thr
65                  70                  75                  80

Tyr Glu Arg Pro Lys Asp Ser Met Ile Trp Asp Cys Thr Cys Ile Gly
                85                  90                  95

Ala Gly Arg Gly Arg Ile Ser Cys Thr Ile Ala Asn Arg Cys His Glu
            100                 105                 110

Gly Gly Gln Ser Tyr Lys Ile Gly Asp Thr Trp Arg Arg Pro His Glu
        115                 120                 125

Thr Gly Gly Tyr Met Leu Glu Cys Val Cys Leu Gly Asn Gly Lys Gly
    130                 135                 140

Glu Trp Thr Cys Lys Pro Ile Ala Glu Lys Cys Phe Asp His Ala Ala
145                 150                 155                 160

Gly Thr Ser Tyr Val Val Gly Glu Thr Trp Glu Lys Pro Tyr Gln Gly
                165                 170                 175

Trp Met Met Val Asp Cys Thr Cys Leu Gly Glu Gly Ser Gly Arg Ile
            180                 185                 190

Thr Cys Thr Ser Arg Asn Arg Cys Asn Asp Gln Asp Thr Arg Thr Ser
        195                 200                 205

Tyr Arg Ile Gly Asp Thr Trp Ser Lys Lys Asp Asn Arg Gly Asn Leu
    210                 215                 220

Leu Gln Cys Ile Cys Thr Gly Asn Gly Arg Gly Glu Trp Lys Cys Glu
225                 230                 235                 240

Arg His Thr Ser Val Gln Thr Thr Ser Ser Gly Ser Gly Pro Phe Thr
                245                 250                 255

Asp Val Arg Ala Ala Val Tyr Gln Pro Gln Pro His Pro Gln Pro Pro
            260                 265                 270

Pro Tyr Gly His Cys Val Thr Asp Ser Gly Val Val Tyr Ser Val Gly
        275                 280                 285

Met Gln Trp Leu Lys Thr Gln Gly Asn Lys Gln Met Leu Cys Thr Cys
    290                 295                 300

Leu Gly Asn Gly Val Ser Cys Gln Glu Thr Ala Val Thr Gln Thr Tyr
305                 310                 315                 320

Gly Gly Asn Ser Asn Gly Glu Pro Cys Val Leu Pro Phe Thr Tyr Asn
                325                 330                 335

Gly Arg Thr Phe Tyr Ser Cys Thr Thr Glu Gly Arg Gln Asp Gly His
            340                 345                 350

Leu Trp Cys Ser Thr Thr Ser Asn Tyr Glu Gln Asp Gln Lys Tyr Ser
        355                 360                 365
```

```
Phe Cys Thr Asp His Thr Val Leu Val Gln Thr Gln Gly Gly Asn Ser
    370                 375                 380

Asn Gly Ala Leu Cys His Phe Pro Phe Leu Tyr Asn Asn His Asn Tyr
385                 390                 395                 400

Thr Asp Cys Thr Ser Glu Gly Arg Arg Asp Asn Met Lys Trp Cys Gly
            405                 410                 415

Thr Thr Gln Asn Tyr Asp Ala Asp Gln Lys Phe Gly Phe Cys Pro Met
        420                 425                 430

Ala Ala His Glu Glu Ile Cys Thr Thr Asn Glu Gly Val Met Tyr Arg
            435                 440                 445

Ile Gly Asp Gln Trp Asp Lys Gln His Asp Met Gly His Met Met Arg
        450                 455                 460

Cys Thr Cys Val Gly Asn Gly Arg Gly Glu Trp Thr Cys Ile Ala Tyr
465                 470                 475                 480

Ser Gln Leu Arg Asp Gln Cys Ile Val Asp Asp Ile Thr Tyr Asn Val
            485                 490                 495

Asn Asp Thr Phe His Lys Arg His Glu Glu Gly His Met Leu Asn Cys
            500                 505                 510

Thr Cys Phe Gly Gln Gly Arg Gly Arg Trp Lys Cys Asp Pro Val Asp
        515                 520                 525

Gln Cys Gln Asp Ser Glu Thr Gly Thr Phe Tyr Gln Ile Gly Asp Ser
530                 535                 540

Trp Glu Lys Tyr Val His Gly Val Arg Tyr Gln Cys Tyr Cys Tyr Gly
545                 550                 555                 560

Arg Gly Ile Gly Glu Trp His Cys Gln Pro Leu Gln Thr Tyr Pro Ser
            565                 570                 575

Ser Ser Gly Pro Val Glu Val Phe Ile Thr Glu Thr Pro Ser Gln Pro
        580                 585                 590

Asn Ser His Pro Ile Gln Trp Asn Ala Pro Gln Pro Ser His Ile Ser
        595                 600                 605

Lys Tyr Ile Leu Arg Trp Arg Pro Lys Asn Ser Val Gly Arg Trp Lys
        610                 615                 620

Glu Ala Thr Ile Pro Gly His Leu Asn Ser Tyr Thr Ile Lys Gly Leu
625                 630                 635                 640

Lys Pro Gly Val Val Tyr Glu Gly Gln Leu Ile Ser Ile Gln Gln Tyr
            645                 650                 655

Gly His Gln Glu Val Thr Arg Phe Asp Phe Thr Thr Ser Thr Ser
            660                 665                 670

Thr Pro Val Thr Ser Asn Thr Val Thr Gly Glu Thr Thr Pro Phe Ser
        675                 680                 685

Pro Leu Val Ala Thr Ser Glu Ser Val Thr Glu Ile Thr Ala Ser Ser
        690                 695                 700

Phe Val Val Ser Trp Val Ser Ala Ser Asp Thr Val Ser Gly Phe Arg
705                 710                 715                 720

Val Glu Tyr Glu Leu Ser Glu Glu Gly Asp Glu Pro Gln Tyr Leu Asp
            725                 730                 735

Leu Pro Ser Thr Ala Thr Ser Val Asn Ile Pro Asp Leu Leu Pro Gly
            740                 745                 750

Arg Lys Tyr Ile Val Asn Val Tyr Gln Ile Ser Glu Asp Gly Glu Gln
        755                 760                 765

Ser Leu Ile Leu Ser Thr Ser Gln Thr Thr Ala Pro Asp Ala Pro Pro
770                 775                 780

Asp Pro Thr Val Asp Gln Val Asp Asp Thr Ser Ile Val Val Arg Trp
```

-continued

```
                785                 790                 795                 800
Ser Arg Pro Gln Ala Pro Ile Thr Gly Tyr Arg Ile Val Tyr Ser Pro
                    805                 810                 815
Ser Val Glu Gly Ser Ser Thr Glu Leu Asn Leu Pro Glu Thr Ala Asn
                    820                 825                 830
Ser Val Thr Leu Ser Asp Leu Gln Pro Gly Val Gln Tyr Asn Ile Thr
                    835                 840                 845
Ile Tyr Ala Val Glu Glu Asn Gln Glu Ser Thr Pro Val Val Ile Gln
            850                 855                 860
Gln Glu Thr Thr Gly Thr Pro Arg Ser Asp Thr Val Pro Ser Pro Arg
865                 870                 875                 880
Asp Leu Gln Phe Val Glu Val Thr Asp Val Lys Val Thr Ile Met Trp
                        885                 890                 895
Thr Pro Pro Glu Ser Ala Val Thr Gly Tyr Arg Val Asp Val Ile Pro
                    900                 905                 910
Val Asn Leu Pro Gly Glu His Gly Gln Arg Leu Pro Ile Ser Arg Asn
                    915                 920                 925
Thr Phe Ala Glu Val Thr Gly Leu Ser Pro Gly Val Thr Tyr Tyr Phe
        930                 935                 940
Lys Val Phe Ala Val Ser His Gly Arg Glu Ser Lys Pro Leu Thr Ala
945                 950                 955                 960
Gln Gln Thr Thr Lys Leu Asp Ala Pro Thr Asn Leu Gln Phe Val Asn
                    965                 970                 975
Glu Thr Asp Ser Thr Val Leu Val Arg Trp Thr Pro Pro Arg Ala Gln
                980                 985                 990
Ile Thr Gly Tyr Arg Leu Thr Val  Gly Leu Thr Arg Arg  Gly Gln Pro
                    995                 1000                1005
Arg Gln  Tyr Asn Val Gly Pro  Ser Val Ser Lys Tyr  Pro Leu Arg
    1010                1015                1020
Asn Leu  Gln Pro Ala Ser Glu  Tyr Thr Val Ser Leu  Val Ala Ile
    1025                1030                1035
Lys Gly  Asn Gln Glu Ser Pro  Lys Ala Thr Gly Val  Phe Thr Thr
    1040                1045                1050
Leu Gln  Pro Gly Ser Ser Ile  Pro Pro Tyr Asn Thr  Glu Val Thr
    1055                1060                1065
Glu Thr  Thr Ile Val Ile Thr  Trp Thr Pro Ala Pro  Arg Ile Gly
    1070                1075                1080
Phe Lys  Leu Gly Val Arg Pro  Ser Gln Gly Gly Glu  Ala Pro Arg
    1085                1090                1095
Glu Val  Thr Ser Asp Ser Gly  Ser Ile Val Val Ser  Gly Leu Thr
    1100                1105                1110
Pro Gly  Val Glu Tyr Val Tyr  Thr Ile Gln Val Leu  Arg Asp Gly
    1115                1120                1125
Gln Glu  Arg Asp Ala Pro Ile  Val Asn Lys Val Val  Thr Pro Leu
    1130                1135                1140
Ser Pro  Pro Thr Asn Leu His  Leu Glu Ala Asn Pro  Asp Thr Gly
    1145                1150                1155
Val Leu  Thr Val Ser Trp Glu  Arg Ser Thr Thr Pro  Asp Ile Thr
    1160                1165                1170
Gly Tyr  Arg Ile Thr Thr Thr  Pro Thr Asn Gly Gln  Gln Gly Asn
    1175                1180                1185
Ser Leu  Glu Glu Val Val His  Ala Asp Gln Ser Ser  Cys Thr Phe
    1190                1195                1200
```

-continued

```
Asp Asn Leu Ser Pro Gly Leu Glu Tyr Asn Val Ser Val Tyr Thr
1205                1210                1215
Val Lys Asp Asp Lys Glu Ser Val Pro Ile Ser Asp Thr Ile Ile
1220                1225                1230
Pro Ala Val Pro Pro Thr Asp Leu Arg Phe Thr Asn Ile Gly
1235                1240                1245
Pro Asp Thr Met Arg Val Thr Trp Ala Pro Pro Ser Ile Asp
1250                1255                1260
Leu Thr Asn Phe Leu Val Arg Tyr Ser Pro Val Lys Asn Glu Glu
1265                1270                1275
Asp Val Ala Glu Leu Ser Ile Ser Pro Ser Asp Asn Ala Val Val
1280                1285                1290
Leu Thr Asn Leu Leu Pro Gly Thr Glu Tyr Val Val Ser Val Ser
1295                1300                1305
Ser Val Tyr Glu Gln His Glu Ser Thr Pro Leu Arg Gly Arg Gln
1310                1315                1320
Lys Thr Gly Leu Asp Ser Pro Thr Gly Ile Asp Phe Ser Asp Ile
1325                1330                1335
Thr Ala Asn Ser Phe Thr Val His Trp Ile Ala Pro Arg Ala Thr
1340                1345                1350
Ile Thr Gly Tyr Arg Ile Arg His His Pro Glu His Phe Ser Gly
1355                1360                1365
Arg Pro Arg Glu Asp Arg Val Pro His Ser Arg Asn Ser Ile Thr
1370                1375                1380
Leu Thr Asn Leu Thr Pro Gly Thr Glu Tyr Val Val Ser Ile Val
1385                1390                1395
Ala Leu Asn Gly Arg Glu Glu Ser Pro Leu Leu Ile Gly Gln Gln
1400                1405                1410
Ser Thr Val Ser Asp Val Pro Arg Asp Leu Glu Val Val Ala Ala
1415                1420                1425
Thr Pro Thr Ser Leu Leu Ile Ser Trp Asp Ala Pro Ala Val Thr
1430                1435                1440
Val Arg Tyr Tyr Arg Ile Thr Tyr Gly Glu Thr Gly Gly Asn Ser
1445                1450                1455
Pro Val Gln Glu Phe Thr Val Pro Gly Ser Lys Ser Thr Ala Thr
1460                1465                1470
Ile Ser Gly Leu Lys Pro Gly Val Asp Tyr Thr Ile Thr Val Tyr
1475                1480                1485
Ala Val Thr Gly Arg Gly Asp Ser Pro Ala Ser Ser Lys Pro Ile
1490                1495                1500
Ser Ile Asn Tyr Arg Thr Glu Ile Asp Lys Pro Ser Gln Met Gln
1505                1510                1515
Val Thr Asp Val Gln Asp Asn Ser Ile Ser Val Lys Trp Leu Pro
1520                1525                1530
Ser Ser Ser Pro Val Thr Gly Tyr Arg Val Thr Thr Thr Pro Lys
1535                1540                1545
Asn Gly Pro Gly Pro Thr Lys Thr Lys Thr Ala Gly Pro Asp Gln
1550                1555                1560
Thr Glu Met Thr Ile Glu Gly Leu Gln Pro Thr Val Glu Tyr Val
1565                1570                1575
Val Ser Val Tyr Ala Gln Asn Pro Ser Gly Glu Ser Gln Pro Leu
1580                1585                1590
```

-continued

```
Val Gln Thr Ala Val Thr Asn Ile Asp Arg Pro Lys Gly Leu Ala
    1595                1600            1605

Phe Thr Asp Val Asp Val Asp Ser Ile Lys Ile Ala Trp Glu Ser
    1610                1615            1620

Pro Gln Gly Gln Val Ser Arg Tyr Arg Val Thr Tyr Ser Ser Pro
    1625                1630            1635

Glu Asp Gly Ile His Glu Leu Phe Pro Ala Pro Asp Gly Glu Glu
    1640                1645            1650

Asp Thr Ala Glu Leu Gln Gly Leu Arg Pro Gly Ser Glu Tyr Thr
    1655                1660            1665

Val Ser Val Val Ala Leu His Asp Asp Met Glu Ser Gln Pro Leu
    1670                1675            1680

Ile Gly Thr Gln Ser Thr Ala Ile Pro Ala Pro Thr Asp Leu Lys
    1685                1690            1695

Phe Thr Gln Val Thr Pro Thr Ser Leu Ser Ala Gln Trp Thr Pro
    1700                1705            1710

Pro Asn Val Gln Leu Thr Gly Tyr Arg Val Arg Val Thr Pro Lys
    1715                1720            1725

Glu Lys Thr Gly Pro Met Lys Glu Ile Asn Leu Ala Pro Asp Ser
    1730                1735            1740

Ser Ser Val Val Val Ser Gly Leu Met Val Ala Thr Lys Tyr Glu
    1745                1750            1755

Val Ser Val Tyr Ala Leu Lys Asp Thr Leu Thr Ser Arg Pro Ala
    1760                1765            1770

Gln Gly Val Val Thr Thr Leu Glu Asn Val Ser Pro Pro Arg Arg
    1775                1780            1785

Ala Arg Val Thr Asp Ala Thr Glu Thr Thr Ile Thr Ile Ser Trp
    1790                1795            1800

Arg Thr Lys Thr Glu Thr Ile Thr Gly Phe Gln Val Asp Ala Val
    1805                1810            1815

Pro Ala Asn Gly Gln Thr Pro Ile Gln Arg Thr Ile Lys Pro Asp
    1820                1825            1830

Val Arg Ser Tyr Thr Ile Thr Gly Leu Gln Pro Gly Thr Asp Tyr
    1835                1840            1845

Lys Ile Tyr Leu Tyr Thr Leu Asn Asp Asn Ala Arg Ser Ser Pro
    1850                1855            1860

Val Val Ile Asp Ala Ser Thr Ala Ile Asp Ala Pro Ser Asn Leu
    1865                1870            1875

Arg Phe Leu Ala Thr Thr Pro Asn Ser Leu Leu Val Ser Trp Gln
    1880                1885            1890

Pro Pro Arg Ala Arg Ile Thr Gly Tyr Ile Ile Lys Tyr Glu Lys
    1895                1900            1905

Pro Gly Ser Pro Pro Arg Glu Val Val Pro Arg Pro Arg Pro Gly
    1910                1915            1920

Val Thr Glu Ala Thr Ile Thr Gly Leu Glu Pro Gly Thr Glu Tyr
    1925                1930            1935

Thr Ile Tyr Val Ile Ala Leu Lys Asn Asn Gln Lys Ser Glu Pro
    1940                1945            1950

Leu Ile Gly Arg Lys Lys Thr Asp Glu Leu Pro Gln Leu Val Thr
    1955                1960            1965

Leu Pro His Pro Asn Leu His Gly Pro Glu Ile Leu Asp Val Pro
    1970                1975            1980

Ser Thr Val Gln Lys Thr Pro Phe Val Thr His Pro Gly Tyr Asp
```

-continued

```
            1985                1990                1995
Thr Gly Asn Gly Ile Gln Leu Pro Gly Thr Ser Gly Gln Gln Pro
    2000                2005                2010

Ser Val Gly Gln Gln Met Ile Phe Glu Glu His Gly Phe Arg Arg
    2015                2020                2025

Thr Thr Pro Pro Thr Thr Ala Thr Pro Ile Arg His Arg Pro Arg
    2030                2035                2040

Pro Tyr Pro Pro Asn Val Gly Glu Glu Ile Gln Ile Gly His Ile
    2045                2050                2055

Pro Arg Glu Asp Val Asp Tyr His Leu Tyr Pro His Gly Pro Gly
    2060                2065                2070

Leu Asn Pro Asn Ala Ser Thr Gly Gln Glu Ala Leu Ser Gln Thr
    2075                2080                2085

Thr Ile Ser Trp Ala Pro Phe Gln Asp Thr Ser Glu Tyr Ile Ile
    2090                2095                2100

Ser Cys His Pro Val Gly Thr Asp Glu Glu Pro Leu Gln Phe Arg
    2105                2110                2115

Val Pro Gly Thr Ser Thr Ser Ala Thr Leu Thr Gly Leu Thr Arg
    2120                2125                2130

Gly Ala Thr Tyr Asn Ile Ile Val Glu Ala Leu Lys Asp Gln Gln
    2135                2140                2145

Arg His Lys Val Arg Glu Glu Val Val Thr Val Gly Asn Ser Val
    2150                2155                2160

Asn Glu Gly Leu Asn Gln Pro Thr Asp Asp Ser Cys Phe Asp Pro
    2165                2170                2175

Tyr Thr Val Ser His Tyr Ala Val Gly Asp Glu Trp Glu Arg Met
    2180                2185                2190

Ser Glu Ser Gly Phe Lys Leu Leu Cys Gln Cys Leu Gly Phe Gly
    2195                2200                2205

Ser Gly His Phe Arg Cys Asp Ser Ser Arg Trp Cys His Asp Asn
    2210                2215                2220

Gly Val Asn Tyr Lys Ile Gly Glu Lys Trp Asp Arg Gln Gly Glu
    2225                2230                2235

Asn Gly Gln Met Met Ser Cys Thr Cys Leu Gly Asn Gly Lys Gly
    2240                2245                2250

Glu Phe Lys Cys Asp Pro His Glu Ala Thr Cys Tyr Asp Asp Gly
    2255                2260                2265

Lys Thr Tyr His Val Gly Glu Gln Trp Gln Lys Glu Tyr Leu Gly
    2270                2275                2280

Ala Ile Cys Ser Cys Thr Cys Phe Gly Gly Gln Arg Gly Trp Arg
    2285                2290                2295

Cys Asp Asn Cys Arg Arg Pro Gly Gly Glu Pro Ser Pro Glu Gly
    2300                2305                2310

Thr Thr Gly Gln Ser Tyr Asn Gln Tyr Ser Gln Arg Tyr His Gln
    2315                2320                2325

Arg Thr Asn Thr Asn Val Asn Cys Pro Ile Glu Cys Phe Met Pro
    2330                2335                2340

Leu Asp Val Gln Ala Asp Arg Glu Asp Ser Arg Glu
    2345                2350                2355

<210> SEQ ID NO 236
<211> LENGTH: 831
<212> TYPE: PRT
<213> ORGANISM: Artificial Sequence
```

<220> FEATURE:
<223> OTHER INFORMATION: sequence of fibrinogen

<400> SEQUENCE: 236

```
Gly Pro Arg Val Val Glu Arg His Gln Ser Ala Cys Lys Asp Ser Asp
1               5                   10                  15

Trp Pro Phe Cys Ser Asp Glu Asp Trp Asn Tyr Lys Cys Pro Ser Gly
            20                  25                  30

Cys Arg Met Lys Gly Leu Ile Asp Glu Val Asn Gln Asp Phe Thr Asn
        35                  40                  45

Arg Ile Asn Lys Leu Lys Asn Ser Leu Phe Glu Tyr Gln Lys Asn Asn
    50                  55                  60

Lys Asp Ser His Ser Leu Thr Thr Asn Ile Met Glu Ile Leu Arg Gly
65                  70                  75                  80

Asp Phe Ser Ser Ala Asn Asn Arg Asp Asn Thr Tyr Asn Arg Val Ser
                85                  90                  95

Glu Asp Leu Arg Ser Arg Ile Glu Val Leu Lys Arg Lys Val Ile Glu
            100                 105                 110

Lys Val Gln His Ile Gln Leu Leu Gln Lys Asn Val Arg Ala Gln Leu
        115                 120                 125

Val Asp Met Lys Arg Leu Glu Val Asp Ile Asp Ile Lys Ile Arg Ser
    130                 135                 140

Cys Arg Gly Ser Cys Ser Arg Ala Leu Ala Arg Glu Val Asp Leu Lys
145                 150                 155                 160

Asp Tyr Glu Asp Gln Gln Lys Gln Leu Glu Gln Val Ile Ala Lys Asp
                165                 170                 175

Leu Leu Pro Ser Arg Asp Arg Gln His Leu Pro Leu Ile Lys Met Lys
            180                 185                 190

Pro Val Pro Asp Leu Val Pro Gly Asn Phe Lys Ser Gln Leu Gln Lys
        195                 200                 205

Val Pro Pro Glu Trp Lys Ala Leu Thr Asp Met Pro Gln Met Arg Met
    210                 215                 220

Glu Leu Glu Arg Pro Gly Gly Asn Glu Ile Thr Arg Gly Gly Ser Thr
225                 230                 235                 240

Ser Tyr Gly Thr Gly Ser Glu Thr Glu Ser Pro Arg Asn Pro Ser Ser
                245                 250                 255

Ala Gly Ser Trp Asn Ser Gly Ser Ser Gly Pro Gly Ser Thr Gly Asn
            260                 265                 270

Arg Asn Pro Gly Ser Ser Gly Thr Gly Gly Thr Ala Thr Trp Lys Pro
        275                 280                 285

Gly Ser Ser Gly Pro Gly Ser Thr Gly Ser Trp Asn Ser Gly Ser Ser
    290                 295                 300

Gly Thr Gly Ser Thr Gly Asn Gln Asn Pro Gly Ser Pro Arg Pro Gly
305                 310                 315                 320

Ser Thr Gly Thr Trp Asn Pro Gly Ser Ser Glu Arg Gly Ser Ala Gly
                325                 330                 335

His Trp Thr Ser Glu Ser Ser Val Ser Gly Ser Thr Gly Gln Trp His
            340                 345                 350

Ser Glu Ser Gly Ser Phe Arg Pro Asp Ser Pro Gly Ser Gly Asn Ala
        355                 360                 365

Arg Pro Asn Asn Pro Asp Trp Gly Thr Phe Glu Glu Val Ser Gly Asn
    370                 375                 380

Val Ser Pro Gly Thr Arg Arg Glu Tyr His Thr Glu Lys Leu Val Thr
385                 390                 395                 400
```

-continued

```
Ser Lys Gly Asp Lys Glu Leu Arg Thr Gly Lys Glu Lys Val Thr Ser
                405                 410                 415
Gly Ser Thr Thr Thr Arg Arg Ser Cys Ser Lys Thr Val Thr Lys
            420                 425                 430
Thr Val Ile Gly Pro Asp Gly His Lys Glu Val Thr Lys Glu Val Val
            435                 440                 445
Thr Ser Glu Asp Gly Ser Asp Cys Pro Glu Ala Met Asp Leu Gly Thr
    450                 455                 460
Leu Ser Gly Ile Gly Thr Leu Asp Gly Phe Arg His Arg His Pro Asp
465                 470                 475                 480
Glu Ala Ala Phe Phe Asp Thr Ala Ser Thr Gly Lys Thr Phe Pro Gly
                485                 490                 495
Phe Phe Ser Pro Met Leu Gly Glu Phe Val Ser Glu Thr Glu Ser Arg
            500                 505                 510
Gly Ser Glu Ser Gly Ile Phe Thr Asn Thr Lys Glu Ser Ser Ser His
            515                 520                 525
His Pro Gly Ile Ala Glu Phe Pro Ser Arg Gly Lys Ser Ser Ser Tyr
    530                 535                 540
Ser Lys Gln Phe Thr Ser Ser Thr Ser Tyr Asn Arg Gly Asp Ser Thr
545                 550                 555                 560
Phe Glu Ser Lys Ser Tyr Lys Met Ala Asp Glu Ala Gly Ser Glu Ala
                565                 570                 575
Asp His Glu Gly Thr His Ser Thr Lys Arg Gly His Ala Lys Ser Arg
            580                 585                 590
Pro Val Arg Asp Cys Asp Asp Val Leu Gln Thr His Pro Ser Gly Thr
            595                 600                 605
Gln Ser Gly Ile Phe Asn Ile Lys Leu Pro Gly Ser Ser Lys Ile Phe
    610                 615                 620
Ser Val Tyr Cys Asp Gln Glu Thr Ser Leu Gly Gly Trp Leu Leu Ile
625                 630                 635                 640
Gln Gln Arg Met Asp Gly Ser Leu Asn Phe Asn Arg Thr Trp Gln Asp
                645                 650                 655
Tyr Lys Arg Gly Phe Gly Ser Leu Asn Asp Glu Gly Glu Gly Glu Phe
            660                 665                 670
Trp Leu Gly Asn Asp Tyr Leu His Leu Leu Thr Gln Arg Gly Ser Val
            675                 680                 685
Leu Arg Val Glu Leu Glu Asp Trp Ala Gly Asn Glu Ala Tyr Ala Glu
    690                 695                 700
Tyr His Phe Arg Val Gly Ser Glu Ala Glu Gly Tyr Ala Leu Gln Val
705                 710                 715                 720
Ser Ser Tyr Glu Gly Thr Ala Gly Asp Ala Leu Ile Glu Gly Ser Val
                725                 730                 735
Glu Glu Gly Ala Glu Tyr Thr Ser His Asn Asn Met Gln Phe Ser Thr
            740                 745                 750
Phe Asp Arg Asp Ala Asp Gln Trp Glu Glu Asn Cys Ala Glu Val Tyr
            755                 760                 765
Gly Gly Gly Trp Trp Tyr Asn Asn Cys Gln Ala Ala Asn Leu Asn Gly
    770                 775                 780
Ile Tyr Tyr Pro Gly Gly Ser Tyr Asp Pro Arg Asn Asn Ser Pro Tyr
785                 790                 795                 800
Glu Ile Glu Asn Gly Val Val Trp Val Ser Phe Arg Gly Ala Asp Tyr
                805                 810                 815
```

```
Ser Leu Arg Ala Val Arg Met Lys Ile Arg Pro Leu Val Thr Gln
            820                 825                 830

<210> SEQ ID NO 237
<211> LENGTH: 177
<212> TYPE: PRT
<213> ORGANISM: Artificial Sequence
<220> FEATURE:
<223> OTHER INFORMATION: sequence of filgrastim

<400> SEQUENCE: 237

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Val Ser Glu Cys Ala Thr Tyr Lys Leu Cys His Pro Glu
        35                  40                  45

Glu Leu Val Leu Leu Gly His Ser Leu Gly Ile Pro Trp Ala Pro Leu
    50                  55                  60

Ser Ser Cys Pro Ser Gln Ala Leu Gln Leu Ala Gly Cys Leu Ser Gln
65                  70                  75                  80

Leu His Ser Gly Leu Phe Leu Tyr Gln Gly Leu Leu Gln Ala Leu Glu
                85                  90                  95

Gly Ile Ser Pro Glu Leu Gly Pro Thr Leu Asp Thr Leu Gln Leu Asp
            100                 105                 110

Val Ala Asp Phe Ala Thr Thr Ile Trp Gln Gln Met Glu Glu Leu Gly
        115                 120                 125

Met Ala Pro Ala Leu Gln Pro Thr Gln Gly Ala Met Pro Ala Phe Ala
    130                 135                 140

Ser Ala Phe Gln Arg Arg Ala Gly Gly Val Leu Val Ala Ser His Leu
145                 150                 155                 160

Gln Ser Phe Leu Glu Val Ser Tyr Arg Val Leu Arg His Leu Ala Gln
                165                 170                 175

Pro

<210> SEQ ID NO 238
<211> LENGTH: 96
<212> TYPE: PRT
<213> ORGANISM: Artificial Sequence
<220> FEATURE:
<223> OTHER INFORMATION: sequence of follitropin alpha

<400> SEQUENCE: 238

Phe Pro Asx Gly Glx Phe Thr Met Glx Gly Cys Pro Glx Cys Lys Leu
1               5                   10                  15

Lys Glx Asx Lys Tyr Phe Ser Lys Leu Gly Ala Pro Ile Tyr Glx Cys
            20                  25                  30

Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glx Ala Thr Cys Cys
    50                  55                  60

Val Ala Lys Ala Phe Thr Lys Ala Thr Val Met Gly Asx Ala Arg Val
65                  70                  75                  80

Glx Asn His Thr Glx Cys His Cys Ser Thr Cys Tyr Tyr His Lys Ser
                85                  90                  95

<210> SEQ ID NO 239
<211> LENGTH: 110
```

```
<212> TYPE: PRT
<213> ORGANISM: Artificial Sequence
<220> FEATURE:
<223> OTHER INFORMATION: sequence of follitropin beta

<400> SEQUENCE: 239

Ser Cys Glu Leu Thr Asn Ile Thr Ile Ala Ile Glu Lys Glu Glu Cys
1               5                   10                  15

Arg Phe Cys Ile Ser Ile Asn Thr Thr Trp Cys Ala Gly Tyr Cys Tyr
            20                  25                  30

Thr Arg Asp Leu Val Tyr Lys Asp Pro Ala Arg Pro Lys Ile Gln Lys
        35                  40                  45

Thr Cys Thr Phe Lys Glu Leu Val Tyr Glu Thr Val Arg Val Pro Gly
    50                  55                  60

Cys Ala His His Ala Asp Ser Leu Tyr Thr Tyr Pro Val Ala Thr Gln
65                  70                  75                  80

Cys His Cys Gly Lys Cys Asp Ser Asp Ser Thr Asp Cys Thr Val Arg
                85                  90                  95

Gly Leu Gly Pro Ser Tyr Cys Ser Phe Gly Glu Met Lys Glu
            100                 105                 110

<210> SEQ ID NO 240
<211> LENGTH: 45
<212> TYPE: PRT
<213> ORGANISM: Artificial Sequence
<220> FEATURE:
<223> OTHER INFORMATION: sequence of growth hormone releasing hormone

<400> SEQUENCE: 240

His Ala Asp Gly Leu Leu Asp Arg Ala Leu Arg Asp Ile Leu Val Gln
1               5                   10                  15

Leu Ser Ala Arg Lys Tyr Leu His Ser Leu Thr Ala Val Arg Val Gly
            20                  25                  30

Glu Glu Glu Glu Asp Glu Asp Ser Glu Pro Leu Ser
        35                  40                  45

<210> SEQ ID NO 241
<211> LENGTH: 37
<212> TYPE: PRT
<213> ORGANISM: Artificial Sequence
<220> FEATURE:
<223> OTHER INFORMATION: sequence of pituitary adenylate cyclase activa
      ting polypeptide

<400> SEQUENCE: 241

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Arg Arg Tyr Arg
            20                  25                  30

Gln Arg Phe Arg Asn
        35

<210> SEQ ID NO 242
<211> LENGTH: 474
<212> TYPE: PRT
<213> ORGANISM: Artificial Sequence
<220> FEATURE:
<223> OTHER INFORMATION: sequence of hyaluronidase

<400> SEQUENCE: 242

Leu Asn Phe Arg Ala Pro Pro Val Ile Pro Asn Val Pro Phe Leu Trp
1               5                   10                  15
```

```
Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
            35                  40                  45

Thr Gly Gln Gly Val Thr Ile Phe Tyr Val Asp Arg Leu Gly Tyr Tyr
            50                  55                  60

Pro Tyr Ile Asp Ser Ile Thr Gly Val Thr Val Asn Gly Gly Ile Pro
 65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
            115                 120                 125

Tyr Lys Asn Arg Ser Ile Glu Leu Val Gln Gln Asn Val Gln Leu
            130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
            165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
            195                 200                 205

Lys Arg Asn Asp Asp Leu Ser Trp Leu Trp Asn Glu Ser Thr Ala Leu
            210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
            245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
            275                 280                 285

Thr Phe Gly Glu Thr Val Ala Leu Gly Ala Ser Gly Ile Val Ile Trp
            290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
            325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
            355                 360                 365

Asn Phe Ala Ile Gln Leu Glu Lys Gly Gly Lys Phe Thr Val Arg Gly
            370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
            405                 410                 415

Thr Asp Ala Val Asp Val Cys Ile Ala Asp Gly Val Cys Ile Asp Ala
            420                 425                 430
```

```
Phe Leu Lys Pro Pro Met Glu Thr Glu Glu Pro Gln Ile Phe Tyr Asn
            435                 440                 445

Ala Ser Pro Ser Thr Leu Ser Ala Thr Met Phe Ile Val Ser Ile Leu
        450                 455                 460

Phe Leu Ile Ile Ser Ser Val Ala Ser Leu
465                 470

<210> SEQ ID NO 243
<211> LENGTH: 65
<212> TYPE: PRT
<213> ORGANISM: Artificial Sequence
<220> FEATURE:
<223> OTHER INFORMATION: sequence of hirudin II

<400> SEQUENCE: 243

Ile Thr Tyr Thr Asp Cys Thr Glu Ser Gly Gln Asp Leu Cys Leu Cys
1               5                   10                  15

Glu Gly Ser Asn Val Cys Gly Lys Gly Asn Lys Cys Ile Leu Gly Ser
            20                  25                  30

Asn Gly Glu Glu Asn Gln Cys Val Thr Gly Glu Gly Thr Pro Lys Pro
        35                  40                  45

Gln Ser His Asn Asp Gly Asp Phe Glu Glu Ile Pro Glu Glu Tyr Leu
    50                  55                  60

Gln
65

<210> SEQ ID NO 244
<211> LENGTH: 497
<212> TYPE: PRT
<213> ORGANISM: Artificial Sequence
<220> FEATURE:
<223> OTHER INFORMATION: sequence of imiglucerase

<400> SEQUENCE: 244

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190
```

```
Gly Lys Gly Ser Leu Lys Gly Gln Pro Gly Asp Ile Tyr His Gln Thr
            195                 200                 205
Trp Ala Arg Tyr Phe Val Lys Phe Leu Asp Ala Tyr Ala Glu His Lys
        210                 215                 220
Leu Gln Phe Trp Ala Val Thr Ala Glu Asn Glu Pro Ser Ala Gly Leu
225                 230                 235                 240
Leu Ser Gly Tyr Pro Phe Gln Cys Leu Gly Phe Thr Pro Glu His Gln
                245                 250                 255
Arg Asp Phe Ile Ala Arg Asp Leu Gly Pro Thr Leu Ala Asn Ser Thr
            260                 265                 270
His His Asn Val Arg Leu Leu Met Leu Asp Asp Gln Arg Leu Leu Leu
        275                 280                 285
Pro His Trp Ala Lys Val Val Leu Thr Asp Pro Glu Ala Ala Lys Tyr
    290                 295                 300
Val His Gly Ile Ala Val His Trp Tyr Leu Asp Phe Leu Ala Pro Ala
305                 310                 315                 320
Lys Ala Thr Leu Gly Glu Thr His Arg Leu Phe Pro Asn Thr Met Leu
                325                 330                 335
Phe Ala Ser Glu Ala Cys Val Gly Ser Lys Phe Trp Glu Gln Ser Val
            340                 345                 350
Arg Leu Gly Ser Trp Asp Arg Gly Met Gln Tyr Ser His Ser Ile Ile
        355                 360                 365
Thr Asn Leu Leu Tyr His Val Val Gly Trp Thr Asp Trp Asn Leu Ala
370                 375                 380
Leu Asn Pro Glu Gly Gly Pro Asn Trp Val Arg Asn Phe Val Asp Ser
385                 390                 395                 400
Pro Ile Ile Val Asp Ile Thr Lys Asp Thr Phe Tyr Lys Gln Pro Met
                405                 410                 415
Phe Tyr His Leu Gly His Phe Ser Lys Phe Ile Pro Glu Gly Ser Gln
            420                 425                 430
Arg Val Gly Leu Val Ala Ser Gln Lys Asn Asp Leu Asp Ala Val Ala
        435                 440                 445
Leu Met His Pro Asp Gly Ser Ala Val Val Val Leu Asn Arg Ser
450                 455                 460
Ser Lys Asp Val Pro Leu Thr Ile Lys Asp Pro Ala Val Gly Phe Leu
465                 470                 475                 480
Glu Thr Ile Ser Pro Gly Tyr Ser Ile His Thr Tyr Leu Trp His Arg
                485                 490                 495
Gln

<210> SEQ ID NO 245
<211> LENGTH: 133
<212> TYPE: PRT
<213> ORGANISM: Artificial Sequence
<220> FEATURE:
<223> OTHER INFORMATION: sequence of interleukin 2

<400> SEQUENCE: 245

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
```

```
Lys Ala Thr Glu Leu Lys His Leu Gln Cys Leu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 246
<211> LENGTH: 166
<212> TYPE: PRT
<213> ORGANISM: Artificial Sequence
<220> FEATURE:
<223> OTHER INFORMATION: sequence of interferon alpha-4

<400> SEQUENCE: 246

Cys Asp Leu Pro Glu Thr His Ser Leu Asp Asn Arg Arg Thr Leu Met
 1               5                  10                  15

Leu Leu Ala Gln Met Ser Arg Ile Ser Pro Ser Ser Cys Leu Met Asp
                 20                  25                  30

Arg His Asp Phe Gly Phe Pro Gln Glu Glu Phe Asp Gly Asn Gln Phe
             35                  40                  45

Gln Lys Ala Pro Ala Ile Ser Val Leu His Glu Leu Ile Gln Gln Ile
     50                  55                  60

Phe Asn Leu Phe Thr Thr Lys Asp Ser Ser Ala Ala Trp Asp Glu Asp
 65                  70                  75                  80

Leu Leu Asp Lys Phe Cys Thr Glu Leu Tyr Gln Gln Leu Asn Asp Leu
                 85                  90                  95

Glu Ala Cys Val Met Gln Glu Glu Arg Val Gly Glu Thr Pro Leu Met
                100                 105                 110

Asn Ala Asp Ser Ile Leu Ala Val Lys Lys Tyr Phe Arg Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 247
<211> LENGTH: 161
<212> TYPE: PRT
<213> ORGANISM: Artificial Sequence
<220> FEATURE:
<223> OTHER INFORMATION: sequence of interferon beta

<400> SEQUENCE: 247

Ile Asn Tyr Lys Gln Leu Gln Leu Gln Glu Arg Thr Asn Ile Arg Lys
 1               5                  10                  15

Cys Gln Glu Leu Leu Glu Gln Leu Asn Gly Lys Ile Asn Leu Thr Tyr
                 20                  25                  30

Arg Ala Asp Phe Lys Ile Pro Met Glu Met Thr Glu Lys Met Gln Lys
             35                  40                  45
```

```
Ser Tyr Thr Ala Phe Ala Ile Gln Glu Met Leu Gln Asn Val Phe Leu
 50                  55                  60

Val Phe Arg Asn Asn Phe Ser Ser Thr Gly Trp Asn Glu Thr Ile Val
 65                  70                  75                  80

Val Arg Leu Leu Asp Glu Leu His Gln Gln Thr Val Phe Leu Lys Thr
                 85                  90                  95

Val Leu Glu Glu Lys Gln Glu Glu Arg Leu Thr Trp Glu Met Ser Ser
            100                 105                 110

Thr Ala Leu His Leu Lys Ser Tyr Tyr Trp Arg Val Gln Arg Tyr Leu
            115                 120                 125

Lys Leu Met Lys Tyr Asn Ser Tyr Ala Trp Met Val Val Arg Ala Glu
            130                 135                 140

Ile Phe Arg Asn Phe Leu Ile Ile Arg Arg Leu Thr Arg Asn Phe Gln
145                 150                 155                 160

Asn

<210> SEQ ID NO 248
<211> LENGTH: 399
<212> TYPE: PRT
<213> ORGANISM: Artificial Sequence
<220> FEATURE:
<223> OTHER INFORMATION: sequence of intrinsic factor

<400> SEQUENCE: 248

Ser Thr Gln Thr Gln Ser Ser Cys Ser Val Pro Ser Ala Gln Glu Pro
 1               5                  10                  15

Leu Val Asn Gly Ile Gln Val Leu Met Glu Asn Ser Val Thr Ser Ser
             20                  25                  30

Ala Tyr Pro Asn Pro Ser Ile Leu Ile Ala Met Asn Leu Ala Gly Ala
         35                  40                  45

Tyr Asn Leu Lys Ala Gln Lys Leu Leu Thr Tyr Gln Leu Met Ser Ser
 50                  55                  60

Asp Asn Asn Asp Leu Thr Ile Gly His Leu Gly Leu Thr Ile Met Ala
 65                  70                  75                  80

Leu Thr Ser Ser Cys Arg Asp Pro Gly Asp Lys Val Ser Ile Leu Gln
                 85                  90                  95

Arg Gln Met Glu Asn Trp Ala Pro Ser Pro Asn Ala Glu Ala Ser
            100                 105                 110

Ala Phe Tyr Gly Pro Ser Leu Ala Ile Leu Ala Leu Cys Gln Lys Asn
            115                 120                 125

Ser Glu Ala Thr Leu Pro Ile Ala Val Arg Phe Ala Lys Thr Leu Leu
            130                 135                 140

Ala Asn Ser Ser Pro Phe Asn Val Asp Thr Gly Ala Met Ala Thr Leu
145                 150                 155                 160

Ala Leu Thr Cys Met Tyr Asn Lys Ile Pro Val Gly Ser Glu Glu Gly
                165                 170                 175

Tyr Arg Ser Leu Phe Gly Gln Val Leu Lys Asp Ile Val Glu Lys Ile
            180                 185                 190

Ser Met Lys Ile Lys Asp Asn Gly Ile Ile Gly Asp Ile Tyr Ser Thr
            195                 200                 205

Gly Leu Ala Met Gln Ala Leu Ser Val Thr Pro Glu Pro Ser Lys Lys
            210                 215                 220

Glu Trp Asn Cys Lys Lys Thr Thr Asp Met Ile Leu Asn Glu Ile Lys
225                 230                 235                 240
```

```
Gln Gly Lys Phe His Asn Pro Met Ser Ile Ala Gln Ile Leu Pro Ser
                245                 250                 255

Leu Lys Gly Lys Thr Tyr Leu Asp Val Pro Gln Val Thr Cys Ser Pro
            260                 265                 270

Asp His Glu Val Gln Pro Thr Leu Pro Ser Asn Pro Gly Pro Gly Pro
        275                 280                 285

Thr Ser Ala Ser Asn Ile Thr Val Ile Tyr Thr Ile Asn Asn Gln Leu
    290                 295                 300

Arg Gly Val Glu Leu Leu Phe Asn Glu Thr Ile Asn Val Ser Val Lys
305                 310                 315                 320

Ser Gly Ser Val Leu Leu Val Val Leu Glu Glu Ala Gln Arg Lys Asn
                325                 330                 335

Pro Met Phe Lys Phe Glu Thr Thr Met Thr Ser Trp Gly Leu Val Val
            340                 345                 350

Ser Ser Ile Asn Asn Ile Ala Glu Asn Val Asn His Lys Thr Tyr Trp
        355                 360                 365

Gln Phe Leu Ser Gly Val Thr Pro Leu Asn Glu Gly Val Ala Asp Tyr
    370                 375                 380

Ile Pro Phe Asn His Glu His Ile Thr Ala Asn Phe Thr Gln Tyr
385                 390                 395

<210> SEQ ID NO 249
<211> LENGTH: 413
<212> TYPE: PRT
<213> ORGANISM: Artificial Sequence
<220> FEATURE:
<223> OTHER INFORMATION: sequence of invertase

<400> SEQUENCE: 249

Met Phe Asn Phe Asn Ala Ser Arg Trp Thr Arg Ala Gln Ala Met Lys
1               5                   10                  15

Val Asn Lys Phe Asp Leu Thr Thr Ser Met Pro Glu Ile Gly Thr Asp
            20                  25                  30

Phe Pro Ile Met Arg Asp Asp Leu Trp Leu Trp Asp Thr Trp Pro Leu
        35                  40                  45

Arg Asp Ile Asn Gly Asn Pro Val Ser Phe Lys Gly Trp Asn Val Ile
    50                  55                  60

Phe Ser Leu Val Ala Asp Arg Asn Ile Pro Trp Asn Asp Arg His Ser
65                  70                  75                  80

His Ala Arg Ile Gly Tyr Phe Tyr Ser Lys Asp Gly Lys Ser Trp Val
                85                  90                  95

Tyr Gly Gly His Leu Leu Gln Glu Ser Ala Asn Thr Arg Thr Ala Glu
            100                 105                 110

Trp Ser Gly Gly Thr Ile Met Ala Pro Gly Ser Arg Asn Gln Val Glu
        115                 120                 125

Thr Phe Phe Thr Ser Thr Leu Phe Asp Lys Asn Gly Val Arg Glu Ala
    130                 135                 140

Val Ala Ala Val Thr Lys Gly Arg Ile Tyr Ala Asp Ser Glu Gly Val
145                 150                 155                 160

Trp Phe Lys Gly Phe Asp Gln Ser Thr Asp Leu Phe Gln Ala Asp Gly
                165                 170                 175

Leu Phe Tyr Gln Asn Tyr Ala Glu Asn Asn Leu Trp Asn Phe Arg Asp
            180                 185                 190

Pro His Val Phe Ile Asn Pro Glu Asp Gly Glu Thr Tyr Ala Leu Phe
        195                 200                 205
```

-continued

```
Glu Ala Asn Val Ala Thr Val Arg Gly Glu Asp Asp Ile Gly Glu Asp
    210                 215                 220
Glu Ile Gly Pro Val Pro Ala Asn Thr Val Val Pro Lys Asp Ala Asn
225                 230                 235                 240
Leu Cys Ser Ala Ser Ile Gly Ile Ala Arg Cys Leu Ser Pro Asp Arg
                245                 250                 255
Thr Glu Trp Glu Leu Leu Pro Pro Leu Leu Thr Ala Phe Gly Val Asn
            260                 265                 270
Asp Gln Met Glu Arg Pro His Val Ile Phe Gln Asn Gly Leu Thr Tyr
        275                 280                 285
Leu Phe Thr Ile Ser His Asp Ser Thr Tyr Ala Asp Gly Leu Thr Gly
    290                 295                 300
Ser Asp Gly Leu Tyr Gly Phe Val Ser Glu Asn Gly Ile Phe Gly Pro
305                 310                 315                 320
Tyr Glu Pro Leu Asn Gly Ser Gly Leu Val Leu Gly Gly Pro Ala Ser
                325                 330                 335
Gln Pro Thr Glu Ala Tyr Ala His Tyr Ile Met Asn Asn Gly Leu Val
            340                 345                 350
Glu Ser Phe Ile Asn Glu Ile Ile Asp Pro Lys Ser Gly Lys Val Ile
        355                 360                 365
Ala Gly Gly Ser Leu Ala Pro Thr Val Arg Val Glu Leu Gln Gly His
    370                 375                 380
Glu Thr Phe Ala Thr Glu Val Phe Asp Tyr Gly Tyr Ile Pro Ala Ser
385                 390                 395                 400
Tyr Ala Trp Pro Val Trp Pro Phe Pro Asp Arg Arg Lys
                405                 410

<210> SEQ ID NO 250
<211> LENGTH: 65
<212> TYPE: PRT
<213> ORGANISM: Artificial Sequence
<220> FEATURE:
<223> OTHER INFORMATION: sequence of lepirudin

<400> SEQUENCE: 250

Val Val Tyr Thr Asp Cys Thr Glu Ser Gly Gln Asn Leu Cys Leu Cys
1               5                   10                  15
Glu Gly Ser Asn Val Cys Gly Gln Gly Asn Lys Cys Ile Leu Gly Ser
                20                  25                  30
Asp Gly Glu Lys Asn Gln Cys Val Thr Gly Glu Gly Thr Pro Lys Pro
            35                  40                  45
Gln Ser His Asn Asp Gly Asp Phe Glu Glu Ile Pro Glu Glu Tyr Leu
        50                  55                  60
Gln
65

<210> SEQ ID NO 251
<211> LENGTH: 121
<212> TYPE: PRT
<213> ORGANISM: Artificial Sequence
<220> FEATURE:
<223> OTHER INFORMATION: sequence of lutropin beta

<400> SEQUENCE: 251

Ser Arg Glu Pro Leu Arg Pro Trp Cys His Pro Ile Asn Ala Ile Leu
1               5                   10                  15
Ala Val Glu Lys Glu Gly Cys Pro Val Cys Ile Thr Val Asn Thr Thr
                20                  25                  30
```

-continued

```
Ile Cys Ala Gly Tyr Cys Pro Thr Met Met Arg Val Leu Gln Ala Val
             35                  40                  45

Leu Pro Pro Leu Pro Gln Val Val Cys Thr Tyr Arg Asp Val Arg Phe
 50                  55                  60

Glu Ser Ile Arg Leu Pro Gly Cys Pro Arg Gly Val Asp Pro Val Val
 65                  70                  75                  80

Ser Phe Pro Val Ala Leu Ser Cys Arg Cys Gly Pro Cys Arg Arg Ser
             85                  90                  95

Thr Ser Asp Cys Gly Gly Pro Lys Asp His Pro Leu Thr Cys Asp His
            100                 105                 110

Pro Gln Leu Ser Gly Leu Leu Phe Leu
            115                 120

<210> SEQ ID NO 252
<211> LENGTH: 316
<212> TYPE: PRT
<213> ORGANISM: Artificial Sequence
<220> FEATURE:
<223> OTHER INFORMATION: sequence of lysozyme

<400> SEQUENCE: 252

Met Asp Pro Arg Leu Arg Glu Glu Val Val Arg Leu Ile Ala Leu
 1               5                  10                  15

Thr Ser Asp Asn Gly Ala Ser Leu Ser Lys Arg Leu Gln Ser Arg Val
             20                  25                  30

Ser Ala Leu Glu Lys Thr Ser Gln Ile His Ser Asp Thr Ile Leu Arg
             35                  40                  45

Ile Thr Gln Gly Leu Asp Asp Ala Asn Lys Arg Ile Ile Ala Leu Glu
 50                  55                  60

Gln Ser Arg Asp Asp Leu Val Ala Ser Val Ser Asp Ala Gln Leu Ala
 65                  70                  75                  80

Ile Ser Arg Leu Glu Ser Ser Ile Gly Ala Leu Gln Thr Val Val Asn
             85                  90                  95

Gly Leu Asp Ser Ser Val Thr Gln Leu Gly Ala Arg Val Gly Gln Leu
            100                 105                 110

Glu Thr Gly Leu Ala Asp Val Arg Val Asp His Asp Asn Leu Val Ala
            115                 120                 125

Arg Val Asp Thr Ala Glu Arg Asn Ile Gly Ser Leu Thr Thr Glu Leu
130                 135                 140

Ser Thr Leu Thr Leu Arg Val Thr Ser Ile Gln Ala Asp Phe Glu Ser
145                 150                 155                 160

Arg Ile Ser Thr Leu Glu Arg Thr Ala Val Thr Ser Ala Gly Ala Pro
                165                 170                 175

Leu Ser Ile Arg Asn Asn Arg Ile Thr Met Gly Leu Asn Asp Gly Leu
            180                 185                 190

Thr Leu Ser Gly Asn Asn Leu Ala Ile Arg Leu Pro Gly Asn Thr Gly
            195                 200                 205

Leu Asn Ile Gln Asn Gly Gly Leu Gln Phe Arg Phe Asn Thr Asp Gln
    210                 215                 220

Phe Gln Ile Val Asn Asn Asn Leu Thr Leu Lys Thr Thr Val Phe Asp
225                 230                 235                 240

Ser Ile Asn Ser Arg Ile Gly Ala Thr Glu Gln Ser Tyr Val Ala Ser
                245                 250                 255

Ala Val Thr Pro Leu Arg Leu Asn Ser Ser Thr Lys Val Leu Asp Met
            260                 265                 270
```

```
Leu Ile Asp Met Ser Thr Leu Glu Ile Asn Ser Ser Gly Gln Leu Thr
        275                 280                 285

Val Arg Ser Thr Ser Pro Asn Leu Arg Tyr Pro Ile Ala Asp Val Ser
        290                 295                 300

Gly Gly Ile Gly Met Ser Pro Asn Tyr Arg Phe Arg
305                 310                 315

<210> SEQ ID NO 253
<211> LENGTH: 194
<212> TYPE: PRT
<213> ORGANISM: Artificial Sequence
<220> FEATURE:
<223> OTHER INFORMATION: sequence of metalloproteinase inhibitor

<400> SEQUENCE: 253

Cys Ser Cys Ser Pro Val His Pro Gln Gln Ala Phe Cys Asn Ala Asp
1               5                   10                  15

Val Val Ile Arg Ala Lys Ala Val Ser Glu Lys Glu Val Asp Ser Gly
            20                  25                  30

Asn Asp Ile Tyr Gly Asn Pro Ile Lys Arg Ile Gln Tyr Glu Ile Lys
        35                  40                  45

Gln Ile Lys Met Phe Lys Gly Pro Glu Lys Asp Ile Glu Phe Ile Tyr
    50                  55                  60

Thr Ala Pro Ser Ser Ala Val Cys Gly Val Ser Leu Asp Val Gly Gly
65                  70                  75                  80

Lys Lys Glu Tyr Leu Ile Ala Gly Lys Ala Glu Gly Asp Gly Lys Met
                85                  90                  95

His Ile Thr Leu Cys Asp Phe Ile Val Pro Trp Asp Thr Leu Ser Thr
            100                 105                 110

Thr Gln Lys Lys Ser Leu Asn His Arg Tyr Gln Met Gly Cys Glu Cys
        115                 120                 125

Lys Ile Thr Arg Cys Pro Met Ile Pro Cys Tyr Ile Ser Ser Pro Asp
    130                 135                 140

Glu Cys Leu Trp Met Asp Trp Val Thr Glu Lys Asn Ile Asn Gly His
145                 150                 155                 160

Gln Ala Lys Phe Phe Ala Cys Ile Lys Arg Ser Asp Gly Ser Cys Ala
                165                 170                 175

Trp Tyr Arg Gly Ala Ala Pro Pro Lys Gln Glu Phe Leu Asp Ile Glu
            180                 185                 190

Asp Pro

<210> SEQ ID NO 254
<211> LENGTH: 93
<212> TYPE: PRT
<213> ORGANISM: Artificial Sequence
<220> FEATURE:
<223> OTHER INFORMATION: sequence of neurophysin

<400> SEQUENCE: 254

Ala Met Ser Asp Leu Glu Leu Arg Gln Cys Leu Pro Cys Gly Pro Gly
1               5                   10                  15

Gly Lys Gly Arg Cys Phe Gly Pro Ser Ile Cys Cys Ala Asp Glu Leu
            20                  25                  30

Gly Cys Phe Val Gly Thr Ala Glu Ala Leu Arg Cys Gln Glu Glu Asn
        35                  40                  45

Tyr Leu Pro Ser Pro Cys Gln Ser Gly Gln Lys Ala Cys Gly Ser Gly
    50                  55                  60
```

```
Gly Arg Cys Ala Ala Phe Gly Val Cys Asn Asp Glu Ser Cys Val
 65                  70                  75                  80

Thr Glu Pro Glu Cys Arg Glu Gly Phe His Arg Arg Ala
                 85                  90
```

<210> SEQ ID NO 255
<211> LENGTH: 327
<212> TYPE: PRT
<213> ORGANISM: Artificial Sequence
<220> FEATURE:
<223> OTHER INFORMATION: sequence of papain

<400> SEQUENCE: 255

```
Val Tyr Met Gly Leu Ser Phe Gly Asp Phe Ser Ile Val Gly Tyr Ser
  1               5                  10                  15

Gln Asn Asp Leu Thr Ser Thr Glu Arg Leu Ile Gln Leu Phe Glu Ser
                 20                  25                  30

Trp Met Leu Lys His Asn Lys Ile Tyr Lys Asn Ile Asp Glu Lys Ile
             35                  40                  45

Tyr Arg Phe Glu Ile Phe Lys Asp Asn Leu Lys Tyr Ile Asp Glu Thr
 50                  55                  60

Asn Lys Lys Asn Asn Ser Tyr Trp Leu Gly Leu Asn Val Phe Ala Asp
 65                  70                  75                  80

Met Ser Asn Asp Glu Phe Lys Glu Lys Tyr Thr Gly Ser Ile Ala Gly
                 85                  90                  95

Asn Tyr Thr Thr Thr Glu Leu Ser Tyr Glu Glu Val Leu Asn Asp Gly
                100                 105                 110

Asp Val Asn Ile Pro Glu Tyr Val Asp Trp Arg Gln Lys Gly Ala Val
            115                 120                 125

Thr Pro Val Lys Asn Gln Gly Ser Cys Gly Ser Cys Trp Ala Phe Ser
130                 135                 140

Ala Val Val Thr Ile Glu Gly Ile Ile Lys Ile Arg Thr Gly Asn Leu
145                 150                 155                 160

Asn Glu Tyr Ser Glu Gln Glu Leu Leu Asp Cys Asp Arg Arg Ser Tyr
                165                 170                 175

Gly Cys Asn Gly Gly Tyr Pro Trp Ser Ala Leu Gln Leu Val Ala Gln
            180                 185                 190

Tyr Gly Ile His Tyr Arg Asn Thr Tyr Pro Tyr Glu Gly Val Gln Arg
        195                 200                 205

Tyr Cys Arg Ser Arg Glu Lys Gly Pro Tyr Ala Ala Lys Thr Asp Gly
    210                 215                 220

Val Arg Gln Val Gln Pro Tyr Asn Glu Gly Ala Leu Leu Tyr Ser Ile
225                 230                 235                 240

Ala Asn Gln Pro Val Ser Val Val Leu Glu Ala Ala Gly Lys Asp Phe
                245                 250                 255

Gln Leu Tyr Arg Gly Gly Ile Phe Val Gly Pro Cys Gly Asn Lys Val
            260                 265                 270

Asp His Ala Val Ala Ala Val Gly Tyr Gly Pro Asn Tyr Ile Leu Ile
        275                 280                 285

Lys Asn Ser Trp Gly Thr Gly Trp Gly Glu Asn Gly Tyr Ile Arg Ile
    290                 295                 300

Lys Arg Gly Thr Gly Asn Ser Tyr Gly Val Cys Gly Leu Tyr Thr Ser
305                 310                 315                 320

Ser Phe Tyr Pro Val Lys Asn
                325
```

<210> SEQ ID NO 256
<211> LENGTH: 326
<212> TYPE: PRT
<213> ORGANISM: Artificial Sequence
<220> FEATURE:
<223> OTHER INFORMATION: sequence of pepsin

<400> SEQUENCE: 256

```
Val Asp Glu Gln Pro Leu Glu Asn Tyr Leu Asp Met Glu Tyr Phe Gly
1               5                   10                  15

Thr Ile Gly Ile Gly Thr Pro Ala Gln Asp Phe Thr Val Val Phe Asp
            20                  25                  30

Thr Gly Ser Ser Asn Leu Trp Val Pro Ser Val Tyr Cys Ser Ser Leu
        35                  40                  45

Ala Cys Thr Asn His Asn Arg Phe Asn Pro Glu Asp Ser Ser Thr Tyr
    50                  55                  60

Gln Ser Thr Ser Glu Thr Val Ser Ile Thr Tyr Gly Thr Gly Ser Met
65                  70                  75                  80

Thr Gly Ile Leu Gly Tyr Asp Thr Val Gln Val Gly Gly Ile Ser Asp
                85                  90                  95

Thr Asn Gln Ile Phe Gly Leu Ser Glu Thr Glu Pro Gly Ser Phe Leu
            100                 105                 110

Tyr Tyr Ala Pro Phe Asp Gly Ile Leu Gly Leu Ala Tyr Pro Ser Ile
        115                 120                 125

Ser Ser Ser Gly Ala Thr Pro Val Phe Asp Asn Ile Trp Asn Gln Gly
    130                 135                 140

Leu Val Ser Gln Asp Leu Phe Ser Val Tyr Leu Ser Ala Asp Asp Gln
145                 150                 155                 160

Ser Gly Ser Val Val Ile Phe Gly Gly Ile Asp Ser Ser Tyr Tyr Thr
                165                 170                 175

Gly Ser Leu Asn Trp Val Pro Val Thr Val Glu Gly Tyr Trp Gln Ile
            180                 185                 190

Thr Val Asp Ser Ile Thr Met Asn Gly Glu Ala Ile Ala Cys Ala Glu
        195                 200                 205

Gly Cys Gln Ala Ile Val Asp Thr Gly Thr Ser Leu Leu Thr Gly Pro
    210                 215                 220

Thr Ser Pro Ile Ala Asn Ile Gln Ser Asp Ile Gly Ala Ser Glu Asn
225                 230                 235                 240

Ser Asp Gly Asp Met Val Val Ser Cys Ser Ala Ile Ser Ser Leu Pro
                245                 250                 255

Asp Ile Val Phe Thr Ile Asn Gly Val Gln Tyr Pro Val Pro Pro Ser
            260                 265                 270

Ala Tyr Ile Leu Gln Ser Glu Gly Ser Cys Ile Ser Gly Phe Gln Gly
        275                 280                 285

Met Asn Leu Pro Thr Glu Ser Gly Glu Leu Trp Ile Leu Gly Asp Val
    290                 295                 300

Phe Ile Arg Gln Tyr Phe Thr Val Phe Asp Arg Ala Asn Asn Gln Val
305                 310                 315                 320

Gly Leu Ala Pro Val Ala
                325
```

<210> SEQ ID NO 257
<211> LENGTH: 791
<212> TYPE: PRT
<213> ORGANISM: Artificial Sequence
<220> FEATURE:
<223> OTHER INFORMATION: sequence of plasminogen

<400> SEQUENCE: 257

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Cys Ala Ala
            20                  25                  30

Lys Cys Glu Glu Asp Glu Glu Phe Thr Cys Arg Ala Phe Gln Tyr His
            35                  40                  45

Ser Lys Glu Gln Gln Cys Val Ile Met Ala Glu Asn Arg Lys Ser Ser
50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
                100                 105                 110

Pro His Arg Pro Arg Phe Ser Pro Ala Thr His Pro Ser Glu Gly Leu
            115                 120                 125

Glu Glu Asn Tyr Cys Arg Asn Pro Asp Asn Asp Pro Gln Gly Pro Trp
130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
                180                 185                 190

Gln Ser Pro His Ala His Gly Tyr Ile Pro Ser Lys Phe Pro Asn Lys
            195                 200                 205

Asn Leu Lys Lys Asn Tyr Cys Arg Asn Pro Asp Arg Glu Leu Arg Pro
210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Pro Ser Ser Gly Pro Thr Tyr Gln Cys
                245                 250                 255

Leu Lys Gly Thr Gly Glu Asn Tyr Arg Gly Asn Val Ala Val Thr Val
                260                 265                 270

Ser Gly His Thr Cys Gln His Trp Ser Ala Gln Thr Pro His Thr His
            275                 280                 285

Asn Arg Thr Pro Glu Asn Phe Pro Cys Lys Asn Leu Asp Glu Asn Tyr
290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
            355                 360                 365

Thr Ser Ser Thr Thr Thr Thr Gly Lys Lys Cys Gln Ser Trp Ser Ser
        370                 375                 380

Met Thr Pro His Arg His Gln Lys Thr Pro Glu Asn Tyr Pro Asn Ala
385                 390                 395                 400
```

```
Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Ala Pro Pro Val
        435                 440                 445

Val Leu Leu Pro Asp Val Glu Thr Pro Ser Glu Asp Cys Met Phe
450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
        515                 520                 525

Pro Arg Lys Leu Tyr Asp Tyr Cys Asp Val Pro Gln Cys Ala Ala Pro
    530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
        595                 600                 605

Pro Arg Pro Ser Ser Tyr Lys Val Ile Leu Gly Ala His Gln Glu Val
    610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
        675                 680                 685

Gln Gly Thr Phe Gly Ala Gly Leu Leu Lys Glu Ala Gln Leu Pro Val
    690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
        755                 760                 765

Asn Lys Pro Gly Val Tyr Val Arg Val Ser Arg Phe Val Thr Trp Ile
    770                 775                 780

Glu Gly Val Met Arg Asn Asn
785                 790

<210> SEQ ID NO 258
<211> LENGTH: 102
```

```
<212> TYPE: PRT
<213> ORGANISM: Artificial Sequence
<220> FEATURE:
<223> OTHER INFORMATION: sequence of protamine

<400> SEQUENCE: 258

Met Val Arg Tyr Arg Val Arg Ser Leu Ser Glu Arg Ser His Glu Val
1               5                   10                  15

Tyr Arg Gln Gln Leu His Gly Gln Glu Gln Gly His His Gly Gln Glu
                20                  25                  30

Glu Gln Gly Leu Ser Pro Glu His Val Glu Val Tyr Glu Arg Thr His
            35                  40                  45

Gly Gln Ser His Tyr Arg Arg Arg His Cys Ser Arg Arg Arg Leu His
        50                  55                  60

Arg Ile His Arg Arg Gln His Arg Ser Cys Arg Arg Arg Lys Arg Arg
65                  70                  75                  80

Ser Cys Arg His Arg Arg Arg His Arg Arg Gly Cys Arg Thr Arg Lys
                85                  90                  95

Arg Thr Cys Arg Arg His
            100

<210> SEQ ID NO 259
<211> LENGTH: 2196
<212> TYPE: PRT
<213> ORGANISM: Artificial Sequence
<220> FEATURE:
<223> OTHER INFORMATION: sequence of prothrombin

<400> SEQUENCE: 259

Ala Gln Leu Arg Gln Phe Tyr Val Ala Ala Gln Gly Ile Ser Trp Ser
1               5                   10                  15

Tyr Arg Pro Glu Pro Thr Asn Ser Ser Leu Asn Leu Ser Val Thr Ser
                20                  25                  30

Phe Lys Lys Ile Val Tyr Arg Glu Tyr Glu Pro Tyr Phe Lys Lys Glu
            35                  40                  45

Lys Pro Gln Ser Thr Ile Ser Gly Leu Leu Gly Pro Thr Leu Tyr Ala
        50                  55                  60

Glu Val Gly Asp Ile Ile Lys Val His Phe Lys Asn Lys Ala Asp Lys
65                  70                  75                  80

Pro Leu Ser Ile His Pro Gln Gly Ile Arg Tyr Ser Lys Leu Ser Glu
                85                  90                  95

Gly Ala Ser Tyr Leu Asp His Thr Phe Pro Ala Glu Lys Met Asp Asp
                100                 105                 110

Ala Val Ala Pro Gly Arg Glu Tyr Thr Tyr Glu Trp Ser Ile Ser Glu
            115                 120                 125

Asp Ser Gly Pro Thr His Asp Asp Pro Pro Cys Leu Thr His Ile Tyr
        130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                165                 170                 175

Lys Thr Phe Asp Lys Gln Ile Val Leu Leu Phe Ala Val Phe Asp Glu
                180                 185                 190

Ser Lys Ser Trp Ser Gln Ser Ser Ser Leu Met Tyr Thr Val Asn Gly
            195                 200                 205

Tyr Val Asn Gly Thr Met Pro Asp Ile Thr Val Cys Ala His Asp His
        210                 215                 220
```

```
Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                245                 250                 255

Ala Ile Thr Leu Val Ser Ala Thr Ser Thr Ala Asn Met Thr Val
                260                 265                 270

Gly Pro Glu Gly Lys Trp Ile Ile Ser Ser Leu Thr Pro Lys His Leu
                275                 280                 285

Gln Ala Gly Met Gln Ala Tyr Ile Asp Ile Lys Asn Cys Pro Lys Lys
                290                 295                 300

Thr Arg Asn Leu Lys Lys Ile Thr Arg Glu Gln Arg His Met Lys
305                 310                 315                 320

Arg Trp Glu Tyr Phe Ile Ala Ala Glu Glu Val Ile Trp Asp Tyr Ala
                325                 330                 335

Pro Val Ile Pro Ala Asn Met Asp Lys Lys Tyr Arg Ser Gln His Leu
                340                 345                 350

Asp Asn Phe Ser Asn Gln Ile Gly Lys His Tyr Lys Lys Val Met Tyr
                355                 360                 365

Thr Gln Tyr Glu Asp Glu Ser Phe Thr Lys His Thr Val Asn Pro Asn
                370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
                405                 410                 415

Ile Tyr Pro His Gly Val Thr Phe Ser Pro Tyr Glu Asp Glu Val Asn
                420                 425                 430

Ser Ser Phe Thr Ser Gly Arg Asn Asn Thr Met Ile Arg Ala Val Gln
                435                 440                 445

Pro Gly Glu Thr Tyr Thr Tyr Lys Trp Asn Ile Leu Glu Phe Asp Glu
                450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu Leu
                485                 490                 495

Ile Cys Lys Ser Arg Ser Leu Asp Arg Arg Gly Ile Gln Arg Ala Ala
                500                 505                 510

Asp Ile Glu Gln Gln Ala Val Phe Ala Val Phe Asp Glu Asn Lys Ser
                515                 520                 525

Trp Tyr Leu Glu Asp Asn Ile Asn Lys Phe Cys Glu Asn Pro Asp Glu
                530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
                565                 570                 575

Asp Asp Thr Val Gln Trp His Phe Cys Ser Val Gly Thr Gln Asn Glu
                580                 585                 590

Ile Leu Thr Ile His Phe Thr Gly His Ser Phe Ile Tyr Gly Lys Arg
                595                 600                 605

His Glu Asp Thr Leu Thr Leu Phe Pro Met Arg Gly Glu Ser Val Thr
                610                 615                 620

Val Thr Met Asp Asn Val Gly Thr Trp Met Leu Thr Ser Met Asn Ser
625                 630                 635                 640
```

-continued

```
Ser Pro Arg Ser Lys Lys Leu Arg Leu Lys Phe Arg Asp Val Lys Cys
            645                 650                 655

Ile Pro Asp Asp Glu Asp Ser Tyr Glu Ile Phe Glu Pro Pro Glu
            660                 665                 670

Ser Thr Val Met Ala Thr Arg Lys Met His Asp Arg Leu Glu Pro Glu
            675                 680                 685

Asp Glu Glu Ser Asp Ala Asp Tyr Asp Tyr Gln Asn Arg Leu Ala Ala
    690                 695                 700

Ala Leu Gly Ile Arg Ser Phe Arg Asn Ser Ser Leu Asn Gln Glu Glu
705                 710                 715                 720

Glu Glu Phe Asn Leu Thr Ala Leu Ala Leu Glu Asn Gly Thr Glu Phe
                725                 730                 735

Val Ser Ser Asn Thr Asp Ile Ile Val Gly Ser Asn Tyr Ser Ser Pro
                740                 745                 750

Ser Asn Ile Ser Lys Phe Thr Val Asn Asn Leu Ala Glu Pro Gln Lys
                755                 760                 765

Ala Pro Ser His Gln Gln Ala Thr Thr Ala Gly Ser Pro Leu Arg His
            770                 775                 780

Leu Ile Gly Lys Asn Ser Val Leu Asn Ser Ser Thr Ala Glu His Ser
785                 790                 795                 800

Ser Pro Tyr Ser Glu Asp Pro Ile Glu Asp Pro Leu Gln Pro Asp Val
                805                 810                 815

Thr Gly Ile Arg Leu Leu Ser Leu Gly Ala Gly Glu Phe Lys Ser Gln
                820                 825                 830

Glu His Ala Lys His Lys Gly Pro Lys Val Glu Arg Asp Gln Ala Ala
            835                 840                 845

Lys His Arg Phe Ser Trp Met Lys Leu Leu Ala His Lys Val Gly Arg
            850                 855                 860

His Leu Ser Gln Asp Thr Gly Ser Pro Ser Gly Met Arg Pro Trp Glu
865                 870                 875                 880

Asp Leu Pro Ser Gln Asp Thr Gly Ser Pro Ser Arg Met Arg Pro Trp
                885                 890                 895

Lys Asp Pro Pro Ser Asp Leu Leu Leu Leu Lys Gln Ser Asn Ser Ser
            900                 905                 910

Lys Ile Leu Val Gly Arg Trp His Leu Ala Ser Glu Lys Gly Ser Tyr
        915                 920                 925

Glu Ile Ile Gln Asp Thr Asp Glu Asp Thr Ala Val Asn Asn Trp Leu
    930                 935                 940

Ile Ser Pro Gln Asn Ala Ser Arg Ala Trp Gly Glu Ser Thr Pro Leu
945                 950                 955                 960

Ala Asn Lys Pro Gly Lys Gln Ser Gly His Pro Lys Phe Pro Arg Val
                965                 970                 975

Arg His Lys Ser Leu Gln Val Arg Gln Asp Gly Gly Lys Ser Arg Leu
            980                 985                 990

Lys Lys Ser Gln Phe Leu Ile Lys  Thr Arg Lys Lys  Lys Glu Lys
        995                 1000                1005

His Thr  His His Ala Pro Leu  Ser Pro Arg Thr Phe  His Pro Leu
    1010                1015                    1020

Arg Ser  Glu Ala Tyr Asn Thr  Phe Ser Glu Arg Arg  Leu Lys His
    1025                1030                    1035

Ser Leu  Val Leu His Lys Ser  Asn Glu Thr Ser Leu  Pro Thr Asp
    1040                1045                    1050

Leu Asn  Gln Thr Leu Pro Ser  Met Asp Phe Gly Trp  Ile Ala Ser
```

-continued

```
                    1055                1060                1065

Leu Pro Asp His Asn Gln Asn Ser Ser Asn Asp Thr Gly Gln Ala
    1070                1075                1080

Ser Cys Pro Pro Gly Leu Tyr Gln Thr Val Pro Glu Glu His
    1085                1090                1095

Tyr Gln Thr Phe Pro Ile Gln Asp Pro Asp Gln Met His Ser Thr
    1100                1105                1110

Ser Asp Pro Ser His Arg Ser Ser Pro Glu Leu Ser Glu Met
    1115                1120                1125

Leu Glu Tyr Asp Arg Ser His Lys Ser Phe Pro Thr Asp Ile Ser
    1130                1135                1140

Gln Met Ser Pro Ser Ser Glu His Glu Val Trp Gln Thr Val Ile
    1145                1150                1155

Ser Pro Asp Leu Ser Gln Val Thr Leu Ser Pro Glu Leu Ser Gln
    1160                1165                1170

Thr Asn Leu Ser Pro Asp Leu Ser His Thr Thr Leu Ser Pro Glu
    1175                1180                1185

Leu Ile Gln Arg Asn Leu Ser Pro Ala Leu Gly Gln Met Pro Ile
    1190                1195                1200

Ser Pro Asp Leu Ser His Thr Thr Leu Ser Pro Asp Leu Ser His
    1205                1210                1215

Thr Thr Leu Ser Leu Asp Leu Ser Gln Thr Asn Leu Ser Pro Glu
    1220                1225                1230

Leu Ser Gln Thr Asn Leu Ser Pro Ala Leu Gly Gln Met Pro Leu
    1235                1240                1245

Ser Pro Asp Leu Ser His Thr Thr Leu Ser Leu Asp Phe Ser Gln
    1250                1255                1260

Thr Asn Leu Ser Pro Glu Leu Ser His Met Thr Leu Ser Pro Glu
    1265                1270                1275

Leu Ser Gln Thr Asn Leu Ser Pro Ala Leu Gly Gln Met Pro Ile
    1280                1285                1290

Ser Pro Asp Leu Ser His Thr Thr Leu Ser Leu Asp Phe Ser Gln
    1295                1300                1305

Thr Asn Leu Ser Pro Glu Leu Ser Gln Thr Asn Leu Ser Pro Ala
    1310                1315                1320

Leu Gly Gln Met Pro Leu Ser Pro Asp Pro Ser His Thr Thr Leu
    1325                1330                1335

Ser Leu Asp Leu Ser Gln Thr Asn Leu Ser Pro Glu Leu Ser Gln
    1340                1345                1350

Thr Asn Leu Ser Pro Asp Leu Ser Glu Met Pro Leu Phe Ala Asp
    1355                1360                1365

Leu Ser Gln Ile Pro Leu Thr Pro Asp Leu Asp Gln Met Thr Leu
    1370                1375                1380

Ser Pro Asp Leu Gly Glu Thr Asp Leu Ser Pro Asn Phe Gly Gln
    1385                1390                1395

Met Ser Leu Ser Pro Asp Leu Ser Gln Val Thr Leu Ser Pro Asp
    1400                1405                1410

Ile Ser Asp Thr Thr Leu Leu Pro Asp Leu Ser Gln Ile Ser Pro
    1415                1420                1425

Pro Pro Asp Leu Asp Gln Ile Phe Tyr Pro Ser Glu Ser Ser Gln
    1430                1435                1440

Ser Leu Leu Leu Gln Glu Phe Asn Glu Ser Phe Pro Tyr Pro Asp
    1445                1450                1455
```

-continued

```
Leu Gly Gln Met Pro Ser Pro Ser Ser Pro Thr Leu Asn Asp Thr
    1460             1465             1470

Phe Leu Ser Lys Glu Phe Asn Pro Leu Val Ile Val Gly Leu Ser
    1475             1480             1485

Lys Asp Gly Thr Asp Tyr Ile Glu Ile Ile Pro Lys Glu Glu Val
    1490             1495             1500

Gln Ser Ser Glu Asp Asp Tyr Ala Glu Ile Asp Tyr Val Pro Tyr
    1505             1510             1515

Asp Asp Pro Tyr Lys Thr Asp Val Arg Thr Asn Ile Asn Ser Ser
    1520             1525             1530

Arg Asp Pro Asp Asn Ile Ala Ala Trp Tyr Leu Arg Ser Asn Asn
    1535             1540             1545

Gly Asn Arg Arg Asn Tyr Tyr Ile Ala Ala Glu Glu Ile Ser Trp
    1550             1555             1560

Asp Tyr Ser Glu Phe Val Gln Arg Glu Thr Asp Ile Glu Asp Ser
    1565             1570             1575

Asp Asp Ile Pro Glu Asp Thr Thr Tyr Lys Lys Val Val Phe Arg
    1580             1585             1590

Lys Tyr Leu Asp Ser Thr Phe Thr Lys Arg Asp Pro Arg Gly Glu
    1595             1600             1605

Tyr Glu Glu His Leu Gly Ile Leu Gly Pro Ile Ile Arg Ala Glu
    1610             1615             1620

Val Asp Asp Val Ile Gln Val Arg Phe Lys Asn Leu Ala Ser Arg
    1625             1630             1635

Pro Tyr Ser Leu His Ala His Gly Leu Ser Tyr Glu Lys Ser Ser
    1640             1645             1650

Glu Gly Lys Thr Tyr Glu Asp Asp Ser Pro Glu Trp Phe Lys Glu
    1655             1660             1665

Asp Asn Ala Val Gln Pro Asn Ser Ser Tyr Thr Tyr Val Trp His
    1670             1675             1680

Ala Thr Glu Arg Ser Gly Pro Glu Ser Pro Gly Ser Ala Cys Arg
    1685             1690             1695

Ala Trp Ala Tyr Tyr Ser Ala Val Asn Pro Glu Lys Asp Ile His
    1700             1705             1710

Ser Gly Leu Ile Gly Pro Leu Leu Ile Cys Gln Lys Gly Ile Leu
    1715             1720             1725

His Lys Asp Ser Asn Met Pro Val Asp Met Arg Glu Phe Val Leu
    1730             1735             1740

Leu Phe Met Thr Phe Asp Glu Lys Lys Ser Trp Tyr Tyr Glu Lys
    1745             1750             1755

Lys Ser Arg Ser Ser Trp Arg Leu Thr Ser Ser Glu Met Lys Lys
    1760             1765             1770

Ser His Glu Phe His Ala Ile Asn Gly Met Ile Tyr Ser Leu Pro
    1775             1780             1785

Gly Leu Lys Met Tyr Glu Gln Glu Trp Val Arg Leu His Leu Leu
    1790             1795             1800

Asn Ile Gly Gly Ser Gln Asp Ile His Val Val His Phe His Gly
    1805             1810             1815

Gln Thr Leu Leu Glu Asn Gly Asn Lys Gln His Gln Leu Gly Val
    1820             1825             1830

Trp Pro Leu Leu Pro Gly Ser Phe Lys Thr Leu Glu Met Lys Ala
    1835             1840             1845
```

-continued

Ser Lys Pro Gly Trp Trp Leu Leu Asn Thr Glu Val Gly Glu Asn
1850                1855                1860

Gln Arg Ala Gly Met Gln Thr Pro Phe Leu Ile Met Asp Arg Asp
1865                1870                1875

Cys Arg Met Pro Met Gly Leu Ser Thr Gly Ile Ile Ser Asp Ser
1880                1885                1890

Gln Ile Lys Ala Ser Glu Phe Leu Gly Tyr Trp Glu Pro Arg Leu
1895                1900                1905

Ala Arg Leu Asn Asn Gly Gly Ser Tyr Asn Ala Trp Ser Val Glu
1910                1915                1920

Lys Leu Ala Ala Glu Phe Ala Ser Lys Pro Trp Ile Gln Val Asp
1925                1930                1935

Met Gln Lys Glu Val Ile Ile Thr Gly Ile Gln Thr Gln Gly Ala
1940                1945                1950

Lys His Tyr Leu Lys Ser Cys Tyr Thr Thr Glu Phe Tyr Val Ala
1955                1960                1965

Tyr Ser Ser Asn Gln Ile Asn Trp Gln Ile Phe Lys Gly Asn Ser
1970                1975                1980

Thr Arg Asn Val Met Tyr Phe Asn Gly Asn Ser Asp Ala Ser Thr
1985                1990                1995

Ile Lys Glu Asn Gln Phe Asp Pro Pro Ile Val Ala Arg Tyr Ile
2000                2005                2010

Arg Ile Ser Pro Thr Arg Ala Tyr Asn Arg Pro Thr Leu Arg Leu
2015                2020                2025

Glu Leu Gln Gly Cys Glu Val Asn Gly Cys Ser Thr Pro Leu Gly
2030                2035                2040

Met Glu Asn Gly Lys Ile Glu Asn Lys Gln Ile Thr Ala Ser Ser
2045                2050                2055

Phe Lys Lys Ser Trp Trp Gly Asp Tyr Trp Glu Pro Phe Arg Ala
2060                2065                2070

Arg Leu Asn Ala Gln Gly Arg Val Asn Ala Trp Gln Ala Lys Ala
2075                2080                2085

Asn Asn Asn Lys Gln Trp Leu Glu Ile Asp Leu Leu Lys Ile Lys
2090                2095                2100

Lys Ile Thr Ala Ile Ile Thr Gln Gly Cys Lys Ser Leu Ser Ser
2105                2110                2115

Glu Met Tyr Val Lys Ser Tyr Thr Ile His Tyr Ser Glu Gln Gly
2120                2125                2130

Val Glu Trp Lys Pro Tyr Arg Leu Lys Ser Ser Met Val Asp Lys
2135                2140                2145

Ile Phe Glu Gly Asn Thr Asn Thr Lys Gly His Val Lys Asn Phe
2150                2155                2160

Phe Asn Pro Pro Ile Ile Ser Arg Phe Ile Arg Val Ile Pro Lys
2165                2170                2175

Thr Trp Asn Gln Ser Ile Thr Leu Arg Leu Glu Leu Phe Gly Cys
2180                2185                2190

Asp Ile Tyr
2195

<210> SEQ ID NO 260
<211> LENGTH: 218
<212> TYPE: PRT
<213> ORGANISM: Artificial Sequence
<220> FEATURE:
<223> OTHER INFORMATION: sequence of protirelin -continued

```
<400> SEQUENCE: 260

Gln Pro Glu Ala Ala Gln Glu Ala Val Thr Ala Ala Glu His Pro
1               5                   10                  15

Gly Leu Asp Asp Phe Leu Arg Gln Val Glu Arg Leu Leu Phe Leu Arg
                20                  25                  30

Glu Asn Ile Gln Arg Leu Gln Gly Asp Gln Gly Glu His Ser Ala Ser
            35                  40                  45

Gln Ile Phe Gln Ser Asp Trp Leu Ser Lys Arg Gln His Pro Gly Lys
        50                  55                  60

Arg Glu Glu Glu Glu Glu Gly Val Glu Glu Glu Glu Glu Glu Glu Glu
65                  70                  75                  80

Gly Gly Ala Val Gly Pro His Lys Arg Gln His Pro Gly Arg Arg Glu
                85                  90                  95

Asp Glu Ala Ser Trp Ser Val Asp Val Thr Gln His Lys Arg Gln His
                100                 105                 110

Pro Gly Arg Arg Ser Pro Trp Leu Ala Tyr Ala Val Pro Lys Arg Gln
            115                 120                 125

His Pro Gly Arg Arg Leu Ala Asp Pro Lys Ala Gln Arg Ser Trp Glu
        130                 135                 140

Glu Glu Glu Glu Glu Glu Arg Glu Asp Leu Met Pro Glu Lys
145                 150                 155                 160

Arg Gln His Pro Gly Lys Arg Ala Leu Gly Gly Pro Cys Gly Pro Gln
                165                 170                 175

Gly Ala Tyr Gly Gln Ala Gly Leu Leu Leu Gly Leu Leu Asp Asp Leu
            180                 185                 190

Ser Arg Ser Gln Gly Ala Glu Glu Lys Arg Gln His Pro Gly Arg Arg
        195                 200                 205

Ala Ala Trp Val Arg Glu Pro Leu Glu Glu
    210                 215

<210> SEQ ID NO 261
<211> LENGTH: 112
<212> TYPE: PRT
<213> ORGANISM: Artificial Sequence
<220> FEATURE:
<223> OTHER INFORMATION: sequence of SC3

<400> SEQUENCE: 261

Gly Gly His Pro Gly Thr Thr Thr Pro Pro Val Thr Thr Val Thr
1               5                   10                  15

Val Thr Thr Pro Pro Ser Thr Thr Thr Ile Ala Ala Gly Thr Cys
                20                  25                  30

Thr Thr Gly Ser Leu Ser Cys Cys Asn Gln Val Gln Ser Ala Ser Ser
            35                  40                  45

Ser Pro Val Thr Ala Leu Leu Gly Leu Leu Gly Ile Val Leu Ser Asp
        50                  55                  60

Leu Asn Val Leu Val Gly Ile Ser Cys Ser Pro Leu Thr Val Ile Gly
65                  70                  75                  80

Val Gly Gly Ser Gly Cys Ser Ala Gln Thr Val Cys Cys Glu Asn Thr
                85                  90                  95

Gln Phe Asn Gly Leu Ile Asn Ile Gly Cys Thr Pro Ile Asn Ile Leu
            100                 105                 110

<210> SEQ ID NO 262
<211> LENGTH: 44
```

```
<212> TYPE: PRT
<213> ORGANISM: Artificial Sequence
<220> FEATURE:
<223> OTHER INFORMATION: sequence of Sermorelin

<400> SEQUENCE: 262

Tyr Ala Asp Ala Ile Phe Thr Asn Ser Tyr Arg Lys Val Leu Gly Gln
1               5                   10                  15
Leu Ser Ala Arg Lys Leu Leu Gln Asp Ile Met Ser Arg Gln Gln Gly
            20                  25                  30
Glu Ser Asn Gln Glu Arg Gly Ala Arg Ala Arg Leu
        35                  40

<210> SEQ ID NO 263
<211> LENGTH: 303
<212> TYPE: PRT
<213> ORGANISM: Artificial Sequence
<220> FEATURE:
<223> OTHER INFORMATION: sequence of streptodornase

<400> SEQUENCE: 263

Ile Pro Pro Tyr His His Asn Thr Val Leu Ala Lys Thr Val Ser Val
1               5                   10                  15
Asn Gln Thr Tyr Gly Glu Tyr Lys Asp Tyr Tyr Thr Val Ile Gly Glu
            20                  25                  30
Ser Asn Ile Asp Gln Ser Ala Phe Pro Lys Ile Tyr Lys Thr Thr Glu
        35                  40                  45
Arg Val Tyr Lys Gly Gln Gly Thr Ser Glu Lys Arg Val Thr Val Ser
    50                  55                  60
Asp Val Val Tyr Asn Pro Leu Asp Gly Tyr Lys Arg Ser Thr Gly Ala
65                  70                  75                  80
Tyr Gly Val Val Thr Lys Asp Met Ile Asp Met Ser Lys Gly Tyr Arg
                85                  90                  95
Glu Lys Trp Glu Thr Asn Pro Glu Pro Ser Gly Trp Phe Arg Phe Tyr
            100                 105                 110
Asn Arg Ala Asp Asn Glu Glu Ile Ser Glu Lys Glu Tyr Asp Ser Arg
        115                 120                 125
Arg Thr Lys Ser Tyr Lys Val Thr Asn Asn Val Pro Val Val Leu Thr
    130                 135                 140
Thr Leu Lys Gly Lys Lys Tyr Asn Ser His Leu Phe Val Ala Ser His
145                 150                 155                 160
Leu Phe Ala Asp Ser Leu Gly Gly Lys Ser Ile Arg Lys Asn Ala Ile
                165                 170                 175
Thr Gly Thr Gln Met Gln Asn Val Gly Thr Arg Lys Gly Gly Met Gln
            180                 185                 190
Tyr Ile Glu Lys Lys Val Leu Ser His Ile Thr Lys Asn Pro Asp Val
        195                 200                 205
Tyr Val Phe Tyr Ser Ala Ile Pro Glu Tyr Gln Gly Ala Glu Leu Leu
    210                 215                 220
Ala Arg Ser Val Leu Val Ser Ala Leu Ser Ser Asp Gly Val Ile Asn
225                 230                 235                 240
Glu Thr Val Arg Val Phe Asn Thr Ala Asp Gly Phe Asn Ile Asn Tyr
                245                 250                 255
Glu Lys Gly Gly Leu Leu Thr Glu Ser Pro Val Ser Glu Ile Asp Asn
            260                 265                 270
Ile Glu Asp Ser Thr Thr Asp Glu Ile Glu Asn Ser Val Asp Ser
        275                 280                 285
```

```
Glu Glu Ile Val Tyr Asn Asp Thr Thr Thr Glu Glu Glu Asn
    290                 295                 300
```

<210> SEQ ID NO 264
<211> LENGTH: 413
<212> TYPE: PRT
<213> ORGANISM: Artificial Sequence
<220> FEATURE:
<223> OTHER INFORMATION: sequence of streptokinase

<400> SEQUENCE: 264

```
Ile Ala Gly Pro Glu Trp Leu Leu Asp Arg Pro Ser Val Asn Asn Ser
1               5                   10                  15

Gln Leu Val Val Ser Val Ala Gly Thr Val Glu Gly Thr Asn Gln Asp
            20                  25                  30

Ile Ser Leu Lys Phe Phe Glu Ile Asp Leu Thr Ser Arg Pro Ala His
        35                  40                  45

Gly Gly Lys Thr Glu Gln Gly Leu Ser Pro Lys Ser Lys Pro Phe Ala
    50                  55                  60

Thr Asp Ser Gly Ala Met Ser His Lys Leu Glu Lys Ala Asp Leu Leu
65                  70                  75                  80

Lys Ala Ile Gln Glu Gln Leu Ile Ala Asn Val His Ser Asn Asp Asp
                85                  90                  95

Tyr Phe Glu Val Ile Asp Phe Ala Ser Asp Ala Thr Ile Thr Asp Arg
            100                 105                 110

Asn Gly Lys Val Tyr Phe Ala Asp Lys Asp Gly Ser Val Thr Leu Pro
        115                 120                 125

Thr Gln Pro Val Gln Glu Phe Leu Leu Ser Gly His Val Arg Val Arg
    130                 135                 140

Pro Tyr Lys Glu Lys Pro Ile Gln Asn Gln Ala Lys Ser Val Asp Val
145                 150                 155                 160

Glu Tyr Thr Val Gln Phe Thr Pro Leu Asn Pro Asp Asp Asp Phe Arg
                165                 170                 175

Pro Gly Leu Lys Asp Thr Lys Leu Leu Lys Thr Leu Ala Ile Gly Asp
            180                 185                 190

Thr Ile Thr Ser Gln Glu Leu Leu Ala Gln Ala Gln Ser Ile Leu Asn
        195                 200                 205

Lys Asn His Pro Gly Tyr Thr Ile Tyr Glu Arg Asp Ser Ser Ile Val
    210                 215                 220

Thr His Asp Asn Asp Ile Phe Arg Thr Ile Leu Pro Met Asp Gln Glu
225                 230                 235                 240

Phe Thr Tyr Arg Val Lys Asn Arg Glu Gln Ala Tyr Arg Ile Asn Lys
                245                 250                 255

Lys Ser Gly Leu Asn Glu Glu Ile Asn Asn Thr Asp Leu Ile Ser Glu
            260                 265                 270

Lys Tyr Tyr Val Leu Lys Lys Gly Glu Lys Pro Tyr Asp Pro Phe Asp
        275                 280                 285

Arg Ser His Leu Lys Leu Phe Thr Ile Lys Tyr Val Asp Val Asp Thr
    290                 295                 300

Asn Glu Leu Leu Lys Ser Glu Gln Leu Leu Thr Ala Ser Glu Arg Asn
305                 310                 315                 320

Leu Asp Phe Arg Asp Leu Tyr Asp Pro Arg Asp Lys Ala Lys Leu Leu
                325                 330                 335

Tyr Asn Asn Leu Asp Ala Phe Gly Ile Met Asp Tyr Thr Leu Thr Gly
            340                 345                 350
```

-continued

```
Lys Val Glu Asp Asn His Asp Asp Thr Asn Arg Ile Ile Thr Val Tyr
            355                 360                 365

Met Gly Lys Arg Pro Glu Gly Glu Asn Ala Ser Tyr His Leu Ala Tyr
            370                 375                 380

Asp Lys Asp Arg Tyr Thr Glu Glu Arg Glu Val Tyr Ser Tyr Leu
385                 390                 395                 400

Arg Tyr Thr Gly Thr Pro Ile Pro Asp Asn Pro Asn Asp
                    405                 410
```

<210> SEQ ID NO 265
<211> LENGTH: 2749
<212> TYPE: PRT
<213> ORGANISM: Artificial Sequence
<220> FEATURE:
<223> OTHER INFORMATION: sequence of thyroglobulin

<400> SEQUENCE: 265

```
Asn Ile Phe Glu Tyr Gln Val Asp Ala Gln Pro Leu Arg Pro Cys Glu
1               5                   10                  15

Leu Gln Arg Glu Thr Ala Phe Leu Lys Gln Ala Asp Tyr Val Pro Gln
            20                  25                  30

Cys Ala Glu Asp Gly Ser Phe Gln Thr Val Gln Cys Gln Asn Asp Gly
        35                  40                  45

Arg Ser Cys Trp Cys Val Gly Ala Asn Gly Ser Glu Val Leu Gly Ser
    50                  55                  60

Arg Gln Pro Gly Arg Pro Val Ala Cys Leu Ser Phe Cys Gln Leu Gln
65                  70                  75                  80

Lys Gln Gln Ile Leu Leu Ser Gly Tyr Ile Asn Ser Thr Asp Thr Ser
                85                  90                  95

Tyr Leu Pro Gln Cys Gln Asp Ser Gly Asp Tyr Ala Pro Val Gln Cys
            100                 105                 110

Asp Val Gln Gln Val Gln Cys Trp Cys Val Asp Ala Glu Gly Met Glu
        115                 120                 125

Val Tyr Gly Thr Arg Gln Leu Gly Arg Pro Lys Arg Cys Pro Arg Ser
    130                 135                 140

Cys Glu Ile Arg Asn Arg Arg Leu Leu His Gly Val Gly Asp Lys Ser
145                 150                 155                 160

Pro Pro Gln Cys Ser Ala Glu Gly Glu Phe Met Pro Val Gln Cys Lys
                165                 170                 175

Phe Val Asn Thr Thr Asp Met Met Ile Phe Asp Leu Val His Ser Tyr
            180                 185                 190

Asn Arg Phe Pro Asp Ala Phe Val Thr Phe Ser Ser Phe Gln Arg Arg
        195                 200                 205

Phe Pro Glu Val Ser Gly Tyr Cys His Cys Ala Asp Ser Gln Gly Arg
    210                 215                 220

Glu Leu Ala Glu Thr Gly Leu Glu Leu Leu Asp Glu Ile Tyr Asp
225                 230                 235                 240

Thr Ile Phe Ala Gly Leu Asp Leu Pro Ser Thr Phe Thr Glu Thr Thr
                245                 250                 255

Leu Tyr Arg Ile Leu Gln Arg Arg Phe Leu Ala Val Gln Ser Val Ile
            260                 265                 270

Ser Gly Arg Phe Arg Cys Pro Thr Lys Cys Glu Val Glu Arg Phe Thr
        275                 280                 285

Ala Thr Ser Phe Gly His Pro Tyr Val Pro Ser Cys Arg Arg Asn Gly
    290                 295                 300
```

-continued

```
Asp Tyr Gln Ala Val Gln Cys Gln Thr Glu Gly Pro Cys Trp Cys Val
305                 310                 315                 320

Asp Ala Gln Gly Lys Glu Met His Gly Thr Arg Gln Gln Gly Glu Pro
            325                 330                 335

Pro Ser Cys Ala Glu Gly Gln Ser Cys Ala Ser Glu Arg Gln Gln Ala
            340                 345                 350

Leu Ser Arg Leu Tyr Phe Gly Thr Ser Gly Tyr Phe Ser Gln His Asp
            355                 360                 365

Leu Phe Ser Ser Pro Glu Lys Arg Trp Ala Ser Pro Arg Val Ala Arg
370                 375                 380

Phe Ala Thr Ser Cys Pro Pro Thr Ile Lys Glu Leu Phe Val Asp Ser
385                 390                 395                 400

Gly Leu Leu Arg Pro Met Val Glu Gly Gln Ser Gln Phe Ser Val
                405                 410                 415

Ser Glu Asn Leu Leu Lys Glu Ala Ile Arg Ala Ile Phe Pro Ser Arg
            420                 425                 430

Gly Leu Ala Arg Leu Ala Leu Gln Phe Thr Thr Asn Pro Lys Arg Leu
            435                 440                 445

Gln Gln Asn Leu Phe Gly Gly Lys Phe Leu Val Asn Val Gly Gln Phe
450                 455                 460

Asn Leu Ser Gly Ala Leu Gly Thr Arg Gly Thr Phe Asn Phe Ser Gln
465                 470                 475                 480

Phe Phe Gln Gln Leu Gly Leu Ala Ser Phe Leu Asn Gly Gly Arg Gln
            485                 490                 495

Glu Asp Leu Ala Lys Pro Leu Ser Val Gly Leu Asp Ser Asn Ser Ser
            500                 505                 510

Thr Gly Thr Pro Glu Ala Ala Lys Lys Asp Gly Thr Met Asn Lys Pro
            515                 520                 525

Thr Val Gly Ser Phe Gly Phe Glu Ile Asn Leu Gln Glu Asn Gln Asn
            530                 535                 540

Ala Leu Lys Phe Leu Ala Ser Leu Leu Glu Leu Pro Glu Phe Leu Leu
545                 550                 555                 560

Phe Leu Gln His Ala Ile Ser Val Pro Glu Asp Val Ala Arg Asp Leu
                565                 570                 575

Gly Asp Val Met Glu Thr Val Leu Ser Ser Gln Thr Cys Glu Gln Thr
            580                 585                 590

Pro Glu Arg Leu Phe Val Pro Ser Cys Thr Thr Glu Gly Ser Tyr Glu
            595                 600                 605

Asp Val Gln Cys Phe Ser Gly Glu Cys Trp Cys Val Asn Ser Trp Gly
610                 615                 620

Lys Glu Leu Pro Gly Ser Arg Val Arg Gly Gln Pro Arg Cys Pro
625                 630                 635                 640

Thr Asp Cys Glu Lys Gln Arg Ala Arg Met Gln Ser Leu Met Gly Ser
                645                 650                 655

Gln Pro Ala Gly Ser Thr Leu Phe Val Pro Ala Cys Thr Ser Glu Gly
            660                 665                 670

His Phe Leu Pro Val Gln Cys Phe Asn Ser Glu Cys Tyr Cys Val Asp
            675                 680                 685

Ala Glu Gly Gln Ala Ile Pro Gly Thr Arg Ser Ala Ile Gly Lys Pro
690                 695                 700

Lys Lys Cys Pro Thr Pro Cys Gln Leu Gln Ser Glu Gln Ala Phe Leu
705                 710                 715                 720
```

-continued

```
Arg Thr Val Gln Ala Leu Leu Ser Asn Ser Ser Met Leu Pro Thr Leu
            725                 730                 735
Ser Asp Thr Tyr Ile Pro Gln Cys Ser Thr Asp Gly Gln Trp Arg Gln
            740                 745                 750
Val Gln Cys Asn Gly Pro Pro Glu Gln Val Phe Glu Leu Tyr Gln Arg
            755                 760                 765
Trp Glu Ala Gln Asn Lys Gly Gln Asp Leu Thr Pro Ala Lys Leu Leu
770                 775                 780
Val Lys Ile Met Ser Tyr Arg Glu Ala Ala Ser Gly Asn Phe Ser Leu
785                 790                 795                 800
Phe Ile Gln Ser Leu Tyr Glu Ala Gly Gln Gln Asp Val Phe Pro Val
                805                 810                 815
Leu Ser Gln Tyr Pro Ser Leu Gln Asp Val Pro Leu Ala Ala Leu Glu
            820                 825                 830
Gly Lys Arg Pro Gln Pro Arg Glu Asn Ile Leu Leu Glu Pro Tyr Leu
            835                 840                 845
Phe Trp Gln Ile Leu Asn Gly Gln Leu Ser Gln Tyr Pro Gly Ser Tyr
850                 855                 860
Ser Asp Phe Ser Thr Pro Leu Ala His Phe Asp Leu Arg Asn Cys Trp
865                 870                 875                 880
Cys Val Asp Glu Ala Gly Gln Glu Leu Glu Gly Met Arg Ser Glu Pro
                885                 890                 895
Ser Lys Leu Pro Thr Cys Pro Gly Ser Cys Glu Glu Ala Lys Leu Arg
            900                 905                 910
Val Leu Gln Phe Ile Arg Glu Thr Glu Glu Ile Val Ser Ala Ser Asn
            915                 920                 925
Ser Ser Arg Phe Pro Leu Gly Glu Ser Phe Leu Val Ala Lys Gly Ile
930                 935                 940
Arg Leu Arg Asn Glu Asp Leu Gly Leu Pro Pro Leu Phe Pro Pro Arg
945                 950                 955                 960
Glu Ala Phe Ala Glu Gln Phe Leu Arg Gly Ser Asp Tyr Ala Ile Arg
                965                 970                 975
Leu Ala Ala Gln Ser Thr Leu Ser Phe Tyr Gln Arg Arg Arg Phe Ser
            980                 985                 990
Pro Asp Asp Ser Ala Gly Ala Ser  Ala Leu Leu Arg Ser  Gly Pro Tyr
            995                  1000                1005
Met Pro  Gln Cys Asp Ala Phe  Gly Ser Trp Glu Pro  Val Gln Cys
1010                 1015                1020
His Ala  Gly Thr Gly His Cys  Trp Cys Val Asp Glu  Lys Gly Gly
    1025                 1030                1035
Phe Ile  Pro Gly Ser Leu Thr  Ala Arg Ser Leu Gln  Ile Pro Gln
    1040                 1045                1050
Cys Pro  Thr Thr Cys Glu Lys  Ser Arg Thr Ser Gly  Leu Leu Ser
    1055                 1060                1065
Ser Trp  Lys Gln Ala Arg Ser  Gln Glu Asn Pro Ser  Pro Lys Asp
    1070                 1075                1080
Leu Phe  Val Pro Ala Cys Leu  Glu Thr Gly Glu Tyr  Ala Arg Leu
    1085                 1090                1095
Gln Ala  Ser Gly Ala Gly Thr  Trp Cys Val Asp Pro  Ala Ser Gly
    1100                 1105                1110
Glu Glu  Leu Arg Pro Gly Ser  Ser Ser Ser Ala Gln  Cys Pro Ser
    1115                 1120                1125
Leu Cys  Asn Val Leu Lys Ser  Gly Val Leu Ser Arg  Arg Val Ser
```

-continued

```
            1130                 1135                 1140
Pro Gly Tyr Val Pro Ala Cys Arg Ala Glu Asp Gly Gly Phe Ser
    1145                 1150                 1155
Pro Val Gln Cys Asp Gln Ala Gln Gly Ser Cys Trp Cys Val Met
    1160                 1165                 1170
Asp Ser Gly Glu Glu Val Pro Gly Thr Arg Val Thr Gly Gly Gln
    1175                 1180                 1185
Pro Ala Cys Glu Ser Pro Arg Cys Pro Leu Pro Phe Asn Ala Ser
    1190                 1195                 1200
Glu Val Val Gly Gly Thr Ile Leu Cys Glu Thr Ile Ser Gly Pro
    1205                 1210                 1215
Thr Gly Ser Ala Met Gln Gln Cys Gln Leu Leu Cys Arg Gln Gly
    1220                 1225                 1230
Ser Trp Ser Val Phe Pro Pro Gly Pro Leu Ile Cys Ser Leu Glu
    1235                 1240                 1245
Ser Gly Arg Trp Glu Ser Gln Leu Pro Gln Pro Arg Ala Cys Gln
    1250                 1255                 1260
Arg Pro Gln Leu Trp Gln Thr Ile Gln Thr Gln Gly His Phe Gln
    1265                 1270                 1275
Leu Gln Leu Pro Pro Gly Lys Met Cys Ser Ala Asp Tyr Ala Gly
    1280                 1285                 1290
Leu Leu Gln Thr Phe Gln Val Phe Ile Leu Asp Glu Leu Thr Ala
    1295                 1300                 1305
Arg Gly Phe Cys Gln Ile Gln Val Lys Thr Phe Gly Thr Leu Val
    1310                 1315                 1320
Ser Ile Pro Val Cys Asn Asn Ser Ser Val Gln Val Gly Cys Leu
    1325                 1330                 1335
Thr Arg Glu Arg Leu Gly Val Asn Val Thr Trp Lys Ser Arg Leu
    1340                 1345                 1350
Glu Asp Ile Pro Val Ala Ser Leu Pro Asp Leu His Asp Ile Glu
    1355                 1360                 1365
Arg Ala Leu Val Gly Lys Asp Leu Leu Gly Arg Phe Thr Asp Leu
    1370                 1375                 1380
Ile Gln Ser Gly Ser Phe Gln Leu His Leu Asp Ser Lys Thr Phe
    1385                 1390                 1395
Pro Ala Glu Thr Ile Arg Phe Leu Gln Gly Asp His Phe Gly Thr
    1400                 1405                 1410
Ser Pro Arg Thr Trp Phe Gly Cys Ser Glu Gly Phe Tyr Gln Val
    1415                 1420                 1425
Leu Thr Ser Glu Ala Ser Gln Asp Gly Leu Gly Cys Val Lys Cys
    1430                 1435                 1440
Pro Glu Gly Ser Tyr Ser Gln Asp Glu Glu Cys Ile Pro Cys Pro
    1445                 1450                 1455
Val Gly Phe Tyr Gln Glu Gln Ala Gly Ser Leu Ala Cys Val Pro
    1460                 1465                 1470
Cys Pro Val Gly Arg Thr Thr Ile Ser Ala Gly Ala Phe Ser Gln
    1475                 1480                 1485
Thr His Cys Val Thr Asp Cys Gln Arg Asn Glu Ala Gly Leu Gln
    1490                 1495                 1500
Cys Asp Gln Asn Gly Gln Tyr Arg Ala Ser Gln Lys Asp Arg Gly
    1505                 1510                 1515
Ser Gly Lys Ala Phe Cys Val Asp Gly Glu Gly Arg Arg Leu Pro
    1520                 1525                 1530
```

-continued

```
Trp Trp Glu Thr Glu Ala Pro Leu Glu Asp Ser Gln Cys Leu Met
1535                1540                1545

Met Gln Lys Phe Glu Lys Val Pro Glu Ser Lys Val Ile Phe Asp
1550                1555                1560

Ala Asn Ala Pro Val Ala Val Arg Ser Lys Val Pro Asp Ser Glu
    1565                1570                1575

Phe Pro Val Met Gln Cys Leu Thr Asp Cys Thr Glu Asp Glu Ala
    1580                1585                1590

Cys Ser Phe Phe Thr Val Ser Thr Thr Glu Pro Glu Ile Ser Cys
    1595                1600                1605

Asp Phe Tyr Ala Trp Thr Ser Asp Asn Val Ala Cys Met Thr Ser
    1610                1615                1620

Asp Gln Lys Arg Asp Ala Leu Gly Asn Ser Lys Ala Thr Ser Phe
    1625                1630                1635

Gly Ser Leu Arg Cys Gln Val Lys Val Arg Ser His Gly Gln Asp
    1640                1645                1650

Ser Pro Ala Val Tyr Leu Lys Lys Gly Gln Gly Ser Thr Thr Thr
    1655                1660                1665

Leu Gln Lys Arg Phe Glu Pro Thr Gly Phe Gln Asn Met Leu Ser
    1670                1675                1680

Gly Leu Tyr Asn Pro Ile Val Phe Ser Ala Ser Gly Ala Asn Leu
    1685                1690                1695

Thr Asp Ala His Leu Phe Cys Leu Leu Ala Cys Asp Arg Asp Leu
    1700                1705                1710

Cys Cys Asp Gly Phe Val Leu Thr Gln Val Gln Gly Gly Ala Ile
    1715                1720                1725

Ile Cys Gly Leu Leu Ser Ser Pro Ser Val Leu Leu Cys Asn Val
    1730                1735                1740

Lys Asp Trp Met Asp Pro Ser Glu Ala Trp Ala Asn Ala Thr Cys
    1745                1750                1755

Pro Gly Val Thr Tyr Asp Gln Glu Ser His Gln Val Ile Leu Arg
    1760                1765                1770

Leu Gly Asp Gln Glu Phe Ile Lys Ser Leu Thr Pro Leu Glu Gly
    1775                1780                1785

Thr Gln Asp Thr Phe Thr Asn Phe Gln Gln Val Tyr Leu Trp Lys
    1790                1795                1800

Asp Ser Asp Met Gly Ser Arg Pro Glu Ser Met Gly Cys Arg Lys
    1805                1810                1815

Asp Thr Val Pro Arg Pro Ala Ser Pro Thr Glu Ala Gly Leu Thr
    1820                1825                1830

Thr Glu Leu Phe Ser Pro Val Asp Leu Asn Gln Val Ile Val Asn
    1835                1840                1845

Gly Asn Gln Ser Leu Ser Ser Gln Lys His Trp Leu Phe Lys His
    1850                1855                1860

Leu Phe Ser Ala Gln Gln Ala Asn Leu Trp Cys Leu Ser Arg Cys
    1865                1870                1875

Val Gln Glu His Ser Phe Cys Gln Leu Ala Glu Ile Thr Glu Ser
    1880                1885                1890

Ala Ser Leu Tyr Phe Thr Cys Thr Leu Tyr Pro Glu Ala Gln Val
    1895                1900                1905

Cys Asp Asp Ile Met Glu Ser Asn Ala Gln Gly Cys Arg Leu Ile
    1910                1915                1920
```

-continued

```
Leu Pro Gln Met Pro Lys Ala Leu Phe Arg Lys Lys Val Ile Leu
1925                1930                1935

Glu Asp Lys Val Lys Asn Phe Tyr Thr Arg Leu Pro Phe Gln Lys
1940                1945                1950

Leu Met Gly Ile Ser Ile Arg Asn Lys Val Pro Met Ser Glu Lys
1955                1960                1965

Ser Ile Ser Asn Gly Phe Phe Glu Cys Glu Arg Arg Cys Asp Ala
1970                1975                1980

Asp Pro Cys Cys Thr Gly Phe Gly Phe Leu Asn Val Ser Gln Leu
1985                1990                1995

Lys Gly Gly Glu Val Thr Cys Leu Thr Leu Asn Ser Leu Gly Ile
2000                2005                2010

Gln Met Cys Ser Glu Glu Asn Gly Gly Ala Trp Arg Ile Leu Asp
2015                2020                2025

Cys Gly Ser Pro Asp Ile Glu Val His Thr Tyr Pro Phe Gly Trp
2030                2035                2040

Tyr Gln Lys Pro Ile Ala Gln Asn Asn Ala Pro Ser Phe Cys Pro
2045                2050                2055

Leu Val Val Leu Pro Ser Leu Thr Glu Lys Val Ser Leu Asp Ser
2060                2065                2070

Trp Gln Ser Leu Ala Leu Ser Ser Val Val Asp Pro Ser Ile
2075                2080                2085

Arg His Phe Asp Val Ala His Val Ser Thr Ala Ala Thr Ser Asn
2090                2095                2100

Phe Ser Ala Val Arg Asp Leu Cys Leu Ser Glu Cys Ser Gln His
2105                2110                2115

Glu Ala Cys Leu Ile Thr Thr Leu Gln Thr Gln Pro Gly Ala Val
2120                2125                2130

Arg Cys Met Phe Tyr Ala Asp Thr Gln Ser Cys Thr His Ser Leu
2135                2140                2145

Gln Gly Gln Asn Cys Arg Leu Leu Leu Arg Glu Glu Ala Thr His
2150                2155                2160

Ile Tyr Arg Lys Pro Gly Ile Ser Leu Leu Ser Tyr Glu Ala Ser
2165                2170                2175

Val Pro Ser Val Pro Ile Ser Thr His Gly Arg Leu Leu Gly Arg
2180                2185                2190

Ser Gln Ala Ile Gln Val Gly Thr Ser Trp Lys Gln Val Asp Gln
2195                2200                2205

Phe Leu Gly Val Pro Tyr Ala Ala Pro Pro Leu Ala Glu Arg Arg
2210                2215                2220

Phe Gln Ala Pro Glu Pro Leu Asn Trp Thr Gly Ser Trp Asp Ala
2225                2230                2235

Ser Lys Pro Arg Ala Ser Cys Trp Gln Pro Gly Thr Arg Thr Ser
2240                2245                2250

Thr Ser Pro Gly Val Ser Glu Asp Cys Leu Tyr Leu Asn Val Phe
2255                2260                2265

Ile Pro Gln Asn Val Ala Pro Asn Ala Ser Val Leu Val Phe Phe
2270                2275                2280

His Asn Thr Met Asp Arg Glu Glu Ser Glu Gly Trp Pro Ala Ile
2285                2290                2295

Asp Gly Ser Phe Leu Ala Ala Val Gly Asn Leu Ile Val Val Thr
2300                2305                2310

Ala Ser Tyr Arg Val Gly Val Phe Gly Phe Leu Ser Ser Gly Ser
```

-continued

```
        2315                2320                2325
Gly Glu Val Ser Gly Asn Trp Gly Leu Leu Asp Gln Val Ala Ala
        2330                2335                2340
Leu Thr Trp Val Gln Thr His Ile Arg Gly Phe Gly Gly Asp Pro
        2345                2350                2355
Arg Arg Val Ser Leu Ala Ala Asp Arg Gly Gly Ala Asp Val Ala
        2360                2365                2370
Ser Ile His Leu Leu Thr Ala Arg Ala Thr Asn Ser Gln Leu Phe
        2375                2380                2385
Arg Arg Ala Val Leu Met Gly Gly Ser Ala Leu Ser Pro Ala Ala
        2390                2395                2400
Val Ile Ser His Glu Arg Ala Gln Gln Gln Ala Ile Ala Leu Ala
        2405                2410                2415
Lys Glu Val Ser Cys Pro Met Ser Ser Ser Gln Glu Val Val Ser
        2420                2425                2430
Cys Leu Arg Gln Lys Pro Ala Asn Val Leu Asn Asp Ala Gln Thr
        2435                2440                2445
Lys Leu Leu Ala Val Ser Gly Pro Phe His Tyr Trp Gly Pro Val
        2450                2455                2460
Ile Asp Gly His Phe Leu Arg Glu Pro Pro Ala Arg Ala Leu Lys
        2465                2470                2475
Arg Ser Leu Trp Val Glu Val Asp Leu Leu Ile Gly Ser Ser Gln
        2480                2485                2490
Asp Asp Gly Leu Ile Asn Arg Ala Lys Ala Val Lys Gln Phe Glu
        2495                2500                2505
Glu Ser Arg Gly Arg Thr Ser Ser Lys Thr Ala Phe Tyr Gln Ala
        2510                2515                2520
Leu Gln Asn Ser Leu Gly Gly Glu Asp Ser Asp Ala Arg Val Glu
        2525                2530                2535
Ala Ala Ala Thr Trp Tyr Tyr Ser Leu Glu His Ser Thr Asp Asp
        2540                2545                2550
Tyr Ala Ser Phe Ser Arg Ala Leu Glu Asn Ala Thr Arg Asp Tyr
        2555                2560                2565
Phe Ile Ile Cys Pro Ile Ile Asp Met Ala Ser Ala Trp Ala Lys
        2570                2575                2580
Arg Ala Arg Gly Asn Val Phe Met Tyr His Ala Pro Glu Asn Tyr
        2585                2590                2595
Gly His Gly Ser Leu Glu Leu Leu Ala Asp Val Gln Phe Ala Leu
        2600                2605                2610
Gly Leu Pro Phe Tyr Pro Ala Tyr Glu Gly Gln Phe Ser Leu Glu
        2615                2620                2625
Glu Lys Ser Leu Ser Leu Lys Ile Met Gln Tyr Phe Ser His Phe
        2630                2635                2640
Ile Arg Ser Gly Asn Pro Asn Tyr Pro Tyr Glu Phe Ser Arg Lys
        2645                2650                2655
Val Pro Thr Phe Ala Thr Pro Trp Pro Asp Phe Val Pro Arg Ala
        2660                2665                2670
Gly Gly Glu Asn Tyr Lys Glu Phe Ser Glu Leu Leu Pro Asn Arg
        2675                2680                2685
Gln Gly Leu Lys Lys Ala Asp Cys Ser Phe Trp Ser Lys Tyr Ile
        2690                2695                2700
Ser Ser Leu Lys Thr Ser Ala Asp Gly Ala Lys Gly Gly Gln Ser
        2705                2710                2715
```

```
Ala Glu  Ser Glu Glu Glu  Leu Thr Ala Gly Ser  Gly Leu Arg
    2720         2725              2730

Glu Asp  Leu Leu Ser Leu Gln  Glu Pro Gly Ser Lys  Thr Tyr Ser
    2735             2740                  2745

Lys

<210> SEQ ID NO 266
<211> LENGTH: 445
<212> TYPE: PRT
<213> ORGANISM: Artificial Sequence
<220> FEATURE:
<223> OTHER INFORMATION: sequence of urokinase

<400> SEQUENCE: 266

Met Arg Ala Leu Leu Ala Arg Leu Leu Leu Cys Val Leu Val Val Ser
1               5                   10                  15

Asp Ser Lys Gly Ser Asn Glu Leu His Gln Val Pro Ser Asn Cys Asp
            20                  25                  30

Cys Leu Asn Gly Gly Thr Cys Val Ser Asn Lys Tyr Phe Phe Thr Ser
        35                  40                  45

Asn Ile His Trp Cys Asn Cys Pro Lys Lys Phe Gly Gly Gln His Cys
    50                  55                  60

Glu Ile Asp Lys Ser Lys Thr Cys Tyr Glu Gly Asn Gly His Phe Tyr
65                  70                  75                  80

Arg Gly Lys Ala Ser Thr Asp Thr Met Gly Arg Pro Cys Leu Pro Trp
                85                  90                  95

Asn Ser Ala Thr Val Leu Gln Gln Thr Tyr Phe Thr His Ala His Arg
            100                 105                 110

Ser Asp Ala Leu Gln Leu Gly Leu Gly Lys His Asn Tyr Cys Arg Asn
        115                 120                 125

Pro Asp Asn Arg Arg Arg Pro Trp Cys Tyr Val Gln Val Gly Leu Lys
    130                 135                 140

Pro Leu Val Gln Glu Cys Met Val His Asp Cys Ala Asp Gly Lys Lys
145                 150                 155                 160

Pro Ser Ser Pro Pro Glu Glu Phe Thr Leu Lys Phe Gln Cys Gly Gln
                165                 170                 175

Lys Thr Leu Arg Pro Arg Phe Lys Ile Ile Gly Gly Glu Phe Thr Thr
            180                 185                 190

Ile Glu Asn Gln Pro Trp Phe Ala Ala Ile Tyr Arg Arg His Arg Gly
        195                 200                 205

Gly Ser Val Thr Tyr Val Cys Gly Gly Ser Leu Ile Ser Pro Cys Trp
    210                 215                 220

Val Ile Ser Ala Phe Thr Thr His Cys Phe Ile Asp Tyr Pro Lys Lys
225                 230                 235                 240

Glu Asp Tyr Ile Val Tyr Leu Gly Arg Ser Arg Leu Asn Ser Asn Thr
                245                 250                 255

Gln Gly Glu Met Lys Phe Glu Val Glu Asn Leu Ile Leu His Lys Asp
            260                 265                 270

Tyr Ser Ala Asp Thr Leu Ala His His Asn Asp Ile Ala Leu Leu Lys
        275                 280                 285

Ile Phe Thr Arg Ser Lys Glu Gly Arg Cys Ala Gln Pro Ser Arg Thr
    290                 295                 300

Ile Gln Thr Ile Cys Leu Pro Ser Met Tyr Asn Asp Pro Gln Phe Gly
305                 310                 315                 320
```

-continued

```
Thr Ser Cys Glu Ile Thr Gly Phe Gly Lys Glu Asn Ser Thr Asp Tyr
            325                 330                 335

Leu Tyr Pro Glu Gln Leu Lys Met Thr Val Val Lys Leu Ile Phe Thr
            340                 345                 350

Ser His Arg Glu Cys Gln Gln Pro His Tyr Tyr Gly Ser Glu Val Thr
            355                 360                 365

Thr Lys Met Leu Cys Ala Ala Asp Pro Gln Trp Lys Thr Asp Ser Cys
        370                 375                 380

Gln Gly Asp Ser Gly Gly Pro Leu Val Cys Ser Leu Gln Gly Arg Met
385                 390                 395                 400

Thr Leu Thr Gly Ile Val Ser Trp Gly Arg Gly Phe Thr Cys Ala Leu
                405                 410                 415

Lys Asp Lys Pro Gly Val Tyr Thr Arg Val Ser His Phe Leu Pro Trp
                420                 425                 430

Ile Arg Ser His Thr Lys Glu Glu Asn Gly Leu Ala Leu
            435                 440                 445

<210> SEQ ID NO 267
<211> LENGTH: 26
<212> TYPE: PRT
<213> ORGANISM: Artificial Sequence
<220> FEATURE:
<223> OTHER INFORMATION: leader peptide Epicidin-280

<400> SEQUENCE: 267

Met Glu Asn Lys Lys Asp Leu Phe Asp Leu Glu Ile Lys Lys Asp Asn
1               5                   10                  15

Met Glu Asn Asn Asn Glu Leu Glu Ala Gln
            20                  25

<210> SEQ ID NO 268
<211> LENGTH: 26
<212> TYPE: PRT
<213> ORGANISM: Artificial Sequence
<220> FEATURE:
<223> OTHER INFORMATION: leader peptide Pep-5

<400> SEQUENCE: 268

Met Lys Asn Asn Lys Asn Leu Phe Asp Leu Glu Ile Lys Lys Glu Thr
1               5                   10                  15

Ser Gln Asn Thr Asp Glu Leu Glu Pro Gln
            20                  25

<210> SEQ ID NO 269
<211> LENGTH: 24
<212> TYPE: PRT
<213> ORGANISM: Artificial Sequence
<220> FEATURE:
<223> OTHER INFORMATION: leader peptide Epilancin-K7

<400> SEQUENCE: 269

Met Asn Asn Ser Leu Phe Asp Leu Asn Leu Asn Lys Gly Val Glu Thr
1               5                   10                  15

Gln Lys Ser Asp Leu Ser Pro Gln
            20

<210> SEQ ID NO 270
<211> LENGTH: 23
<212> TYPE: PRT
<213> ORGANISM: Artificial Sequence
<220> FEATURE:
<223> OTHER INFORMATION: leader peptide Nisin-A/Z
```

```
<400> SEQUENCE: 270

Met Ser Thr Lys Asp Phe Asn Leu Asp Leu Val Ser Val Ser Lys Lys
1               5                   10                  15

Asp Ser Gly Ala Ser Pro Arg
            20

<210> SEQ ID NO 271
<211> LENGTH: 24
<212> TYPE: PRT
<213> ORGANISM: Artificial Sequence
<220> FEATURE:
<223> OTHER INFORMATION: leader peptide Subtilin

<400> SEQUENCE: 271

Met Ser Lys Phe Asp Asp Phe Asp Leu Asp Val Val Lys Val Ser Lys
1               5                   10                  15

Gln Asp Ser Lys Ile Thr Pro Gln
            20

<210> SEQ ID NO 272
<211> LENGTH: 30
<212> TYPE: PRT
<213> ORGANISM: Artificial Sequence
<220> FEATURE:
<223> OTHER INFORMATION: leader peptide Epidermin

<400> SEQUENCE: 272

Met Glu Ala Val Lys Glu Lys Asn Asp Leu Phe Asn Leu Asp Val Lys
1               5                   10                  15

Val Asn Ala Lys Glu Ser Asn Asp Ser Gly Ala Glu Pro Arg
            20                  25                  30

<210> SEQ ID NO 273
<211> LENGTH: 30
<212> TYPE: PRT
<213> ORGANISM: Artificial Sequence
<220> FEATURE:
<223> OTHER INFORMATION: leader peptide Gallidermin

<400> SEQUENCE: 273

Met Glu Ala Val Lys Glu Lys Asn Glu Leu Phe Asp Leu Asp Val Lys
1               5                   10                  15

Val Asn Ala Lys Glu Ser Asn Asp Ser Gly Ala Glu Pro Arg
            20                  25                  30

<210> SEQ ID NO 274
<211> LENGTH: 41
<212> TYPE: PRT
<213> ORGANISM: Artificial Sequence
<220> FEATURE:
<223> OTHER INFORMATION: leader peptide Mutacin-1140/III

<400> SEQUENCE: 274

Met Ser Asn Thr Gln Leu Leu Glu Val Leu Gly Thr Glu Thr Phe Asp
1               5                   10                  15

Val Gln Glu Asp Leu Phe Ala Phe Asp Thr Thr Asp Thr Thr Ile Val
            20                  25                  30

Ala Ser Asn Asp Asp Pro Asp Thr Arg
            35                  40

<210> SEQ ID NO 275
<211> LENGTH: 24
```

```
<212> TYPE: PRT
<213> ORGANISM: Artificial Sequence
<220> FEATURE:
<223> OTHER INFORMATION: leader peptide Lacticin-481

<400> SEQUENCE: 275

Met Lys Glu Gln Asn Ser Phe Asn Leu Leu Gln Glu Val Thr Glu Ser
1               5                   10                  15

Glu Leu Asp Leu Ile Leu Gly Ala
            20

<210> SEQ ID NO 276
<211> LENGTH: 22
<212> TYPE: PRT
<213> ORGANISM: Artificial Sequence
<220> FEATURE:
<223> OTHER INFORMATION: leader peptide Variacin

<400> SEQUENCE: 276

Met Thr Asn Ala Phe Gln Ala Leu Asp Glu Val Thr Asp Ala Glu Leu
1               5                   10                  15

Asp Ala Ile Leu Gly Gly
            20

<210> SEQ ID NO 277
<211> LENGTH: 26
<212> TYPE: PRT
<213> ORGANISM: Artificial Sequence
<220> FEATURE:
<223> OTHER INFORMATION: leader peptide Mutacin-II

<400> SEQUENCE: 277

Met Asn Lys Leu Asn Ser Asn Ala Val Val Ser Leu Asn Glu Val Ser
1               5                   10                  15

Asp Ser Glu Leu Asp Thr Ile Leu Gly Gly
            20                  25

<210> SEQ ID NO 278
<211> LENGTH: 25
<212> TYPE: PRT
<213> ORGANISM: Artificial Sequence
<220> FEATURE:
<223> OTHER INFORMATION: leader peptide Streptococcin-A-FF22

<400> SEQUENCE: 278

Met Glu Lys Asn Asn Glu Val Ile Asn Ser Ile Gln Glu Val Ser Leu
1               5                   10                  15

Glu Glu Leu Asp Gln Ile Ile Gly Ala
            20                  25

<210> SEQ ID NO 279
<211> LENGTH: 29
<212> TYPE: PRT
<213> ORGANISM: Artificial Sequence
<220> FEATURE:
<223> OTHER INFORMATION: leader peptide Salivaricin-A

<400> SEQUENCE: 279

Met Asn Ala Met Lys Asn Ser Lys Asp Ile Leu Asn Asn Ala Ile Glu
1               5                   10                  15

Glu Val Ser Glu Lys Glu Leu Met Glu Val Ala Gly Gly
            20                  25

<210> SEQ ID NO 280
```

```
<210> SEQ ID NO 280
<211> LENGTH: 19
<212> TYPE: PRT
<213> ORGANISM: Artificial Sequence
<220> FEATURE:
<223> OTHER INFORMATION: leader peptide Sublancin

<400> SEQUENCE: 280

Met Glu Lys Leu Phe Lys Glu Val Lys Leu Glu Glu Leu Glu Asn Gln
1               5                   10                  15

Lys Gly Ser

<210> SEQ ID NO 281
<211> LENGTH: 31
<212> TYPE: PRT
<213> ORGANISM: Artificial Sequence
<220> FEATURE:
<223> OTHER INFORMATION: leader peptide Lactocin-S

<400> SEQUENCE: 281

Met Lys Thr Glu Lys Lys Val Leu Asp Glu Leu Ser Leu His Ala Ser
1               5                   10                  15

Ala Lys Met Gly Ala Arg Asp Val Glu Ser Ser Met Asn Ala Asp
            20                  25                  30

<210> SEQ ID NO 282
<211> LENGTH: 23
<212> TYPE: PRT
<213> ORGANISM: Artificial Sequence
<220> FEATURE:
<223> OTHER INFORMATION: leader peptide Ruminococcin A

<400> SEQUENCE: 282

Met Arg Asn Asp Val Leu Thr Leu Thr Asn Pro Met Glu Glu Lys Glu
1               5                   10                  15

Leu Glu Gln Ile Leu Gly Gly
            20

<210> SEQ ID NO 283
<211> LENGTH: 23
<212> TYPE: PRT
<213> ORGANISM: Artificial Sequence
<220> FEATURE:
<223> OTHER INFORMATION: leader peptide Butyrivibriocin OR79A

<400> SEQUENCE: 283

Met Asn Lys Glu Leu Asn Ala Leu Thr Asn Pro Ile Asp Glu Lys Glu
1               5                   10                  15

Leu Glu Gln Ile Leu Gly Gly
            20

<210> SEQ ID NO 284
<211> LENGTH: 25
<212> TYPE: PRT
<213> ORGANISM: Artificial Sequence
<220> FEATURE:
<223> OTHER INFORMATION: leader peptide Streptococcin A-M49

<400> SEQUENCE: 284

Met Thr Lys Glu His Glu Ile Ile Asn Ser Ile Gln Glu Val Ser Leu
1               5                   10                  15

Glu Glu Leu Asp Gln Ile Ile Gly Ala
            20                  25

<210> SEQ ID NO 285
```

-continued

<211> LENGTH: 24
<212> TYPE: PRT
<213> ORGANISM: Artificial Sequence
<220> FEATURE:
<223> OTHER INFORMATION: leader peptide Bacteriocin J46

<400> SEQUENCE: 285

Met Lys Glu Gln Asn Ser Phe Asn Leu Leu Gln Glu Val Thr Glu Ser
1               5                   10                  15

Glu Leu Asp Leu Ile Leu Gly Ala
            20

<210> SEQ ID NO 286
<211> LENGTH: 26
<212> TYPE: PRT
<213> ORGANISM: Artificial Sequence
<220> FEATURE:
<223> OTHER INFORMATION: leader peptide Salivaricin A1

<400> SEQUENCE: 286

Met Lys Asn Ser Lys Asp Ile Leu Thr Asn Ala Thr Glu Glu Val Ser
1               5                   10                  15

Glu Lys Glu Leu Met Glu Val Ala Gly Gly
            20                  25

<210> SEQ ID NO 287
<211> LENGTH: 23
<212> TYPE: PRT
<213> ORGANISM: Artificial Sequence
<220> FEATURE:
<223> OTHER INFORMATION: leader peptide Streptin

<400> SEQUENCE: 287

Met Asn Asn Thr Ile Lys Asp Phe Asp Leu Asp Leu Lys Thr Asn Lys
1               5                   10                  15

Lys Asp Thr Ala Thr Pro Tyr
            20

<210> SEQ ID NO 288
<211> LENGTH: 30
<212> TYPE: PRT
<213> ORGANISM: Artificial Sequence
<220> FEATURE:
<223> OTHER INFORMATION: leader peptide Plantaricin-W alpha

<400> SEQUENCE: 288

Met Lys Ile Ser Lys Ile Glu Ala Gln Ala Arg Lys Asp Phe Phe Lys
1               5                   10                  15

Lys Ile Asp Thr Asn Ser Asn Leu Leu Asn Val Asn Gly Ala
            20                  25                  30

<210> SEQ ID NO 289
<211> LENGTH: 29
<212> TYPE: PRT
<213> ORGANISM: Artificial Sequence
<220> FEATURE:
<223> OTHER INFORMATION: leader peptide Lacticin-3147A1

<400> SEQUENCE: 289

Met Asn Lys Asn Glu Ile Glu Thr Gln Pro Val Thr Trp Leu Glu Glu
1               5                   10                  15

Val Ser Asp Gln Asn Phe Asp Glu Asp Val Phe Gly Ala
            20                  25

```
<210> SEQ ID NO 290
<211> LENGTH: 32
<212> TYPE: PRT
<213> ORGANISM: Artificial Sequence
<220> FEATURE:
<223> OTHER INFORMATION: leader peptide Staphylococcin-C55 alpha

<400> SEQUENCE: 290

Met Lys Ser Ser Phe Leu Glu Lys Asp Ile Glu Glu Gln Val Thr Trp
1               5                   10                  15

Phe Glu Glu Val Ser Glu Gln Glu Phe Asp Asp Asp Ile Phe Gly Ala
            20                  25                  30

<210> SEQ ID NO 291
<211> LENGTH: 35
<212> TYPE: PRT
<213> ORGANISM: Artificial Sequence
<220> FEATURE:
<223> OTHER INFORMATION: leader peptide Plantaricin-W beta

<400> SEQUENCE: 291

Met Thr Lys Thr Ser Arg Arg Lys Asn Ala Ile Ala Asn Tyr Leu Glu
1               5                   10                  15

Pro Val Asp Glu Lys Ser Ile Asn Glu Ser Phe Gly Ala Gly Asp Pro
            20                  25                  30

Glu Ala Arg
        35

<210> SEQ ID NO 292
<211> LENGTH: 36
<212> TYPE: PRT
<213> ORGANISM: Artificial Sequence
<220> FEATURE:
<223> OTHER INFORMATION: leader peptide Lacticin-3147A2

<400> SEQUENCE: 292

Met Lys Glu Lys Asn Met Lys Lys Asn Asp Thr Ile Glu Leu Gln Leu
1               5                   10                  15

Gly Lys Tyr Leu Glu Asp Asp Met Ile Glu Leu Ala Glu Gly Asp Glu
            20                  25                  30

Ser His Gly Gly
        35

<210> SEQ ID NO 293
<211> LENGTH: 35
<212> TYPE: PRT
<213> ORGANISM: Artificial Sequence
<220> FEATURE:
<223> OTHER INFORMATION: leader peptide Staphylococcin-C55 beta

<400> SEQUENCE: 293

Met Lys Asn Glu Leu Gly Lys Phe Leu Glu Glu Asn Glu Leu Glu Leu
1               5                   10                  15

Gly Lys Phe Ser Glu Ser Asp Met Leu Glu Ile Thr Asp Asp Glu Val
            20                  25                  30

Tyr Ala Ala
        35

<210> SEQ ID NO 294
<211> LENGTH: 30
<212> TYPE: PRT
<213> ORGANISM: Artificial Sequence
<220> FEATURE:
<223> OTHER INFORMATION: leader peptide Cytolysin-LL
```

<400> SEQUENCE: 294

Met Glu Asn Leu Ser Val Val Pro Ser Phe Glu Glu Leu Ser Val Glu
1               5                   10                  15

Glu Met Glu Ala Ile Gln Gly Ser Gly Asp Val Gln Ala Glu
            20                  25                  30

<210> SEQ ID NO 295
<211> LENGTH: 42
<212> TYPE: PRT
<213> ORGANISM: Artificial Sequence
<220> FEATURE:
<223> OTHER INFORMATION: leader peptide Cytolysin-LS

<400> SEQUENCE: 295

Met Leu Asn Lys Glu Asn Gln Glu Asn Tyr Tyr Ser Asn Lys Leu Glu
1               5                   10                  15

Leu Val Gly Pro Ser Phe Glu Glu Leu Ser Leu Glu Glu Met Glu Ala
            20                  25                  30

Ile Gln Gly Ser Gly Asp Val Gln Ala Glu
        35                  40

<210> SEQ ID NO 296
<211> LENGTH: 59
<212> TYPE: PRT
<213> ORGANISM: Artificial Sequence
<220> FEATURE:
<223> OTHER INFORMATION: leader peptide Cinnamycin

<400> SEQUENCE: 296

Met Thr Ala Ser Ile Leu Gln Gln Ser Val Val Asp Ala Asp Phe Arg
1               5                   10                  15

Ala Ala Leu Leu Glu Asn Pro Ala Ala Phe Gly Ala Ser Ala Ala Ala
            20                  25                  30

Leu Pro Thr Pro Val Glu Ala Gln Asp Gln Ala Ser Leu Asp Phe Trp
        35                  40                  45

Thr Lys Asp Ile Ala Ala Thr Glu Ala Phe Ala
    50                  55

<210> SEQ ID NO 297
<211> LENGTH: 48
<212> TYPE: PRT
<213> ORGANISM: Artificial Sequence
<220> FEATURE:
<223> OTHER INFORMATION: leader peptide Mersacidin

<400> SEQUENCE: 297

Met Ser Gln Glu Ala Ile Ile Arg Ser Trp Lys Asp Pro Phe Ser Arg
1               5                   10                  15

Glu Asn Ser Thr Gln Asn Pro Ala Gly Asn Pro Phe Ser Glu Leu Lys
            20                  25                  30

Glu Ala Gln Met Asp Lys Leu Val Gly Ala Gly Asp Asn Glu Ala Ala
        35                  40                  45

<210> SEQ ID NO 298
<211> LENGTH: 10
<212> TYPE: PRT
<213> ORGANISM: Artificial Sequence
<220> FEATURE:
<223> OTHER INFORMATION: thioether LHRH

<400> SEQUENCE: 298

```
Gln His Trp Ala Tyr Gly Ala Arg Pro Gly
1               5                   10
```

<210> SEQ ID NO 299
<211> LENGTH: 10
<212> TYPE: PRT
<213> ORGANISM: Artificial Sequence
<220> FEATURE:
<223> OTHER INFORMATION: LHRH1 analogue

<400> SEQUENCE: 299

```
Gln His Trp Ser Tyr Gly Leu Arg Pro Gly
1               5                   10
```

<210> SEQ ID NO 300
<211> LENGTH: 10
<212> TYPE: PRT
<213> ORGANISM: Artificial Sequence
<220> FEATURE:
<223> OTHER INFORMATION: LHRH1 analogue
<220> FEATURE:
<221> NAME/KEY: SITE
<222> LOCATION: (6)..(9)
<223> OTHER INFORMATION: Note = "A" on pos. 6 and 9 are linked by "S"

<400> SEQUENCE: 300

```
Gln His Trp Ala Tyr Ala Leu Arg Ala Gly
1               5                   10
```

<210> SEQ ID NO 301
<211> LENGTH: 10
<212> TYPE: PRT
<213> ORGANISM: Artificial Sequence
<220> FEATURE:
<223> OTHER INFORMATION: LHRH1 analogue
<220> FEATURE:
<221> NAME/KEY: SITE
<222> LOCATION: (4)..(7)
<223> OTHER INFORMATION: Note = "A" on pos. 4 and 7 are linked by "S"

<400> SEQUENCE: 301

```
Gln His Trp Ala Tyr Gly Ala Arg Pro Gly
1               5                   10
```

<210> SEQ ID NO 302
<211> LENGTH: 10
<212> TYPE: PRT
<213> ORGANISM: Artificial Sequence
<220> FEATURE:
<223> OTHER INFORMATION: LHRH1 analogue
<220> FEATURE:
<221> NAME/KEY: SITE
<222> LOCATION: (2)..(4)
<223> OTHER INFORMATION: Note = "A" on pos. 2 and 4 are linked by "S"

<400> SEQUENCE: 302

```
Gln His Trp Ala Tyr Gly Leu Arg Pro Gly
1               5                   10
```

<210> SEQ ID NO 303
<211> LENGTH: 10
<212> TYPE: PRT
<213> ORGANISM: Artificial Sequence
<220> FEATURE:
<223> OTHER INFORMATION: LHRH1 analogue
<220> FEATURE:
<221> NAME/KEY: SITE
<222> LOCATION: (4)..(6)
<223> OTHER INFORMATION: Note = "A" on pos. 4 and 6 are linked by "S"

-continued

```
<400> SEQUENCE: 303

Gln His Trp Ser His Gly Trp Tyr Pro Gly
1               5                   10

<210> SEQ ID NO 304
<211> LENGTH: 10
<212> TYPE: PRT
<213> ORGANISM: Artificial Sequence
<220> FEATURE:
<223> OTHER INFORMATION: LHRH2 analogue

<400> SEQUENCE: 304

Gln His Trp Ser His Gly Trp Tyr Pro Gly
1               5                   10

<210> SEQ ID NO 305
<211> LENGTH: 10
<212> TYPE: PRT
<213> ORGANISM: Artificial Sequence
<220> FEATURE:
<223> OTHER INFORMATION: LHRH2 analogue
<220> FEATURE:
<221> NAME/KEY: SITE
<222> LOCATION: (6)..(9)
<223> OTHER INFORMATION: Note = "A" on pos. 6 and 9 are linked by "S"

<400> SEQUENCE: 305

Gln His Trp Ala His Ala Trp Tyr Ala Gly
1               5                   10

<210> SEQ ID NO 306
<211> LENGTH: 10
<212> TYPE: PRT
<213> ORGANISM: Artificial Sequence
<220> FEATURE:
<223> OTHER INFORMATION: LHRH2 analogue
<220> FEATURE:
<221> NAME/KEY: SITE
<222> LOCATION: (4)..(7)
<223> OTHER INFORMATION: Note = "A" on pos. 4 and 7 are linked by "S"

<400> SEQUENCE: 306

Gln His Trp Ala His Gly Ala Tyr Pro Gly
1               5                   10

<210> SEQ ID NO 307
<211> LENGTH: 10
<212> TYPE: PRT
<213> ORGANISM: Artificial Sequence
<220> FEATURE:
<223> OTHER INFORMATION: LHRH2 analogue
<220> FEATURE:
<221> NAME/KEY: SITE
<222> LOCATION: (2)..(4)
<223> OTHER INFORMATION: Note = "A" on pos. 2 and 4 are linked by "S"

<400> SEQUENCE: 307

Gln Ala Trp Ala His Gly Trp Tyr Pro Gly
1               5                   10

<210> SEQ ID NO 308
<211> LENGTH: 10
<212> TYPE: PRT
<213> ORGANISM: Artificial Sequence
<220> FEATURE:
<223> OTHER INFORMATION: LHRH2 analogue
<220> FEATURE:
<221> NAME/KEY: SITE
<222> LOCATION: (4)..(6)
```

<223> OTHER INFORMATION: Note = "A" on pos. 4 and 6 are linked by "S"

<400> SEQUENCE: 308

Gln His Trp Ala His Ala Trp Tyr Pro Gly
1               5                   10

<210> SEQ ID NO 309
<211> LENGTH: 10
<212> TYPE: PRT
<213> ORGANISM: Artificial Sequence
<220> FEATURE:
<223> OTHER INFORMATION: (Q1,C7)-Sequence of LHRH2

<400> SEQUENCE: 309

Gln His Trp Ser His Gly Cys Tyr Pro Gly
1               5                   10

<210> SEQ ID NO 310
<211> LENGTH: 3
<212> TYPE: PRT
<213> ORGANISM: Artificial Sequence
<220> FEATURE:
<221> NAME/KEY: misc_feature
<222> LOCATION: (2)..(2)
<223> OTHER INFORMATION: Xaa can be from one to twenty naturally
      accuring amino acids

<400> SEQUENCE: 310

Ser Xaa Cys
1

<210> SEQ ID NO 311
<211> LENGTH: 3
<212> TYPE: PRT
<213> ORGANISM: Artificial Sequence
<220> FEATURE:
<221> NAME/KEY: misc_feature
<222> LOCATION: (2)..(2)
<223> OTHER INFORMATION: Xaa can be from one to twenty naturally
      accuring amino acids

<400> SEQUENCE: 311

Thr Xaa Cys
1

<210> SEQ ID NO 312
<211> LENGTH: 3
<212> TYPE: PRT
<213> ORGANISM: Artificial Sequence
<220> FEATURE:
<221> NAME/KEY: misc_feature
<222> LOCATION: (2)..(2)
<223> OTHER INFORMATION: Xaa can be from two to fifteen naturally
      accuring amino acids

<400> SEQUENCE: 312

Ser Xaa Cys
1

<210> SEQ ID NO 313
<211> LENGTH: 3
<212> TYPE: PRT
<213> ORGANISM: Artificial Sequence
<220> FEATURE:
<221> NAME/KEY: misc_feature
<222> LOCATION: (2)..(2)
<223> OTHER INFORMATION: Xaa can be from two to fifteen naturally
      accuring amino acids -continued

<400> SEQUENCE: 313

Thr Xaa Cys
1